United States Patent
Pajouhesh et al.

(10) Patent No.: US 8,377,968 B2
(45) Date of Patent: Feb. 19, 2013

(54) N-PIPERIDINYL ACETAMIDE DERIVATIVES AS CALCIUM CHANNEL BLOCKERS

(75) Inventors: Hassan Pajouhesh, West Vancouver (CA); Ramesh Kaul, Burnaby (CA); Yanbing Ding, Richmond (CA); Yongbao Zhu, Langley (CA); Lingyun Zhang, Vancouver (CA); Nagasree Chakka, Cambridge, MA (US); Mike Grimwood, North Vancouver (CA); Jason Tan, Vancouver (CA); Yuanxi Zhou, Richmond (CA)

(73) Assignee: Zalicus Pharmaceuticals, Ltd., Vancouver, BC (CA)

( * ) Notice: Subject to any disclaimer, the term of this patent is extended or adjusted under 35 U.S.C. 154(b) by 0 days.

(21) Appl. No.: 12/420,793

(22) Filed: Apr. 8, 2009

(65) Prior Publication Data

US 2009/0298883 A1  Dec. 3, 2009

Related U.S. Application Data

(60) Provisional application No. 61/058,179, filed on Jun. 2, 2008.

(51) Int. Cl.
*A61K 31/454* (2006.01)
*A61K 31/445* (2006.01)
*A61P 25/08* (2006.01)
*A61P 25/16* (2006.01)
*A61P 25/18* (2006.01)
*A61P 25/30* (2006.01)
*A61P 25/00* (2006.01)
*A61P 3/10* (2006.01)
*A61P 29/00* (2006.01)
*A61P 35/00* (2006.01)
*A61P 13/10* (2006.01)
*A61P 13/12* (2006.01)
*A61P 15/16* (2006.01)

(52) U.S. Cl. ........ 514/326; 514/331; 514/316; 546/247; 546/203

(58) Field of Classification Search .................... None
See application file for complete search history.

(56) References Cited

U.S. PATENT DOCUMENTS

| | | | |
|---|---|---|---|
| 5,852,014 A | 12/1998 | Gaster et al. | |
| 6,544,997 B1 | 4/2003 | Bosmans et al. | |
| 6,984,637 B2 | 1/2006 | Gong et al. | |
| 7,067,665 B2 | 6/2006 | Nazare et al. | |
| 7,244,758 B2 | 7/2007 | Pajouhesh et al. | |
| 7,259,157 B2 | 8/2007 | Liverton et al. | |
| 7,507,760 B2 | 3/2009 | Pajouhesh et al. | |
| 2003/0086980 A1 | 5/2003 | Shin et al. | |
| 2003/0087799 A1 | 5/2003 | Wolfart et al. | |
| 2003/0125269 A1 | 7/2003 | Li | |
| 2004/0197825 A1 | 10/2004 | Karicheti et al. | |
| 2006/0003985 A1 | 1/2006 | Renger et al. | |
| 2006/0025397 A1 | 2/2006 | Shin et al. | |
| 2009/0298834 A1 | 12/2009 | Pajouhesh et al. | |

FOREIGN PATENT DOCUMENTS

| | | |
|---|---|---|
| CA | 2286870 | 10/1998 |
| FR | 2769914 | 4/1999 |
| GR | 1003885 | 5/2002 |
| WO | WO-03/007953 | 1/2003 |
| WO | WO-04/000311 | 12/2003 |
| WO | WO2004/046110 | 6/2004 |
| WO | WO 2004/046110 * | 6/2004 |
| WO | WO-2005/077082 | 8/2005 |
| WO | WO-2005/086971 | 9/2005 |
| WO | WO-2005/092882 | 10/2005 |
| WO | WO-2007/002361 | 1/2007 |
| WO | WO 2007/002361 * | 1/2007 |
| WO | WO 2007/002884 * | 1/2007 |
| WO | WO-2007/002884 | 1/2007 |
| WO | WO 2007/053819 | 5/2007 |
| WO | WO 2007/077508 | 7/2007 |
| WO | WO 2007/078990 | 7/2007 |
| WO | WO 2008/031227 | 3/2008 |
| WO | WO 2011/032291 | 3/2011 |

OTHER PUBLICATIONS

McCalmont et al. in Bioorganic and Medicinal Chemistry Letters 14 (2004) 3691-3695.*
Coenen et al._Behavior Genetics 33(6) 635-655 (2003).*
Astles et al., Bioorganic & Medicinal Chemistry (2001) 9:2195-2202.
Augustine et al., Annu. Rev. Neurosci. (1987) 10:633-693.
Catterall, Annu. Rev. Cell Dev. Biol. (2000) 16:521-555.
Diouf et al., Eur. J. Med. Chem. (2001) 35:699-706.
Dogrul et al., Pain (2003) 105:159-168.
Gomora et al., Mol. Pharmacol. (2001) 60:1121-1132.
Hayashi et al., Journal of Pharmacological Sciences (2005) 99:221-227.
Heady et al., Jpn. J. Pharmacol. (2001) 85:339-350.
Heo et al., Bioorganic & Medicinal Chemistry Letters (2008) 18:3899-3901.
Huguenard, Annu. Rev. Physiol. (1996) 58:329-348.
Itoh et al., Eur. J. Med. Chem. (1999) 34:329-341.
Itoh et al., Eur. J. Med. Chem. (1999) 34:1101-1108.
Kim et al., Mol. Cell Neurosci. (2001) 18(2):235-245.
Lopez-Rodriguez et al., J. Med. Chem. (2002) 45:4806-4815.

(Continued)

Primary Examiner — Dennis Heyer
(74) Attorney, Agent, or Firm — Clark & Elbing LLP

(57) ABSTRACT

Methods and compounds effective in ameliorating conditions characterized by unwanted calcium channel activity, particularly unwanted T-type calcium channel activity are disclosed. Specifically, a series of compounds containing N-piperidinyl acetamide derivatives as shown in formula (1).

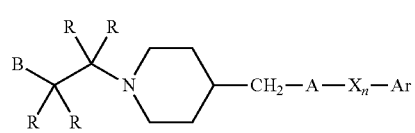

(1)

2 Claims, No Drawings

OTHER PUBLICATIONS

Miller, Science (1987) 235:46-52.

Su et al., J. Neurosci. (2002) 22:3645-3655.

Sui et al., British Journal of Urology International (2007) 99(2):436-441.

Taylor et al., World J. Gastroenterol. (2008) 14(32):4984-4991.

Lopez-Rodriguez et al., "3-D-QSAR/CoMFA and Recognition Models of Benzimidazole Derivatives at the 5-HT$_4$ Receptor," *Bioorg. Med. Chem. Lett.* 11:2807-2811, 2001.

Yang et al., "Discovery of 1,4-Substituted Piperidines as Potent and Selective Inhibitors of T-Type Calcium Channels," *J. Med. Chem.* 51:6471-6477, 2008.

Written Opinion and International Search Report of International Application No. PCT/CA2009/000768 mailed on Sep. 11, 2009.

International Preliminary Report on Patentability (PCT/CA2009/000768), dated Dec. 6, 2010.

López-Rodriguez et al., "Benzimidazole Derivatives. Part I: Synthesis and Structure-Activity Relationships of New Benzimidazole-4-Carboxamides and Carboxylates as Potent and Selective 5-HT$_4$ Receptor Antagonists," *Bioorg. Med. Chem.* 7:2271-2281 (1999).

Shanklin, Jr. et al., "Synthesis, Calcium-Channel Blocking Activity, and Antihypertensive Activity of 4-(Diarylmethyl)-1-[3-(Aryloxy)propyl] Piperidines and Structurally Related Compounds," *J. Med. Chem.* 34:3011-3022 (1991).

Shipe et al., "Design, Synthesis and Evaluation of a Novel 4-Aminomethyl-4-Fluoropiperidine as a T-Type Ca$^{2+}$ Channel Antagonist," *J. Med. Chem.* 51:3692-3695 (2008).

Uebele et al., "Antagonism of T-Type Calcium Channels Inhibits High-Fat Diet-Induced Weight Gain in Mice," *J. Clin. Investigation* 119:1659-1667 (2009).

Extended European Search Report for Application No. 09757002.2-2123, dated Nov. 24, 2011.

* cited by examiner

N-PIPERIDINYL ACETAMIDE DERIVATIVES AS CALCIUM CHANNEL BLOCKERS

CROSS-REFERENCE TO RELATED APPLICATIONS

This application claims benefit of Provisional Application Ser. No. 61/058,179, filed 2 Jun. 2008. The contents of this document are incorporated herein by reference.

TECHNICAL FIELD

The invention relates to compounds useful in treating conditions associated with calcium channel function, and particularly conditions associated with T-type calcium channel activity. More specifically, the invention concerns compounds containing substituted amino N-piperidinyl acetamide derivatives that are useful in treatment of conditions such as cardiovascular disease, epilepsy, cancer and pain.

BACKGROUND ART

The entry of calcium into cells through voltage-gated calcium channels mediates a wide variety of cellular and physiological responses, including excitation-contraction coupling, hormone secretion and gene expression (Miller, R. J., *Science* (1987) 235:46-52; Augustine, G. J. et al., *Annu Rev Neurosci* (1987) 10: 633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazapines all target L-type calcium channels) (Janis, R. J. & Triggle, D. J., Ion Calcium Channels: Their Properties, Functions, Regulation nad Clinical Relevance (1991) CRC Press, London).

Native calcium channels have been classified by their electrophysiological and pharmacological properties into T-, L-, N-, P/Q- and R-types (reviewed in Catterall, W., *Annu Rev Cell Dev Biol* (2000) 16: 521-555; Huguenard, J. R., *Annu Rev Physiol* (1996) 58: 329-348). T-type (or low voltage-activated) channels describe a broad class of molecules that transiently activate at negative potentials and are highly sensitive to changes in resting potential.

The L-, N- and P/Q-type channels activate at more positive potentials (high voltage-activated) and display diverse kinetics and voltage-dependent properties (Catterall (2000); Huguenard (1996)). T-type channels can be distinguished by having a more negative range of activation and inactivation, rapid inactivation, slow deactivation, and smaller single-channel conductances. There are three subtypes of T-type calcium channels that have been molecularly, pharmacologically, and elecrophysiologically identified: these subtypes have been termed $\alpha_{1G}$, $\alpha_{1H}$, and $\alpha_{1I}$ (alternately called Cav 3.1, Cav 3.2 and Cav 3.3 respectively).

T-type calcium channels are involved in various medical conditions. In mice lacking the gene expressing the $\alpha_{1G}$ subunit, resistance to absence seizures was observed (Kim, C. et al., *Mol Cell Neurosci* (2001) 18(2): 235-245). Other studies have also implicated the $\alpha_{1H}$ subunit in the development of epilepsy (Su, H. et al., *J Neurosci* (2002) 22: 3645-3655). There is strong evidence that some existing anticonvulsant drugs, such as ethosuximide, function through the blockade of T-type channels (Gomora, J. C., et al., *Mol Pharmacol* (2001) 60: 1121-1132).

Low voltage-activated calcium channels are highly expressed in tissues of the cardiovascular system. Mibefradil, a calcium channel blocker 10-30 fold selective for T-type over L-type channels, was approved for use in hypertension and angina. It was withdrawn from the market shortly after launch due to interactions with other drugs (Heady, T. N., et al., *Jpn J Pharmacol*. (2001) 85:339-350).

There is also a growing body of evidence that suggests that T-type calcium channels are abnormally expressed in cancerous cells and that blockade of these channels may reduce cell proliferation in addition to inducing apoptosis. Recent studies also show that the expression of T-type calcium channels in breast cancer cells is proliferation state dependent, i.e. the channels are expressed at higher levels during the fast-replication period, and once the cells are in a non-proliferation state, expression of this channel is minimal. Therefore, selectively blocking calcium channel entry into cancerous cells may be a valuable approach for preventing tumor growth (PCT Patent Application Nos. WO 05/086971 and WO 05/77082; Taylor, J. T., et al., *World J. Gastroenterol* (2008) 14(32): 4984-4991; Heo, J. H., et al., *Biorganic & Medicinal Chemistry Letters* (2008) 18:3899-3901).

Growing evidence suggests T-type calcium channels are also involved in pain (see for example: US Patent Application No. 2003/086980; PCT Patent Application Nos. WO 03/007953 and WO 04/000311). Both mibefradil and ethosuximide have shown anti-hyperalgesic activity in the spinal nerve ligation model of neuropathic pain in rats (Dogrul, A., et al., *Pain* (2003) 105:159-168). In addition to cardiovascular disease, epilepsy (see also US Patent Application No. 2006/025397), cancer and chronic and acute pain, T-type calcium channels have been implicated in diabetes (US Patent Application No. 2003/125269), sleep disorders (US Patent Application No. 2006/003985), Parkinson's disease (US Patent Application No. 2003/087799); psychosis such as schizophrenia (US Patent Application No. 2003/087799), overactive bladder (Sui, G.-P., et al., *British Journal of Urology International* (2007) 99(2): 436-441; see also US 2004/197825), renal disease (Hayashi, K., et al., *Journal of Pharmacological Sciences* (2005) 99: 221-227), neuroprotection and male birth control.

All patents, patent applications and publications are herein incorporated by reference in their entirety.

DISCLOSURE OF THE INVENTION

The invention relates to compounds useful in treating conditions modulated by calcium channel activity and in particular conditions mediated by T-type channel activity. The compounds of the invention are N-piperidinyl acetamide derivatives with structural features that enhance the calcium channel blocking activity of the compounds. Thus, in one aspect, the invention is directed to a method of treating conditions mediated by calcium channel activity by administering to patients in need of such treatment at least one compound of formula (1):

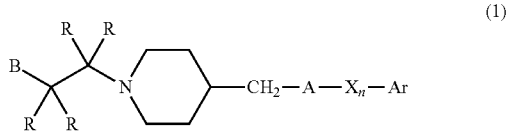

or a pharmaceutically acceptable salt or conjugate thereof, wherein

A is C(O)NR' or NR' C(O) wherein R' is H or methyl;

X is an optionally substituted alkylene (1-4C), heteroalkylene (2-4C), alkenylene (2-4C), or heteroakenylene (2-4C);

n is 0 or 1;

Ar is an optionally substituted aryl (6-10C) or heteroaryl (5-12C);

B is OH or $NY_2$, wherein each Y is independently H, SR", SOR", $SO_2R$", or each Y is an optionally substituted group selected from alkyl (1-10C), alkenyl (2-10C), alkynyl (2-10C), heteroalkyl (2-10C), heteroalkenyl (2-10C), heteroalkynyl (2-10C); or two Y may together form an optionally substituted heterocyclic ring (4-6 ring members);

each R is independently H, halo, CN, $NO_2$, $CF_3$, $OCF_3$, COOR", $CONR"_2$, OR", SR", SOR", $SO_2R"$, $NR"_2$, NR"(CO)R", and $NR"SO_2R"$; or each R is independently optionally substituted groups selected from alkyl (1-6C), alkenyl (2-6C), alkynyl (2-6C), heteroalkyl (2-6C), heteroalkenyl (2-6C), heteroalkynyl (2-6C); or two R on the same carbon atom taken together are =O, =NOR" or =NCN; or two R together form an optionally substituted cyclic or heterocyclic ring (3-6 ring members); or if B is $NY_2$, one R and one Y together form an optionally substituted heterocyclic ring (4-6 ring members);

each R" is independently H or an optionally substituted group selected from alkyl (1-6C), alkenyl (2-6C), alkynyl (2-6C), heteroalkyl (2-6C) heteroalkenyl (2-6), heteroalkynyl (2-6C), wherein the optional substituents on Y, R and R" may be one or more halo, =O, =NOR', CN, $NO_2$, $CF_3$, $OCF_3$, COOR', $CONR'_2$, OR', SR', SOR', $SO_2R'$, $NR'_2$, NR'(CO)R', and $NR'SO_2R'$, alkyl (1-6C), alkenyl (2-6C), alkynyl (2-6C), heteroalkyl (2-6C), heteroalkenyl (2-6C), heteroalkynyl (2-6C);

wherein the optional substituents on X and Ar may be one or more halo, CN, $CF_3$, $OCF_3$, COOR", $CONR"_2$, OR", SR", SOR", $SO_2R"$, alkyl (1-6C), alkenyl (2-6C), alkynyl (2-6C), heteroalkyl (2-6C), heteroalkenyl (2-6C), heteroalkynyl (2-6C); aryl (6-10C), heteroaryl (5-12 ring members), O-aryl (6-10C), O-heteroaryl (5-12 ring members), aryl (6-12C)-alkyl (1-6) or heteroaryl (5-12 ring members)-alkyl (1-6C); and wherein optional substituents on X may be additionally selected from =O, =NOR", $NO_2$, $NR"_2$, NR"(CO)R", and $NR"SO_2R"$; and wherein two substituents on Ar or X may together form a cyclic or heterocyclic ring (4-7 ring members).

The invention is also directed to the use of compounds of formula (1) for the preparation of medicaments for the treatment of conditions requiring modulation of calcium channel activity, and in particular T-type calcium channel activity. In another aspect, the invention is directed to pharmaceutical compositions containing compounds of formula (1) in admixture with a pharmaceutically acceptable excipient with the additional proviso that Ar is not a benzimidazolyl and to the use of these compositions for treating conditions requiring modulation of calcium channel activity, and particularly T-type calcium channel activity. The invention is also directed to compounds of formula (1) useful to modulate calcium channel activity, particularly T-type channel activity.

DETAILED DESCRIPTION

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. Typically, the alkyl, alkenyl and alkynyl groups contain 1-10C (alkyl) or 2-10C (alkenyl or alkynyl). In some embodiments, they contain 1-8C, 1-6C, 1-4C, 1-3C or 1-2C (alkyl); or 2-8C, 2-6C, 2-4C or 2-3C (alkenyl or alkynyl). Further, any hydrogen atom on one of these groups can be replaced with a halogen atom, and in particular a fluoro or chloro, and still be within the scope of the definition of alkyl, alkenyl and alkynyl. For example, $CF_3$ is a 1C alkyl. These groups may be also be substituted by other substituents.

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N.

The designated number of carbons in heteroforms of alkyl, alkenyl and alkynyl includes the heteroatom count. For example, if heteroalkyl is defined as 1-6C, it will contain 1-6 C, N, O, or S atoms such that the heteroalkyl contains at least one C atom and at least one heteroatom, for example 1-5C and 1N or 1-4C and 2N. Similarly, when heteroalkyl is defined as 1-6C or 1-4C, it would contain 1-5C or 1-3C respectively, i.e., at least one C is replaced by O, N or S. Accordingly, when heteroalkenyl or heteroalkynyl is defined as 2-6C (or 2-4C), it would contain 2-6 or 2-4 C, N, O, or S atoms, since the heteroalkenyl or heteroalkynyl contains at least one carbon atom and at least one heteroatom, e.g. 2-5C and 1N or 2-4C and 2O. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_nNR_2$, OR, COOR, $CONR_2$, $(CH_2)_nOR$, $(CH_2)_nCOR$, $(CH_2)_nCOOR$, $(CH_2)_nSR$, $(CH_2)_nSOR$, $(CH_2)_nSO_2R$, $(CH_2)_nCONR_2$, NRCOR, NRCOOR, $OCONR_2$, OCOR and the like wherein the group contains at least one C and the size of the substituent is consistent with the definition of alkyl, alkenyl and alkynyl.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/ heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, indolyl. Even more particularly, such moiety is phenyl, pyridyl, or pyrimidyl and even more particularly, it is phenyl.

"O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of 1-8C, 1-6C or more particularly 1-4C or 1-3C when saturated or 2-8C, 2-6C, 2-4C or 2-3C when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(6-12C)alkyl(1-8C), aryl(6-12C)alkenyl(2-8C), or aryl(6-12C)alkynyl(2-8C), plus the heteroforms, A typical example is phenylmethyl, commonly referred to as benzyl.

Typical optional substituents on aromatic or heteroaromatic groups include independently halo, CN, $NO_2$, $CF_3$, $OCF_3$, COOR', CONR'$_2$, OR', SR', SOR', $SO_2$R', NR'$_2$, NR'(CO)R', NR'C(O)OR', NR'C(O)NR'$_2$, NR'$SO_2$NR'$_2$, or NR'$SO_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group, are typically selected from the same list of substituents suitable for aromatic or heteroaromatic groups and may further be selected from =O and =NOR' where R' is H or an optionally substituted group selected from alkyl, alkenyl, alkynyl, heteroalkyl, heteroalkenyl, heteralkynyl, heteroaryl, and aryl (all as defined above).

Halo may be any halogen atom, especially F, Cl, Br, or I, and more particularly it is fluoro, chloro or bromo and even more particularly it is fluoro or chloro.

In general, any alkyl, alkenyl, alkynyl, or aryl (including all heteroforms defined above) group contained in a substituent may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included.

A is C(O)NH or NHC(O). "n" is 0 or 1 indicating that X is present when n is 1 and X is absent when n is 0. X is an optionally substituted alkylene (1-4C), heteroalkylene (2-4C), alkenylene (2-4C), or heteralkenylene (2-4C). In more particular embodiments X is absent (i.e. n=0) or X is an optionally substituted alkylene (1-2C) or X is an optionally substituted alkenylene (2C). When X is present, the substituents on X are as defined above, however, in particular embodiments X may be unsubstituted or be substituted with an optionally substituted phenyl. When X is an unsubstituted alkenylene, in particular embodiments, X is in the trans configuration.

Ar is an optionally substituted aryl (6-10C) or heteroaryl (5-12C). In particular embodiments, Ar is an optionally substituted phenyl, pyrazolyl, imidazolyl, pyridinyl, isoxazolyl, benzimidazolyl, thiazolyl, benzothiazolyl or indolyl. In more particular embodiments, Ar is an optionally substituted phenyl. Optional substituents on Ar are as defined above, however, in more particular embodiments such optional substituents may independently be selected from fluoro, bromo, chloro, trifluoromethyl, methyl, difluoromethoxy, trifluoromethoxy, methylsulfonyl, t-butyl, t-butyloxy, methoxy, phenoxy, pyrrolidinyl, pyridinyloxy, morpholinomethyl, hydroxyl, $(CH_3)_3COC(O)$. In addition, two optional substitents on Ar may together form a cyclic or heterocyclic ring with Ar. For example, in some embodiments, the two substituents on Ar together form —O—$CH_2$—O—, —O—$CF_2$—O, or —O—$CH_2CH_2$—. In even more particular embodiments, Ar is a phenyl and as such, the Ar group, including substituents that together form a 5 membered heterocyclic ring, is a benzodioxole, 2,2-difluorobenzodioxole, or dihydrobenzofuran.

Each R is independently is independently H, halo, CN, $NO_2$, $CF_3$, $OCF_3$, COOR", CONR"$_2$, OR", SR", SOR", $SO_2$R", NR"$_2$, NR"(CO)R", and NR"$SO_2$R"; or each R is independently optionally substituted groups selected from alkyl, alkenyl, alkynyl, heteroalkyl, heteroalkenyl, heteroalkynyl; or two R on the same carbon atom taken together are =O, =NOR" or =NCN; or two R together form an optionally substituted cyclic or heterocyclic ring (3-6 ring members). In many embodiments, each R is H. In other embodiments, one or more R may be an optionally substituted alkyl or heteroalkyl. In some embodiments, two R together form =O or a 4-6 membered optionally substituted cyclic or heterocylic ring. R" is independently H or an optionally substituted group selected from alkyl, alkenyl, alkynyl, heteroalkyl, heteroalkenyl, heteroalkynyl.

In compounds of formula (1), there are two carbon atoms between the piperidine nitrogen and B. The alpha carbon is immediately adjacent to the piperidine nitrogen and the beta carbon is immediately adjacent to B. In many embodiments, the two R on the beta carbon together form =O or a 4-6 membered optionally substituted cyclic or heterocyclic ring. In many alternate or concurrent embodiments, the two R on the alpha carbon are H or together form =O.

B may be a hydroxyl or $NY_2$ where Y is H, SR", SOR", $SO_2$R", or each Y is an optionally substituted group selected from alkyl, alkenyl, alkynyl, heteroalkyl, heteroalkenyl, heteroalkynyl; or two Y may together form an optionally substituted heterocyclic ring (4-6 ring members). In some embodiments, at least one Y is a hydrogen whereas in other embodiments both Y are hydrogen. In many embodiments, at least one Y is an alkyl or a heteroalkyl. In many embodiments, a carbonyl or a sulfonyl in Y is adjacent to the N in B. In some embodiments, a ureido functionality (NC(O)N) is created with Y and the N in B. In some embodiments, one Y and one R together form an optionally substituted heterocyclic ring, and even more particularly, the R is on the beta carbon as defined above. In other embodiments, two Y together form an optionally substituted heterocyclic ring. In yet other embodiments, one Y is H or methyl and one Y is an optionally substituted alkyl (1-6C) or $SO_2R^4$ wherein $R^4$ is an optionally substituted alkyl (1-5C).

In some embodiments, the compound is of formula (2):

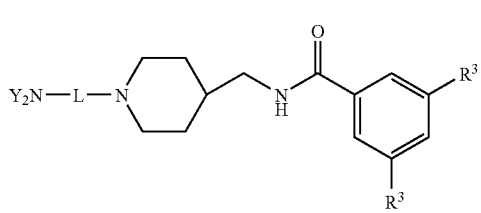

(2)

Wherein Y is as defined above, L is $C(O)CH_2$ or $CH_2CH_2$ and $R^3$ is H, halo, $CF_3$, $CH_3$, $OCH_3$ or $OCF_3$.

In some preferred embodiments, two or more of the particularly described groups are combined into one compound: it is often suitable to combine one of the specified embodiments of one feature as described above with a specified embodiment or embodiments of one or more other features as described above. For example, a specified embodiment includes a compound of formula (1) with Ar equal to phenyl, and another specified embodiment has n equal to 0. Thus one preferred embodiment combines both of these features together, i.e., Ar is phenyl in combination with n=0. In some specific embodiments, B is OH and in others A is NHC(O). Thus additional preferred embodiments include B as OH in combination with any of the preferred combinations set forth above; other preferred combinations include A as NHC(O) in combination with any of the preferred combinations set forth above.

The compounds of the invention may be in the form of pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed.

Compounds of formula (1) are also useful for the manufacture of a medicament useful to treat conditions characterized by undesired T-type calcium channel activities.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to the compounds of formula (1) when modified so as to be included in a conjugate of this type.

Merck & Co., Inc. has filed two patent applications directed towards T-type calcium channel blockers with a similar piperidinyl acetamide core to that disclosed in the present invention, namely Patent Cooperation Treaty applications WO 2007/002361 and WO 2007/002884 (the '361 and '884 patent applications). However, in the '361 patent it is essential that the piperidinyl group be substituted by a fluoro at the 3 position while in the '884 application, it is essential that the piperidinyl group be substituted by a fluoro at the 4 position. Not only does Merck view the presence of fluorine on the piperidinyl ring as required but also that the position on the ring gives rise to two separate inventions. No experimental data is provided for any of the compounds in either patent, no explanation is given for the role of the fluorine in either patent application, nor is it even clear what subtype of the T-type calcium channel is affected by their compounds (i.e. $\alpha_{1G}$, $\alpha_{1H}$ or $\alpha_{1I}$). Surprisingly, we have found that the central piperidinyl core does not need to be fluorinated in order to obtain activity against the T-type calcium channel. Of more importance is the presence of a nitrogen or hydroxy on the beta carbon spaced from the piperidinyl nitrogen which, unexpectantly, also provides selectivity against the hERG $K^+$ channel. Activity against the $\alpha_{1G}$ and $\alpha_{1H}$ T-type calcium channel subtypes as well as against the hERG $K^+$ channel are shown for selected compounds below in tables 4 and 5.

Modes of Carrying out the Invention

The compounds of formula (1) are useful in the methods of the invention and, while not bound by theory, are believed to exert their desirable effects through their ability to modulate the activity of calcium channels, particularly the activity of T-type calcium channels. This makes them useful for treatment of certain conditions where modulation of T-type calcium channels is desired, including: cardiovascular disease; epilepsy; diabetes; cancer; pain, including both chronic and acute pain; sleep disorders; Parkinson's disease; psychosis such as schizophrenia; overactive bladder; renal disease, neuroprotection, addiction and male birth control.

Cardiovascular disease as used herein includes but is not limited to hypertension, pulmonary hypertension, arrhythmia (such as atrial fibrillation and ventricular fibrillation), congestive heart failure, angina pectoris, arteriosclerosis, atherosclerosis, and stroke.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adrenocarcinoma, insulinoma, lung carcinoma, melanoma, and ovarian cancer.

Acute pain as used herein includes but is not limited to nociceptive pain and post-operative pain. Chronic pain includes but is not limited by: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome;

inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

For greater certainty, in treating osteoarthritic pain, joint mobility will also improve as the underlying chronic pain is reduced. Thus, use of compounds of the present invention to treat osteoarthritic pain inherently includes use of such compounds to improve joint mobility in patients suffering from osteoarthritis.

Addiction includes but is not limited to dependence, withdrawal and/or relapse of cocaine, opioid, alcohol and nicotine It is known that calcium channel activity is involved in a multiplicity of disorders, and particular types of channels are associated with particular conditions. The association of T-type channels in conditions associated with neural transmission would indicate that compounds of the invention which target T-type receptors are most useful in these conditions. Many of the members of the genus of compounds of formula (1) exhibit high affinity for T-type channels. Thus, as described below, they are screened for their ability to interact with T-type channels as an initial indication of desirable function. It is particularly desirable that the compounds exhibit $IC_{50}$ values of <1 µM. The $IC_{50}$ is the concentration which inhibits 50% of the calcium, barium or other permeant divalent cation flux at a particular applied potential.

In order to be maximally useful in treatment, it is also helpful to assess the side reactions which might occur. Thus, in addition to being able to modulate a particular calcium channel, it is desirable that the compound has very low activity with respect to the hERG $K^+$ channel which is expressed in the heart. Compounds that block this channel with high potency may cause reactions which are fatal. Thus, for a compound that modulates the calcium channel, it is preferred that the hERG $K^+$ channel is not inhibited. Some inhibition of the hERG $K^+$ channel may be tolerated in a drug as long as the compound is sufficiently selective for the target of interest over the hERG $K^+$ channel. For example, 10 fold selectivity of a T-type calcium channel over the hERG $K^+$ channel would be beneficial and more preferably 30 fold selectivity or 100 fold selectivity.

Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Furthermore, the compounds of the invention are selective against the hERG $K^+$ channel. Typical assays are described hereinbelow in Example 17.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109-115; Salemme, F. R., et al., *Structure* (1997) 5:319-324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, e.g., the N-type channel. In addition, using standard screening protocols, the libraries may be screened for compounds that block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium, barium or other permeant divalent cation and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz. Finally, resting channel blockers would diminish the peak current amplitude during the very first depolarization after drug application without additional inhibition during the depolarization.

Accordingly, a library of compounds of formula (1) can be used to identify a compound having a desired combination of activities that includes activity against at least one type of calcium channel. For example, the library can be used to identify a compound having a suitable level of activity on T-type calcium channels while having minimal activity on HERG K+ channels.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, the compounds of formula (1) may be used alone, as mixtures of two or more compounds of formula (1) or in combination with other pharmaceuticals. An example of other potential pharmaceuticals to combine with the compounds of formula (1) would include pharmaceuticals for the treatment of the same indication but having a different mechanism of action from T-type calcium channel blocking. For example, in the treatment of pain, a compound of formula (1) may be combined with another pain relief treatment such as an NSAID, or a compound which selectively inhibits COX-2, or an opioid, or an adjuvant analgesic such as an antidepressant. Another example of a potential pharmaceutical to combine with the compounds of formula (1) would include pharmaceuticals for the treatment of different yet associated or related symptoms or indications. Depending on the mode of administration, the compounds will be formulated into suitable compositions to permit facile delivery.

The compounds of the invention may be prepared and used as pharmaceutical compositions comprising an effective amount of at least one compound of formula (1) admixed with a pharmaceutically acceptable carrier or excipient, as is well known in the art. Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.01-15 mg/kg, preferably 0.1-10 mg/kg. However, dosage levels are highly dependent on the nature of the condition, drug efficacy, the condition of the patient, the judgment of the practitioner, and the frequency and mode of administration. Optimization of the dosage for a particular subject is within the ordinary level of skill in the art.

Synthesis of the Invention Compounds

The following reaction schemes and examples are intended to illustrate the synthesis of a representative number of compounds. Accordingly, the following examples are intended to illustrate but not to limit the invention. Additional compounds not specifically exemplified may be synthesized using conventional methods in combination with the methods described hereinbelow.

EXAMPLE 1

Synthesis of N-((1-((1-(ethylsulfonamido)cyclopentyl)methyl)piperidin-4-yl)methyl)-3,5-bis(trifluoromethyl)benzamide (Compound 3)

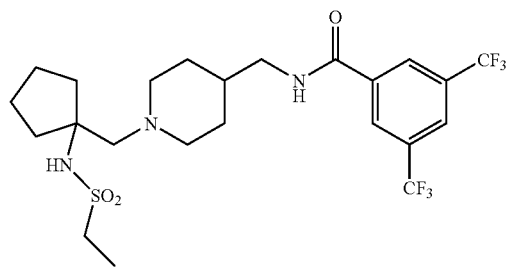

-continued

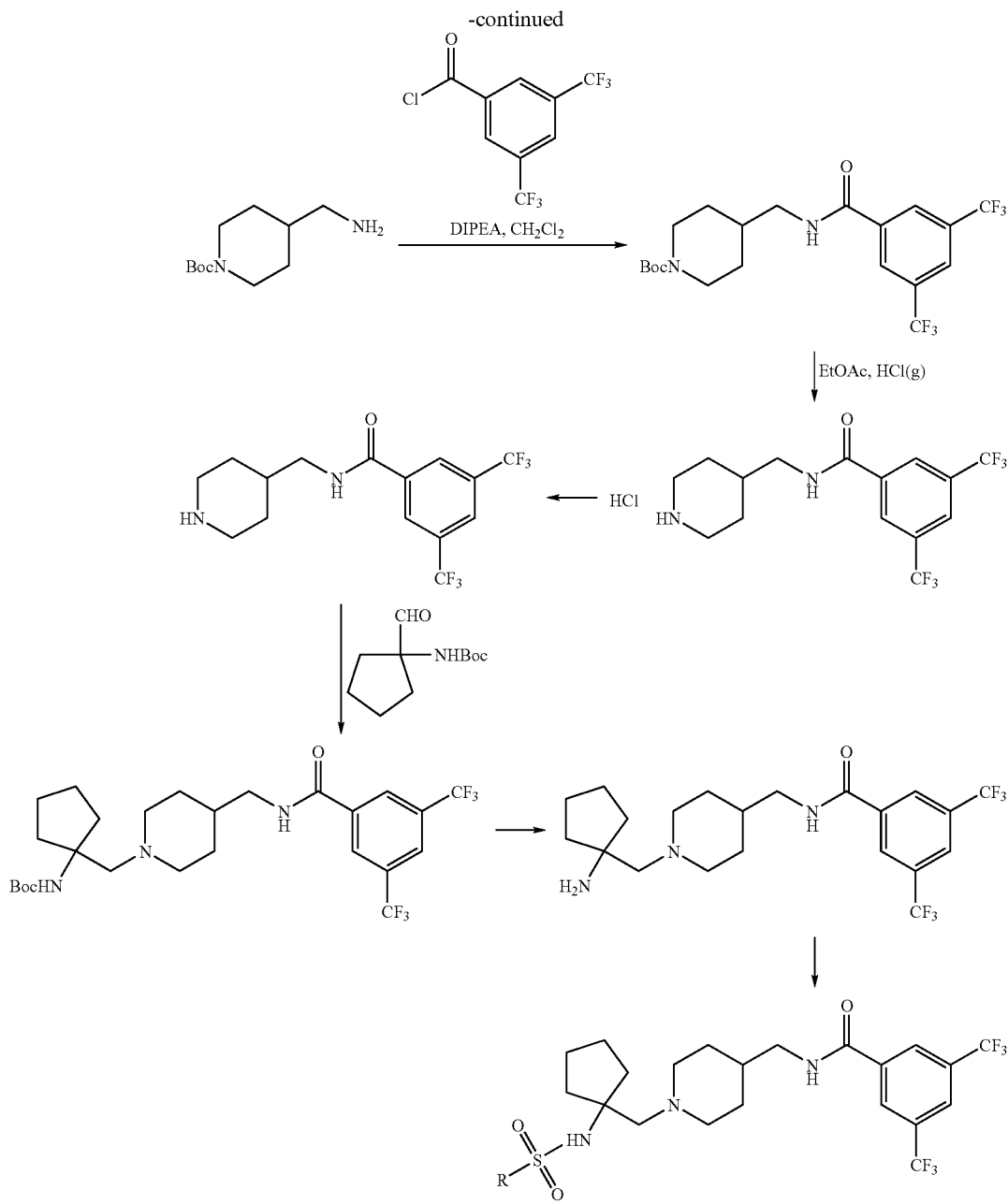

A. Synthesis of N-(piperidin-4-ylmethyl)-3,5-bis(trifluoromethyl)benzamide

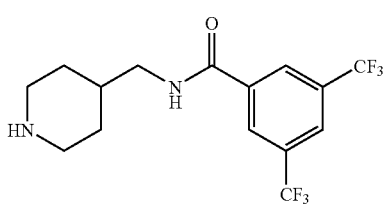 [SMILES: O=C(NCC1CCNCC1)c1cc(C(F)(F)F)cc(C(F)(F)F)c1]

To a solution of 1-Boc-4-(aminomethyl)piperidine (18.0 g, 84.1 mmol) and DIPEA (12.9 g, 100 mmol) in anhydrous CH$_2$Cl$_2$ (200 mL) at 15° C. was added 3,5-bis-(trifluoromethyl)benzoyl chloride (23.4 g, 85.0 mmol) slowly. After the reaction mixture was stirred at room temperature for 30 min, water (50 mL) was added followed by adding aqueous HCl (0.5 N, 100 mL). The organic fraction was collected. The aqueous fraction was extracted with CH$_2$Cl$_2$ (100 mL). The combined organic solution was dried over anhydrous Na$_2$SO$_4$ and passed through a silica gel plug. The desired compound was eluted off with EtOAc/petroleum ether (1:3 in v/v). Solvents were removed and the product was dissolved in EtOAc (200 mL). To the solution HCl (g) bubbled for 5 min to form a white suspension. The suspension was stirred at room temperature for 30 min, and then concentrated to around 100 mL. Diethyl ether (150 mL) was added and the suspension was cooled at 7° C. for 1 h. A white HCl salt was collected by filtration. The salt was dissolved in a mixture of methanol/ water (30/300 mL), and aqueous NaOH (2 N) was added until pH=~11. The mixture was extracted with CH$_2$Cl$_2$ (5×200 ML) and the combined organic solution was dried over anhydrous Na$_2$SO$_4$. After filtration the filtrate was concentrated in vacuo to give pale yellow sticky foam (28.8 g, 97%).).

B. Synthesis of N-((1-((1-aminocyclopentyl)methyl) piperidin-4-yl)methyl)-3,5-bis(trifluoromethyl)benzamide

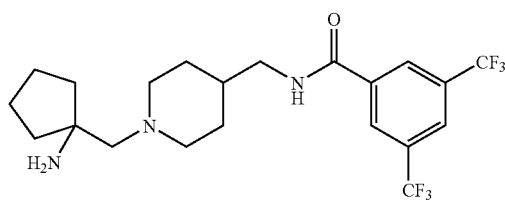 [SMILES: NC1(CN2CCC(CNC(=O)c3cc(C(F)(F)F)cc(C(F)(F)F)c3)CC2)CCCC1]

To a solution of N-(piperidin-4-ylmethyl)-3,5-bis(trifluoromethyl)benzamide (546 mg, 1.54 mmol) and N—BOC-cycloleucinal (329 mg, 1.54 mmol) in CH$_2$Cl$_2$ (15 mL) was added NaBH(OAC)$_3$ (481 mg, 2.16 mmol). The resulting mixture was allowed to stir at room temperature for 18 hours and then diluted with ethyl acetate. The organic fraction was washed with sat. NaHCO$_3$ (30 mL), brine (30 mL) and dried over Na$_2$SO$_4$. The solvent was removed in vacuo to provide crude tert-butyl 1-((4-((3,5-bis(trifluoromethyl)benzamido) methyl)piperidin-1-yl)methyl) cyclopentyl carbamate as an oil.

The above crude tert-butyl 1-((4-((3,5-bis(trifluoromethyl) benzamido) methyl)piperidin-1-yl)methyl)cyclopentyl carbamate dissolved in CH$_2$Cl$_2$ (3 mL) and TFA (2 mL) was added at room temperature. The reaction was allowed to stir at room temperature for 2 hours and then diluted with CH$_2$Cl$_2$ (15 mL). The organic mixture was washed with the mixture of sat. NaHCO$_3$ (10 mL) and 2 N NaOH (5 mL), dried over Na$_2$SO$_4$. Removal of solvent in vacuo provided oil. The crude oil was purified by Biotage (10% MeOH in CH$_2$Cl$_2$) to yield N-((1-((1-aminocyclopentyl)methyl)piperidin-4-yl)methyl)-3,5-bis(trifluoromethyl) benzamide (379 mg, 56% over two steps).

C. Synthesis of N-((1-((1-(ethylsulfonamido)cyclopentyl)methyl)piperidin-4-yl)methyl)-3,5-bis(trifluoromethyl)benzamide (Compound 3)

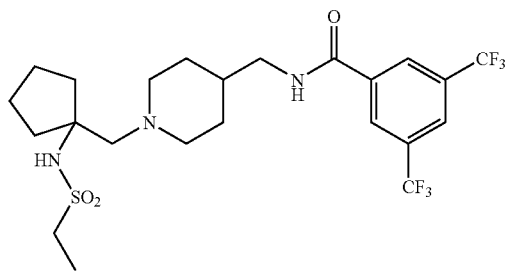 [SMILES: CCS(=O)(=O)NC1(CN2CCC(CNC(=O)c3cc(C(F)(F)F)cc(C(F)(F)F)c3)CC2)CCCC1]

To a solution of N-((1-((1-aminocyclopentyl)methyl)piperidin-4-yl)methyl)-3,5-bis(trifluoromethyl) benzamide (100 mg, 0.28 mmol) and i-Pr$_2$NEt (0.2 mL, 1.1 mmol) in CH$_2$Cl$_2$ (5 mL) was added ethanesulfonyl chloride (0.05 mL, 0.53 mmol). The reaction mixture was allowed to stir at room temperature for 18 hours and then diluted with ethyl acetate. The organic fraction was washed with sat. NaHCO$_3$, and then brine and dried over Na$_2$SO$_4$. The solvent was removed and the crude was purified by High Throughput Purification System (HiTOPs) to provide N-((1-((1-(ethylsulfonamido)cyclopentyl)methyl) piperidin-4-yl)methyl)-3,5-bis(trifluoromethyl)benzamide.

EXAMPLE 2

Synthesis of N-((1-((1-(3-ethylureido)cyclopentyl) methyl)piperidin-4-yl)methyl)-3,5-bis(trifluoromethyl)benzamide (Compound 11)

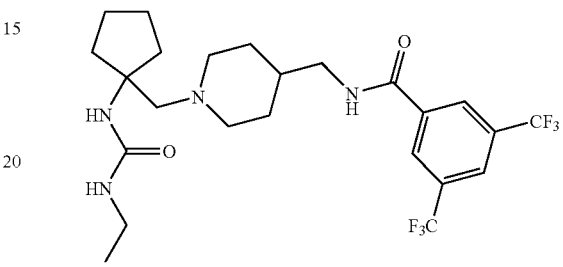

To a solution of N-((1-((1-aminocyclopentyl)methyl)piperidin-4-yl)methyl)-3,5-bis(trifluoromethyl) benzamide (100 mg, 0.28 mmol) in CH$_2$Cl$_2$ (5 mL) was added ethyl isocyanate (0.05 mL, 0.63 mmol). The reaction mixture was allowed to stir at room temperature for 18 hours and then diluted with ethyl acetate. The organic fraction was washed with sat. NaHCO$_3$, and then brine and dried over Na$_2$SO$_4$. The solvent was removed and the crude was purified by HiTOPs to provide N-((1-((1-(3-ethylureido)cyclopentyl) methyl)piperidin-4-yl)methyl)-3,5-bis(trifluoromethyl)benzamide.

EXAMPLE 3

Synthesis of ethyl 1-((4-((3,5-bis(trifluoromethyl) benzamido)methyl)piperidin-1-yl)methyl)cyclopentylcarbamate (Compound 17)

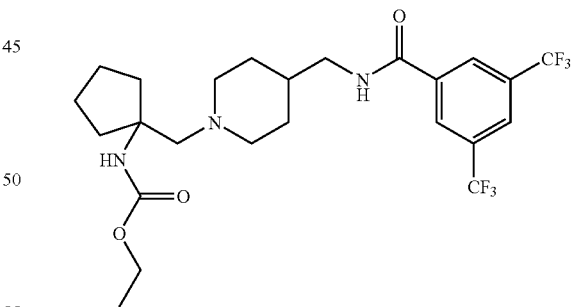

To a solution of N-((1-((1-aminocyclopentyl)methyl)piperidin-4-yl)methyl)-3,5-bis(trifluoromethyl) benzamide (100 mg, 0.28 mmol) and i-Pr$_2$NEt (0.2 mL, 1.1 mmol) in CH$_2$Cl$_2$ (5 mL) was added ethyl chloroformate (0.05 mL, 0.53 mmol). The reaction mixture was allowed to stir at room temperature for 18 hours and then diluted with ethyl acetate. The organic fraction was washed with sat. NaHCO$_3$, and then brine and dried over Na$_2$SO$_4$. The solvent was removed and the crude was purified by HiTOPs to provide ethyl 1-((4-((3,5-bis(trifluoromethyl)benzamido)methyl)piperidin-1-yl)methyl)cyclopentylcarbamate.

EXAMPLE 4
Synthesis of synthesis of N-((1-(2-(1-methylethylsulfonamido)ethyl)piperidin-4-yl)methyl)-3,5-bis(trifluoromethyl)benzamide (Compound 20)
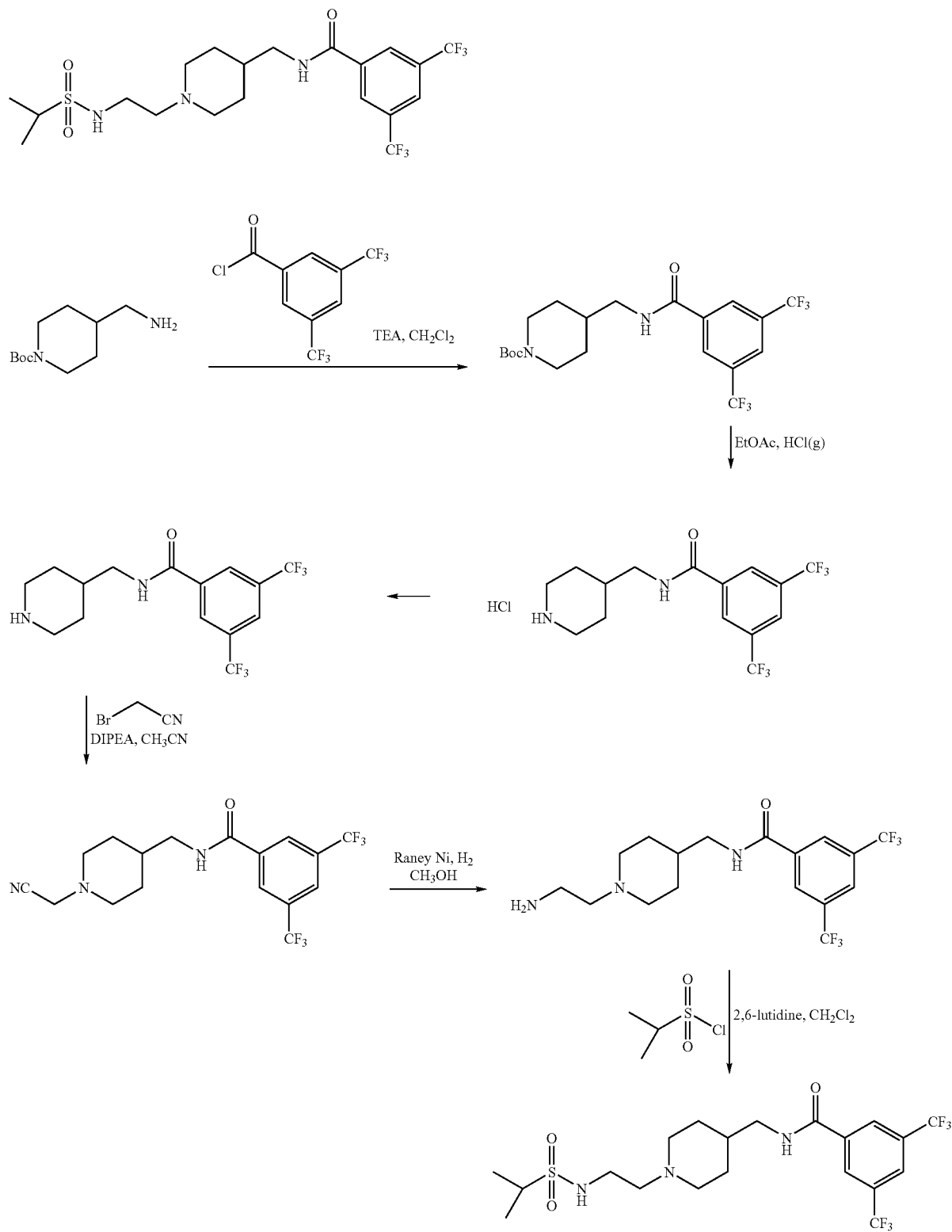

A. Synthesis of N-((1-(cyanomethyl)piperidin-4-yl)methyl)-3,5-bis(trifluoromethyl)benzamide

C. Synthesis of N-((1-(2-(1-methylethylsulfonamido)ethyl)piperidin-4-yl)methyl)-3,5-bis(trifluoromethyl)benzamide (Compound 20)

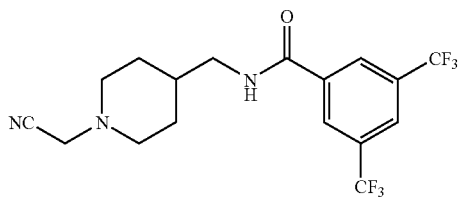

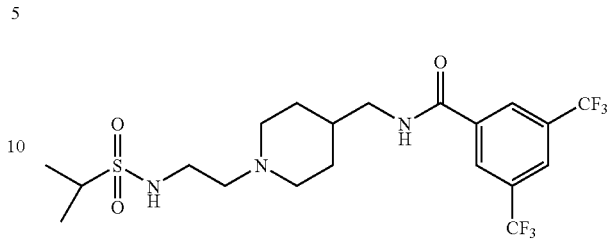

A solution of N-((1-(2-aminoethyl)piperidin-4-yl)methyl)-3,5-bis(trifluoromethyl)benzamide (70 mg, 0.18 mmol) and 2,6-lutidine (123 µL, 0.882 mmol) in $CH_2Cl_2$ (2 mL) was treated with isopropylsulfonyl chloride (49.9 mg, 0.35 mmol). The reaction was stirred overnight and then transferred to a test tube containing saturated aqueous $NaHCO_3$ (4 mL) and EtOAc (4 mL). The biphasic mixture was mixed vigourously and allowed to separate for 15 min. After separation, the mixture was cooled to −20° C. until the aqueous layer was frozen. The organic layer was then poured off and the solvent was removed under reduced pressure at 50° C. The resulting residue was purified by HiTOPs N-(piperidin-4-ylmethyl)-3,5-bis(trifluoromethyl)benzamide (3.54 g, 10.0 mmol) was dissolved in $CH_3CN$ (100 mL). DIPEA (1.94 g, 15.0 mmol) and bromoacetonitrile (1.32 g, 11.0 mmol) were added. The reaction mixture was heated at 50° C. overnight. The solvent was removed in vacuo. Saturated $NaHCO_3$ (40 mL) was added and the mixture was extracted with $CH_2Cl_2$ (4×30 mL). The combined organic solution was dried over anhydrous $Na_2SO_4$ and passed through a silica gel plug. The desired compound was eluted off with EtOAc. The product was further purified by crystallization from EtOAc/petroleum ether as a white solid (3.62 g, 92%).

EXAMPLE 5

Synthesis of ethyl 2-(4-((3,5-bis(trifluoromethyl)benzamido)methyl)piperidin-1-yl)ethylcarbamate (Compound 36)

B. Synthesis of N-((1-(2-aminoethyl)piperidin-4-yl)methyl)-3,5-bis(trifluoromethyl)benzamide

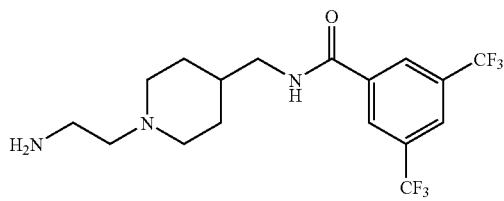 [SMILES: NCCN1CCC(CNC(=O)c2cc(C(F)(F)F)cc(C(F)(F)F)c2)CC1]

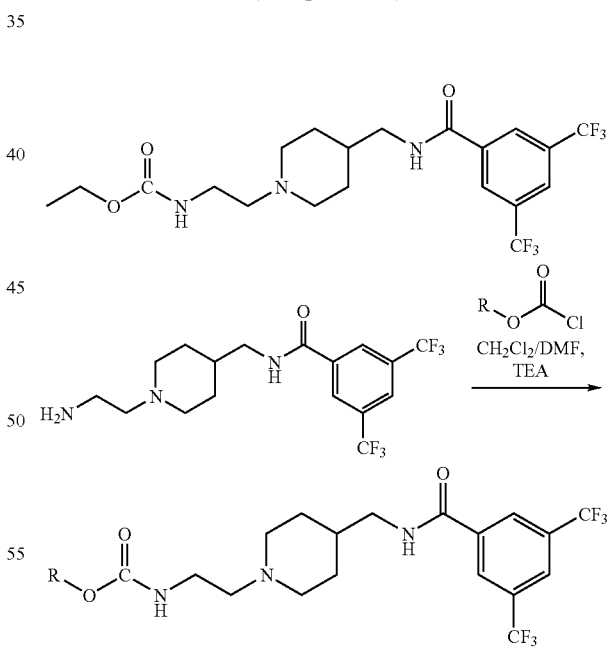

Hydrogenation flask charged with a solution of N-((1-(cyanomethyl)piperidin-4-yl)methyl)-3,5-bis(trifluoromethyl)benzamide (2.80 g, 7.13 mmol) in methanol (20 mL) and Raney nickel (~1 g, rinsed with methanol). The flask was shaken at room temperature under hydrogen (40 psi) overnight. The reaction mixture was then filtered through a celite cake, and the filtrate was concentrated to give sticky foam which was used in the next step without further purification.

A solution of N-((1-(2-aminoethyl)piperidin-4-yl)methyl)-3,5-bis(trifluoromethyl)benzamide (66 mg, 0.17 mmol) in a 2:1 mixture of $CH_2Cl_2$:DMF (3 mL) and TEA (69 µL, 0.50 mmol) was treated with ethyl chloroformate (27 mg, 0.25 mmol). The reaction mixture was allowed to stir overnight, then the solvent was removed in vacuo and the residue was purified by HiTOPs.

EXAMPLE 6

Synthesis of tert-butyl 2-(4-((3-fluoro-5-(trifluoromethyl)benzamido)methyl)piperidin-1-yl)ethylcarbamate (Compound 38)

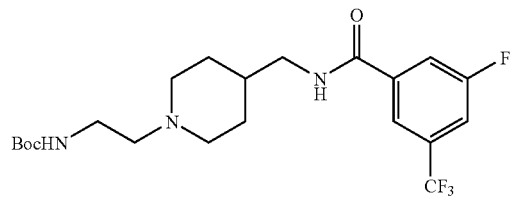

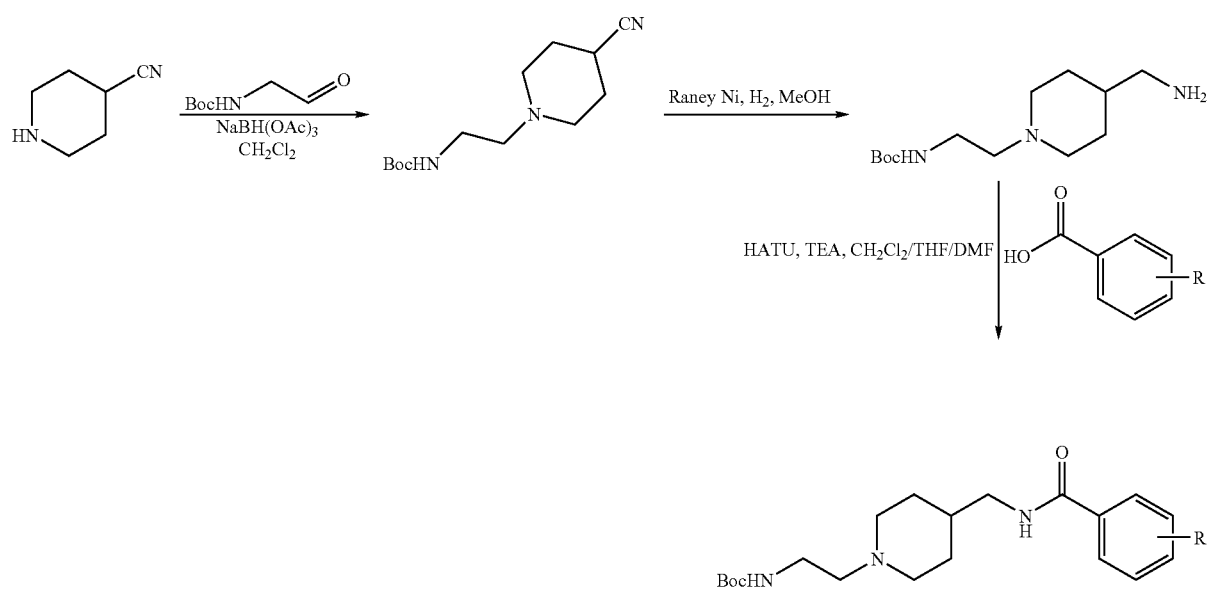

A. Synthesis of tert-butyl 2-(4-cyanopiperidin-1-yl)ethylcarbamate

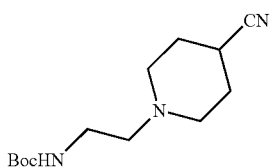 [SMILES: CC(C)(C)OC(=O)NCCN1CCC(C#N)CC1]

A mixture of piperidine-4-carbonitrile (1.10 g, 10 mmol), tert-butyl 2-oxoethylcarbamate (1.59 g, 10 mmol) and sodium triacetoxy borohydride (2.5 g, 12 mmol) in 25 ml of $CH_2Cl_2$ was stirred at room temperature overnight. Solvent was evaporated and ethyl acetate was added and washed with water. The solvent was removed in vacuo to provide oil. The crude oil was purified by column chromatography (100% ethyl acetate) to yield colorless oil (2.3 g, 91%).

B. Synthesis of tert-butyl 2-(4-aminomethyl)piperidin-1-yl)ethylcarbamate

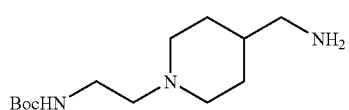 [SMILES: CC(C)(C)OC(=O)NCCN1CCC(CN)CC1]

To a mixture of tert-butyl 2-(4-cyanopiperidin-1-yl)ethylcarbamate (2.3 g, 9.05 mmol) and Raney Nickel (1.1 g) in $CH_3OH$ (50 mL) was bubbled ammonia gas for 5 min. The reaction mixture was shaken at room temperature under hydrogen (40 psi) overnight. The catalyst was filtered through celite. The solvent was removed in vacuo to provide oil (2.3 g, 98.5%).

C. Synthesis of tert-butyl 2-(4-((3-fluoro-5-(trifluoromethyl)benzamido)methyl)piperidin-1-yl)ethylcarbamate (Compound 38)

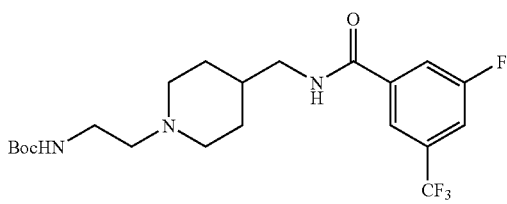 [SMILES: CC(C)(C)OC(=O)NCCN1CCC(CNC(=O)c2cc(F)cc(C(F)(F)F)c2)CC1]

A solution of tert-butyl 2-(4-(aminomethyl)piperidin-1-yl)ethylcarbamate (50 mg, 0.19 mmol), TEA (135 μL, 0.972 mmol), and 3-fluoro-5-(trifluoromethyl)benzoic acid (48 mg, 0.23 mmol) in a mixture of 1:1 CH$_2$Cl$_2$:THF (2 mL) was treated with a solution of HATU (111 mg, 0.292 mmol) in DMF (1 mL). The resulting solution was stirred overnight, then transferred to a test tube containing saturated aqueous NaHCO$_3$ (4 mL) and EtOAc (4 mL). The biphasic mixture was mixed vigorously and allowed to separate for 15 minutes. After separation, the mixture was cooled to −20° C. until the aqueous layer was frozen. The organic layer was then poured off and the solvent was removed under reduced pressure at 50° C. The resulting residue was purified by HiTOPs.

EXAMPLE 7

Synthesis of tert-butyl 2-(4-((2,2-difluorobenzo[d][1,3]dioxole-5-carboxamido)methyl)piperidin-1-yl)ethylcarbamate (Compound 54)

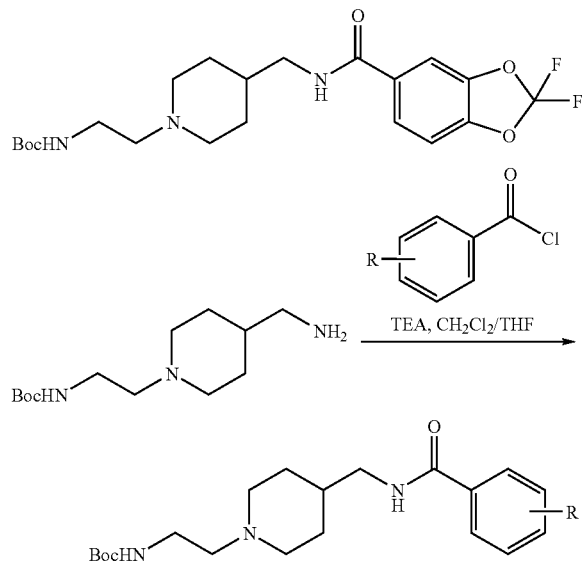

A solution of tert-butyl 2-(4-(aminomethyl)piperidin-1-yl)ethylcarbamate (50 mg, 0.19 mmol) and TEA (135 μL, 0.972 mmol) in a mixture of 1:1 CH$_2$Cl$_2$:THF (2.5 mL) was treated with 2,2-difluorobenzo[d][1,3]dioxole-5-carbonyl chloride (51 mg, 0.23 mmol). The resulting solution was stirred overnight, then transferred to a test tube containing saturated aqueous NaHCO$_3$ (4 mL) and EtOAc (4 mL). The biphasic mixture was mixed vigorously and allowed to separate for 15 minutes. After separation, the mixture was cooled to −20° C. until the aqueous layer was frozen. The organic layer was then poured off and the solvent was removed under reduced pressure at 50° C. The resulting residue was purified by HiTOPs.

EXAMPLE 8

Synthesis of N-((1-(2-pivalamidoethyl)piperidin-4-yl)methyl)-3,5-bis(trifluoromethyl)benzamide (Compound 60)

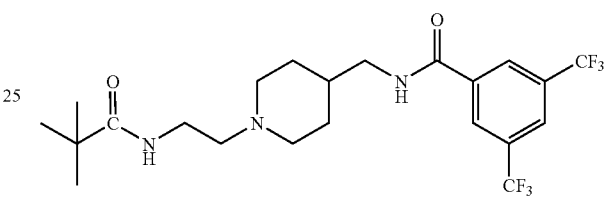

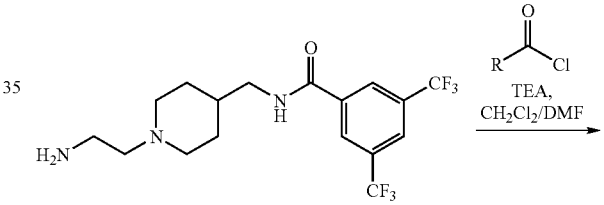

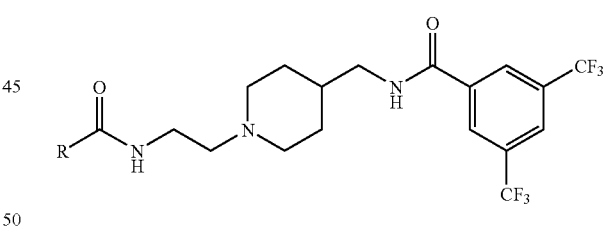

A solution of N-((1-(2-aminoethyl)piperidin-4-yl)methyl)-3,5-bis(trifluoromethyl)benzamide (70 mg, 0.18 mmol) and TEA (123 μL, 0.881 mmol) in a 1:1 mixture of CH$_2$Cl$_2$:DMF (2 mL) was treated with pivaloyl chloride (42 mg, 0.35 mmol). The reaction mixture was stirred overnight then transferred to a test tube containing saturated aqueous NaHCO$_3$ (4 mL) and EtOAc (4 mL). The biphasic mixture was mixed vigorously and allowed to separate for 15 min. After separation, the mixture was cooled to −20° C. until the aqueous layer was frozen. The organic layer was then poured off and the solvent was removed under reduced pressure at 50° C. The resulting residue was purified by HiTOPs.

EXAMPLE 9

Synthesis of N-((1-(2-(2-cyclopropylacetamido)ethyl)piperidin-4-yl)methyl)-3,5-bis(trifluoromethyl)benzamide (Compound 63)

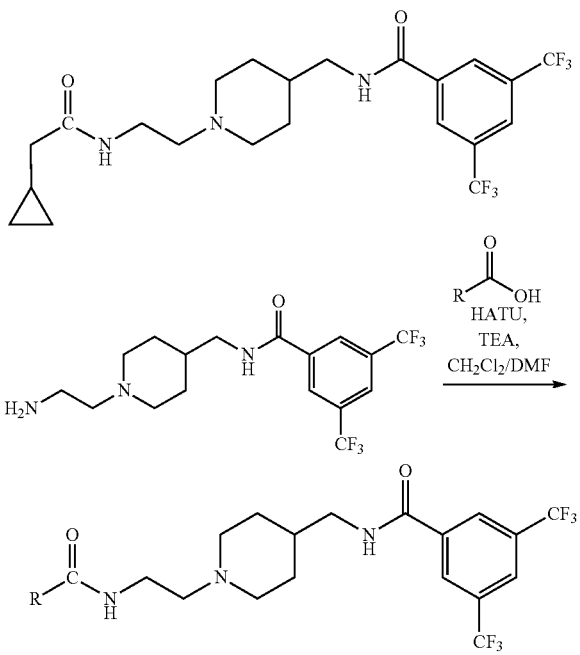

A solution of N-((1-(2-aminoethyl)piperidin-4-yl)methyl)-3,5-bis(trifluoromethyl)benzamide (70 mg, 0.18 mmol), TEA (123 μL, 0.881 mmol), and 2-cyclopropylacetic acid (35 mg, 0.35 mmol) in a 1:1 mixture of CH₂Cl₂:DMF (2 mL) was treated with a solution of HATU (100 mg, 0.264 mmol) in DMF (1 mL). The reaction was stirred over night then transferred to a test tube containing saturated aqueous NaHCO₃ (4 mL) and EtOAc (4 mL). The biphasic mixture was mixed vigorously and allowed to separate for 15 min. After separation, the mixture was cooled to −20° C. until the aqueous layer was frozen. The organic layer was then poured off and the solvent was removed under reduced pressure at 50° C. The resulting residue was purified by HiTOPs.

EXAMPLE 10

Synthesis of N-((1-(2-(3-tert-butylureido)ethyl)piperidin-4-yl)methyl)-3,5-bis(trifluoromethyl)benzamide (Compound 72)

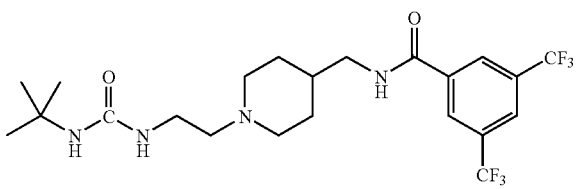

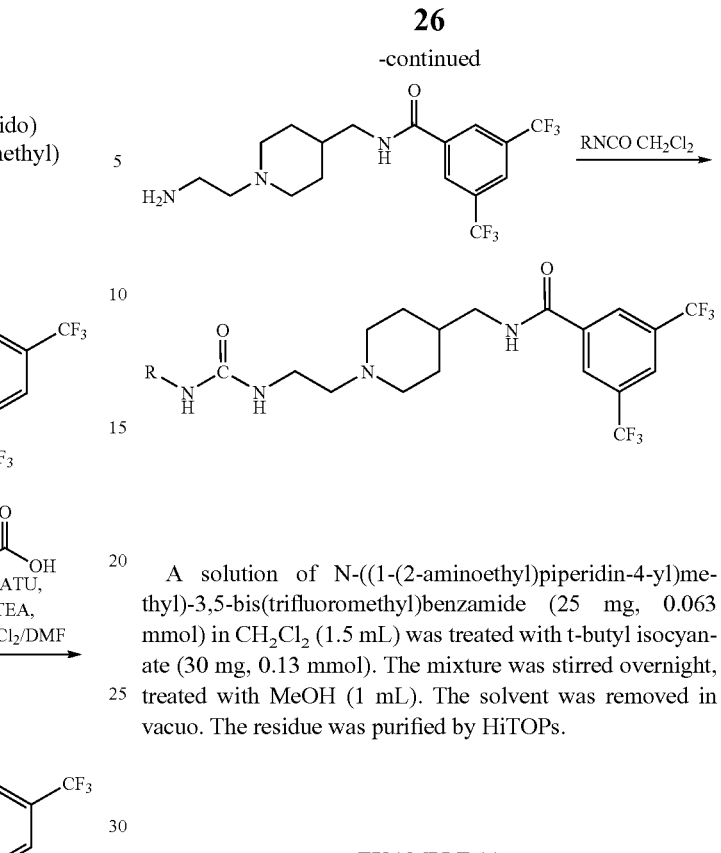

A solution of N-((1-(2-aminoethyl)piperidin-4-yl)methyl)-3,5-bis(trifluoromethyl)benzamide (25 mg, 0.063 mmol) in CH₂Cl₂ (1.5 mL) was treated with t-butyl isocyanate (30 mg, 0.13 mmol). The mixture was stirred overnight, treated with MeOH (1 mL). The solvent was removed in vacuo. The residue was purified by HiTOPs.

EXAMPLE 11

Synthesis of (R)—N-((1-(5-oxopyrrolidine-2-carbonyl)piperidin-4-yl)methyl)-3,5-bis(trifluoromethyl)benzamide (Compound 83)

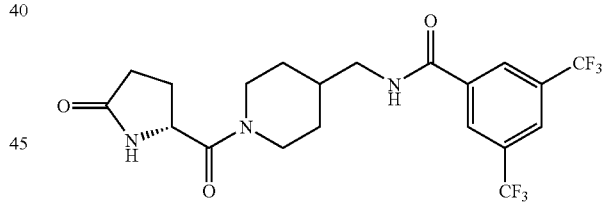

A solution of N-(piperidin-4-ylmethyl)-3,5-bis(trifluoromethyl)benzamide (48 mg, 0.14 mmol), TEA (95 μL, 0.68 mmol), and (R)-5-oxopyrrolidine-2-carboxylic acid (20.66 mg, 0.16 mmol) in DMF (1.5 mL) was treated with a solution of HATU (77 mg, 0.20 mmol) in DMF (1 mL). The reaction mixture was stirred overnight then transferred to a test tube containing saturated aqueous NaHCO₃ (4 mL) and EtOAc (4 mL). The biphasic mixture was mixed vigorously and allowed to separate for 15 min. After separation, the mixture was cooled to −20° C. until the aqueous layer was frozen. The organic layer was then poured off and the solvent was removed in vacuo at 50° C. The resulting residue was dissolved in CH₂Cl₂ (1 mL) and treated with 2M HCl in Et₂O (3 mL) and allowed to stir overnight at room temperature. The solvent was removed under reduced pressure and the crude solid was purified by HiTOPs.

EXAMPLE 12

Synthesis of N-((1-(2-(cyclopentylamino)-2-oxoethyl)piperidin-4-yl)methyl)-3,5-bis(trifluoromethyl)benzamide (Compound 93)

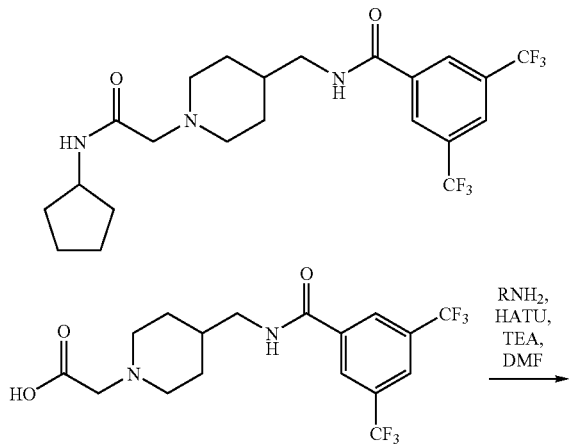

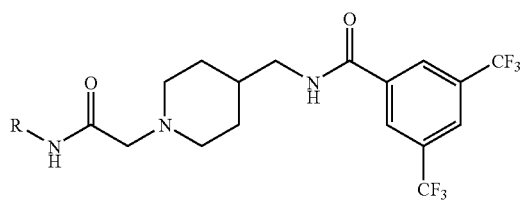

A solution of 2-(4-((3,5-bis(trifluoromethyl)benzamido)methyl)piperidin-1-yl)acetic acid (73 mg, 0.18 mmol), TEA (123 μL, 0.88 mmol), and cyclopentylamine (30 mg, 0.35 mmol) in DMF (1 mL) was treated with a solution of HATU (100 mg, 0.26 mmol) in DMF (1 mL). The reaction mixture was stirred overnight then transferred to a test tube containing saturated aqueous NaHCO$_3$ (4 mL) and EtOAc (4 mL). The biphasic mixture was mixed vigourously and allowed to separate for 15 min. After separation, the mixture was cooled to −20° C. until the aqueous layer was frozen. The organic layer was then poured off and the solvent was removed under reduced pressure at 50° C. The resulting residue was purified by HiTOPs.

EXAMPLE 13

Synthesis of 3-bromo-5-(trifluoromethyl)-N-((1-(2-(trifluoromethylsulfonamido)ethyl)piperidin-4-yl)methyl)benzamide (Compound 116)

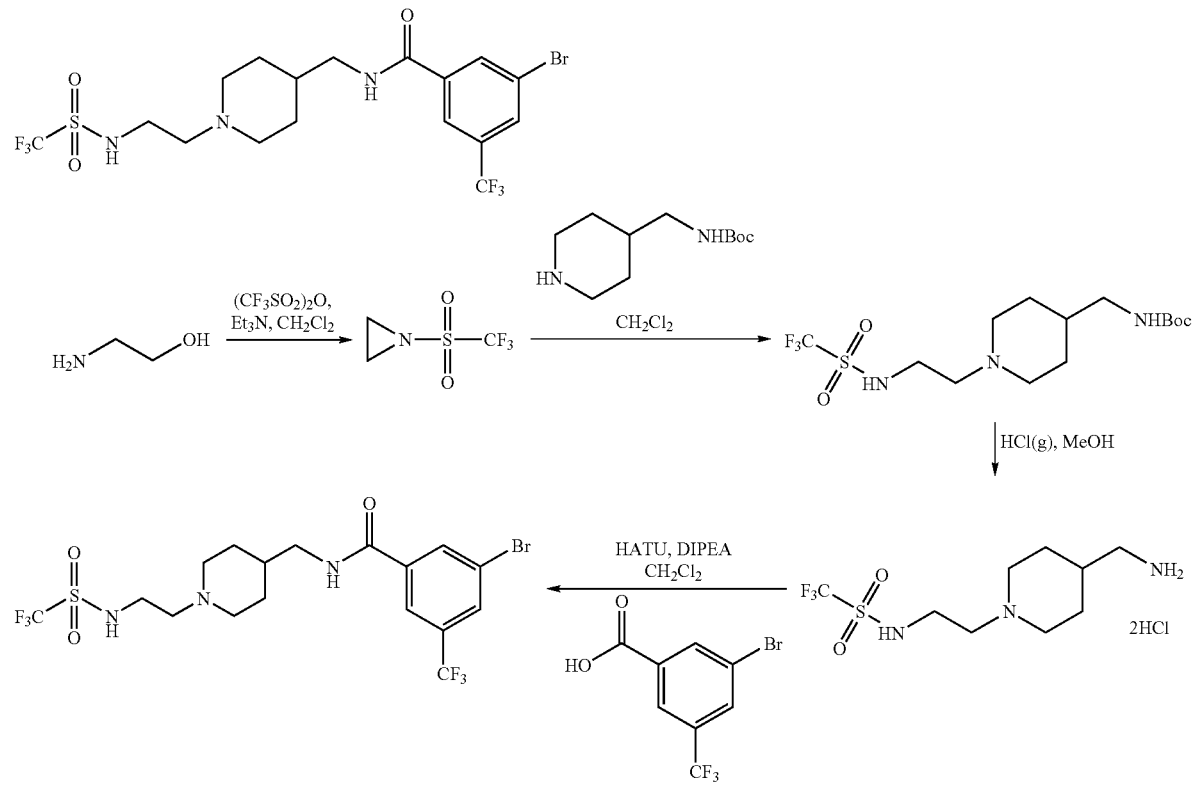

A. Synthesis of tert-butyl (1-(2-(trifluoromethylsulfonamido)ethyl)piperidin-4-yl)methylcarbamate

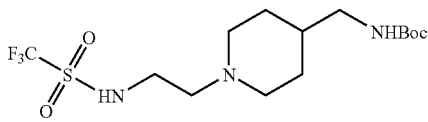 [SMILES: CC(C)(C)OC(=O)NCC1CCN(CCNS(=O)(=O)C(F)(F)F)CC1]

To a solution of 2-aminoethanol (0.84 g, 13.8 mmol) and triethylamine (3.85 mL, 27.7 mmol) in $CH_2Cl_2$ (100 mL) at −78° C. was added slowly trifluoromethanesulfonic anhydride (8.4 g, 29.8 mmol). The reaction mixture was stirred at −78° C. for 2 hrs, warmed to −40° C. and stirred at −40° C. overnight. The reaction mixture was then diluted with $CH_2Cl_2$ (50 mL), washed with cold 0.1N aqueous HCl (2×150 mL) and cold saturated aqueous $NaHCO_3$ (150 mL), and dried over anhydrous $Na_2SO_4$. After filtration to the filtrate was added tert-butyl piperidin-4-ylmethylcarbamate (3.00 g, 14.0 mmol). The reaction mixture was concentrated at 0° C. to 50 mL and stirred at room temperature for 3 hrs. The solvent was then removed, and the residue was purified by flash chromatography (3-8% MeOH in $CH_2Cl_2$) to provide tert-butyl (1-(2-(trifluoromethyl sulfonamido) ethyl)piperidin-4-yl)methylcarbamate (1.40 g, 26%).

B. Synthesis of N-(2-(4-(aminomethyl)piperidin-1-yl)ethyl)-1,1,1-trifluoromethanesulfonamide di-HCl salt

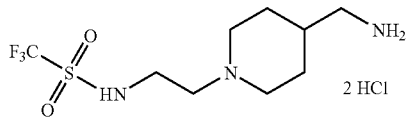 [SMILES: NCC1CCN(CCNS(=O)(=O)C(F)(F)F)CC1 ; "2 HCl"]

tert-Butyl (1-(2-(trifluoromethylsulfonamido)ethyl)piperidin-4-yl)methylcarbamate (1.25 g, 3.21 mmol) was dissolved in $CH_3OH$ (15 mL) and bubbled with HCl(g) for 30 sec. After the reaction mixture was stirred at room temperature for 15 min the solvent was removed in vacuo to provide N-(2-(4-(aminomethyl) piperidin-1-yl)ethyl)-1,1,1-trifluoromethanesulfonamide di-HCl salt as a white solid (1.01 g, 87%).

C. Synthesis of 3-bromo-5-(trifluoromethyl)-N-((1-(2-(trifluoromethylsulfonamido)ethyl)piperidin-4-yl)methyl)benzamide (Compound 116)

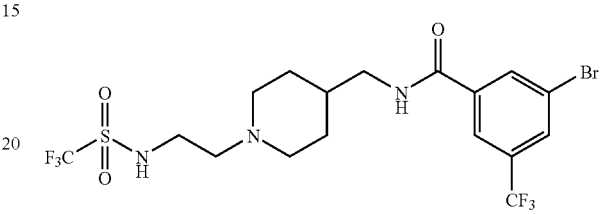

To a solution of 3-bromo-5-(trifluoromethyl)benzoic acid (0.1 g, 0.37 mmol) in $CH_2Cl_2$ (4 mL) was added DIPEA (0.3 mL, 1.8 mmol), N-(2-(4-(aminomethyl) piperidin-1-yl) ethyl)-1,1,1-trifluoromethanesulfonamide dihydrochloride salt (0.1 g, 0.3 mmol) and HATU (0.17 g, 0.4 mmol). The reaction mixture was stirred at room temperature for 2 h. The organic layer was washed with sat. $NaHCO_3$ aq. (8 mL), dried over $Na_2SO_4$, and concentrated to give crude product as gummy solid. Purification of the crude material was done using High Throughput Purification System (HiTOPs).

EXAMPLE 14

Synthesis of 3,5-dichloro-N-((1-(2-(cyclopropanesulfonamido)ethyl)piperidin-4-yl)methyl)benzamide (Compound 131)

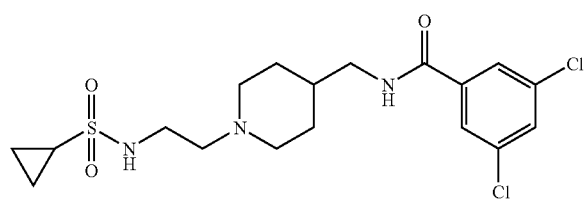

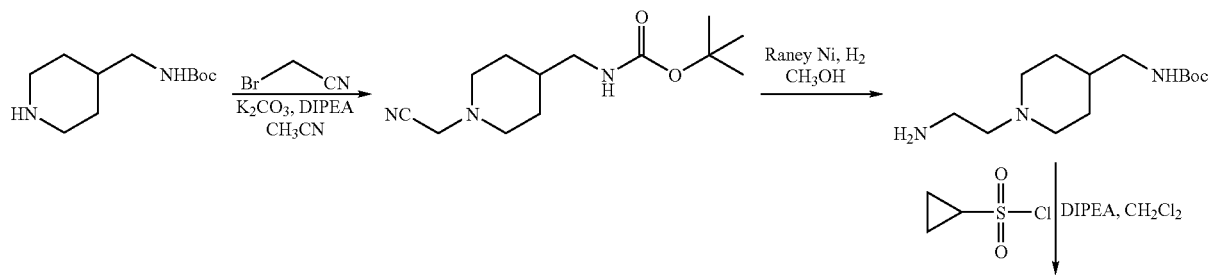

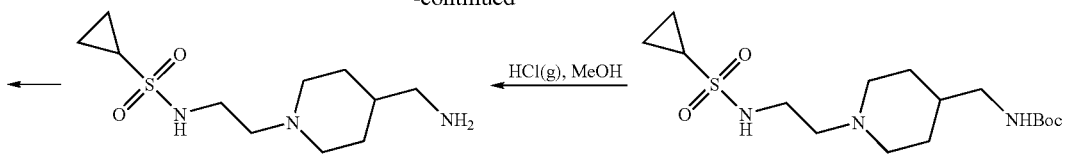

A. Synthesis of tert-butyl (1-(cyanomethyl)piperidin-4-yl)methylcarbamate

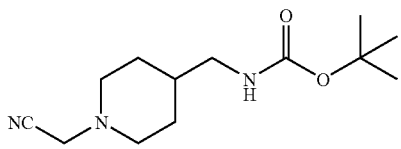

tert-Butyl piperidin-4-ylmethylcarbamate (5 g, 23.2 mmol) was dissolved in CH$_3$CN (40 mL). Potassium carbonate (3.5 g, 25 mmol), DIPEA (4.4 mL, 25 mmol) and bromoacetonitrile (2.77 g, 23.2 mmol) were added, and the mixture was stirred at room temperature overnight. The solution was then concentrated and saturated NaHCO$_3$ (40 mL) was added. The mixture was extracted with CH$_2$Cl$_2$ (4×30 mL). The extract was dried over anhydrous Na2SO4. The dried extract was passed through a silica gel plug, and the desired compound was eluted off with EtOAc. The product was further purified by crystallization from EtOAc/petroleum ether as a white solid (5.4 g, 92%).

B. Synthesis of tert-butyl (1-(2-aminoethyl)piperidin-4-yl)methylcarbamate

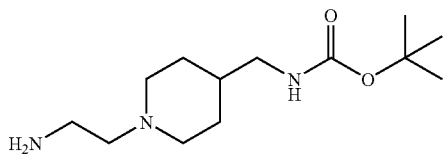 [SMILES: CC(C)(C)OC(=O)NCC1CCN(CCN)CC1]

To a hydrogenation flask charged with a solution of tert-butyl (1-(cyanomethyl)piperidin-4-yl)methylcarbamate (5.4 g, 21.3 mmol) in CH$_3$OH (20 mL) was added Raney nickel (~1 g, rinsed with CH$_3$OH). The flask was shaken at room temperature under hydrogen (40 psi) overnight. The reaction mixture was then filtered through a celite cake, and the filtrate was concentrated to give sticky foam which was used in the next step without further purification.

C. Synthesis of tert-butyl (1-(2-(cyclopropanesulfonamido)ethyl)piperidin-4-yl)methylcarbamate

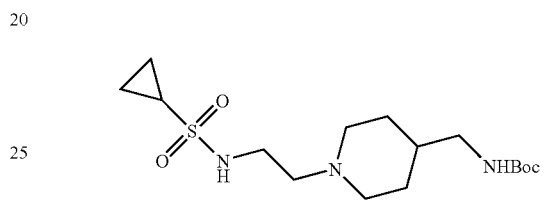

At 15° C., to a solution of tert-butyl (1-(2-aminoethyl)piperidin-4-yl)methylcarbamate (2.00 g, 7.78 mmol) and DIPEA (3.00 g, 23.3 mmol) in CH$_2$Cl$_2$ (40 mL) was added slowly cyclopropylsulfonyl chloride (3.40 g, 25.0 mmol) under Ar. The reaction mixture was stirred at room temperature for 2 hrs. Water (30 mL) was added, and the mixture was extracted with CH$_2$Cl$_2$ (3×30 mL). The combined extract was washed with saturated NaHCO$_3$ (40 mL) and dried over anhydrous Na$_2$SO$_4$. After filtration the solvent was removed in vacuo, and the residue was applied to flash column chromatography (3-7% CH$_3$OH in CH$_2$Cl$_2$) to provide tert-butyl (1-(2-(cyclopropanesulfonamido)ethyl)piperidin-4-yl)methylcarbamate as pale yellow oil (2.2 g, 78%).

D. Synthesis of N-(2-(4-(aminomethyl)piperidin-1-yl)ethyl)cyclopropanesulfonamide di-HCl salt

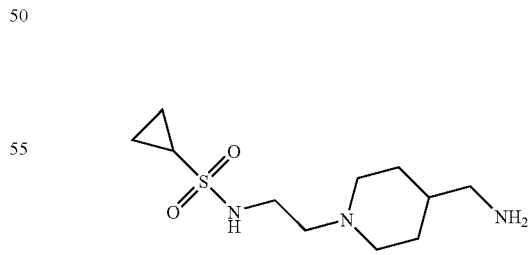

tert-Butyl (1-(2-(cyclopropanesulfonamido)ethyl)piperidin-4-yl)methylcarbamate (2.20 g, 6.09 mmol) was dissolved in CH$_3$OH (15 mL) and bubbled with HCl(g) for 30 sec. After the reaction mixture was stirred at room temperature for 30 min the solvent was removed in vacuo to provide N-(2-(4-(aminomethyl) piperidin-1-yl)ethyl)cyclopropanesulfonamide di-HCl salt as a white solid (1.8 g, 89%).

E. Synthesis of 3,5-dichloro-N-((1-(2-(cyclopropane-sulfonamido)ethyl)piperidin-4-yl)methyl)benzamide (Compound 131)

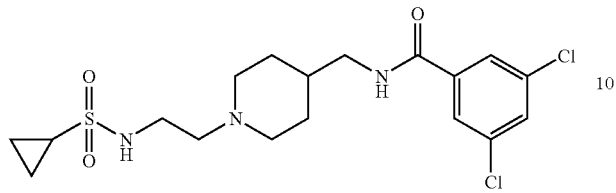

To a solution of 3,5-dichlorobenzoic acid (23 mg, 0.12 mmol) in DMF (2 mL) was added DIPEA (0.1 mL, 0.6 mmol), N-(2-(4-(aminomethyl) piperidin-1-yl)ethyl)-1,1,1-trifluoromethanesulfonamide dihydrochloride salt (40 mg, 0.12 mmol) and HATU (60 mg, 0.15 mmol). The reaction mixture was stirred at room temperature overnight. The organic layer was washed with sat. NaHCO$_3$ aq. (8 mL), dried over Na$_2$SO$_4$, and concentrated to give crude product which was subsequently purified by High Throughput Purification System (HiTOPs).

EXAMPLE 15

Synthesis of N-((1-(2-(tert-butylamino)acetyl)piperidin-4-yl)methyl)-3,5-bis(trifluoromethyl)benzamide (Compound 242)

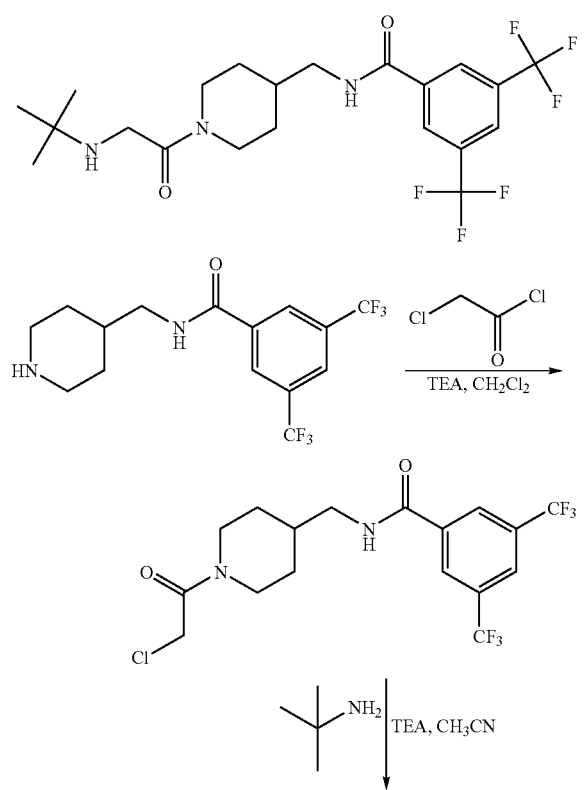

A. Synthesis of N-((1-(2-chloroacetyl)piperidin-4-yl)methyl)-3,5-bis(trifluoromethyl)benzamide

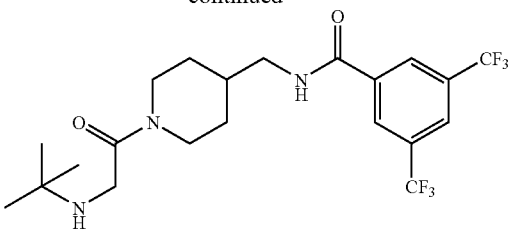

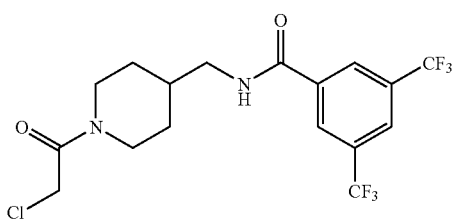 [SMILES: O=C(NCC1CCN(C(=O)CCl)CC1)c1cc(C(F)(F)F)cc(C(F)(F)F)c1]

A solution of N-(piperidin-4-ylmethyl)-3,5-bis(trifluoromethyl)benzamide (2.0 g, 5.66 mmol) and DIPEA (1.2 mL) in CH$_2$Cl$_2$ (10 mL) was added 2-chloroacetyl chloride (0.64, 5.66 mmol) dropwise, the mixture was stirred overnight. The mixture was washed with water, dried with Na$_2$SO$_4$, filtered, and the solvent was removed in vacuo. The residue was purified by automated flash chromatography to yield the product (2.0 g, 82%).

B. Synthesis of N-((1-(2-(tert-butylamino)acetyl)piperidin-4-yl)methyl)-3,5-bis(trifluoromethyl)benzamide (Compound 242)

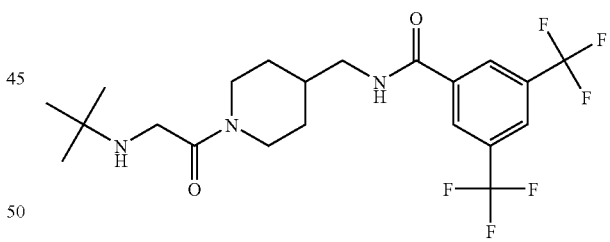

A solution of N-((1-(2-chloroacetyl)piperidin-4-yl)methyl)-3,5-bis(trifluoromethyl)benzamide (50 mg, 0.12 mmol) and TEA (65 µL, 0.46 mmol) in CH$_3$CN (1 mL) was stirred at room temperature overnight. The reaction mixture was then diluted with EtOAc (4 mL) and washed with saturated aqueous NaHCO$_3$ (4 mL). The layers were allowed to separate and the mixture was cooled to −20° C. in the freezer. After the aqueous layer had frozen, the organic layer was poured off, and the solvent was removed in vacuo. The crude residue was purified by reverse phase HPLC

EXAMPLE 16

Following the general procedures set forth in Examples 1-15, the following compounds listed in Table 1 below were prepared. Mass spectrometry was employed with the final compound and at various stages throughout the synthesis as a confirmation of the identity of the product obtained (M+1). For the mass spectrometric analysis, samples were prepared at an approximate concentration of 1 μg/mL in acetonitrile with 0.1% formic acid. Samples were then manually infused into an Applied Biosystems API3000 triple quadrupole mass spectrometer and scanned in Q1 in the range of 50 to 700 m/z.

TABLE 1

| Cmpd No. | Name | Structure | Mass Spec (m/z) |
|---|---|---|---|
| 1 | N-((1-((1-(methylsulfonamido)cyclopentyl)methyl)piperidin-4-yl)methyl)-3,5-bis(trifluoromethyl)benzamide | 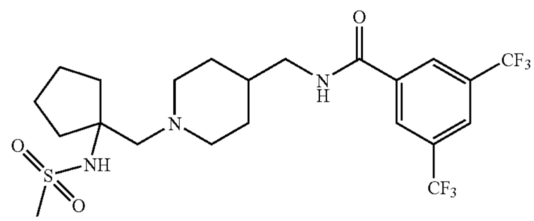 [SMILES: CS(=O)(=O)NC1(CN2CCC(CNC(=O)c3cc(C(F)(F)F)cc(C(F)(F)F)c3)CC2)CCCC1] | 530.18 |
| 2 | N-((1-((1-(cyclopropanesulfonamido)cyclopentyl)methyl)piperidin-4-yl)methyl)-3,5-bis(trifluoromethyl)benzamide | 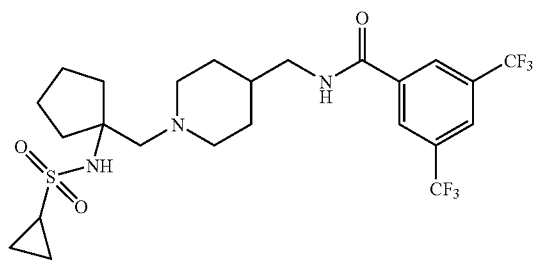 [SMILES: O=C(NCC1CCN(CC2(NS(=O)(=O)C3CC3)CCCC2)CC1)c1cc(C(F)(F)F)cc(C(F)(F)F)c1] | 556.19 |
| 3 | N-((1-((1-(ethylsulfonamido)cyclopentyl)methyl)piperidin-4-yl)methyl)-3,5-bis(trifluoromethyl)benzamide | 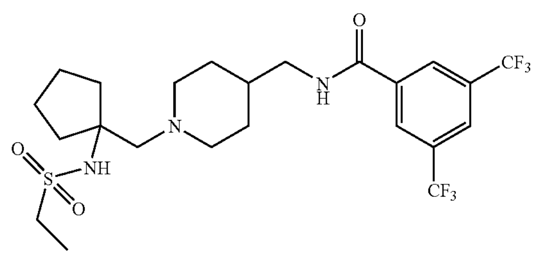 [SMILES: CCS(=O)(=O)NC1(CN2CCC(CNC(=O)c3cc(C(F)(F)F)cc(C(F)(F)F)c3)CC2)CCCC1] | 544.19 |
| 4 | N-((1-((1-(1-methylethylsulfonamido)cyclopentyl)methyl)piperidin-4-yl)methyl)-3,5-bis(trifluoromethyl)benzamide | 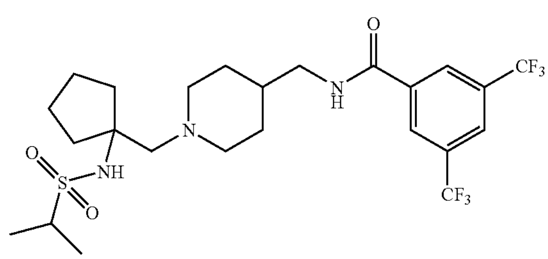 [SMILES: CC(C)S(=O)(=O)NC1(CN2CCC(CNC(=O)c3cc(C(F)(F)F)cc(C(F)(F)F)c3)CC2)CCCC1] | 558.21 |
| 5 | 3,5-bis(trifluoromethyl)-N-((1-((1-(trifluoromethylsulfonamido)cyclopentyl)methyl)piperidin-4-yl)methyl)benzamide | 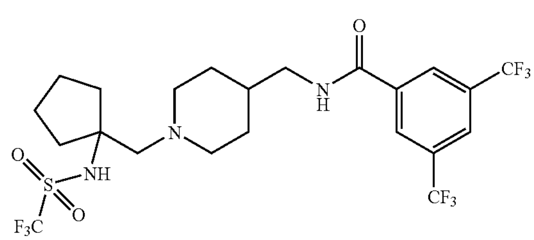 [SMILES: O=C(NCC1CCN(CC2(NS(=O)(=O)C(F)(F)F)CCCC2)CC1)c1cc(C(F)(F)F)cc(C(F)(F)F)c1] | 584.16 |
| 6 | 3-fluoro-N-((1-(2-methyl-2-(trifluoromethylsulfonamido)propyl)piperidin-4-yl)methyl)-5-(trifluoromethyl)benzamide | 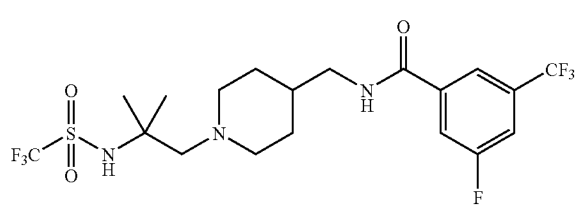 [SMILES: CC(C)(CN1CCC(CNC(=O)c2cc(F)cc(C(F)(F)F)c2)CC1)NS(=O)(=O)C(F)(F)F] | 508.14 |

TABLE 1-continued

| Cmpd No. | Name | Structure | Mass Spec (m/z) |
|---|---|---|---|
| 7 | N-((1-(2-(ethylsulfonamido)-2-methylpropyl)piperidin-4-yl)methyl)-3-fluoro-5-(trifluoromethyl)benzamide | 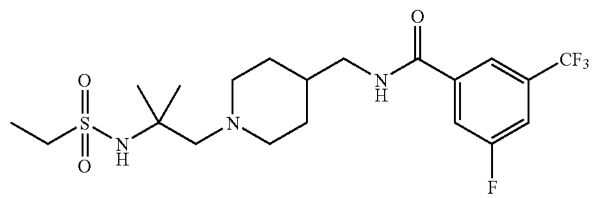 [SMILES: CCS(=O)(=O)NC(C)(C)CN1CCC(CNC(=O)c2cc(F)cc(C(F)(F)F)c2)CC1] | 468.19 |
| 8 | N-((1-(2-(cyclopropanesulfonamido)-2-methylpropyl)piperidin-4-yl)methyl)-3-fluoro-5-(trifluoromethyl)benzamide | 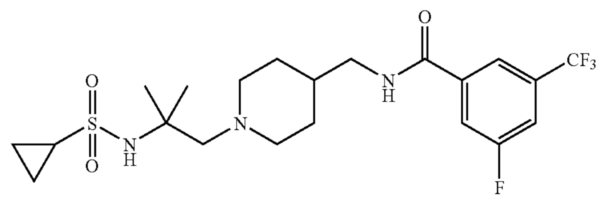 [SMILES: CC(C)(CN1CCC(CNC(=O)c2cc(F)cc(C(F)(F)F)c2)CC1)NS(=O)(=O)C1CC1] | 480.19 |
| 9 | 3-fluoro-N-((1-(2-methyl-2-(1-methylethylsulfonamido)propyl)piperidin-4-yl)methyl)-5-(trifluoromethyl)benzamide | 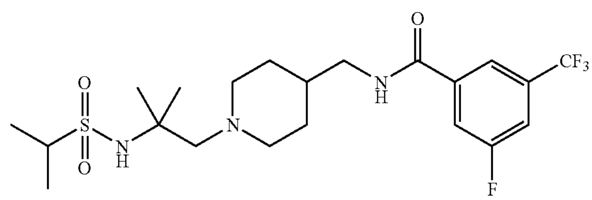 [SMILES: CC(C)S(=O)(=O)NC(C)(C)CN1CCC(CNC(=O)c2cc(F)cc(C(F)(F)F)c2)CC1] | 482.20 |
| 10 | 3-fluoro-N-((1-(2-methyl-2-(2,2,2-trifluoroethylsulfonamido)propyl)piperidin-4-yl)methyl)-5-(trifluoromethyl)benzamide | 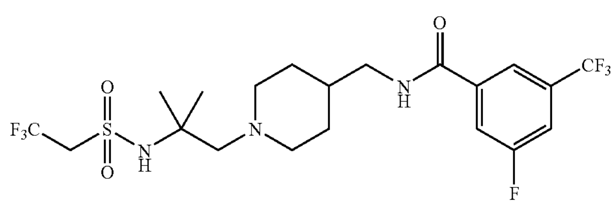 [SMILES: CC(C)(CN1CCC(CNC(=O)c2cc(F)cc(C(F)(F)F)c2)CC1)NS(=O)(=O)CC(F)(F)F] | 522.16 |
| 11 | N-((1-((1-(3-ethylureido)cyclopentyl)methyl)piperidin-4-yl)methyl)-3,5-bis(trifluoromethyl)benzamide | 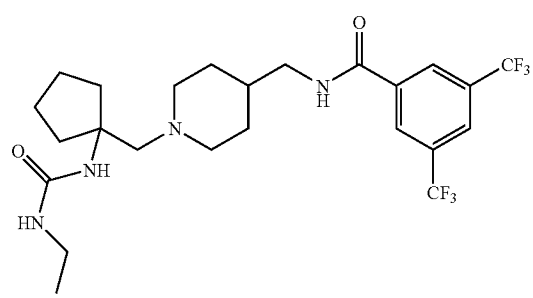 [SMILES: CCNC(=O)NC1(CN2CCC(CNC(=O)c3cc(C(F)(F)F)cc(C(F)(F)F)c3)CC2)CCCC1] | 523.24 |
| 12 | N-((1-((1-(3-tert-butylureido)cyclopentyl)methyl)piperidin-4-yl)methyl)-3,5-bis(trifluoromethyl)benzamide | 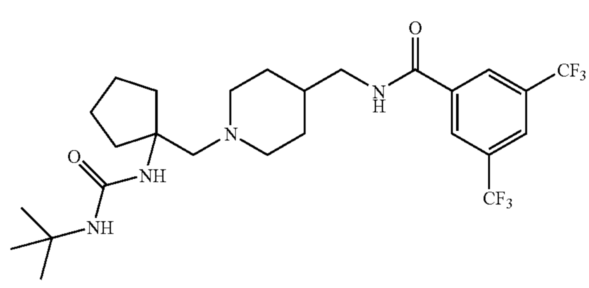 [SMILES: CC(C)(C)NC(=O)NC1(CN2CCC(CNC(=O)c3cc(C(F)(F)F)cc(C(F)(F)F)c3)CC2)CCCC1] | 551.27 |

TABLE 1-continued

| Cmpd No. | Name | Structure | Mass Spec (m/z) |
|---|---|---|---|
| 13 | N-((1-((1-(3-propylureido)cyclopentyl)methyl)piperidin-4-yl)methyl)-3,5-bis(trifluoromethyl)benzamide | 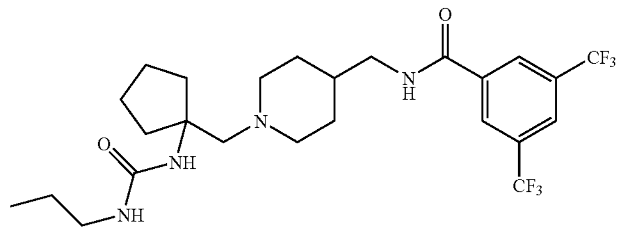 [SMILES: CCCNC(=O)NC1(CN2CCC(CNC(=O)c3cc(C(F)(F)F)cc(C(F)(F)F)c3)CC2)CCCC1] | 537.25 |
| 14 | N-((1-((1-(3-cyclohexylureido)cyclopentyl)methyl)piperidin-4-yl)methyl)-3,5-bis(trifluoromethyl)benzamide | 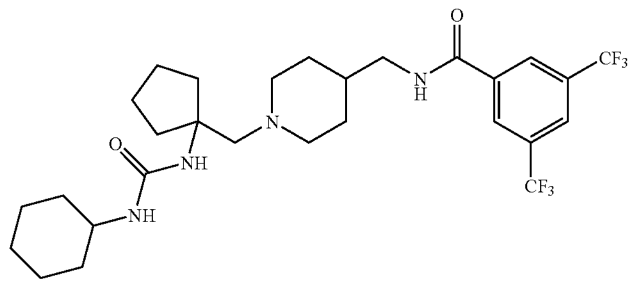 [SMILES: O=C(NC1CCCCC1)NC1(CN2CCC(CNC(=O)c3cc(C(F)(F)F)cc(C(F)(F)F)c3)CC2)CCCC1] | 577.28 |
| 15 | N-((1-((1-(3-isopropylureido)cyclopentyl)methyl)piperidin-4-yl)methyl)-3,5-bis(trifluoromethyl)benzamide | 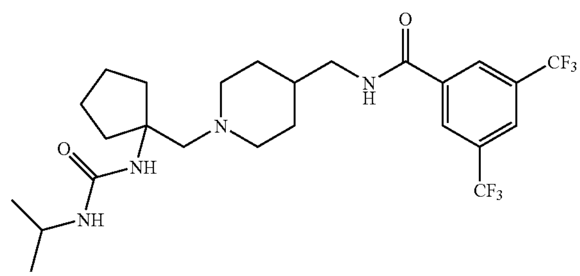 [SMILES: CC(C)NC(=O)NC1(CN2CCC(CNC(=O)c3cc(C(F)(F)F)cc(C(F)(F)F)c3)CC2)CCCC1] | 537.25 |
| 16 | methyl 1-((4-((3,5-bis(trifluoromethyl)benzamido)methyl)piperidin-1-yl)methyl)cyclopentylcarbamate | 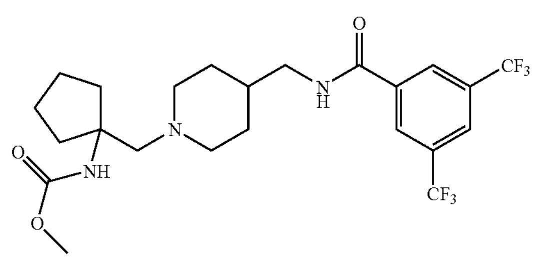 [SMILES: COC(=O)NC1(CN2CCC(CNC(=O)c3cc(C(F)(F)F)cc(C(F)(F)F)c3)CC2)CCCC1] | 510.21 |
| 17 | ethyl 1-((4-((3,5-bis(trifluoromethyl)benzamido)methyl)piperidin-1-yl)methyl)cyclopentylcarbamate | 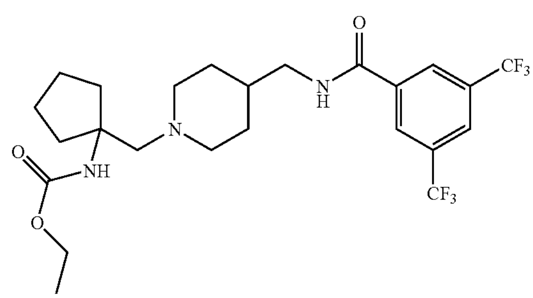 | 524.22 |

TABLE 1-continued

| Cmpd No. | Name | Structure | Mass Spec (m/z) |
|---|---|---|---|
| 18 | isobutyl 1-((4-(((3,5-bis(trifluoromethyl) benzamido)methyl)piperidin-1-yl)methyl)cyclopentylcarbamate | 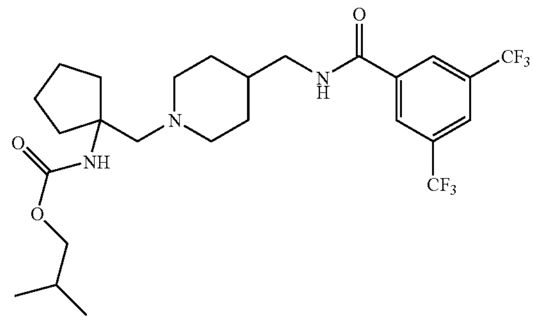 [SMILES: CC(C)COC(=O)NC1(CN2CCC(CNC(=O)c3cc(C(F)(F)F)cc(C(F)(F)F)c3)CC2)CCCC1] | 552.25 |
| 19 | N-((1-(2-(cyclopropanesulfonamido) ethyl)piperidin-4-yl)methyl)-3,5-bis(trifluoromethyl)benzamide | 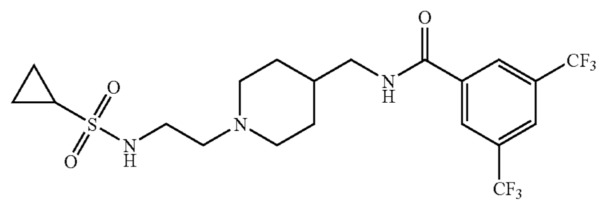 [SMILES: O=C(NCC1CCN(CCNS(=O)(=O)C2CC2)CC1)c1cc(C(F)(F)F)cc(C(F)(F)F)c1] | 502.15 |
| 20 | N-((1-(2-(1-methylethylsulfonamido) ethyl)piperidin-4-yl)methyl)-3,5-bis(trifluoromethyl)benzamide | 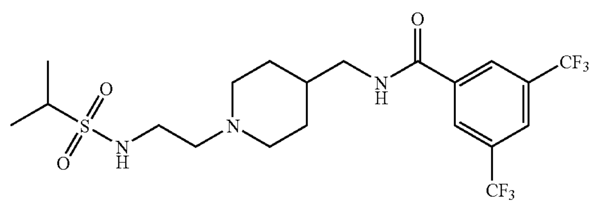 [SMILES: CC(C)S(=O)(=O)NCCN1CCC(CNC(=O)c2cc(C(F)(F)F)cc(C(F)(F)F)c2)CC1] | 504.16 |
| 21 | 3,5-bis(trifluoromethyl)-N-((1-(2-(trifluoromethylsulfonamido)ethyl) piperidin-4-yl)methyl)benzamide | 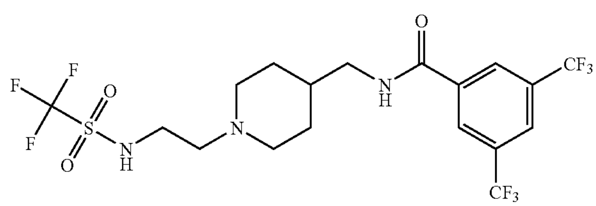 [SMILES: O=C(NCC1CCN(CCNS(=O)(=O)C(F)(F)F)CC1)c1cc(C(F)(F)F)cc(C(F)(F)F)c1] | 530.10 |
| 22 | N-((1-(2-(cyclopropylmethylsulfonamido) ethyl)piperidin-4-yl)methyl)-3,5-bis(trifluoromethyl)benzamide | 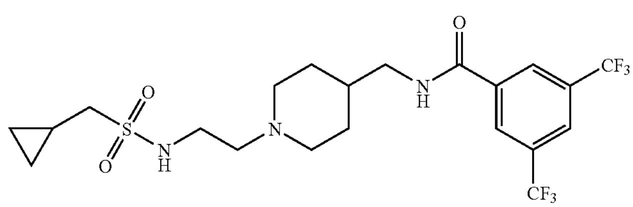 [SMILES: O=C(NCC1CCN(CCNS(=O)(=O)CC2CC2)CC1)c1cc(C(F)(F)F)cc(C(F)(F)F)c1] | 516.17 |
| 23 | 3-fluoro-5-(trifluoromethyl)-N-((1-(2-(3,3,3-trifluoropropylsulfonamido)ethyl) piperidin-4-yl)methyl)benzamide | 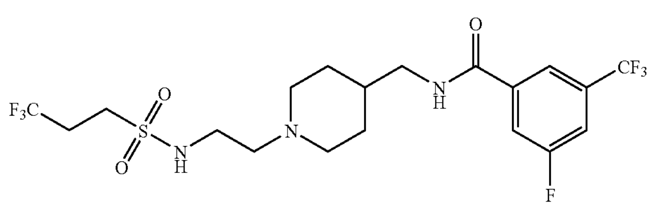 [SMILES: O=C(NCC1CCN(CCNS(=O)(=O)CCC(F)(F)F)CC1)c1cc(F)cc(C(F)(F)F)c1] | 508.14 |
| 24 | N-((1-(2-(cyclopropanesulfonamido) ethyl)piperidin-4-yl)methyl)-3-fluoro-5-(trifluoromethyl)benzamide | 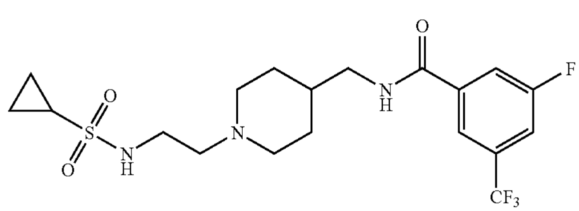 [SMILES: O=C(NCC1CCN(CCNS(=O)(=O)C2CC2)CC1)c1cc(F)cc(C(F)(F)F)c1] | 452.16 |

TABLE 1-continued

| Cmpd No. | Name | Mass Spec (m/z) |
|---|---|---|
| 25 | 3,5-bis(trifluoromethyl)-N-((1-(2-(3,3,3-trifluoropropylsulfonamido)ethyl)piperidin-4-yl)methyl)benzamide | 558.14 |
| 26 | 3-fluoro-N-((1-(2-(2-methylpropylsulfonamido)ethyl)piperidin-4-yl)methyl)-5-(trifluoromethyl)benzamide | 468.19 |
| 27 | N-((1-(2-(2-methylpropylsulfonamido)ethyl)piperidin-4-yl)methyl)-3,5-bis(trifluoromethyl)benzamide | 518.18 |
| 28 | N-((1-(2-(cyclopropylmethylsulfonamido)ethyl)piperidin-4-yl)methyl)-3-fluoro-5-(trifluoromethyl)benzamide | 466.17 |
| 29 | N-((1-(2-(methylsulfonamido)ethyl)piperidin-4-yl)methyl)-3,5-bis(trifluoromethyl)benzamide | 476.14 |
| 30 | N-((1-(2-(ethylsulfonamido)ethyl)piperidin-4-yl)methyl)-3,5-bis(trifluoromethyl)benzamide | 490.15 |
| 31 | N-((1-(2-(2,2,2-trifluoroethylsulfonamido)ethyl)piperidin-4-yl)methyl)-3,5-bis(trifluoromethyl)benzamide | 544.12 |

TABLE 1-continued

| Cmpd No. | Name | Structure | Mass Spec (m/z) |
|---|---|---|---|
| 32 | 3-fluoro-N-((1-(2-(2,2,2-trifluoroethylsulfonamido)ethyl)piperidin-4-yl)methyl)-5-(trifluoromethyl)benzamide | 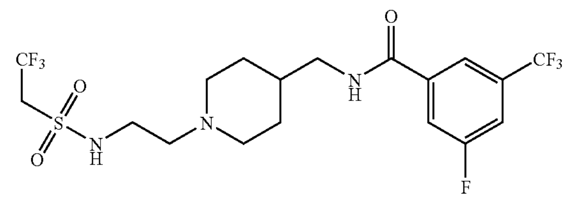 [SMILES: O=C(NCC1CCN(CCNS(=O)(=O)CC(F)(F)F)CC1)c1cc(F)cc(C(F)(F)F)c1] | 494.13 |
| 33 | 3-fluoro-5-(trifluoromethyl)-N-((1-(2-(trifluoromethylsulfonamido)ethyl)piperidin-4-yl)methyl)benzamide | 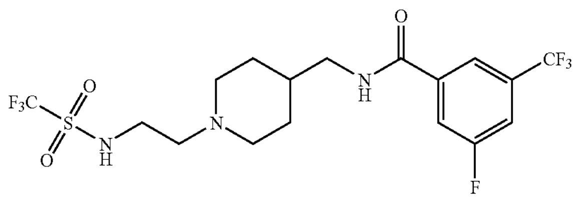 [SMILES: O=C(NCC1CCN(CCNS(=O)(=O)C(F)(F)F)CC1)c1cc(F)cc(C(F)(F)F)c1] | 480.11 |
| 34 | 3-fluoro-N-((1-(2-(1-methylethylsulfonamido)ethyl)piperidin-4-yl)methyl)-5-(trifluoromethyl)benzamide | 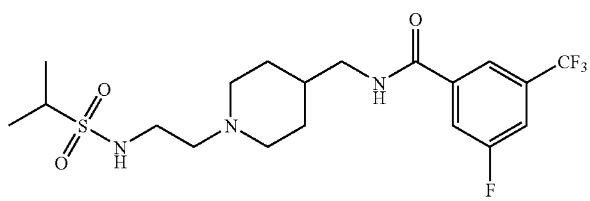 [SMILES: CC(C)S(=O)(=O)NCCN1CCC(CNC(=O)c2cc(F)cc(C(F)(F)F)c2)CC1] | 454.17 |
| 35 | tert-butyl 2-(4-((3,5-bis(trifluoromethyl)benzamido)methyl)piperidin-1-yl)ethylcarbamate | 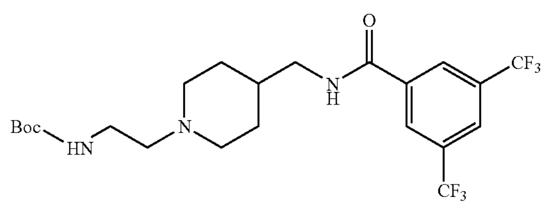 [SMILES: CC(C)(C)OC(=O)NCCN1CCC(CNC(=O)c2cc(C(F)(F)F)cc(C(F)(F)F)c2)CC1] | 498.21 |
| 36 | ethyl 2-(4-((3,5-bis(trifluoromethyl)benzamido)methyl)piperidin-1-yl)ethylcarbamate | 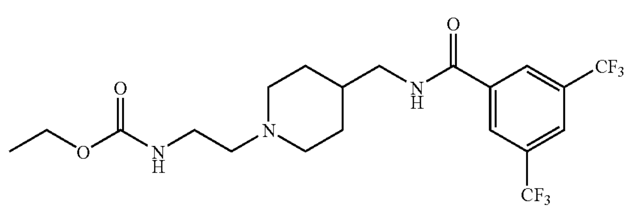 [SMILES: CCOC(=O)NCCN1CCC(CNC(=O)c2cc(C(F)(F)F)cc(C(F)(F)F)c2)CC1] | 470.18 |
| 37 | isobutyl 2-(4-((3,5-bis(trifluoromethyl)benzamido)methyl)piperidin-1-yl)ethylcarbamate | 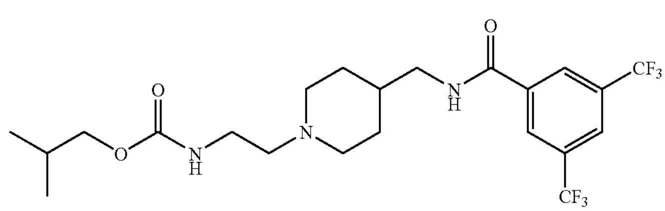 [SMILES: CC(C)COC(=O)NCCN1CCC(CNC(=O)c2cc(C(F)(F)F)cc(C(F)(F)F)c2)CC1] | 498.21 |
| 38 | tert-butyl 2-(4-((3-fluoro-5-(trifluoromethyl)benzamido)methyl)piperidin-1-yl)ethylcarbamate | 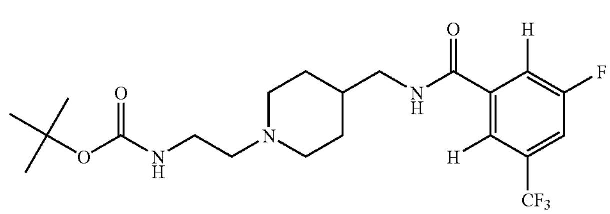 [SMILES: CC(C)(C)OC(=O)NCCN1CCC(CNC(=O)c2cc(F)cc(C(F)(F)F)c2)CC1] | 448.21 |

TABLE 1-continued

| Cmpd No. | Name | Structure | Mass Spec (m/z) |
|---|---|---|---|
| 39 | tert-butyl 2-(4-((3-(trifluoromethyl)benzamido)methyl)piperidin-1-yl)ethylcarbamate | 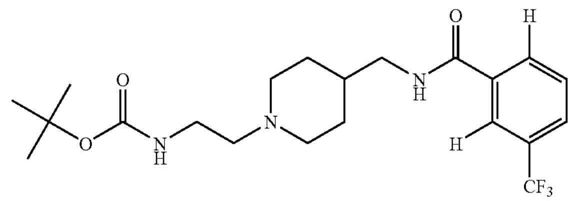 [SMILES: CC(C)(C)OC(=O)NCCN1CCC(CNC(=O)c2cccc(C(F)(F)F)c2)CC1] | 430.22 |
| 40 | tert-butyl 2-(4-((3-chloro-5-(trifluoromethyl)benzamido)methyl)piperidin-1-yl)ethylcarbamate | 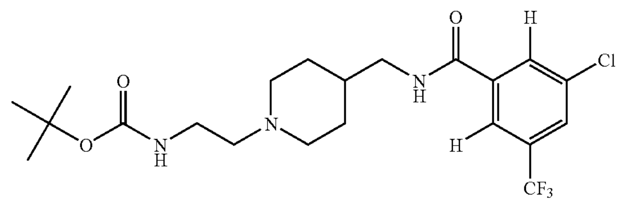 [SMILES: CC(C)(C)OC(=O)NCCN1CCC(CNC(=O)c2cc(Cl)cc(C(F)(F)F)c2)CC1] | 464.18 |
| 41 | tert-butyl 2-(4-((3-bromo-5-(trifluoromethyl)benzamido)methyl)piperidin-1-yl)ethylcarbamate | 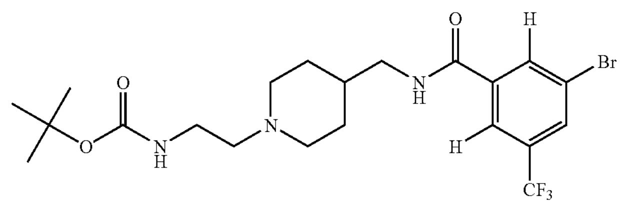 [SMILES: CC(C)(C)OC(=O)NCCN1CCC(CNC(=O)c2cc(Br)cc(C(F)(F)F)c2)CC1] | 508.13 |
| 42 | tert-butyl 2-(4-((3,5-dimethylbenzamido)methyl)piperidin-1-yl)ethylcarbamate | 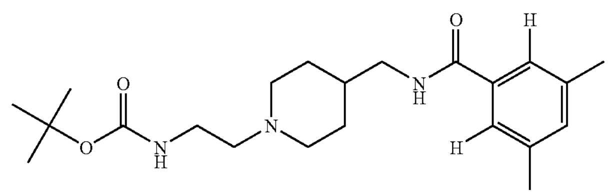 [SMILES: Cc1cc(C)cc(C(=O)NCC2CCN(CCNC(=O)OC(C)(C)C)CC2)c1] | 390.26 |
| 43 | tert-butyl 2-(4-((3,5-dichlorobenzamido)methyl)piperidin-1-yl)ethylcarbamate | 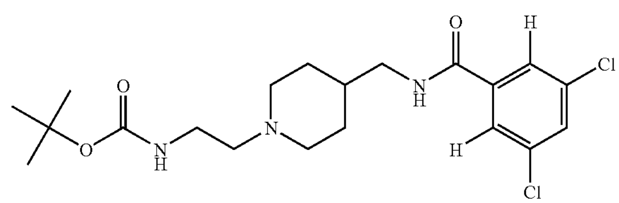 [SMILES: CC(C)(C)OC(=O)NCCN1CCC(CNC(=O)c2cc(Cl)cc(Cl)c2)CC1] | 430.15 |
| 44 | tert-butyl 2-(4-((3-(trifluoromethoxy)benzamido)methyl)piperidin-1-yl)ethylcarbamate | 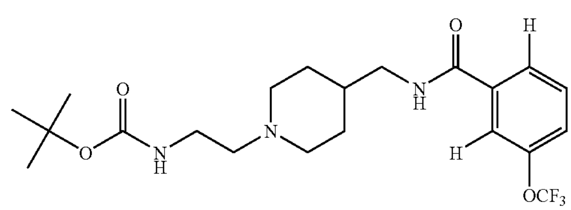 [SMILES: CC(C)(C)OC(=O)NCCN1CCC(CNC(=O)c2cccc(OC(F)(F)F)c2)CC1] | 446.21 |
| 45 | tert-butyl 2-(4-((3-(methylsulfonyl)benzamido)methyl)piperidin-1-yl)ethylcarbamate | 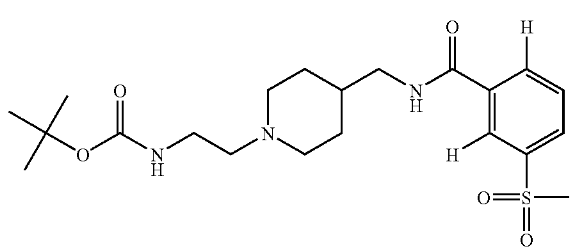 [SMILES: CC(C)(C)OC(=O)NCCN1CCC(CNC(=O)c2cccc(S(C)(=O)=O)c2)CC1] | 440.21 |

TABLE 1-continued

| Cmpd No. | Name | Structure | Mass Spec (m/z) |
|---|---|---|---|
| 46 | tert-butyl 2-(4-((4-(methylsulfonyl)benzamido)methyl)piperidin-1-yl)ethylcarbamate | 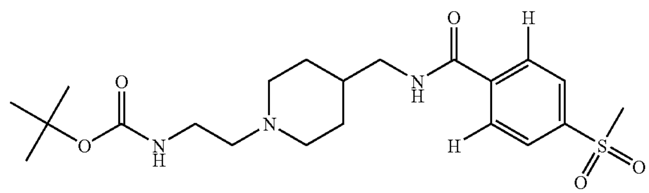 [SMILES: CC(C)(C)OC(=O)NCCN1CCC(CNC(=O)c2ccc(S(C)(=O)=O)cc2)CC1] | 440.21 |
| 47 | tert-butyl 2-(4-((3,5-difluorobenzamido)methyl)piperidin-1-yl)ethylcarbamate | 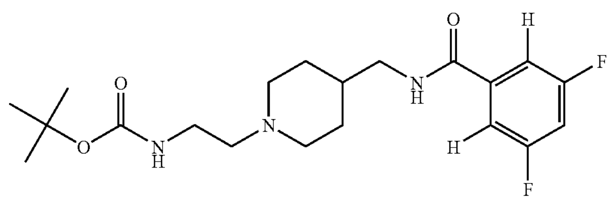 [SMILES: CC(C)(C)OC(=O)NCCN1CCC(CNC(=O)c2cc(F)cc(F)c2)CC1] | 398.21 |
| 48 | tert-butyl 2-(4-((3-chlorobenzamido)methyl)piperidin-1-yl)ethylcarbamate | 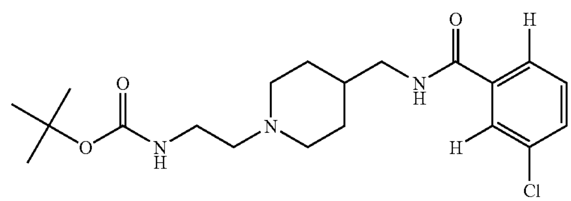 [SMILES: CC(C)(C)OC(=O)NCCN1CCC(CNC(=O)c2cccc(Cl)c2)CC1] | 396.19 |
| 49 | tert-butyl 2-(4-((3,5-di-tert-butylbenzamido)methyl)piperidin-1-yl)ethylcarbamate | 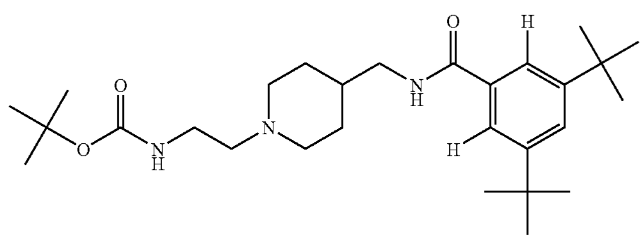 [SMILES: CC(C)(C)OC(=O)NCCN1CCC(CNC(=O)c2cc(C(C)(C)C)cc(C(C)(C)C)c2)CC1] | 474.36 |
| 50 | tert-butyl 2-(4-((3-tert-butoxybenzamido)methyl)piperidin-1-yl)ethylcarbamate | 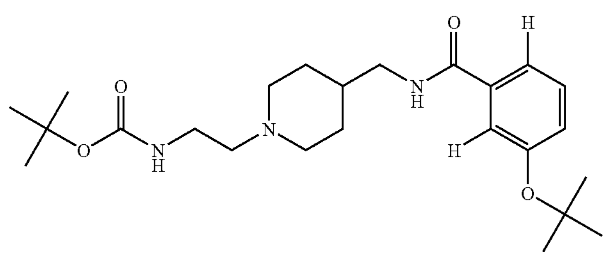 [SMILES: CC(C)(C)OC(=O)NCCN1CCC(CNC(=O)c2cccc(OC(C)(C)C)c2)CC1] | 434.29 |
| 51 | tert-butyl 2-(4-((2,4-difluorobenzamido)methyl)piperidin-1-yl)ethylcarbamate | 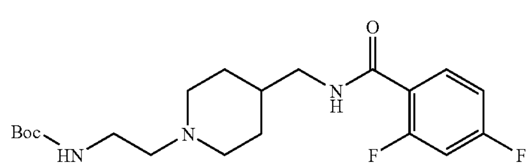 [SMILES: CC(C)(C)OC(=O)NCCN1CCC(CNC(=O)c2ccc(F)cc2F)CC1] | 398.21 |
| 52 | tert-butyl 2-(4-((3,4-dimethoxybenzamido)methyl)piperidin-1-yl)ethylcarbamate | 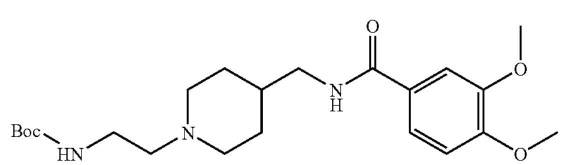 [SMILES: COc1ccc(C(=O)NCC2CCN(CCNC(=O)OC(C)(C)C)CC2)cc1OC] | 422.25 |

TABLE 1-continued

| Cmpd No. | Name | Structure | Mass Spec (m/z) |
|---|---|---|---|
| 53 | tert-butyl 2-(4-((2-(trifluoromethyl)benzamido)methyl)piperidin-1-yl)ethylcarbamate | 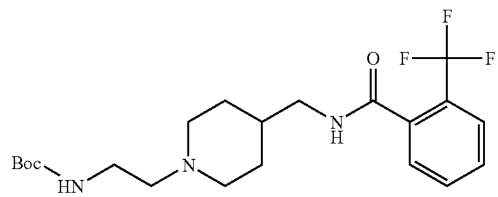 [SMILES: CC(C)(C)OC(=O)NCCN1CCC(CNC(=O)c2ccccc2C(F)(F)F)CC1] | 430.22 |
| 54 | tert-butyl 2-(4-((2,2-difluorobenzo[d][1,3]dioxole-5-carboxamido)methyl)piperidin-1-yl)ethylcarbamate | 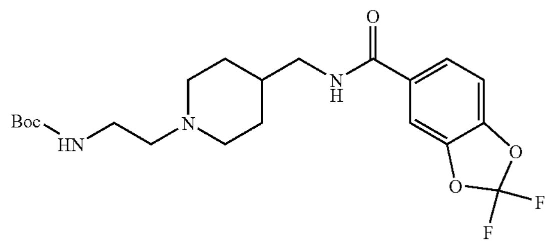 [SMILES: CC(C)(C)OC(=O)NCCN1CCC(CNC(=O)c2ccc3c(c2)OC(F)(F)O3)CC1] | 442.20 |
| 55 | tert-butyl 2-(4-((2-(trifluoromethoxy)benzamido)methyl)piperidin-1-yl)ethylcarbamate | 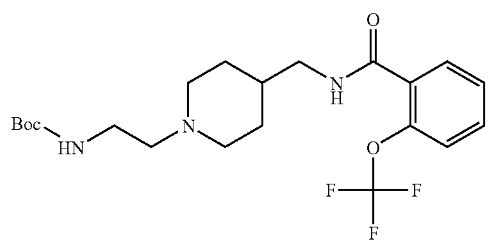 [SMILES: CC(C)(C)OC(=O)NCCN1CCC(CNC(=O)c2ccccc2OC(F)(F)F)CC1] | 446.21 |
| 56 | tert-butyl 2-(4-((3,4,5-trimethoxybenzamido)methyl)piperidin-1-yl)ethylcarbamate | 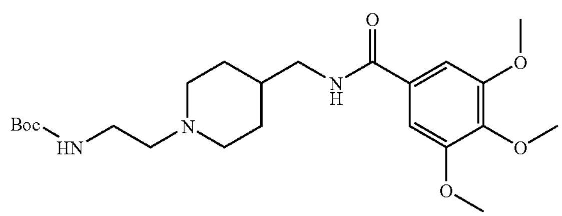 [SMILES: COc1cc(C(=O)NCC2CCN(CCNC(=O)OC(C)(C)C)CC2)cc(OC)c1OC] | 452.26 |
| 57 | tert-butyl 2-(4-((4-phenoxybenzamido)methyl)piperidin-1-yl)ethylcarbamate | 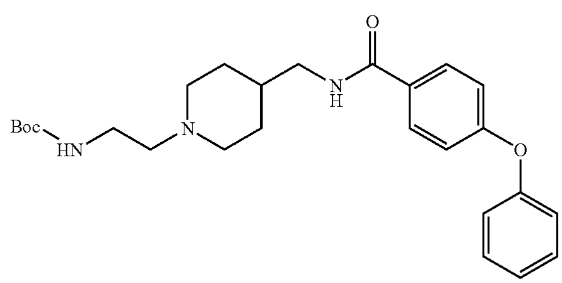 [SMILES: CC(C)(C)OC(=O)NCCN1CCC(CNC(=O)c2ccc(Oc3ccccc3)cc2)CC1] | 454.26 |
| 58 | N-((1-(2-propionamidoethyl)piperidin-4-yl)methyl)-3,5-bis(trifluoromethyl)benzamide | 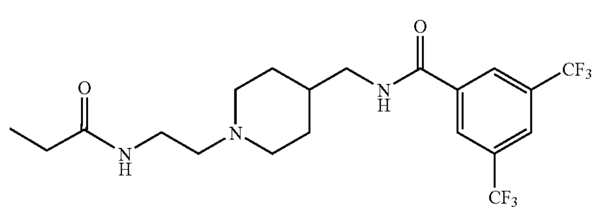 [SMILES: CCC(=O)NCCN1CCC(CNC(=O)c2cc(C(F)(F)F)cc(C(F)(F)F)c2)CC1] | 454.18 |

TABLE 1-continued

| Cmpd No. | Name | Mass Spec (m/z) |
|---|---|---|
| 59 | N-((1-(2-(cyclopropanecarboxamido)ethyl)piperidin-4-yl)methyl)-3,5-bis(trifluoromethyl)benzamide | 466.18 |
| 60 | N-((1-(2-pivalamidoethyl)piperidin-4-yl)methyl)-3,5-bis(trifluoromethyl)benzamide | 482.21 |
| 61 | N-(2-(4-((3,5-bis(trifluoromethyl)benzamido)methyl)piperidin-1-yl)ethyl)-1-methylpiperidine-4-carboxamide | 523.24 |
| 62 | N-((1-(2-(cyclopentanecarboxamido)ethyl)piperidin-4-yl)methyl)-3,5-bis(trifluoromethyl)benzamide | 494.21 |
| 63 | N-((1-(2-(2-cyclopropylacetamido)ethyl)piperidin-4-yl)methyl)-3,5-bis(trifluoromethyl)benzamide | 480.20 |
| 64 | N-((1-(2-((1r,4r)-4-methylcyclohexanecarboxamido)ethyl)piperidin-4-yl)methyl)-3,5-bis(trifluoromethyl)benzamide | 522.24 |
| 65 | N-((1-(2-(2-hydroxy-2-methylpropanamido)ethyl)piperidin-4-yl)methyl)-3,5-bis(trifluoromethyl)benzamide | 484.19 |

TABLE 1-continued

| Cmpd No. | Name | Structure | Mass Spec (m/z) |
|---|---|---|---|
| 66 | N-((1-(2-(4,4,4-trifluorobutanamido)ethyl)piperidin-4-yl)methyl)-3,5-bis(trifluoromethyl)benzamide | 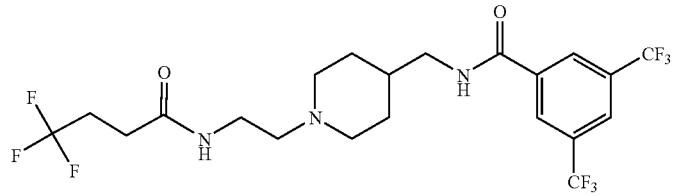 [SMILES: O=C(CCC(F)(F)F)NCCN1CCC(CNC(=O)c2cc(C(F)(F)F)cc(C(F)(F)F)c2)CC1] | 522.17 |
| 67 | (R)-N-(2-(4-((3,5-bis(trifluoromethyl)benzamido)methyl)piperidin-1-yl)ethyl)-5-oxopyrrolidine-2-carboxamide | 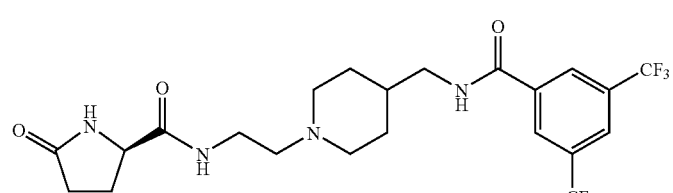 | 509.19 |
| 68 | N-((1-(2-(3-methoxypropanamido)ethyl)piperidin-4-yl)methyl)-3,5-bis(trifluoromethyl)benzamide | 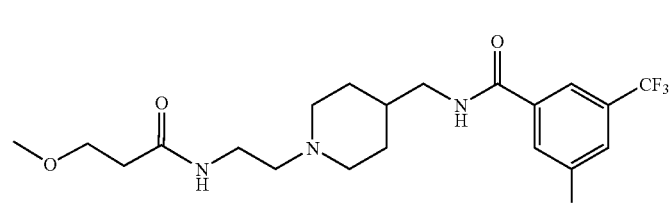 | 484.19 |
| 69 | N-(2-(4-((3,5-bis(trifluoromethyl)benzamido)methyl)piperidin-1-yl)ethyl)-1-methylpiperidine-3-carboxamide | 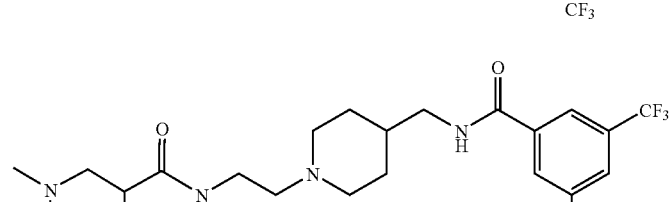 | 523.24 |
| 70 | N-((1-(2-(3-cyclohexylureido)ethyl)piperidin-4-yl)methyl)-3,5-bis(trifluoromethyl)benzamide | 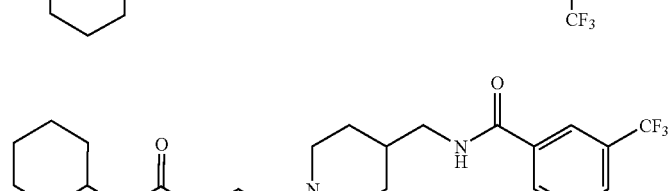 | 523.24 |
| 71 | N-((1-(2-(3-propylureido)ethyl)piperidin-4-yl)methyl)-3,5-bis(trifluoromethyl)benzamide | 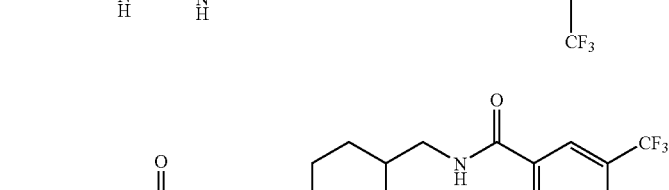 | 483.21 |
| 72 | N-((1-(2-(3-tert-butylureido)ethyl)piperidin-4-yl)methyl)-3,5-bis(trifluoromethyl)benzamide | 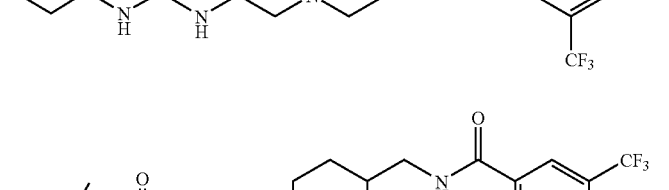 | 410.72 |

TABLE 1-continued

| Cmpd No. | Name | Structure | Mass Spec (m/z) |
|---|---|---|---|
| 73 | N-((1-(2-(3-isopropylureido)ethyl) piperidin-4-yl)methyl)-3,5-bis(trifluoromethyl)benzamide | 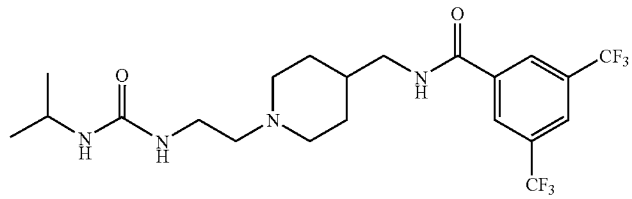 [SMILES: CC(C)NC(=O)NCCN1CCC(CNC(=O)c2cc(C(F)(F)F)cc(C(F)(F)F)c2)CC1] | 483.21 |
| 74 | N-((1-(2-(3-ethylureido)ethyl)piperidin-4-yl)methyl)-3,5-bis(trifluoromethyl) benzamide | 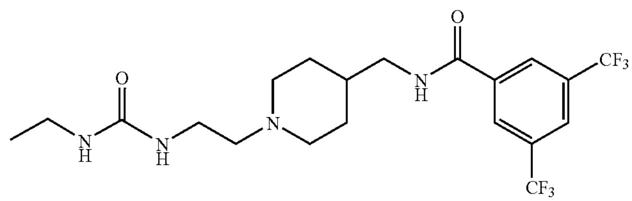 [SMILES: CCNC(=O)NCCN1CCC(CNC(=O)c2cc(C(F)(F)F)cc(C(F)(F)F)c2)CC1] | 461.02 |
| 75 | N-((1-(2-(3-(tetrahydrosulfonylphen-3-yl)ureido)ethyl)piperidin-4-yl)methyl)-3,5-bis(trifluoromethyl)benzamide | 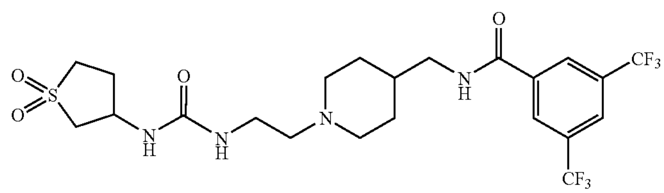 [SMILES: O=C(NCCN1CCC(CNC(=O)c2cc(C(F)(F)F)cc(C(F)(F)F)c2)CC1)NC1CCS(=O)(=O)C1] | 551.01 |
| 76 | (S)-N-((1-(2-hydroxy-3,3-dimethylbutanoyl)piperidin-4-yl)methyl)-3,5-bis(trifluoromethyl)benzamide | 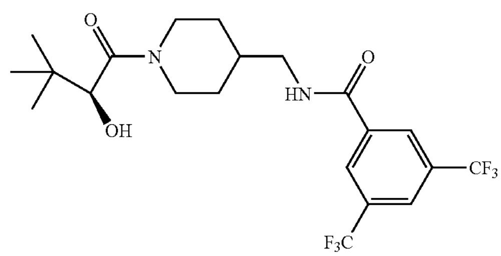 [SMILES: CC(C)(C)[C@H](O)C(=O)N1CCC(CNC(=O)c2cc(C(F)(F)F)cc(C(F)(F)F)c2)CC1] | 469.18 |
| 77 | N-((1-(4-hydroxypiperidine-4-carbonyl) piperidin-4-yl)methyl)-3,5-bis(trifluoromethyl)benzamide | 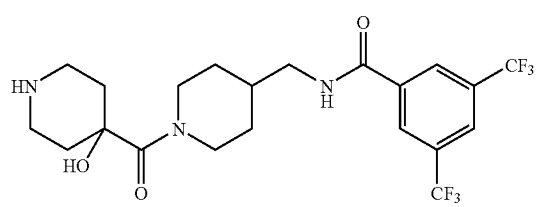 [SMILES: O=C(NCC1CCN(C(=O)C2(O)CCNCC2)CC1)c1cc(C(F)(F)F)cc(C(F)(F)F)c1] | 482.18 |
| 78 | N-((1-(4-aminotetrahydro-2H-pyran-4-carbonyl)piperidin-4-yl)methyl)-3,5-bis(trifluoromethyl)benzamide | 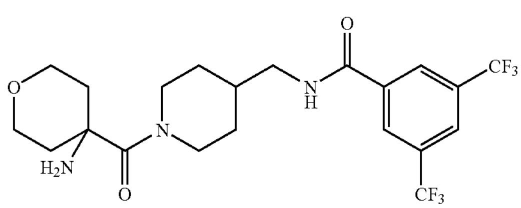 [SMILES: NC1(C(=O)N2CCC(CNC(=O)c3cc(C(F)(F)F)cc(C(F)(F)F)c3)CC2)CCOCC1] | 482.18 |
| 79 | N-((1-(1-aminocyclopropanecarbonyl)piperidin-4-yl)methyl)-3,5-bis(trifluoromethyl)benzamide | 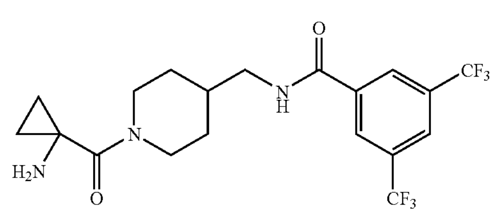 [SMILES: NC1(C(=O)N2CCC(CNC(=O)c3cc(C(F)(F)F)cc(C(F)(F)F)c3)CC2)CC1] | 438.15 |

TABLE 1-continued

| Cmpd No. | Name | Structure | Mass Spec (m/z) |
|---|---|---|---|
| 80 | N-((1-((2R,4R)-4-hydroxypyrrolidine-2-carbonyl)piperidin-4-yl)methyl)-3,5-bis(trifluoromethyl)benzamide | 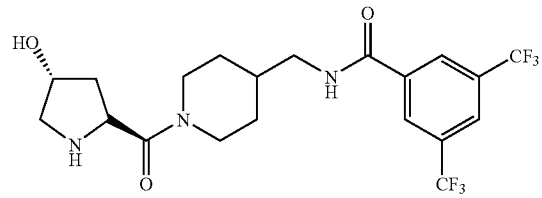 | 468.16 |
| 81 | (R)-N-((1-(pyrrolidine-2-carbonyl)piperidin-4-yl)methyl)-3,5-bis(trifluoromethyl)benzamide | 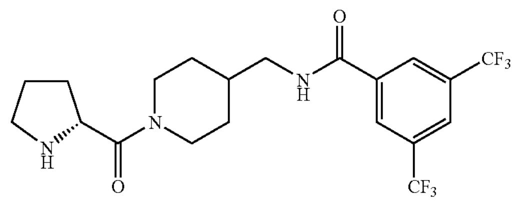 [SMILES: O=C(NCC1CCN(C(=O)[C@H]2CCCN2)CC1)c1cc(C(F)(F)F)cc(C(F)(F)F)c1] | 452.17 |
| 82 | (S)-N-((1-(pyrrolidine-2-carbonyl)piperidin-4-yl)methyl)-3,5-bis(trifluoromethyl)benzamide | 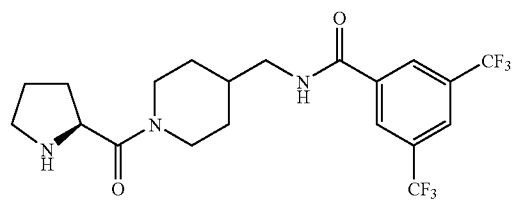 [SMILES: O=C(NCC1CCN(C(=O)[C@@H]2CCCN2)CC1)c1cc(C(F)(F)F)cc(C(F)(F)F)c1] | 452.17 |
| 83 | (R)-N-((1-(5-oxopyrrolidine-2-carbonyl)piperidin-4-yl)methyl)-3,5-bis(trifluoromethyl)benzamide | 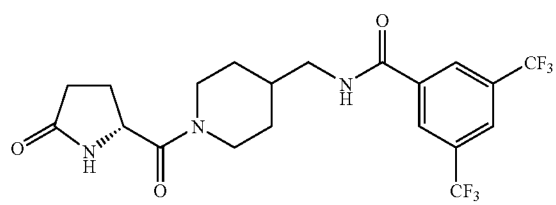 [SMILES: O=C1CC[C@H](C(=O)N2CCC(CNC(=O)c3cc(C(F)(F)F)cc(C(F)(F)F)c3)CC2)N1] | 466.15 |
| 84 | N-((1-(4-hydroxypiperidine-4-carbonyl)piperidin-4-yl)methyl)benzo[d][1,3]dioxole-5-carboxamide | 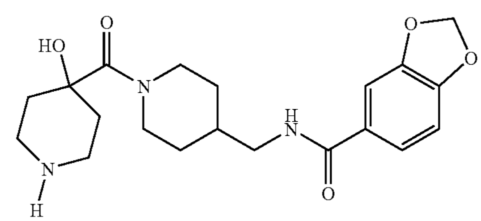 [SMILES: O=C(NCC1CCN(C(=O)C2(O)CCNCC2)CC1)c1ccc2c(c1)OCO2] | 390.20 |
| 85 | N-((1-(1-aminocyclopentanecarbonyl)piperidin-4-yl)methyl)-3,5-bis(trifluoromethyl)benzamide | 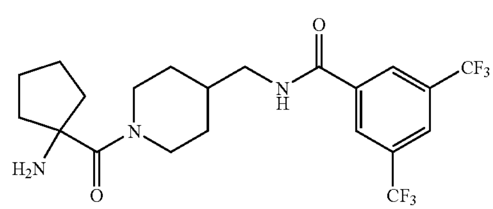 [SMILES: NC1(C(=O)N2CCC(CNC(=O)c3cc(C(F)(F)F)cc(C(F)(F)F)c3)CC2)CCCC1] | 466.19 |
| 86 | N-((1-(1-aminocyclohexanecarbonyl)piperidin-4-yl)methyl)-3,5-bis(trifluoromethyl)benzamide | 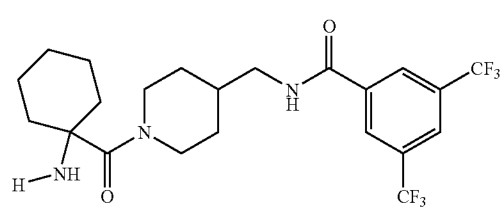 [SMILES: NC1(C(=O)N2CCC(CNC(=O)c3cc(C(F)(F)F)cc(C(F)(F)F)c3)CC2)CCCCC1] | 480.20 |

TABLE 1-continued

| Cmpd No. | Name | Structure | Mass Spec (m/z) |
|---|---|---|---|
| 87 | (R)-N-((1-(pyrrolidine-2-carbonyl) piperidin-4-yl)methyl)-3,5-bis(trifluoromethyl)benzamide | 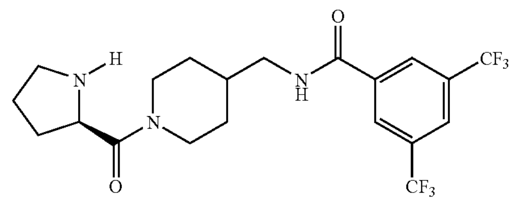 [SMILES: O=C(NCC1CCN(C(=O)[C@H]2CCCN2)CC1)c1cc(C(F)(F)F)cc(C(F)(F)F)c1] | 452.17 |
| 88 | (S)-N-((1-(piperidine-2-carbonyl) piperidin-4-yl)methyl)-3,5-bis(trifluoromethyl)benzamide | 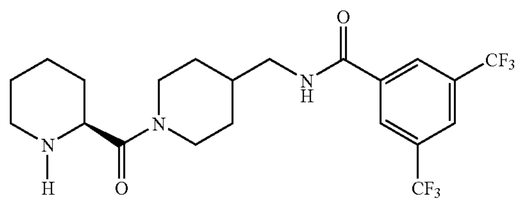 [SMILES: O=C(NCC1CCN(C(=O)[C@@H]2CCCCN2)CC1)c1cc(C(F)(F)F)cc(C(F)(F)F)c1] | 466.19 |
| 89 | N-((1-(2-hydroxy-2,3,3-trimethylbutanoyl)piperidin-4-yl)methyl)-3,5-bis(trifluoromethyl)benzamide | 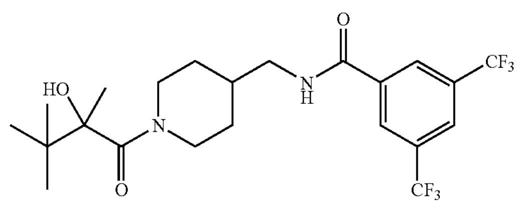 [SMILES: CC(C)(C)C(C)(O)C(=O)N1CCC(CNC(=O)c2cc(C(F)(F)F)cc(C(F)(F)F)c2)CC1] | 483.20 |
| 90 | N-((1-(2-ethyl-2-hydroxy-3,3-dimethylbutanoyl)piperidin-4-yl)methyl)-3,5-bis(trifluoromethyl)benzamide | 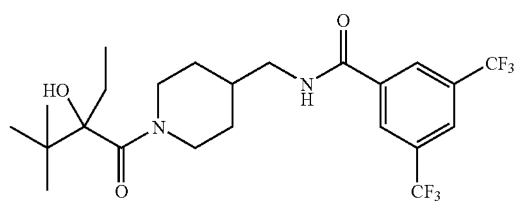 [SMILES: CCC(O)(C(=O)N1CCC(CNC(=O)c2cc(C(F)(F)F)cc(C(F)(F)F)c2)CC1)C(C)(C)C] | 497.22 |
| 91 | N-((1-(2-hydroxy-3,3-dimethylbutanoyl)piperidin-4-yl)methyl)-3,5-bis(trifluoromethyl)benzamide | 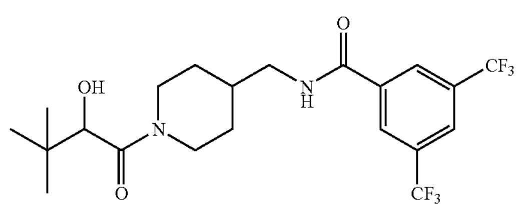 [SMILES: CC(C)(C)C(O)C(=O)N1CCC(CNC(=O)c2cc(C(F)(F)F)cc(C(F)(F)F)c2)CC1] | 469.18 |
| 92 | N-((1-(2-(cyclopentylamino)-2-oxoethyl)piperidin-4-yl)methyl)-3,5-bis(trifluoromethyl)benzamide | 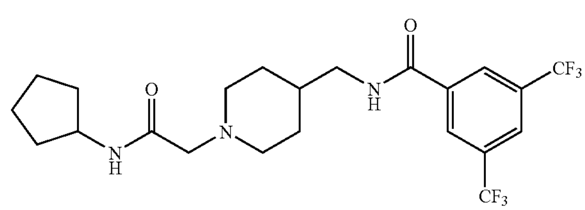 [SMILES: O=C(CN1CCC(CNC(=O)c2cc(C(F)(F)F)cc(C(F)(F)F)c2)CC1)NC1CCCC1] | 480.20 |
| 93 | N-((1-(2-(2-methylcyclohexylamino)-2-oxoethyl)piperidin-4-yl)methyl)-3,5-bis(trifluoromethyl)benzamide | 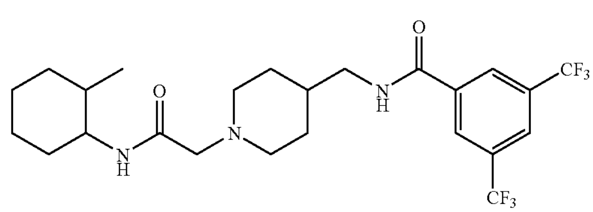 [SMILES: CC1CCCCC1NC(=O)CN1CCC(CNC(=O)c2cc(C(F)(F)F)cc(C(F)(F)F)c2)CC1] | 508.23 |

TABLE 1-continued

| Cmpd No. | Name | Structure | Mass Spec (m/z) |
|---|---|---|---|
| 94 | N-((1-(2-(cyclohexylamino)-2-oxoethyl)piperidin-4-yl)methyl)-3,5-bis(trifluoromethyl)benzamide | 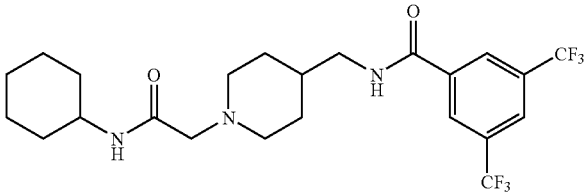 [SMILES: O=C(CN1CCC(CNC(=O)c2cc(C(F)(F)F)cc(C(F)(F)F)c2)CC1)NC1CCCCC1] | 494.22 |
| 95 | N-((1-(2-(cyclopropylamino)-2-oxoethyl)piperidin-4-yl)methyl)-3,5-bis(trifluoromethyl)benzamide | 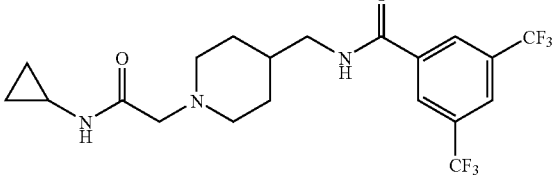 | 452.17 |
| 96 | N-((1-(2-((1r,4r)-4-hydroxycyclohexylamino)-2-oxoethyl)piperidin-4-yl)methyl)-3,5-bis(trifluoromethyl)benzamide | 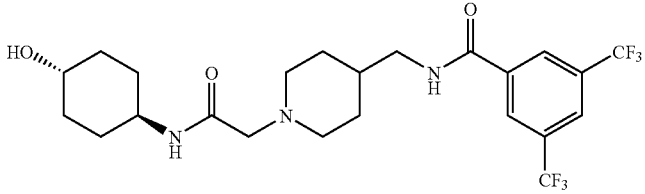 [SMILES: O=C(CN1CCC(CNC(=O)c2cc(C(F)(F)F)cc(C(F)(F)F)c2)CC1)N[C@H]1CC[C@H](O)CC1] | 510.21 |
| 97 | N-((1-(2-((1r,4r)-4-methylcyclohexylamino)-2-oxoethyl)piperidin-4-yl)methyl)-3,5-bis(trifluoromethyl)benzamide | 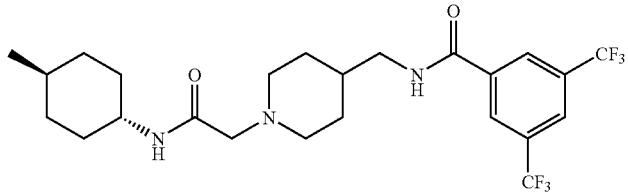 [SMILES: C[C@H]1CC[C@H](NC(=O)CN2CCC(CNC(=O)c3cc(C(F)(F)F)cc(C(F)(F)F)c3)CC2)CC1] | 508.23 |
| 98 | N-((1-(2-(3-hydroxypiperidin-1-yl)-2-oxoethyl)piperidin-4-yl)methyl)-3,5-bis(trifluoromethyl)benzamide | 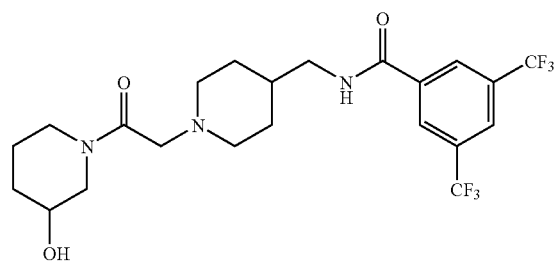 [SMILES: O=C(NCC1CCN(CC(=O)N2CCCC(O)C2)CC1)c1cc(C(F)(F)F)cc(C(F)(F)F)c1] | 496.20 |
| 99 | N-((1-(2-(3-methylpiperidin-1-yl)-2-oxoethyl)piperidin-4-yl)methyl)-3,5-bis(trifluoromethyl)benzamide | 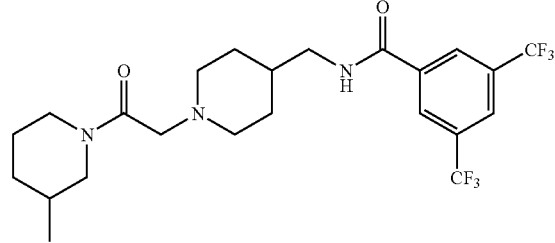 [SMILES: CC1CCCN(C(=O)CN2CCC(CNC(=O)c3cc(C(F)(F)F)cc(C(F)(F)F)c3)CC2)C1] | 494.22 |

TABLE 1-continued

| Cmpd No. | Name | Structure | Mass Spec (m/z) |
|---|---|---|---|
| 100 | N-((1-(2-(2-ethylpiperidin-1-yl)-2-oxoethyl)piperidin-4-yl)methyl)-3,5-bis(trifluoromethyl)benzamide | 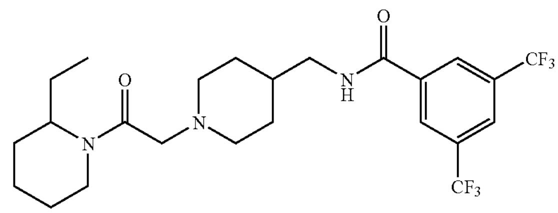 [SMILES: CCC1CCCCN1C(=O)CN1CCC(CNC(=O)c2cc(C(F)(F)F)cc(C(F)(F)F)c2)CC1] | 508.23 |
| 101 | N-((1-(2-(cyclohexyl(methyl)amino)-2-oxoethyl)piperidin-4-yl)methyl)-3,5-bis(trifluoromethyl)benzamide | 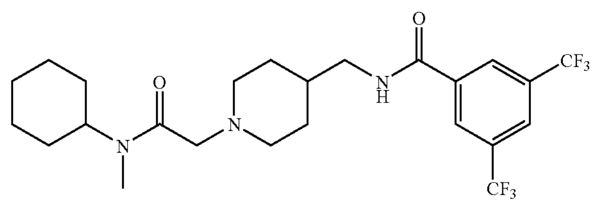 [SMILES: CN(C(=O)CN1CCC(CNC(=O)c2cc(C(F)(F)F)cc(C(F)(F)F)c2)CC1)C1CCCCC1] | 508.23 |
| 102 | N-((1-(2-(4-hydroxypiperidin-1-yl)-2-oxoethyl)piperidin-4-yl)methyl)-3,5-bis(trifluoromethyl)benzamide | 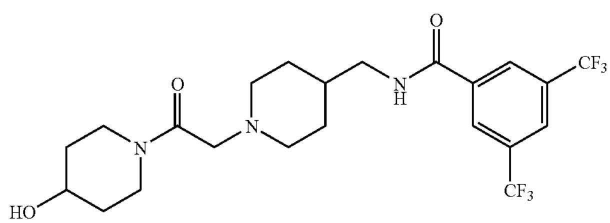 [SMILES: O=C(NCC1CCN(CC(=O)N2CCC(O)CC2)CC1)c1cc(C(F)(F)F)cc(C(F)(F)F)c1] | 496.20 |
| 103 | N-((1-(2-(4-methoxypiperidin-1-yl)-2-oxoethyl)piperidin-4-yl)methyl)-3,5-bis(trifluoromethyl)benzamide | 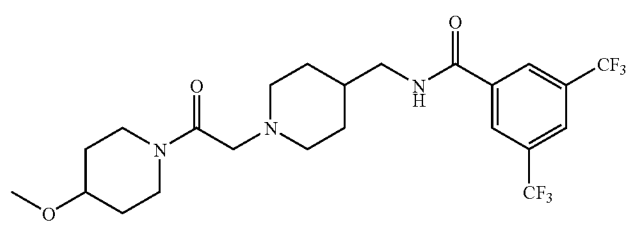 [SMILES: COC1CCN(C(=O)CN2CCC(CNC(=O)c3cc(C(F)(F)F)cc(C(F)(F)F)c3)CC2)CC1] | 510.21 |
| 104 | (R)-N-((1-(2-(2-methylpiperidin-1-yl)-2-oxoethyl)piperidin-4-yl)methyl)-3,5-bis(trifluoromethyl)benzamide | 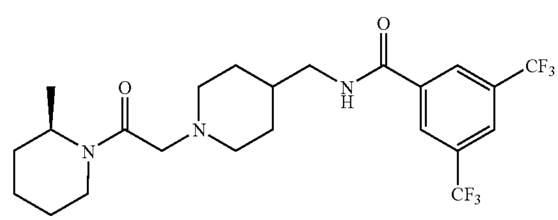 [SMILES: C[C@@H]1CCCCN1C(=O)CN1CCC(CNC(=O)c2cc(C(F)(F)F)cc(C(F)(F)F)c2)CC1] | 494.22 |
| 105 | N-((1-(2-(2-ethylpyrrolidin-1-yl)-2-oxoethyl)piperidin-4-yl)methyl)-3,5-bis(trifluoromethyl)benzamide | 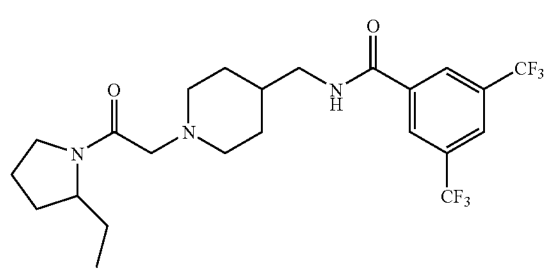 [SMILES: CCC1CCCN1C(=O)CN1CCC(CNC(=O)c2cc(C(F)(F)F)cc(C(F)(F)F)c2)CC1] | 494.22 |

TABLE 1-continued

| Cmpd No. | Name | Structure | Mass Spec (m/z) |
|---|---|---|---|
| 106 | N-((1-(2-(4-(hydroxymethyl)piperidin-1-yl)-2-oxoethyl)piperidin-4-yl)methyl)-3,5-bis(trifluoromethyl)benzamide | 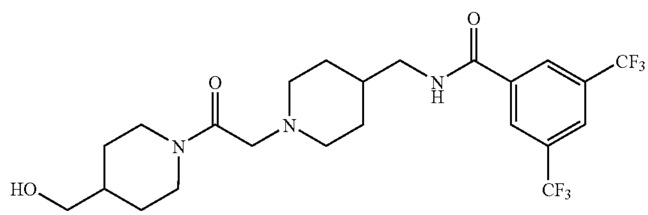 [SMILES: O=C(NCC1CCN(CC(=O)N2CCC(CO)CC2)CC1)c1cc(C(F)(F)F)cc(C(F)(F)F)c1] | 510.21 |
| 107 | N-((1-(2-oxo-2-(2-(trifluoromethyl)pyrrolidin-1-yl)ethyl)piperidin-4-yl)methyl)-3,5-bis(trifluoromethyl)benzamide | 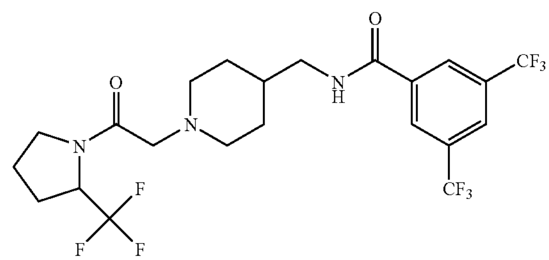 [SMILES: O=C(NCC1CCN(CC(=O)N2CCCC2C(F)(F)F)CC1)c1cc(C(F)(F)F)cc(C(F)(F)F)c1] | 534.17 |
| 108 | N-((1-(2-oxo-2-(4-(trifluoromethyl)piperidin-1-yl)ethyl)piperidin-4-yl)methyl)-3,5-bis(trifluoromethyl)benzamide | 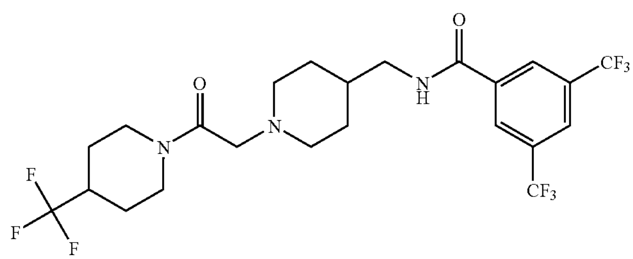 [SMILES: O=C(NCC1CCN(CC(=O)N2CCC(C(F)(F)F)CC2)CC1)c1cc(C(F)(F)F)cc(C(F)(F)F)c1] | 548.19 |
| 109 | N-((1-(2-(3,3-difluoropiperidin-1-yl)-2-oxoethyl)piperidin-4-yl)methyl)-3,5-bis(trifluoromethyl)benzamide | 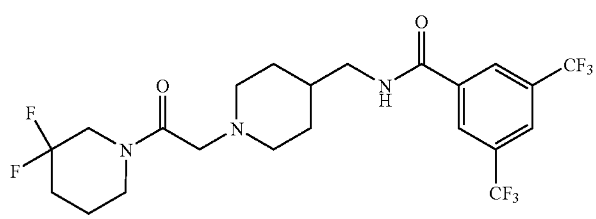 [SMILES: O=C(NCC1CCN(CC(=O)N2CCCC(F)(F)C2)CC1)c1cc(C(F)(F)F)cc(C(F)(F)F)c1] | 516.18 |
| 110 | N-((1-(2-(4,4-difluoropiperidin-1-yl)-2-oxoethyl)piperidin-4-yl)methyl)-3,5-bis(trifluoromethyl)benzamide | 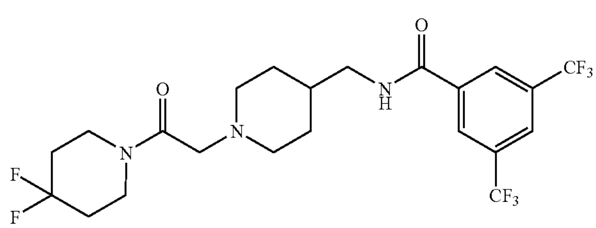 [SMILES: O=C(NCC1CCN(CC(=O)N2CCC(F)(F)CC2)CC1)c1cc(C(F)(F)F)cc(C(F)(F)F)c1] | 516.18 |
| 111 | N-((1-(2-(4-tert-butylpiperidin-1-yl)-2-oxoethyl)piperidin-4-yl)methyl)-3,5-bis(trifluoromethyl)benzamide | 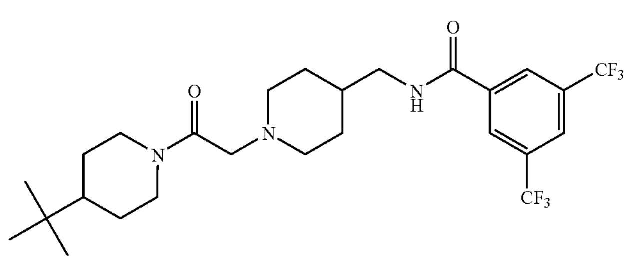 [SMILES: CC(C)(C)C1CCN(C(=O)CN2CCC(CNC(=O)c3cc(C(F)(F)F)cc(C(F)(F)F)c3)CC2)CC1] | 536.26 |

TABLE 1-continued

| Cmpd No. | Name | Structure | Mass Spec (m/z) |
|---|---|---|---|
| 112 | N-((1-(2-(4-cyanopiperidin-1-yl)-2-oxoethyl)piperidin-4-yl)methyl)-3,5-bis(trifluoromethyl)benzamide | 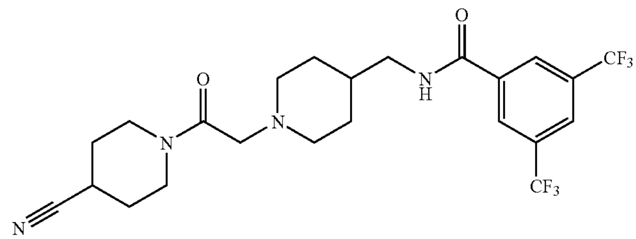 [SMILES: N#CC1CCN(C(=O)CN2CCC(CNC(=O)c3cc(C(F)(F)F)cc(C(F)(F)F)c3)CC2)CC1] | 505.20 |
| 113 | N-((1-(2-(4-morpholinopiperidin-1-yl)-2-oxoethyl)piperidin-4-yl)methyl)-3,5-bis(trifluoromethyl)benzamide | 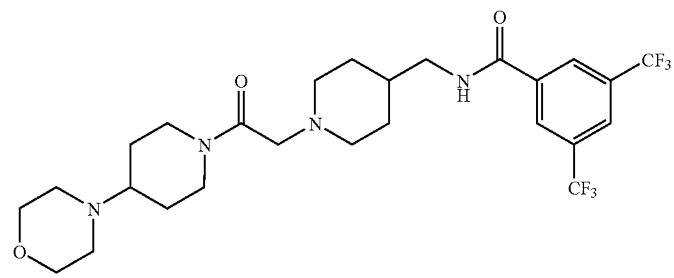 [SMILES: O=C(NCC1CCN(CC(=O)N2CCC(N3CCOCC3)CC2)CC1)c1cc(C(F)(F)F)cc(C(F)(F)F)c1] | 565.25 |
| 114 | N-((1-(2-(2-hydroxybutylamino)-2-oxoethyl)piperidin-4-yl)methyl)-3,5-bis(trifluoromethyl)benzamide | 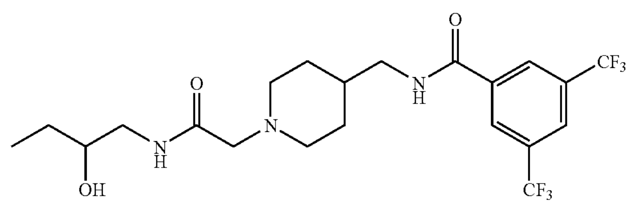 [SMILES: CCC(O)CNC(=O)CN1CCC(CNC(=O)c2cc(C(F)(F)F)cc(C(F)(F)F)c2)CC1] | 484.20 |
| 115 | 3-bromo-5-(trifluoromethyl)-N-((1-(2-(trifluoromethylsulfonamido)ethyl)piperidin-4-yl)methyl)benzamide | 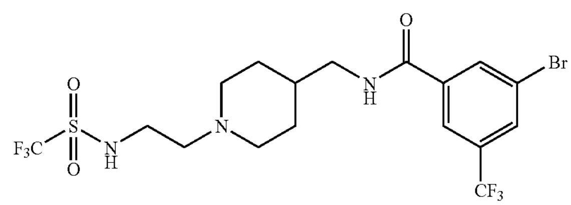 [SMILES: O=C(NCC1CCN(CCNS(=O)(=O)C(F)(F)F)CC1)c1cc(Br)cc(C(F)(F)F)c1] | 540.03 |
| 116 | 3,5-dimethyl-N-((1-(2-(trifluoromethylsulfonamido)ethyl)piperidin-4-yl)methyl)benzamide | 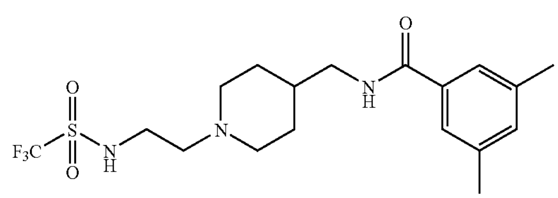 [SMILES: Cc1cc(C)cc(C(=O)NCC2CCN(CCNS(=O)(=O)C(F)(F)F)CC2)c1] | 422.16 |
| 117 | 3-(trifluoromethyl)-N-((1-(2-(trifluoromethylsulfonamido)ethyl)piperidin-4-yl)methyl)benzamide | 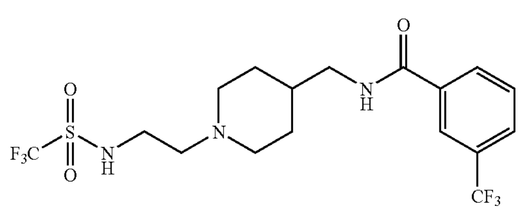 [SMILES: O=C(NCC1CCN(CCNS(=O)(=O)C(F)(F)F)CC1)c1cccc(C(F)(F)F)c1] | 462.12 |
| 118 | 3-chloro-5-(trifluoromethyl)-N-((1-(2-(trifluoromethylsulfonamido)ethyl)piperidin-4-yl)methyl)benzamide | 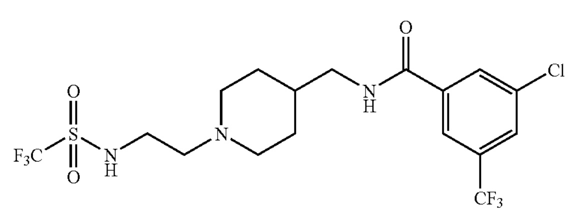 [SMILES: O=C(NCC1CCN(CCNS(=O)(=O)C(F)(F)F)CC1)c1cc(Cl)cc(C(F)(F)F)c1] | 496.08 |

TABLE 1-continued

| Cmpd No. | Name | Structure | Mass Spec (m/z) |
|---|---|---|---|
| 119 | 3,5-dichloro-N-((1-(2-(trifluoromethylsulfonamido)ethyl)piperidin-4-yl)methyl)benzamide | 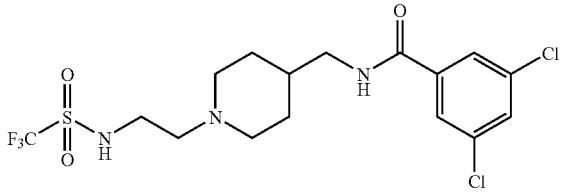 [SMILES: O=C(NCC1CCN(CCNS(=O)(=O)C(F)(F)F)CC1)c1cc(Cl)cc(Cl)c1] | 462.06 |
| 120 | 3-(trifluoromethoxy)-N-((1-(2-(trifluoromethylsulfonamido)ethyl)piperidin-4-yl)methyl)benzamide | 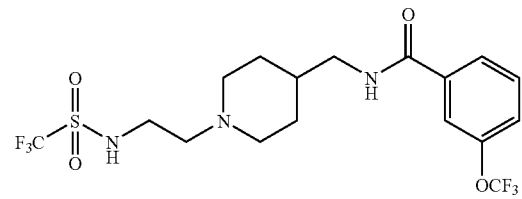 [SMILES: O=C(NCC1CCN(CCNS(=O)(=O)C(F)(F)F)CC1)c1cccc(OC(F)(F)F)c1] | 478.12 |
| 121 | 3,5-difluoro-N-((1-(2-(trifluoromethylsulfonamido)ethyl)piperidin-4-yl)methyl)benzamide | 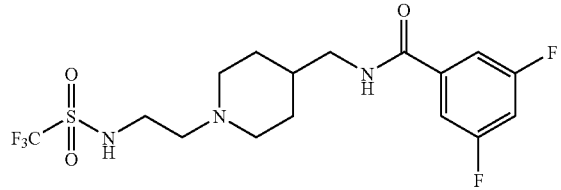 [SMILES: O=C(NCC1CCN(CCNS(=O)(=O)C(F)(F)F)CC1)c1cc(F)cc(F)c1] | 430.11 |
| 122 | 3-chloro-N-((1-(2-(trifluoromethylsulfonamido)ethyl)piperidin-4-yl)methyl)benzamide | 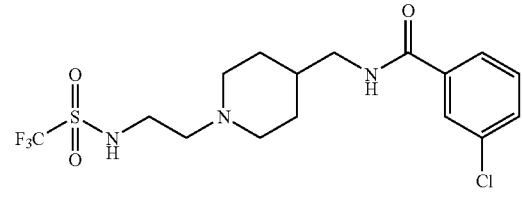 [SMILES: O=C(NCC1CCN(CCNS(=O)(=O)C(F)(F)F)CC1)c1cccc(Cl)c1] | 428.09 |
| 123 | 3,5-dimethoxy-N-((1-(2-(trifluoromethylsulfonamido)ethyl)piperidin-4-yl)methyl)benzamide | 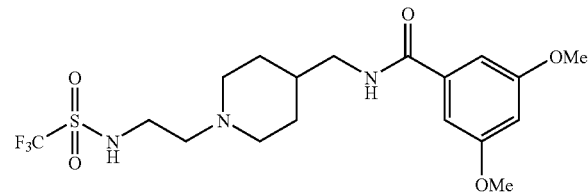 [SMILES: COc1cc(OC)cc(C(=O)NCC2CCN(CCNS(=O)(=O)C(F)(F)F)CC2)c1] | 454.15 |
| 124 | N-((1-(2-(cyclopropanesulfonamido)ethyl)piperidin-4-yl)methyl)-3-(trifluoromethyl)benzamide | 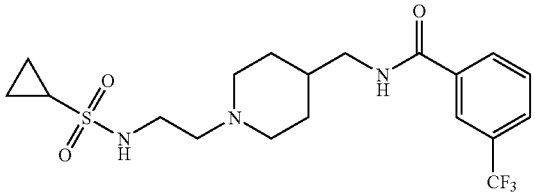 [SMILES: O=C(NCC1CCN(CCNS(=O)(=O)C2CC2)CC1)c1cccc(C(F)(F)F)c1] | 434.16 |
| 125 | 3-chloro-N-((1-(2-(cyclopropanesulfonamido)ethyl)piperidin-4-yl)methyl)-5-(trifluoromethyl)benzamide | 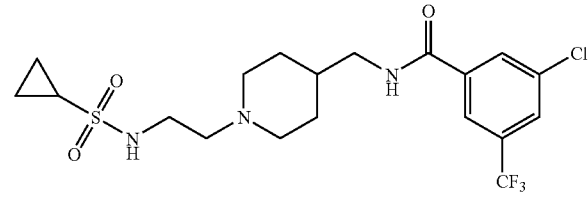 [SMILES: O=C(NCC1CCN(CCNS(=O)(=O)C2CC2)CC1)c1cc(Cl)cc(C(F)(F)F)c1] | 468.13 |

TABLE 1-continued

| Cmpd No. | Name | Structure | Mass Spec (m/z) |
|---|---|---|---|
| 126 | 3-bromo-N-((1-(2-(cyclopropanesulfonamido)ethyl)piperidin-4-yl)methyl)-5-(trifluoromethyl)benzamide | 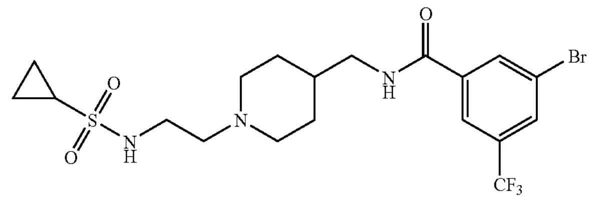 [SMILES: O=C(NCC1CCN(CCNS(=O)(=O)C2CC2)CC1)c1cc(Br)cc(C(F)(F)F)c1] | 512.08 |
| 127 | N-((1-(2-(cyclopropanesulfonamido)ethyl)piperidin-4-yl)methyl)-4-fluoro-3-(trifluoromethyl)benzamide | 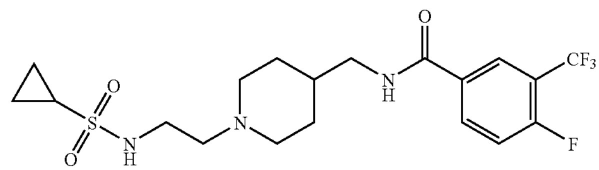 [SMILES: O=C(NCC1CCN(CCNS(=O)(=O)C2CC2)CC1)c1ccc(F)c(C(F)(F)F)c1] | 452.16 |
| 128 | N-((1-(2-(cyclopropanesulfonamido)ethyl)piperidin-4-yl)methyl)-3,5-dimethylbenzamide | 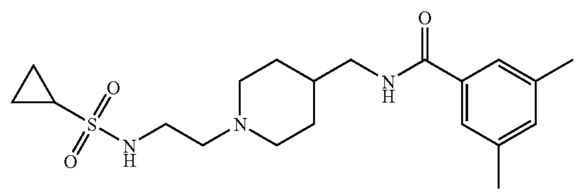 [SMILES: Cc1cc(C)cc(C(=O)NCC2CCN(CCNS(=O)(=O)C3CC3)CC2)c1] | 394.21 |
| 129 | N-((1-(2-(cyclopropanesulfonamido)ethyl)piperazin-4-yl)methyl)-3,5-dimethoxybenzamide | 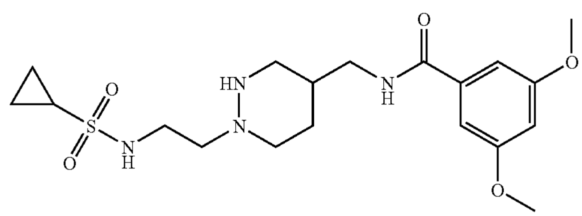 [SMILES: COc1cc(OC)cc(C(=O)NCC2CCN(CCNS(=O)(=O)C3CC3)NC2)c1] | 426.20 |
| 130 | 3,5-dichloro-N-((1-(2-(cyclopropanesulfonamido)ethyl)piperidin-4-yl)methyl)benzamide | 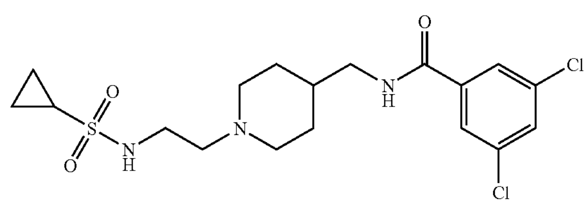 [SMILES: O=C(NCC1CCN(CCNS(=O)(=O)C2CC2)CC1)c1cc(Cl)cc(Cl)c1] | 434.10 |
| 131 | N-((1-(2-(cyclopropanesulfonamido)ethyl)piperidin-4-yl)methyl)-3-(trifluoromethoxy)benzamie | 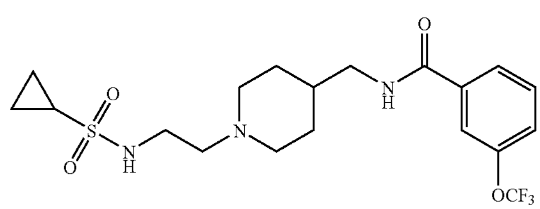 [SMILES: O=C(NCC1CCN(CCNS(=O)(=O)C2CC2)CC1)c1cccc(OC(F)(F)F)c1] | 450.16 |
| 132 | N-((1-(2-(cyclopropanesulfonamido)ethyl)piperidin-4-yl)methyl)-3-(methylsulfonyl)benzamide | 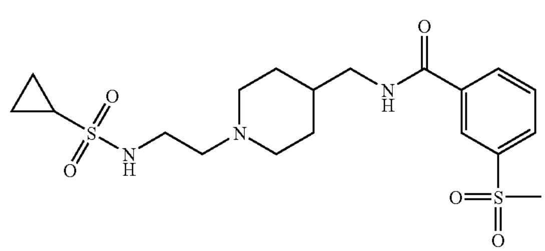 [SMILES: CS(=O)(=O)c1cccc(C(=O)NCC2CCN(CCNS(=O)(=O)C3CC3)CC2)c1] | 444.15 |

TABLE 1-continued

| Cmpd No. | Name | Structure | Mass Spec (m/z) |
|---|---|---|---|
| 133 | N-((1-(2-(cyclopropanesulfonamido)ethyl)piperidin-4-yl)methyl)-4-(methylsulfonyl)benzamide | 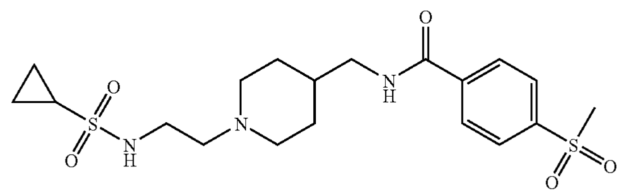 [SMILES: CS(=O)(=O)c1ccc(C(=O)NCC2CCN(CCNS(=O)(=O)C3CC3)CC2)cc1] | 444.15 |
| 134 | N-((1-(2-(cyclopropanesulfonamido)ethyl)piperidin-4-yl)methyl)-3,5-difluorobenzamide | 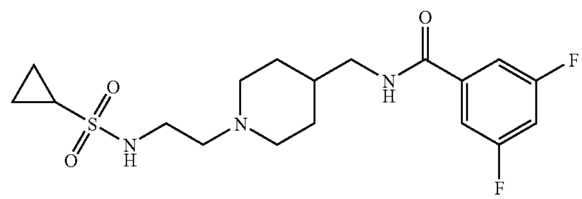 [SMILES: O=C(NCC1CCN(CCNS(=O)(=O)C2CC2)CC1)c1cc(F)cc(F)c1] | 402.16 |
| 135 | 3-chloro-N-((1-(2-(cyclopropanesulfonamido)ethyl)piperidin-4-yl)methyl)benzamide | 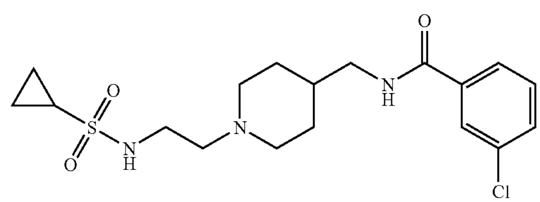 [SMILES: O=C(NCC1CCN(CCNS(=O)(=O)C2CC2)CC1)c1cccc(Cl)c1] | 400.14 |
| 136 | 3-tert-butoxy-N-((1-(2-(cyclopropanesulfonamido)ethyl)piperidin-4-yl)methyl)benzamide | 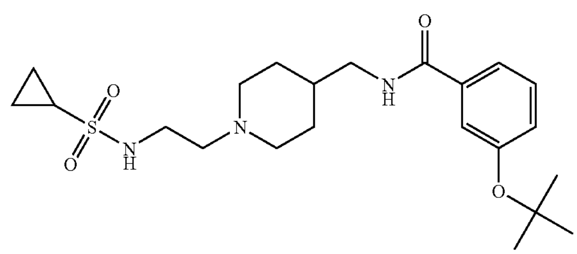 [SMILES: CC(C)(C)Oc1cccc(C(=O)NCC2CCN(CCNS(=O)(=O)C3CC3)CC2)c1] | 438.23 |
| 137 | 4-tert-butyl-N-((1-(2-(cyclopropanesulfonamido)ethyl)piperidin-4-yl)methyl)benzamide | 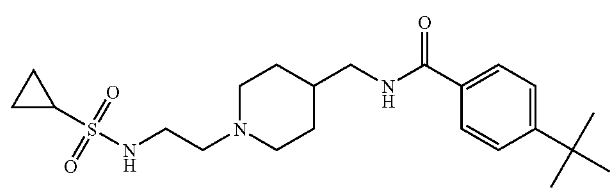 [SMILES: CC(C)(C)c1ccc(C(=O)NCC2CCN(CCNS(=O)(=O)C3CC3)CC2)cc1] | 422.24 |
| 138 | N-((1-(2-(cyclopropanesulfonamido)ethyl)piperidin-4-yl)methyl)-3-methoxy-5-(trifluoromethyl)benzamide | 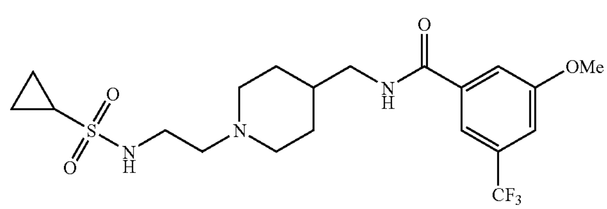 [SMILES: COc1cc(C(=O)NCC2CCN(CCNS(=O)(=O)C3CC3)CC2)cc(C(F)(F)F)c1] | 464.18 |
| 139 | N-((1-(2-(cyclopropanesulfonamido)ethyl)piperidin-4-yl)methyl)-4-(trifluoromethoxy)benzamide | 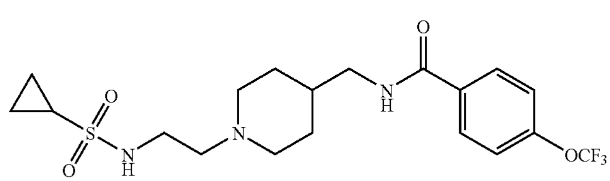 [SMILES: O=C(NCC1CCN(CCNS(=O)(=O)C2CC2)CC1)c1ccc(OC(F)(F)F)cc1] | 450.16 |

TABLE 1-continued

| Cmpd No. | Name | Structure | Mass Spec (m/z) |
|---|---|---|---|
| 140 | 3,5-dimethyl-N-((1-(2-(1-methylethylsulfonamido)ethyl)piperidin-4-yl)methyl)benzamide | 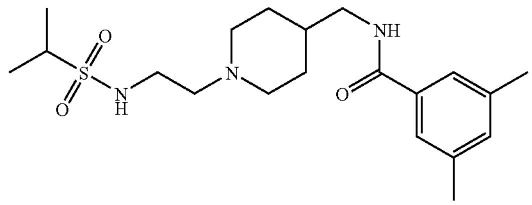 [SMILES: Cc1cc(C)cc(C(=O)NCC2CCN(CCNS(=O)(=O)C(C)C)CC2)c1] | 396.22 |
| 141 | 3-chloro-N-((1-(2-(1-methylethylsulfonamido)ethyl)piperidin-4-yl)methyl)benzamide | 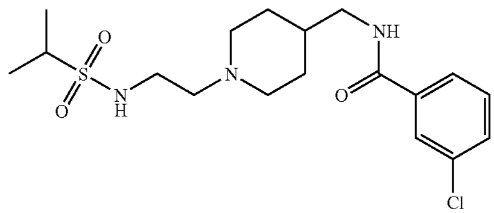 [SMILES: CC(C)S(=O)(=O)NCCN1CCC(CNC(=O)c2cccc(Cl)c2)CC1] | 402.15 |
| 142 | 3,5-difluoro-N-((1-(2-(1-methylethylsulfonamido)ethyl)piperidin-4-yl)methyl)benzamide | 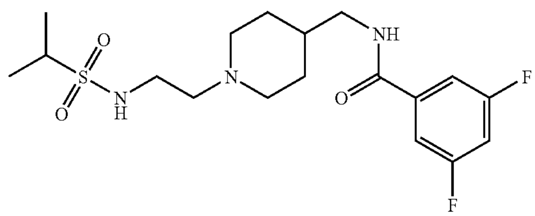 [SMILES: CC(C)S(=O)(=O)NCCN1CCC(CNC(=O)c2cc(F)cc(F)c2)CC1] | 404.17 |
| 143 | 4-tert-butyl-N-((1-(2-(1-methylethylsulfonamido)ethyl)piperidin-4-yl)methyl)benzamide | 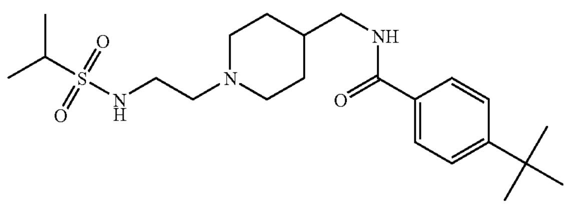 [SMILES: CC(C)S(=O)(=O)NCCN1CCC(CNC(=O)c2ccc(C(C)(C)C)cc2)CC1] | 424.26 |
| 144 | 3,5-dimethoxy-N-((1-(2-(1-methylethylsulfonamido)ethyl)piperidin-4-yl)methyl)benzamide | 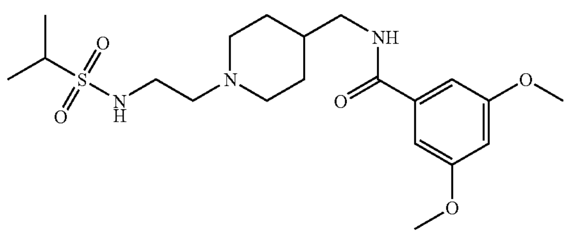 [SMILES: COc1cc(OC)cc(C(=O)NCC2CCN(CCNS(=O)(=O)C(C)C)CC2)c1] | 428.21 |
| 145 | 3,5-dichloro-N-((1-(2-(1-methylethylsulfonamido)ethyl)piperidin-4-yl)methyl)benzamide | 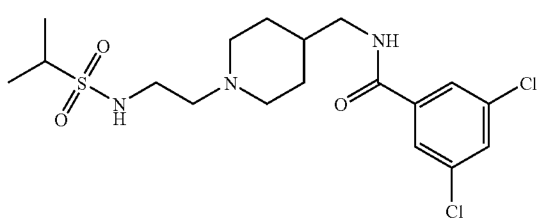 [SMILES: CC(C)S(=O)(=O)NCCN1CCC(CNC(=O)c2cc(Cl)cc(Cl)c2)CC1] | 436.11 |
| 146 | N-((1-(2-(1-methylethylsulfonamido)ethyl)piperidin-4-yl)methyl)-3-(trifluoromethyl)benzamide | 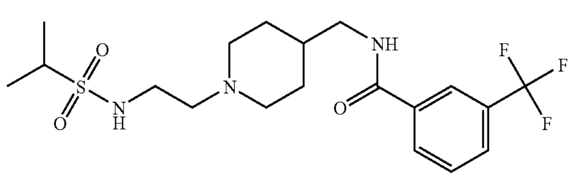 [SMILES: CC(C)S(=O)(=O)NCCN1CCC(CNC(=O)c2cccc(C(F)(F)F)c2)CC1] | 436.18 |

TABLE 1-continued

| Cmpd No. | Name | Structure | Mass Spec (m/z) |
|---|---|---|---|
| 147 | 3-tert-butoxy-N-((1-(2-(1-methylethylsulfonamido)ethyl)piperidin-4-yl)methyl)benzamide | 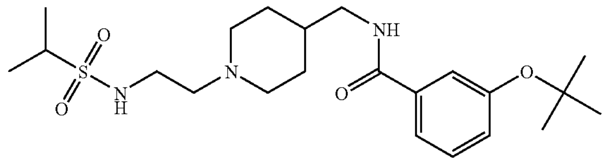 [SMILES: CC(C)S(=O)(=O)NCCN1CCC(CNC(=O)c2cccc(OC(C)(C)C)c2)CC1] | 440.25 |
| 148 | N-((1-(2-(1-methylethylsulfonamido)ethyl)piperidin-4-yl)methyl)-3-(trifluoromethoxy)benzamide | 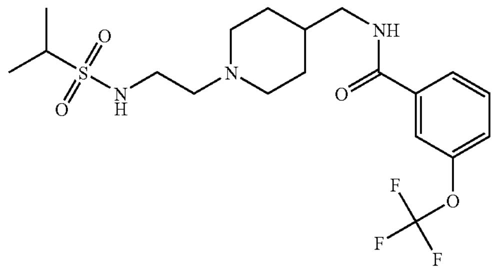 [SMILES: CC(C)S(=O)(=O)NCCN1CCC(CNC(=O)c2cccc(OC(F)(F)F)c2)CC1] | 452.18 |
| 149 | 3-methoxy-N-((1-(2-(1-methylethylsulfonamido)ethyl)piperidin-4-yl)methyl)-5-(trifluoromethyl)benzamide | 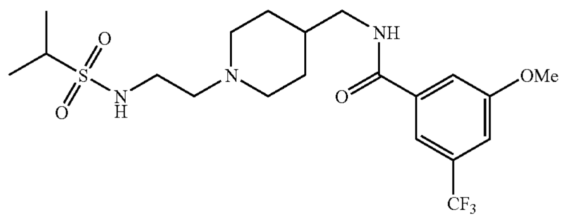 [SMILES: COc1cc(C(=O)NCC2CCN(CCNS(=O)(=O)C(C)C)CC2)cc(C(F)(F)F)c1] | 466.19 |
| 150 | 3-chloro-N-((1-(2-(1-methylethylsulfonamido)ethyl)piperidin-4-yl)methyl)-5-(trifluoromethyl)benzamide | 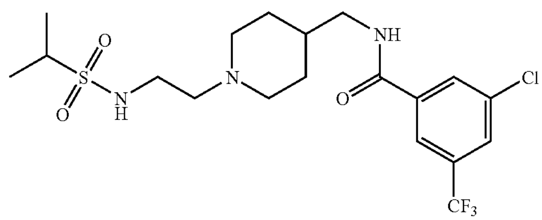 [SMILES: CC(C)S(=O)(=O)NCCN1CCC(CNC(=O)c2cc(Cl)cc(C(F)(F)F)c2)CC1] | 470.14 |
| 151 | 3-bromo-N-((1-(2-(1-methylethylsulfonamido)ethyl)piperidin-4-yl)methyl)-5-(trifluoromethyl)benzamide | 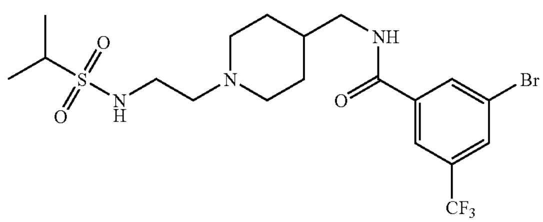 [SMILES: CC(C)S(=O)(=O)NCCN1CCC(CNC(=O)c2cc(Br)cc(C(F)(F)F)c2)CC1] | 514.09 |
| 152 | N-((1-(2-(1-methylethylsulfonamido)ethyl)piperidin-4-yl)methyl)-4-(trifluoromethoxy)benzamide | 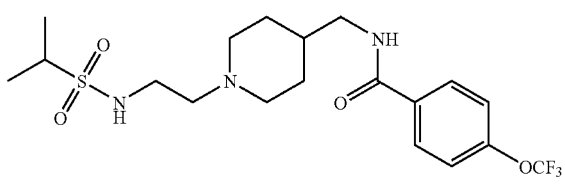 [SMILES: CC(C)S(=O)(=O)NCCN1CCC(CNC(=O)c2ccc(OC(F)(F)F)cc2)CC1] | 452.18 |
| 153 | N-(3,5-bis(trifluoromethyl)phenyl)-2-(1-(2-hydroxy-3,3-dimethylbutyl)piperidin-4-yl)acetamide | 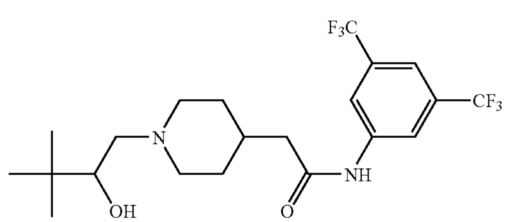 [SMILES: CC(C)(C)C(O)CN1CCC(CC(=O)Nc2cc(C(F)(F)F)cc(C(F)(F)F)c2)CC1] | 455.21 |

TABLE 1-continued

| Cmpd No. | Name | Structure | Mass Spec (m/z) |
|---|---|---|---|
| 154 | N-(3,5-bis(trifluoromethyl)phenyl)-2-(1-(2-hydroxy-2-methylpropanoyl)piperidin-4-yl)acetamide | 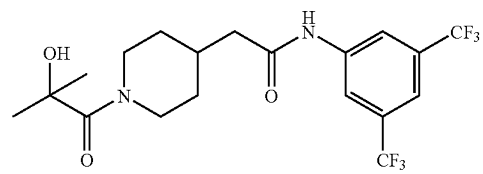 [SMILES: CC(C)(O)C(=O)N1CCC(CC(=O)Nc2cc(C(F)(F)F)cc(C(F)(F)F)c2)CC1] | 441.15 |
| 155 | (R)-N-(3,5-bis(trifluoromethyl)phenyl)-2-(1-(2-hydroxy-3,3-dimethylbutanoyl)piperidin-4-yl)acetamide | 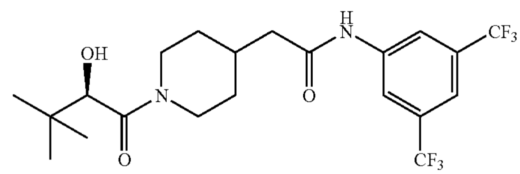 [SMILES: CC(C)(C)[C@@H](O)C(=O)N1CCC(CC(=O)Nc2cc(C(F)(F)F)cc(C(F)(F)F)c2)CC1] | 469.18 |
| 156 | N-(3,5-bis(trifluoromethyl)phenyl)-2-(1-((4-hydroxypiperidin-4-yl)methyl)piperidin-4-yl)acetamide | 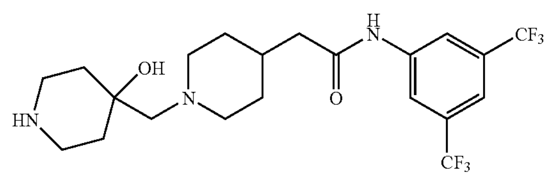 [SMILES: O=C(CC1CCN(CC2(O)CCNCC2)CC1)Nc1cc(C(F)(F)F)cc(C(F)(F)F)c1] | 468.20 |
| 157 | N-(3,5-bis(trifluoromethyl)phenyl)-2-(1-(4-hydroxypiperidine-4-carbonyl)piperidin-4-yl)acetamide | 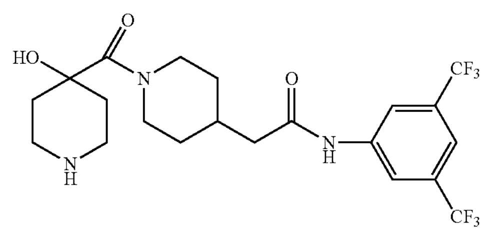 [SMILES: O=C(CC1CCN(C(=O)C2(O)CCNCC2)CC1)Nc1cc(C(F)(F)F)cc(C(F)(F)F)c1] | 482.18 |
| 158 | 2-(1-(2-amino-2-methylpropanoyl)piperidin-4-yl)-N-(3,5-bis(trifluoromethyl)phenyl)acetamide | 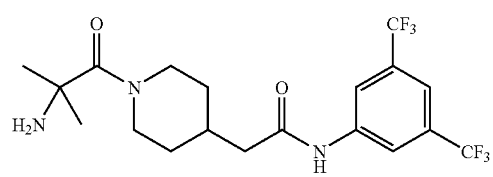 [SMILES: CC(C)(N)C(=O)N1CCC(CC(=O)Nc2cc(C(F)(F)F)cc(C(F)(F)F)c2)CC1] | 440.17 |
| 159 | 2-(1-((1-aminocyclopentyl)methyl)piperidin-4-yl)-N-(3,5-bis(trifluoromethyl)phenyl)acetamide | 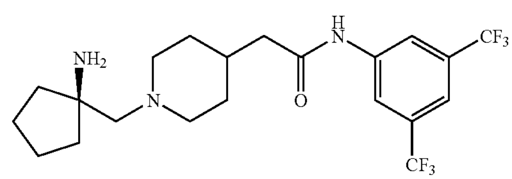 | 452.21 |
| 160 | N-(3,5-bis(trifluoromethyl)phenyl)-2-(1-((1-(methylsulfonamido)cyclopentyl)methyl)piperidin-4-yl)acetamide | 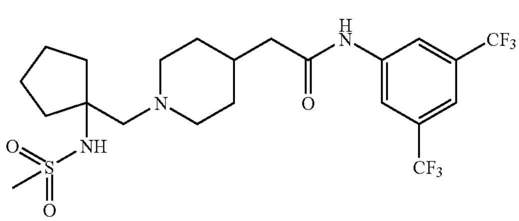 [SMILES: CS(=O)(=O)NC1(CN2CCC(CC(=O)Nc3cc(C(F)(F)F)cc(C(F)(F)F)c3)CC2)CCCC1] | 530.18 |

TABLE 1-continued

| Cmpd No. | Name | Structure | Mass Spec (m/z) |
|---|---|---|---|
| 161 | N-((1,5-dimethyl-1H-pyrazol-3-yl)methyl)-2-(1-(2-hydroxy-3,3-dimethylbutyl)piperidin-4-yl)acetamide | 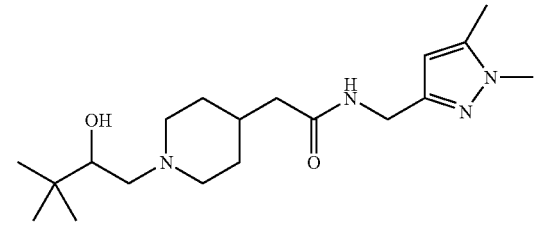 [SMILES: Cc1cc(CNC(=O)CC2CCN(CC(O)C(C)(C)C)CC2)nn1C] | 351.27 |
| 162 | 2-(1-(2-hydroxy-3,3-dimethylbutyl)piperidin-4-yl)-N-((1-methyl-1H-imidazol-4-yl)methyl)acetamide | 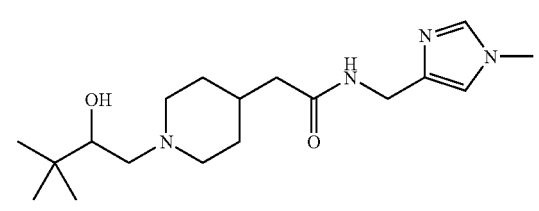 [SMILES: Cn1cnc(CNC(=O)CC2CCN(CC(O)C(C)(C)C)CC2)c1] | 337.25 |
| 163 | N-(5-fluoropyridin-3-yl)-2-(1-(2-hydroxy-3,3-dimethylbutyl)piperidin-4-yl)acetamide | 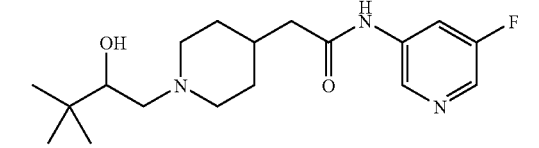 [SMILES: CC(C)(C)C(O)CN1CCC(CC(=O)Nc2cncc(F)c2)CC1] | 338.22 |
| 164 | 2-(1-(2-hydroxy-3,3-dimethylbutyl)piperidin-4-yl)-N-(4-(morpholinomethyl)benzyl)acetamide | 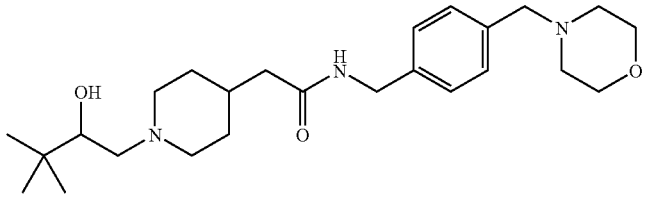 [SMILES: CC(C)(C)C(O)CN1CCC(CC(=O)NCc2ccc(CN3CCOCC3)cc2)CC1] | 432.31 |
| 165 | 2-(1-(2-hydroxy-3,3-dimethylbutyl)piperidin-4-yl)-N-((5-methylisoxazol-3-yl)methyl)acetamide | 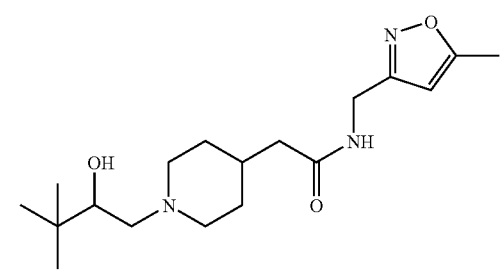 [SMILES: Cc1cc(CNC(=O)CC2CCN(CC(O)C(C)(C)C)CC2)no1] | 338.24 |
| 166 | N-(1H-benzo[d]imidazol-2-yl)-2-(1-(2-hydroxy-3,3-dimethylbutyl)piperidin-4-yl)acetamide | 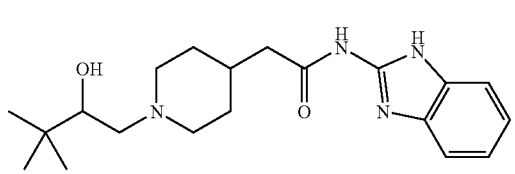 [SMILES: CC(C)(C)C(O)CN1CCC(CC(=O)Nc2nc3ccccc3[nH]2)CC1] | 359.24 |
| 167 | 2-(1-(2-hydroxy-3,3-dimethylbutyl)piperidin-4-yl)-N-(thiazol-2-ylmethyl)acetamide | 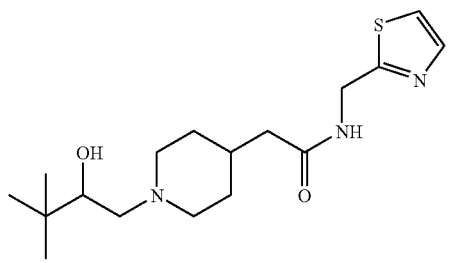 [SMILES: CC(C)(C)C(O)CN1CCC(CC(=O)NCc2nccs2)CC1] | 340.20 |

TABLE 1-continued

| Cmpd No. | Name | Structure | Mass Spec (m/z) |
|---|---|---|---|
| 168 | 2-(1-(2-hydroxy-3,3-dimethylbutyl)piperidin-4-yl)-N-(4-(trifluoromethyl)pyridin-2-yl)acetamide | 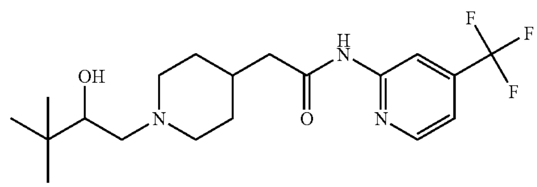 [SMILES: CC(C)(C)C(O)CN1CCC(CC(=O)Nc2cc(C(F)(F)F)ccn2)CC1] | 388.21 |
| 169 | N-(3-fluoro-5-(trifluoromethyl)phenyl)-2-(1-(2-hydroxy-3,3-dimethylbutyl)piperidin-4-yl)acetamide | 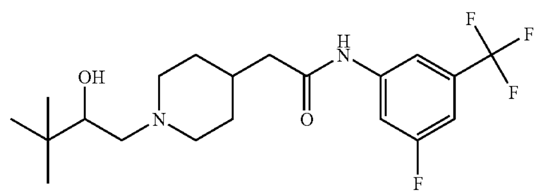 [SMILES: CC(C)(C)C(O)CN1CCC(CC(=O)Nc2cc(F)cc(C(F)(F)F)c2)CC1] | 405.21 |
| 170 | 2-(1-(2-hydroxy-3,3-dimethylbutyl)piperidin-4-yl)-N-(2-hydroxypyridin-3-yl)acetamide | 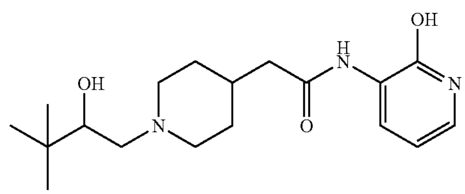 [SMILES: CC(C)(C)C(O)CN1CCC(CC(=O)Nc2cccnc2O)CC1] | 336.22 |
| 171 | 2-(1-(2-hydroxy-3,3-dimethylbutyl)piperidin-4-yl)-N-(4-(pyridin-2-yloxy)benzyl)acetamide | 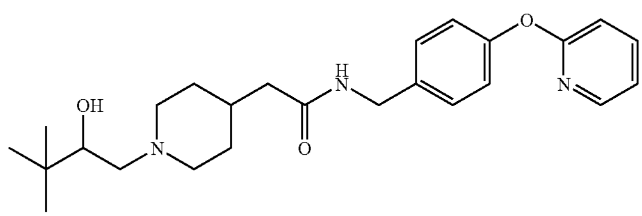 [SMILES: CC(C)(C)C(O)CN1CCC(CC(=O)NCc2ccc(Oc3ccccn3)cc2)CC1] | 426.27 |
| 172 | 2-(1-(2-hydroxy-3,3-dimethylbutyl)piperidin-4-yl)-N-(4-p-tolylthiazol-2-yl)acetamide | 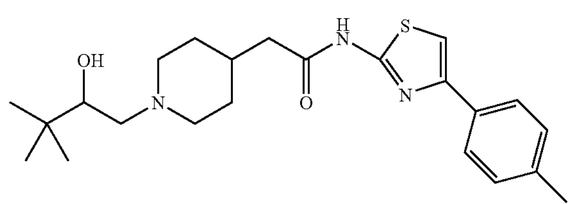 [SMILES: Cc1ccc(-c2csc(NC(=O)CC3CCN(CC(O)C(C)(C)C)CC3)n2)cc1] | 416.23 |
| 173 | N-(benzo[d]thiazol-2-yl)-2-(1-(2-hydroxy-3,3-dimethylbutyl)piperidin-4-yl)acetamide | 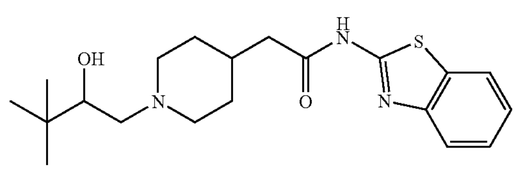 [SMILES: CC(C)(C)C(O)CN1CCC(CC(=O)Nc2nc3ccccc3s2)CC1] | 376.20 |
| 174 | 2-(1-(2-hydroxy-3,3-dimethylbutyl)piperidin-4-yl)-N-(4-phenoxybenzyl)acetamide | 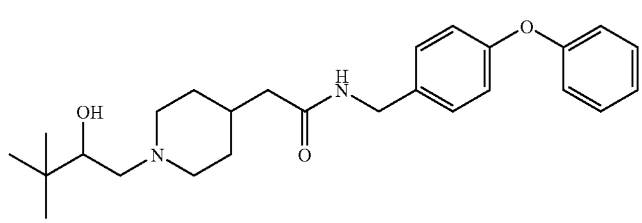 [SMILES: CC(C)(C)C(O)CN1CCC(CC(=O)NCc2ccc(Oc3ccccc3)cc2)CC1] | 425.27 |

TABLE 1-continued

| Cmpd No. | Name | Structure | Mass Spec (m/z) |
|---|---|---|---|
| 175 | N-(3-(difluoromethoxy)benzyl)-2-(1-(2-hydroxy-3,3-dimethylbutyl)piperidin-4-yl)acetamide | 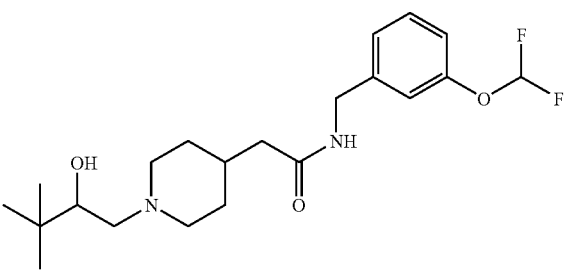 [SMILES: CC(C)(C)C(O)CN1CCC(CC(=O)NCc2cccc(OC(F)F)c2)CC1] | 399.24 |
| 176 | N-((2,3-dihydrobenzofuran-5-yl)methyl)-2-(1-(2-hydroxy-3,3-dimethylbutyl)piperidin-4-yl)acetamide | 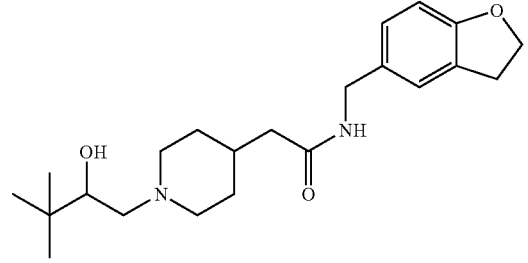 [SMILES: CC(C)(C)C(O)CN1CCC(CC(=O)NCc2ccc3c(c2)CCO3)CC1] | 375.26 |
| 177 | N-(4-fluorophenethyl)-2-(1-(2-hydroxy-3,3-dimethylbutyl)piperidin-4-yl)acetamide | 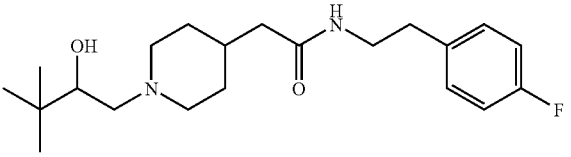 [SMILES: CC(C)(C)C(O)CN1CCC(CC(=O)NCCc2ccc(F)cc2)CC1] | 365.25 |
| 178 | N-(3,5-bis(trifluoromethyl)phenyl)-2-(1-(3,3,3-trifluoro-2-hydroxypropyl)piperidin-4-yl)acetamide | 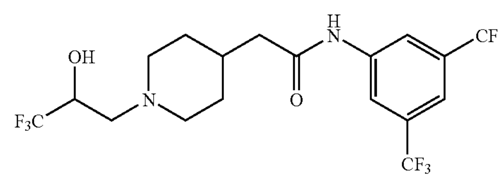 | 467.13 |
| 179 | N-(3,5-bis(trifluoromethyl)phenyl)-2-(1-((1-(cyclopropanesulfonamido)cyclopentyl)methyl)piperidin-4-yl)acetamide | 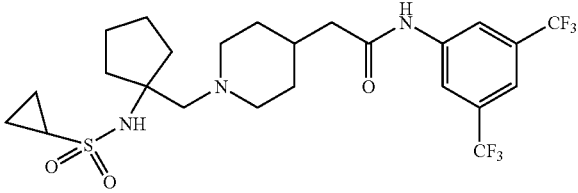 [SMILES: O=C(CC1CCN(CC2(NS(=O)(=O)C3CC3)CCCC2)CC1)Nc1cc(C(F)(F)F)cc(C(F)(F)F)c1] | 556.20 |
| 180 | (2S,4R)-tert-butyl 2-(4-(2-(3,5-bis(trifluoromethyl)phenylamino)-2-oxoethyl)piperidine-1-carbonyl)-4-hydroxypyrrolidine-1-carboxylate | 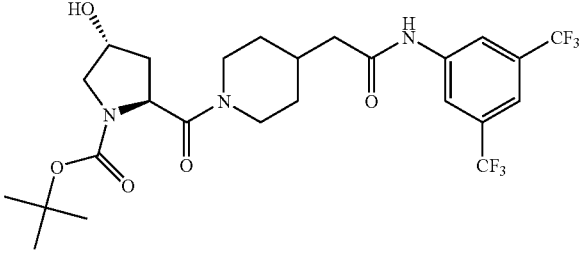 [SMILES: CC(C)(C)OC(=O)N1C[C@H](O)C[C@H]1C(=O)N1CCC(CC(=O)Nc2cc(C(F)(F)F)cc(C(F)(F)F)c2)CC1] | 568.22 |

TABLE 1-continued

| Cmpd No. | Name | Structure | Mass Spec (m/z) |
|---|---|---|---|
| 181 | tert-butyl 1-(4-(2-(3,5-bis(trifluoromethyl)phenylamino)-2-oxoethyl)piperidine-1-carbonyl)cyclohexylcarbamate | 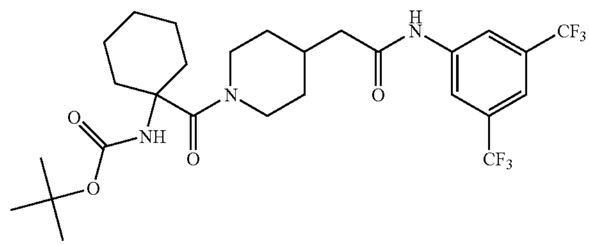 [SMILES: CC(C)(C)OC(=O)NC1(C(=O)N2CCC(CC(=O)Nc3cc(C(F)(F)F)cc(C(F)(F)F)c3)CC2)CCCCC1] | 580.25 |
| 182 | tert-butyl 1-(4-(2-(3,5-bis(trifluoromethyl)phenylamino)-2-oxoethyl)piperidine-1-carbonyl)cyclopropylcarbamate | 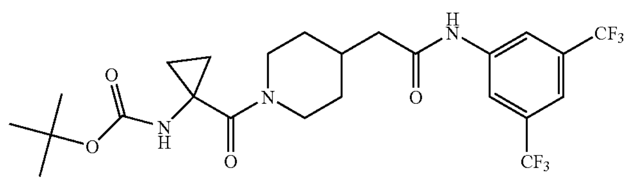 [SMILES: CC(C)(C)OC(=O)NC1(C(=O)N2CCC(CC(=O)Nc3cc(C(F)(F)F)cc(C(F)(F)F)c3)CC2)CC1] | 538.21 |
| 183 | (R)-tert-butyl 2-(4-(2-(3,5-bis(trifluoromethyl)phenylamino)-2-oxoethyl)piperidine-1-carbonyl)pyrrolidine-1-carboxylate | 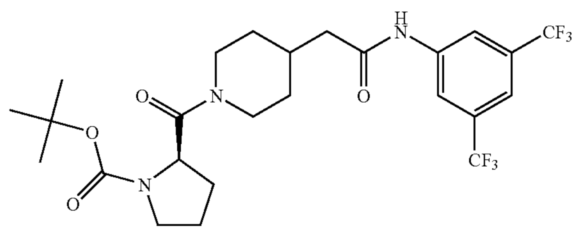 [SMILES: CC(C)(C)OC(=O)N1CCC[C@@H]1C(=O)N1CCC(CC(=O)Nc2cc(C(F)(F)F)cc(C(F)(F)F)c2)CC1] | 552.22 |
| 184 | (S)-tert-butyl 2-(4-(2-(3,5-bis(trifluoromethyl)phenylamino)-2-oxoethyl)piperidine-1-carbonyl)pyrrolidine-1-carboxylate | 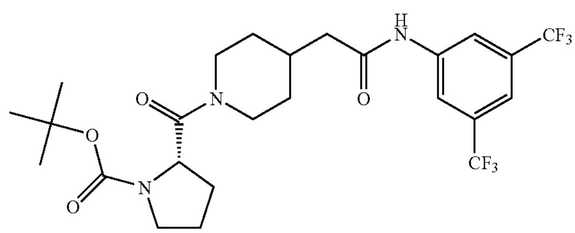 [SMILES: CC(C)(C)OC(=O)N1CCC[C@H]1C(=O)N1CCC(CC(=O)Nc2cc(C(F)(F)F)cc(C(F)(F)F)c2)CC1] | 552.22 |
| 185 | tert-butyl 1-(4-(2-(3,5-bis(trifluoromethyl)phenylamino)-2-oxoethyl)piperidin-1-yl)-2-methyl-1-oxopropan-2-yl(methyl)carbamate | 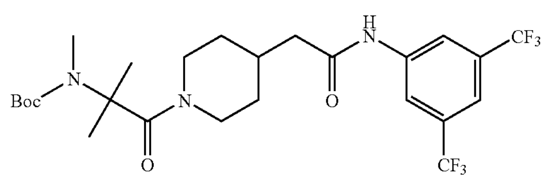 [SMILES: CN(C(=O)OC(C)(C)C)C(C)(C)C(=O)N1CCC(CC(=O)Nc2cc(C(F)(F)F)cc(C(F)(F)F)c2)CC1] | 554.24 |
| 186 | tert-butyl 4-(4-(2-(3,5-bis(trifluoromethyl)phenylamino)-2-oxoethyl)piperidine-1-carbonyl)tetrahydro-2H-pyran-4-ylcarbamate | 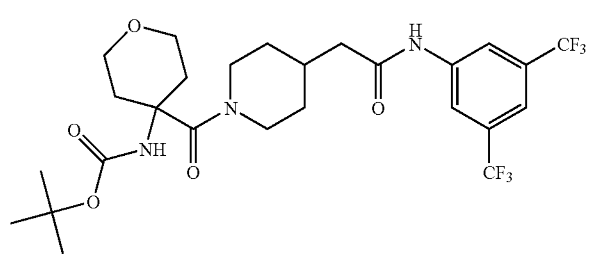 [SMILES: CC(C)(C)OC(=O)NC1(C(=O)N2CCC(CC(=O)Nc3cc(C(F)(F)F)cc(C(F)(F)F)c3)CC2)CCOCC1] | 582.23 |

TABLE 1-continued

| Cmpd No. | Name | Structure | Mass Spec (m/z) |
|---|---|---|---|
| 187 | tert-butyl 2-(4-(2-(3,5-bis(trifluoromethyl)phenylamino)-2-oxoethyl)piperidine-1-carbonyl)piperidine-1-carboxylate | 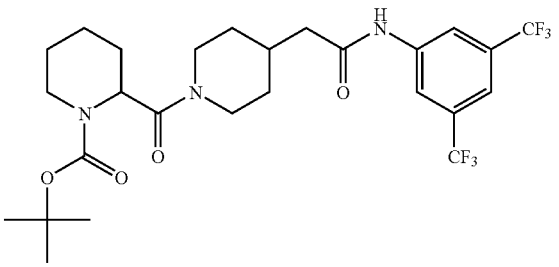 [SMILES: CC(C)(C)OC(=O)N1CCCCC1C(=O)N1CCC(CC(=O)Nc2cc(C(F)(F)F)cc(C(F)(F)F)c2)CC1] | 566.24 |
| 188 | N-(3,5-bis(trifluoromethyl)phenyl)-2-(1-((2S,4R)-4-hydroxypyrrolidine-2-carbonyl)piperidin-4-yl)acetamide | 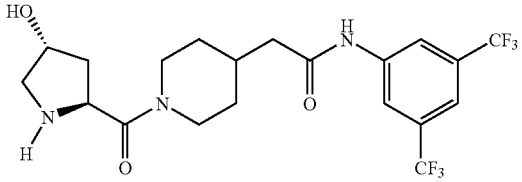 [SMILES: O=C(CC1CCN(C(=O)[C@@H]2C[C@@H](O)CN2)CC1)Nc1cc(C(F)(F)F)cc(C(F)(F)F)c1] | 468.16 |
| 189 | 2-(1-(1-aminocyclohexanecarbonyl)piperidin-4-yl)-N-(3,5-bis(trifluoromethyl)phenyl)acetamide | 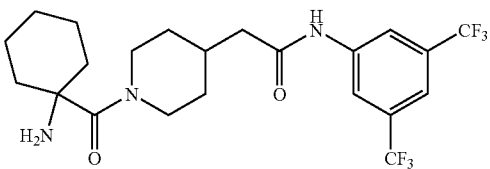 [SMILES: NC1(C(=O)N2CCC(CC(=O)Nc3cc(C(F)(F)F)cc(C(F)(F)F)c3)CC2)CCCCC1] | 480.20 |
| 190 | 2-(1-(1-aminocyclopropanecarbonyl)piperidin-4-yl)-N-(3,5-bis(trifluoromethyl)phenyl)acetamide | 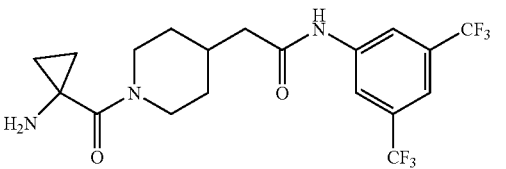 [SMILES: NC1(C(=O)N2CCC(CC(=O)Nc3cc(C(F)(F)F)cc(C(F)(F)F)c3)CC2)CC1] | 438.15 |
| 191 | (R)-N-(3,5-bis(trifluoromethyl)phenyl)-2-(1-(pyrrolidine-2-carbonyl)piperidin-4-yl)acetamide | 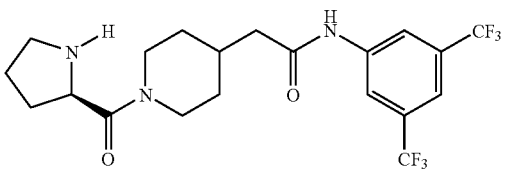 [SMILES: O=C(CC1CCN(C(=O)[C@H]2CCCN2)CC1)Nc1cc(C(F)(F)F)cc(C(F)(F)F)c1] | 452.17 |
| 192 | (S)-N-(3,5-bis(trifluoromethyl)phenyl)-2-(1-(pyrrolidine-2-carbonyl)piperidin-4-yl)acetamide | 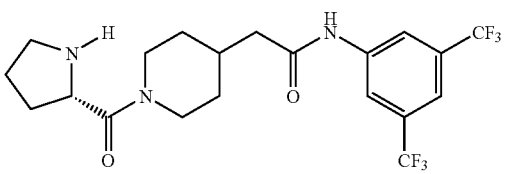 [SMILES: O=C(CC1CCN(C(=O)[C@@H]2CCCN2)CC1)Nc1cc(C(F)(F)F)cc(C(F)(F)F)c1] | 452.17 |
| 193 | N-(3,5-bis(trifluoromethyl)phenyl)-2-(1-(2-methyl-2-(methylamino)propanoyl)piperidin-4-yl)acetamide | 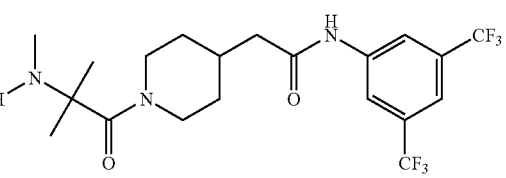 | 454.19 |
| 194 | 2-(1-(4-aminotetrahydro-2H-pyran-4-carbonyl)piperidin-4-yl)-N-(3,5-bis(trifluoromethyl)phenyl)acetamide | 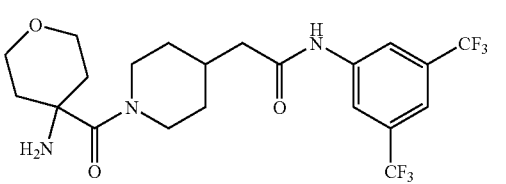 [SMILES: NC1(C(=O)N2CCC(CC(=O)Nc3cc(C(F)(F)F)cc(C(F)(F)F)c3)CC2)CCOCC1] | 482.18 |

TABLE 1-continued

| Cmpd No. | Name | Structure | Mass Spec (m/z) |
|---|---|---|---|
| 195 | (S)-N-(3,5-bis(trifluoromethyl)phenyl)-2-(1-(piperidine-2-carbonyl)piperidin-4-yl)acetamide | 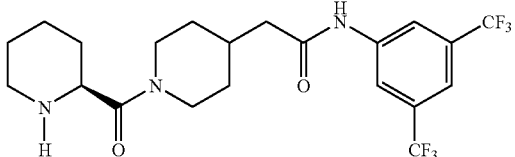 | 466.19 |
| 196 | tert-butyl 1-(4-(2-(2-(5-fluoro-1H-indol-3-yl)ethylamino)-2-oxoethyl)piperidin-1-yl)-3,3-dimethylbutan-2-ylcarbamate | 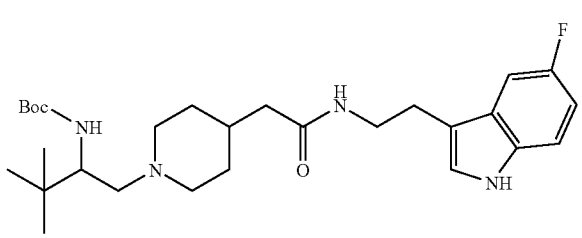 [SMILES: CC(C)(C)OC(=O)NC(CN1CCC(CC(=O)NCCc2c[nH]c3ccc(F)cc23)CC1)C(C)(C)C] | 503.33 |
| 197 | tert-butyl 1-(4-(2-(2-(1H-indol-3-yl)ethylamino)-2-oxoethyl)piperidin-1-yl)-3,3-dimethylbutan-2-ylcarbamate | 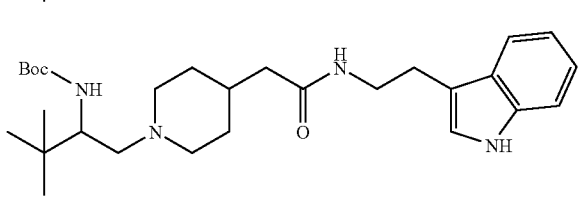 | 485.34 |
| 198 | tert-butyl 1-(4-(2-(3,5-dichlorobenzyl-amino)-2-oxoethyl)piperidin-1-yl)-3,3-dimethylbutan-2-ylcarbamate | 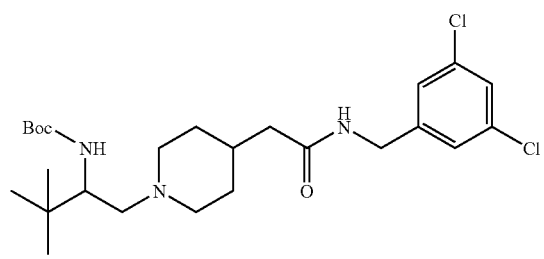 [SMILES: CC(C)(C)OC(=O)NC(CN1CCC(CC(=O)NCc2cc(Cl)cc(Cl)c2)CC1)C(C)(C)C] | 500.24 |
| 199 | 2-(1-(2-amino-3,3-dimethylbutyl)piperidin-4-yl)-N-(2-(5-fluoro-1H-indol-3-yl)ethyl)acetamide | 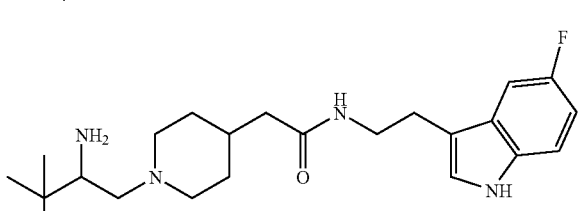 | 403.28 |
| 200 | N-(2-(1H-indol-3-yl)ethyl)-2-(1-(2-amino-3,3-dimethylbutyl)piperidin-4-yl)acetamide | 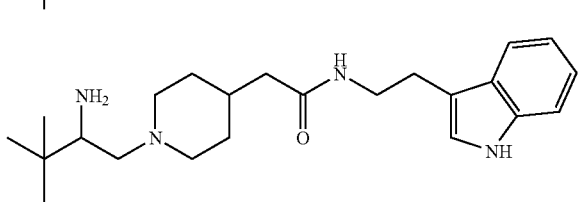 | 385.29 |
| 201 | 2-(1-(2-amino-3,3-dimethylbutyl)piperidin-4-yl)-N-(3,5-dichlorobenzyl)acetamide | 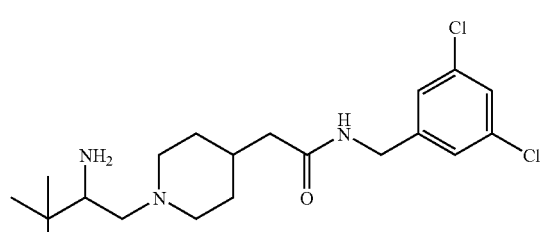 | 400.18 |

TABLE 1-continued

| Cmpd No. | Name | Structure | Mass Spec (m/z) |
|---|---|---|---|
| 202 | 2-(1-(3,3-dimethyl-2-(methylsulfonamido)butyl)piperidin-4-yl)-N-(2-(5-fluoro-1H-indol-3-yl)ethyl)acetamide | 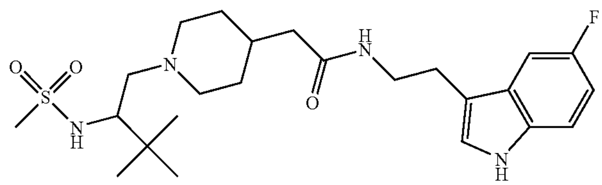 [SMILES: CC(C)(C)C(CN1CCC(CC(=O)NCCc2c[nH]c3ccc(F)cc23)CC1)NS(C)(=O)=O] | 481.26 |
| 203 | 2-(1-(2-(ethylsulfonamido)-3,3-dimethylbutyl)piperidin-4-yl)-N-(2-(5-fluoro-1H-indol-3-yl)ethyl)acetamide | 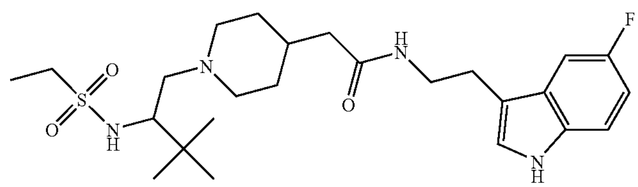 [SMILES: CCS(=O)(=O)NC(CN1CCC(CC(=O)NCCc2c[nH]c3ccc(F)cc23)CC1)C(C)(C)C] | 495.27 |
| 204 | 2-(1-(2-(cyclopropanesulfonamido)-3,3-dimethylbutyl)piperidin-4-yl)-N-(2-(5-fluoro-1H-indol-3-yl)ethyl)acetamide | 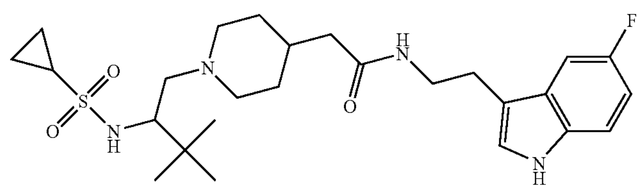 [SMILES: CC(C)(C)C(CN1CCC(CC(=O)NCCc2c[nH]c3ccc(F)cc23)CC1)NS(=O)(=O)C1CC1] | 507.27 |
| 205 | 2-(1-(3,3-dimethyl-2-(trifluoromethylsulfonamido)butyl)piperidin-4-yl)-N-(2-(5-fluoro-1H-indol-3-yl)ethyl)acetamide | 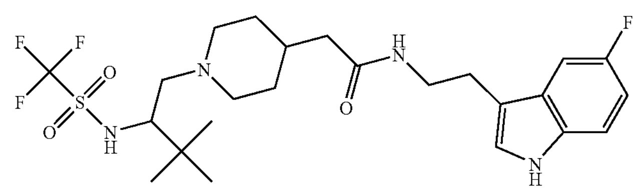 [SMILES: CC(C)(C)C(CN1CCC(CC(=O)NCCc2c[nH]c3ccc(F)cc23)CC1)NS(=O)(=O)C(F)(F)F] | 535.23 |
| 206 | 2-(1-(3,3-dimethyl-2-(1-methylethylsulfonamido)butyl)piperidin-4-yl)-N-(2-(5-fluoro-1H-indol-3-yl)ethyl)acetamide | 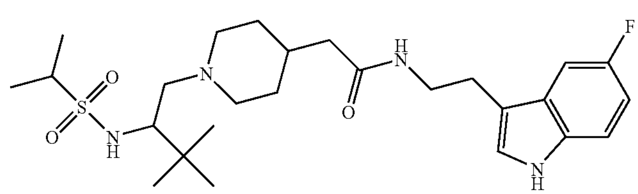 [SMILES: CC(C)S(=O)(=O)NC(CN1CCC(CC(=O)NCCc2c[nH]c3ccc(F)cc23)CC1)C(C)(C)C] | 509.29 |
| 207 | N-(3,5-dichlorobenzyl)-2-(1-(3,3-dimethyl-2-(methylsulfonamido)butyl)piperidin-4-yl)acetamide | 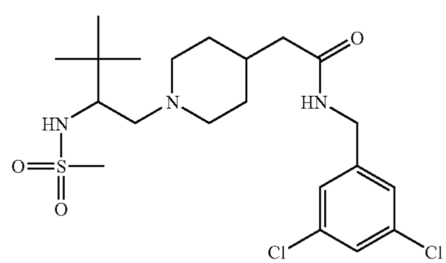 [SMILES: CC(C)(C)C(CN1CCC(CC(=O)NCc2cc(Cl)cc(Cl)c2)CC1)NS(C)(=O)=O] | 478.16 |
| 208 | N-(3,5-dichlorobenzyl)-2-(1-(2-(ethylsulfonamido)-3,3-dimethylbutyl)piperidin-4-yl)acetamide | 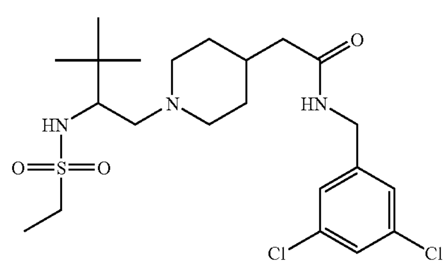 [SMILES: CCS(=O)(=O)NC(CN1CCC(CC(=O)NCc2cc(Cl)cc(Cl)c2)CC1)C(C)(C)C] | 492.18 |

TABLE 1-continued

| Cmpd No. | Name | Structure | Mass Spec (m/z) |
|---|---|---|---|
| 209 | 2-(1-(2-(cyclopropanesulfonamido)-3,3-dimethylbutyl)piperidin-4-yl)-N-(3,5-dichlorobenzyl)acetamide | 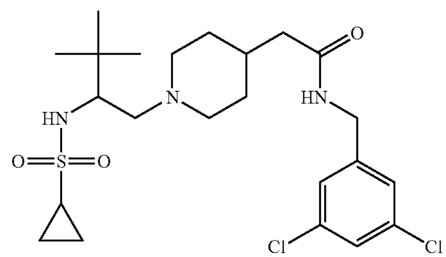 [SMILES: CC(C)(C)C(CN1CCC(CC(=O)NCc2cc(Cl)cc(Cl)c2)CC1)NS(=O)(=O)C1CC1] | 504.18 |
| 210 | N-(3,5-dichlorobenzyl)-2-(1-(3,3-dimethyl-2-(trifluoromethylsulfonamido)butyl)piperidin-4-yl)acetamide | 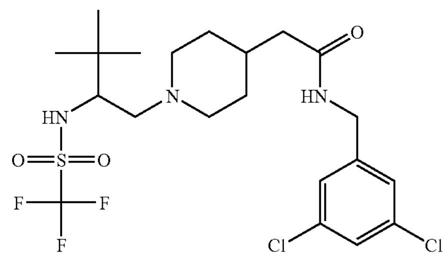 [SMILES: CC(C)(C)C(CN1CCC(CC(=O)NCc2cc(Cl)cc(Cl)c2)CC1)NS(=O)(=O)C(F)(F)F] | 532.13 |
| 211 | N-(3,5-dichlorobenzyl)-2-(1-(3,3-dimethyl-2-(1-methylethylsulfonamido)butyl)piperidin-4-yl)acetamide | 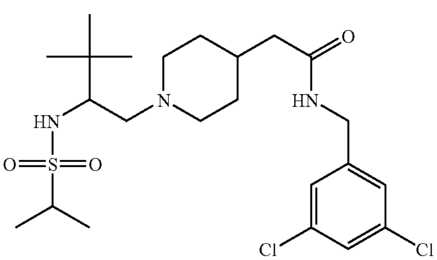 [SMILES: CC(C)S(=O)(=O)NC(CN1CCC(CC(=O)NCc2cc(Cl)cc(Cl)c2)CC1)C(C)(C)C] | 506.19 |
| 212 | N-(2-(1H-indol-3-yl)ethyl)-2-(1-(2-(cyclopropanesulfonamido)-3,3-dimethylbutyl)piperidin-4-yl)acetamide | 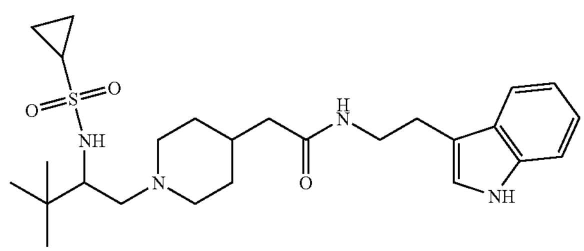 [SMILES: CC(C)(C)C(CN1CCC(CC(=O)NCCc2c[nH]c3ccccc23)CC1)NS(=O)(=O)C1CC1] | 489.28 |
| 213 | N-(2-(1H-indol-3-yl)ethyl)-2-(1-(3,3-dimethyl-2-(methylsulfonamido)butyl)piperidin-4-yl)acetamide | 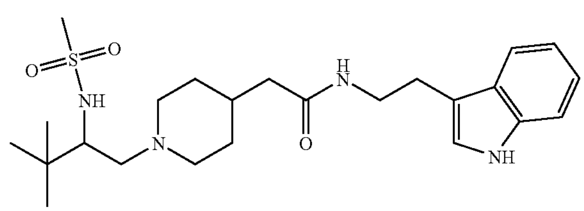 [SMILES: CC(C)(C)C(CN1CCC(CC(=O)NCCc2c[nH]c3ccccc23)CC1)NS(C)(=O)=O] | 463.27 |
| 214 | N-(2-(1H-indol-3-yl)ethyl)-2-(1-(3,3-dimethyl-2-(trifluoromethylsulfonamido)butyl)piperidin-4-yl)acetamide | 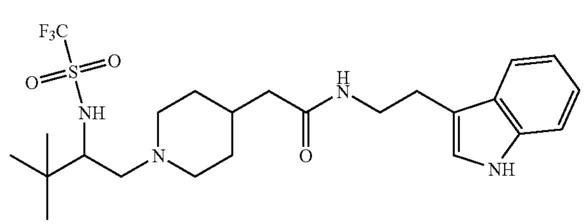 [SMILES: CC(C)(C)C(CN1CCC(CC(=O)NCCc2c[nH]c3ccccc23)CC1)NS(=O)(=O)C(F)(F)F] | 517.24 |

TABLE 1-continued

| Cmpd No. | Name | Structure | Mass Spec (m/z) |
|---|---|---|---|
| 215 | N-(2-(1H-indol-3-yl)ethyl)-2-(1-(3,3-dimethyl-2-(1-methylethylsulfonamido)butyl)piperidin-4-yl)acetamide | 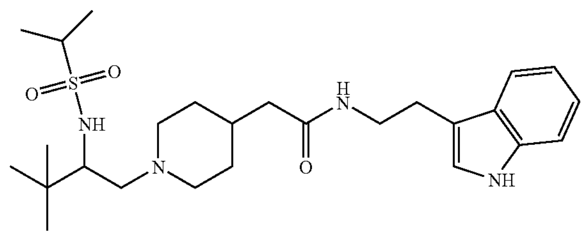 [SMILES: CC(C)S(=O)(=O)NC(CN1CCC(CC(=O)NCCc2c[nH]c3ccccc23)CC1)C(C)(C)C] | 491.30 |
| 216 | tert-butyl 1-(4-(2-(bis(3-fluorophenyl)methylamino)-2-oxoethyl)piperidin-1-yl)-3,3-dimethylbutan-2-ylcarbamate | 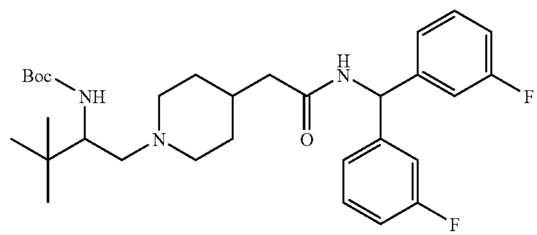 [SMILES: CC(C)(C)OC(=O)NC(CN1CCC(CC(=O)NC(c2cccc(F)c2)c2cccc(F)c2)CC1)C(C)(C)C] | 544.33 |
| 217 | 2-(1-(2-amino-3,3-dimethylbutyl)piperidin-4-yl)-N-(bis(3-fluorophenyl)methyl)acetamide | 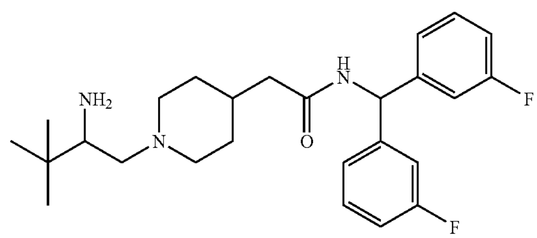 [SMILES: CC(C)(C)C(N)CN1CCC(CC(=O)NC(c2cccc(F)c2)c2cccc(F)c2)CC1] | 444.27 |
| 218 | 2-(1-(1-aminocyclopentanecarbonyl)piperidin-4-yl)-N-(3,5-bis(trifluoromethyl)phenyl)acetamide | 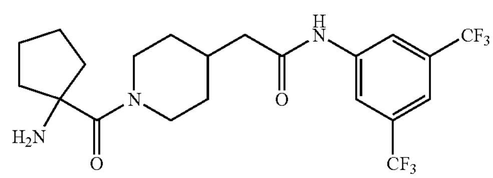 [SMILES: NC1(C(=O)N2CCC(CC(=O)Nc3cc(C(F)(F)F)cc(C(F)(F)F)c3)CC2)CCCC1] | 466.19 |
| 219 | N-(bis(3-fluorophenyl)methyl)-2-(1-(3,3-dimethyl-2-(methylsulfonamido)butyl)piperidin-4-yl)acetamide | 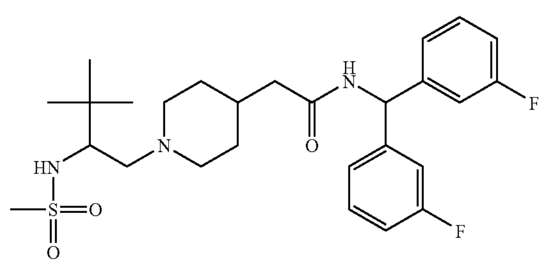 [SMILES: CC(C)(C)C(CN1CCC(CC(=O)NC(c2cccc(F)c2)c2cccc(F)c2)CC1)NS(C)(=O)=O] | 522.25 |
| 220 | N-(bis(3-fluorophenyl)methyl)-2-(1-(2-(ethylsulfonamido)-3,3-dimethylbutyl)piperidin-4-yl)acetamide | 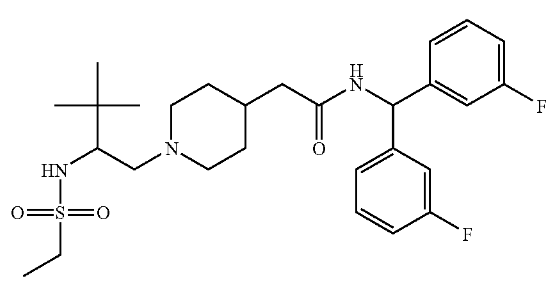 [SMILES: CCS(=O)(=O)NC(CN1CCC(CC(=O)NC(c2cccc(F)c2)c2cccc(F)c2)CC1)C(C)(C)C] | 536.27 |

TABLE 1-continued

| Cmpd No. | Name | Structure | Mass Spec (m/z) |
|---|---|---|---|
| 221 | N-(bis(3-fluorophenyl)methyl)-2-(1-(2-(cyclopropanesulfonamido)-3,3-dimethylbutyl)piperidin-4-yl)acetamide | 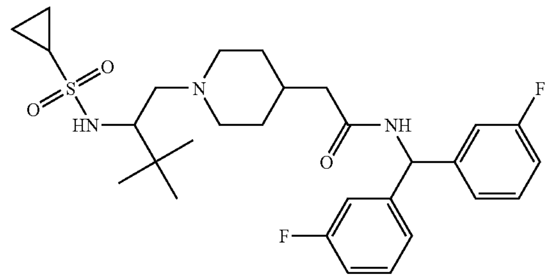 [SMILES: CC(C)(C)C(CN1CCC(CC(=O)NC(c2cccc(F)c2)c2cccc(F)c2)CC1)NS(=O)(=O)C1CC1] | 548.27 |
| 222 | N-(bis(3-fluorophenyl)methyl)-2-(1-(3,3-dimethyl-2-(1-methylethylsulfonamido)butyl)piperidin-4-yl)acetamide | 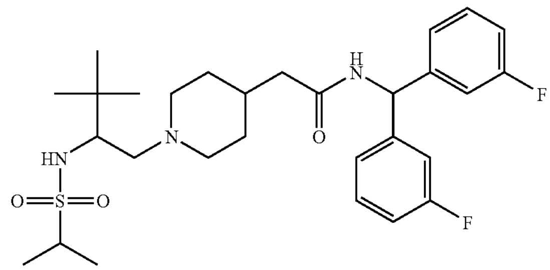 [SMILES: CC(C)S(=O)(=O)NC(CN1CCC(CC(=O)NC(c2cccc(F)c2)c2cccc(F)c2)CC1)C(C)(C)C] | 550.28 |
| 223 | methyl 1-(4-(2-(3,5-dichlorobenzylamino)-2-oxoethyl)piperidin-1-yl)-3,3-dimethylbutan-2-ylcarbamate | 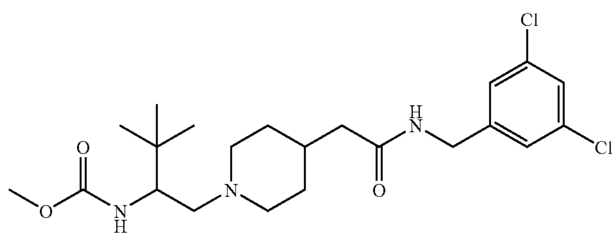 [SMILES: COC(=O)NC(CN1CCC(CC(=O)NCc2cc(Cl)cc(Cl)c2)CC1)C(C)(C)C] | 458.19 |
| 224 | ethyl 1-(4-(2-(3,5-dichlorobenzylamino)-2-oxoethyl)piperidin-1-yl)-3,3-dimethylbutan-2-ylcarbamate | 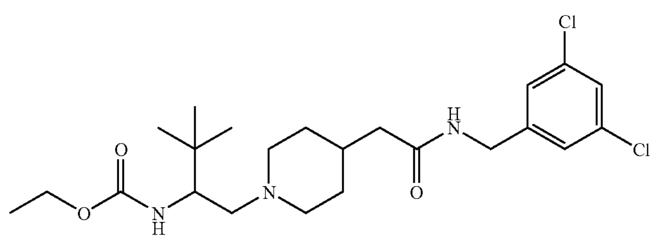 [SMILES: CCOC(=O)NC(CN1CCC(CC(=O)NCc2cc(Cl)cc(Cl)c2)CC1)C(C)(C)C] | 472.21 |
| 225 | isobutyl 1-(4-(2-(3,5-dichlorobenzylamino)-2-oxoethyl)piperidin-1-yl)-3,3-dimethylbutan-2-ylcarbamate | 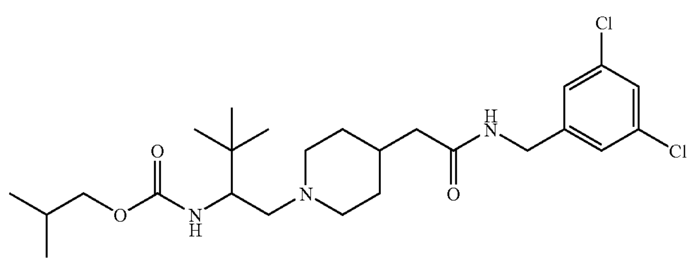 [SMILES: CC(C)COC(=O)NC(CN1CCC(CC(=O)NCc2cc(Cl)cc(Cl)c2)CC1)C(C)(C)C] | 500.24 |
| 226 | N-((1-(2-(3,3-difluoropyrrolidin-1-yl)acetyl)piperidin-4-yl)methyl)-3,5-bis(trifluoromethyl)benzamide | 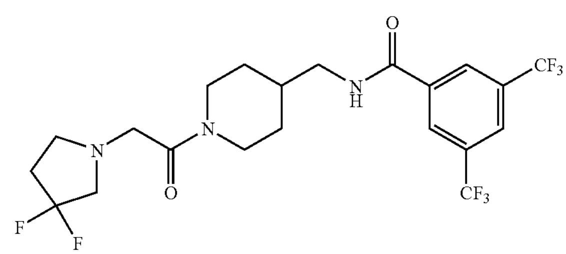 [SMILES: O=C(NCC1CCN(C(=O)CN2CCC(F)(F)C2)CC1)c1cc(C(F)(F)F)cc(C(F)(F)F)c1] | 502.42 |

TABLE 1-continued

| Cmpd No. | Name | Mass Spec (m/z) |
|---|---|---|
| 227 | N-((1-(2-(3,3-difluoropyrrolidin-1-yl)acetyl)piperidin-4-yl)methyl)-3-fluoro-5-(trifluoromethyl)benzamide | 452.41 |
| 228 | N-((1-(2-(cyclopropanesulfonamido)ethyl)piperidin-4-yl)methyl)-3-(trifluoromethyl)benzamide | 434.49 |
| 229 | 3-tert-butoxy-N-((1-(2-(cyclopropanesulfonamido)ethyl)piperidin-4-yl)methyl)benzamide | 438.60 |
| 230 | N-((1-(2-(cyclopropanesulfonamido)ethyl)piperidin-4-yl)methyl)-3-fluoro-5-(trifluoromethyl)benzamide | 452.48 |
| 231 | (E)-N-((1-(2-(cyclopropanesulfonamido)ethyl)piperidin-4-yl)methyl)-3-(3,5-difluorophenyl)acrylamide | 428.51 |
| 232 | N-((1-(2-(cyclopropanesulfonamido)ethyl)piperidin-4-yl)methyl)-4-(trifluoromethoxy)benzamide | 450.49 |

TABLE 1-continued

| Cmpd No. | Name | Mass Spec (m/z) |
|---|---|---|
| 233 | N-((1-(2-(cyclopropanesulfonamido)ethyl)piperidin-4-yl)methyl)-3,5-dimethylbenzamide | 394.55 |
| 234 | N-((1-(2-(cyclopropanesulfonamido)ethyl)piperidin-4-yl)methyl)-3-(trifluoromethoxy)benzamide | 450.49 |
| 235 | N-((1-(2-(cyclopropanesulfonamido)ethyl)piperidin-4-yl)methyl)-3-methoxy-5-(trifluoromethyl)benzamide | 464.52 |
| 236 | 3-chloro-N-((1-(2-(1-methylethylsulfonamido)ethyl)piperidin-4-yl)methyl)benzamide | 402.96 |
| 237 | N-((1-(2-(cyclopropanesulfonamido)ethyl)piperidin-4-yl)methyl)-2-(3-fluorophenyl)acetamide | 398.51 |
| 238 | 4-tert-butyl-N-((1-(2-(cyclopropanesulfonamido)ethyl)piperidin-4-yl)methyl)benzamide | 422.60 |

TABLE 1-continued

| Cmpd No. | Name | Structure | Mass Spec (m/z) |
|---|---|---|---|
| 239 | N-((1-(2-(tert-butylamino)acetyl)piperidin-4-yl)methyl)-3,5-bis(trifluoromethyl)benzamide | 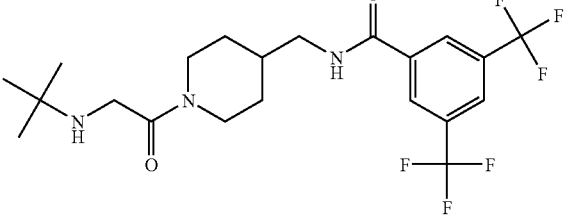 | 468.45 |
| 240 | N-((1-(2-(3-hydroxypiperidin-1-yl)acetyl)piperidin-4-yl)methyl)-3,5-bis(trifluoromethyl)benzamide | 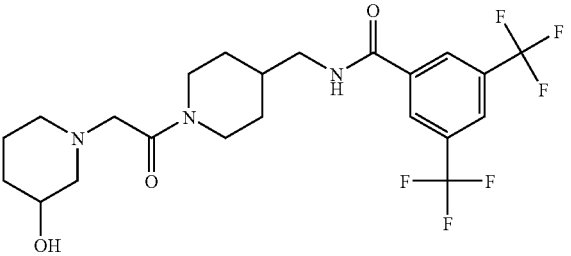 [SMILES: O=C(NCC1CCN(C(=O)CN2CCCC(O)C2)CC1)c1cc(C(F)(F)F)cc(C(F)(F)F)c1] | 496.46 |
| 241 | N-((1-(2-(pentylamino)acetyl)piperidin-4-yl)methyl)-3,5-bis(trifluoromethyl)benzamide | 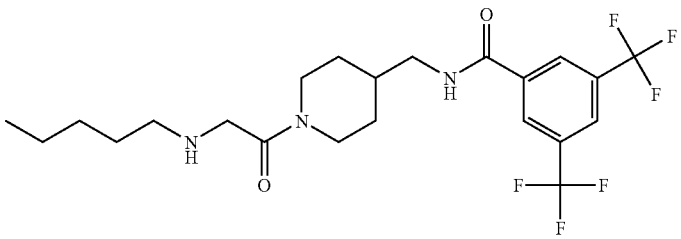 [SMILES: CCCCCNCC(=O)N1CCC(CNC(=O)c2cc(C(F)(F)F)cc(C(F)(F)F)c2)CC1] | 482.48 |
| 242 | N-((1-(2-(3-methylpiperidin-1-yl)acetyl)piperidin-4-yl)methyl)-3,5-bis(trifluoromethyl)benzamide | 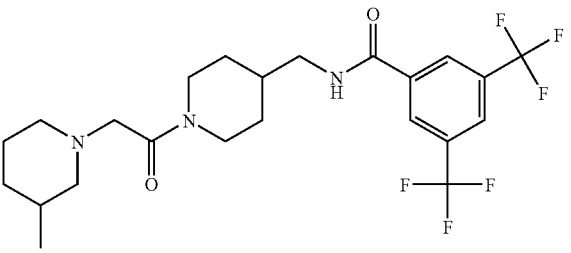 [SMILES: CC1CCCN(CC(=O)N2CCC(CNC(=O)c3cc(C(F)(F)F)cc(C(F)(F)F)c3)CC2)C1] | 494.49 |
| 243 | N-((1-(2-(2-ethylpiperidin-1-yl)acetyl)piperidin-4-yl)methyl)-3,5-bis(trifluoromethyl)benzamide | 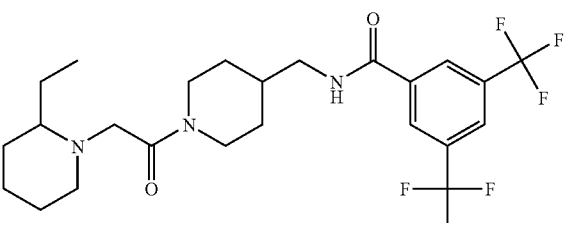 | 508.52 |
| 244 | N-((1-(2-(3-morpholinopropylamino)acetyl)piperidin-4-yl)methyl)-3,5-bis(trifluoromethyl)benzamide | 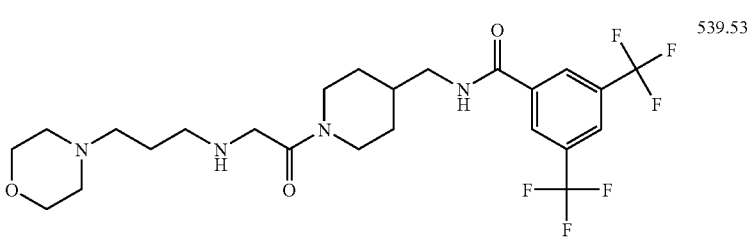 | 539.53 |

TABLE 1-continued

| Cmpd No. | Name | Mass Spec (m/z) |
|---|---|---|
| 245 | N-((1-(2-(3-(dimethylamino)propylamino)acetyl)piperidin-4-yl)methyl)-3,5-bis(trifluoromethyl)benzamide | 497.50 |
| 246 | N-((1-(2-(cyclohexyl(methyl)amino)acetyl)piperidin-4-yl)methyl)-3,5-bis(trifluoromethyl)benzamide | 508.52 |
| 247 | N-((1-(2-(cyclopentylamino)acetyl)piperidin-4-yl)methyl)-3,5-bis(trifluoromethyl)benzamide | 480.46 |
| 248 | N-((1-(2-(2-methylcyclohexylamino)acetyl)piperidin-4-yl)methyl)-3,5-bis(trifluoromethyl)benzamide | 508.52 |
| 249 | N-((1-(2-(cyclohexylamino)acetyl)piperidin-4-yl)methyl)-3,5-bis(trifluoromethyl)benzamide | 494.49 |
| 250 | N-((1-(2-(4-hydroxypiperidin-1-yl)acetyl)piperidin-4-yl)methyl)-3,5-bis(trifluoromethyl)benzamide | 496.46 |

TABLE 1-continued

| Cmpd No. | Name | Structure | Mass Spec (m/z) |
|---|---|---|---|
| 251 | N-((1-(2-(4-methoxypiperidin-1-yl)acetyl)piperidin-4-yl)methyl)-3,5-bis(trifluoromethyl)benzamide | 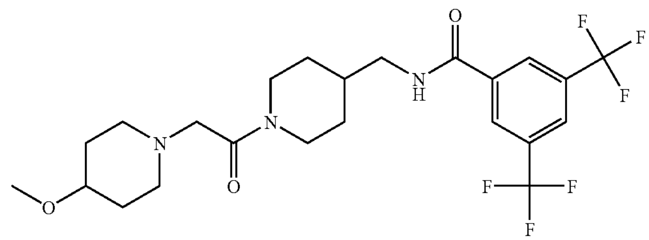 [SMILES: COC1CCN(CC(=O)N2CCC(CNC(=O)c3cc(C(F)(F)F)cc(C(F)(F)F)c3)CC2)CC1] | 510.49 |
| 252 | (R)-N-((1-(2-(2-methylpiperidin-1-yl)acetyl)piperidin-4-yl)methyl)-3,5-bis(trifluoromethyl)benzamide | 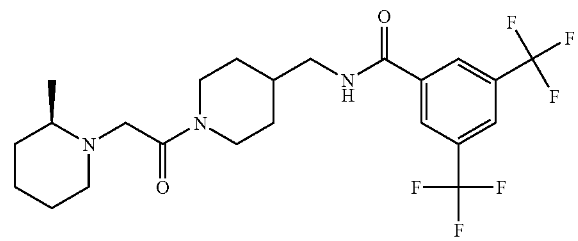 [SMILES: C[C@@H]1CCCCN1CC(=O)N1CCC(CNC(=O)c2cc(C(F)(F)F)cc(C(F)(F)F)c2)CC1] | 494.49 |
| 253 | N-((1-(2-(2-ethylpyrrolidin-1-yl)acetyl)piperidin-4-yl)methyl)-3,5-bis(trifluoromethyl)benzamide | 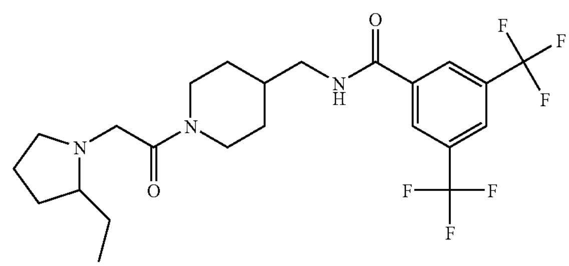 [SMILES: CCC1CCCN1CC(=O)N1CCC(CNC(=O)c2cc(C(F)(F)F)cc(C(F)(F)F)c2)CC1] | 494.49 |
| 254 | N-((1-(2-(4-(hydroxymethyl)piperidin-1-yl)acetyl)piperidin-4-yl)methyl)-3,5-bis(trifluoromethyl)benzamide | 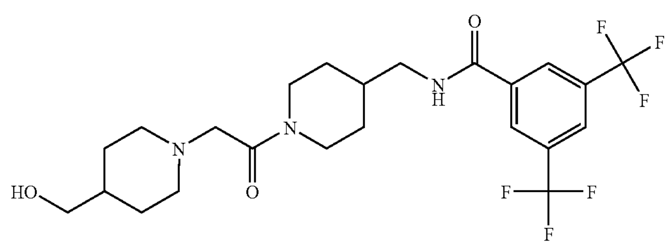 [SMILES: O=C(NCC1CCN(C(=O)CN2CCC(CO)CC2)CC1)c1cc(C(F)(F)F)cc(C(F)(F)F)c1] | 510.49 |
| 255 | 3,5-bis(trifluoromethyl)-N-((1-(2-(3-(trifluoromethyl)piperidin-1-yl)acetyl)piperidin-4-yl)methyl)benzamide | 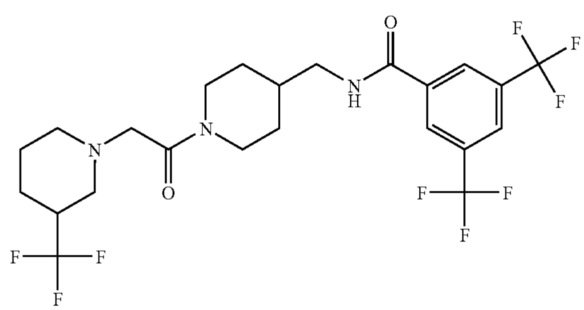 [SMILES: O=C(NCC1CCN(C(=O)CN2CCCC(C(F)(F)F)C2)CC1)c1cc(C(F)(F)F)cc(C(F)(F)F)c1] | 548.46 |
| 256 | N-((1-(2-(3,3-difluoropiperidin-1-yl)acetyl)piperidin-4-yl)methyl)-3,5-bis(trifluoromethyl)benzamide | 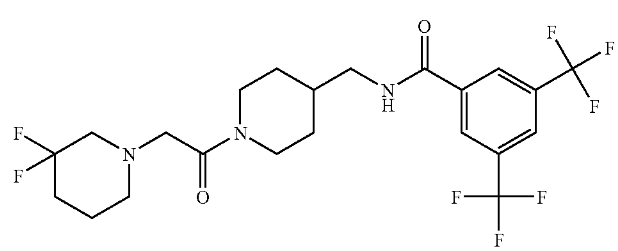 [SMILES: O=C(NCC1CCN(C(=O)CN2CCCC(F)(F)C2)CC1)c1cc(C(F)(F)F)cc(C(F)(F)F)c1] | 516.44 |

TABLE 1-continued

| Cmpd No. | Name | Structure | Mass Spec (m/z) |
|---|---|---|---|
| 257 | N-((1-(2-(cyclopropylamino)acetyl)piperidin-4-yl)methyl)-3,5-bis(trifluoromethyl)benzamide | 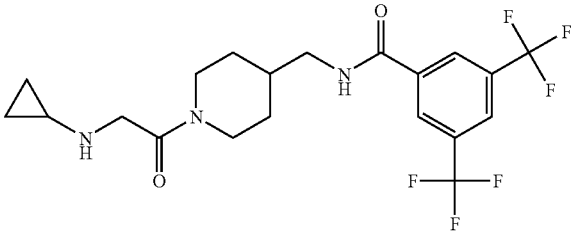 [SMILES: O=C(NCC1CCN(C(=O)CNC2CC2)CC1)c1cc(C(F)(F)F)cc(C(F)(F)F)c1] | 452.41 |
| 258 | N-((1-(2-(4-tert-butylpiperidin-1-yl)acetyl)piperidin-4-yl)methyl)-3,5-bis(trifluoromethyl)benzamide | 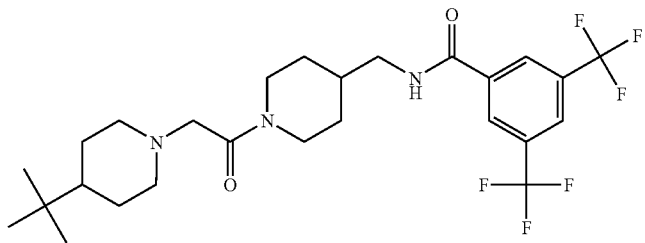 [SMILES: CC(C)(C)C1CCN(CC(=O)N2CCC(CNC(=O)c3cc(C(F)(F)F)cc(C(F)(F)F)c3)CC2)CC1] | 536.57 |
| 259 | N-((1-(2-(4-cyanopiperidin-1-yl)acetyl)piperidin-4-yl)methyl)-3,5-bis(trifluoromethyl)benzamide | 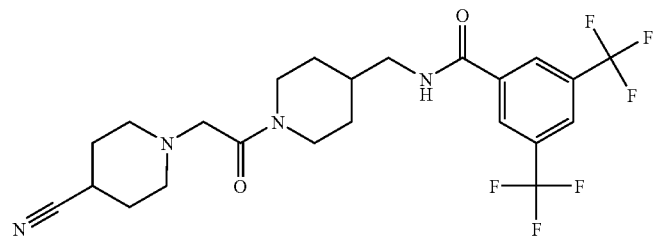 [SMILES: N#CC1CCN(CC(=O)N2CCC(CNC(=O)c3cc(C(F)(F)F)cc(C(F)(F)F)c3)CC2)CC1] | 505.47 |
| 260 | N-((1-(2-(4-morpholinopiperidin-1-yl)acetyl)piperidin-4-yl)methyl)-3,5-bis(trifluoromethyl)benzamide | 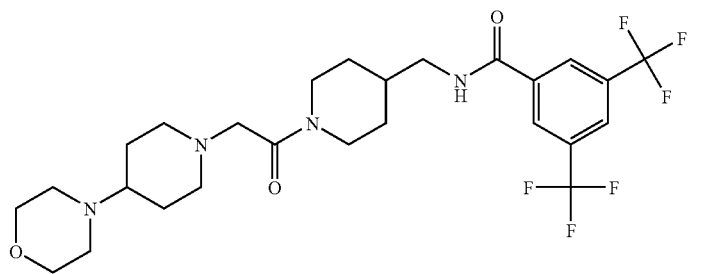 [SMILES: O=C(NCC1CCN(C(=O)CN2CCC(N3CCOCC3)CC2)CC1)c1cc(C(F)(F)F)cc(C(F)(F)F)c1] | 565.57 |
| 261 | N-((1-(2-(2,6-dimethylmorpholino)acetyl)piperidin-4-yl)methyl)-3,5-bis(trifluoromethyl)benzamide | 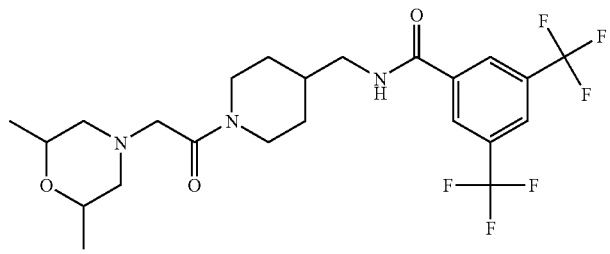 [SMILES: CC1CN(CC(=O)N2CCC(CNC(=O)c3cc(C(F)(F)F)cc(C(F)(F)F)c3)CC2)CC(C)O1] | 510.49 |
| 262 | N-((1-(2-morpholinoacetyl)piperidin-4-yl)methyl)-3,5-bis(trifluoromethyl)benzamide | 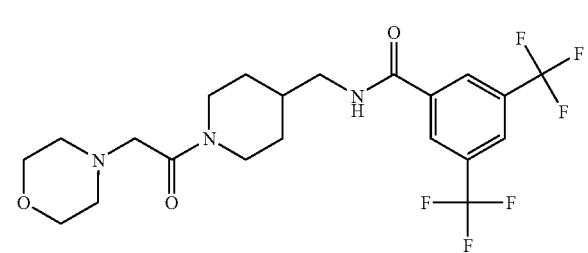 [SMILES: O=C(NCC1CCN(C(=O)CN2CCOCC2)CC1)c1cc(C(F)(F)F)cc(C(F)(F)F)c1] | 482.44 |

TABLE 1-continued

| Cmpd No. | Name | Structure | Mass Spec (m/z) |
|---|---|---|---|
| 263 | (R)-N-((1-(2-(3-hydroxypyrrolidin-1-yl)acetyl)piperidin-4-yl)methyl)-3,5-bis(trifluoromethyl)benzamide | 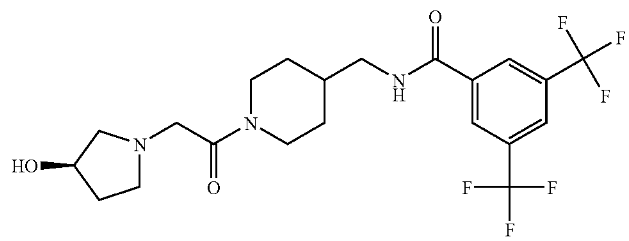 [SMILES: O=C(NCC1CCN(C(=O)CN2CC[C@@H](O)C2)CC1)c1cc(C(F)(F)F)cc(C(F)(F)F)c1] | 482.44 |
| 264 | N-((1-(2-((1r,4r)-4-methylcyclohexyl-amino)acetyl)piperidin-4-yl)methyl)-3,5-bis(trifluoromethyl)benzamide | 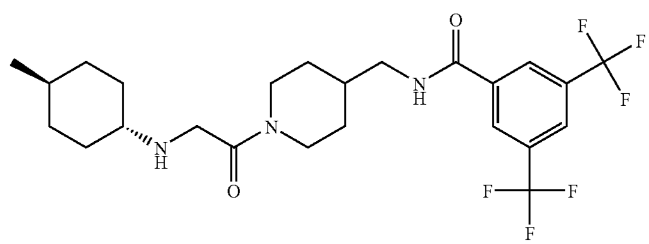 [SMILES: C[C@H]1CC[C@H](NCC(=O)N2CCC(CNC(=O)c3cc(C(F)(F)F)cc(C(F)(F)F)c3)CC2)CC1] | 508.52 |
| 265 | N-((1-(2-(tert-butylamino)acetyl)piperidin-4-yl)methyl)-3-fluoro-5-(trifluoromethyl)benzamide | 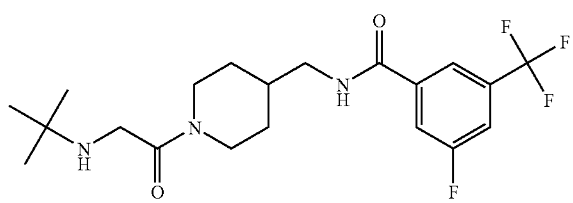 [SMILES: CC(C)(C)NCC(=O)N1CCC(CNC(=O)c2cc(F)cc(C(F)(F)F)c2)CC1] | 418.45 |
| 266 | 3-fluoro-N-((1-(2-(3-hydroxypiperidin-1-yl)acetyl)piperidin-4-yl)methyl)-5-(trifluoromethyl)benzamide | 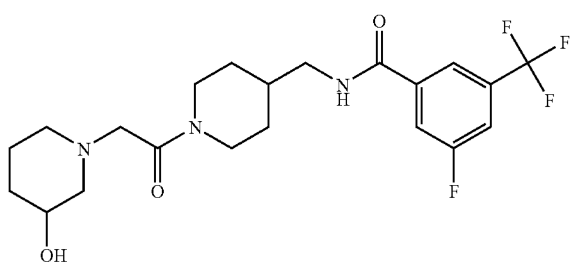 [SMILES: O=C(NCC1CCN(C(=O)CN2CCCC(O)C2)CC1)c1cc(F)cc(C(F)(F)F)c1] | 446.46 |
| 267 | 3-fluoro-N-((1-(2-(pentylamino)acetyl)piperidin-4-yl)methyl)-5-(trifluoromethyl)benzamide | 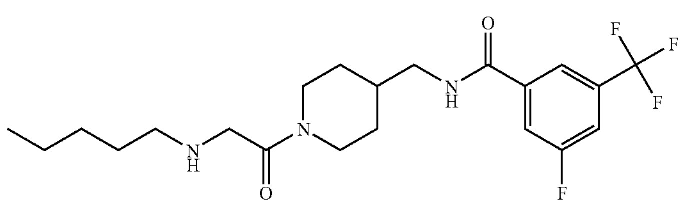 [SMILES: CCCCCNCC(=O)N1CCC(CNC(=O)c2cc(F)cc(C(F)(F)F)c2)CC1] | 432.47 |
| 268 | 3-fluoro-N-((1-(2-(3-methylpiperidin-1-yl)acetyl)piperidin-4-yl)methyl)-5-(trifluoromethyl)benzamide | 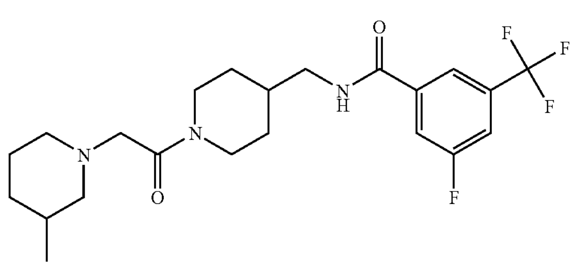 [SMILES: CC1CCCN(CC(=O)N2CCC(CNC(=O)c3cc(F)cc(C(F)(F)F)c3)CC2)C1] | 444.48 |

TABLE 1-continued

| Cmpd No. | Name | Structure | Mass Spec (m/z) |
|---|---|---|---|
| 269 | N-((1-(2-(2-ethylpiperidin-1-yl)acetyl)piperidin-4-yl)methyl)-3-fluoro-5-(trifluoromethyl)benzamide | 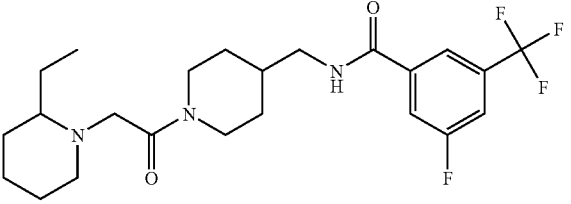 [SMILES: CCC1CCCCN1CC(=O)N1CCC(CNC(=O)c2cc(F)cc(C(F)(F)F)c2)CC1] | 458.51 |
| 270 | 3-fluoro-N-((1-(2-(3-morpholinopropyl-amino)acetyl)piperidin-4-yl)methyl)-5-(trifluoromethyl)benzamide | 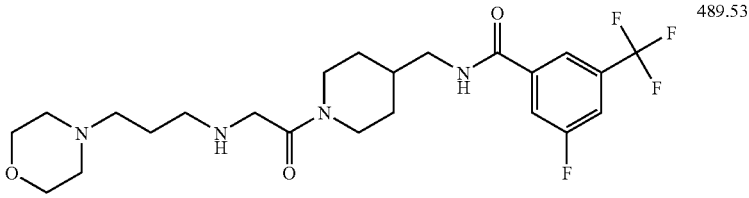 | 489.53 |
| 271 | N-((1-(2-(3-(dimethylamino)propylamino)acetyl)piperidin-4-yl)methyl)-3-fluoro-5-(trifluoromethyl)benzamide | 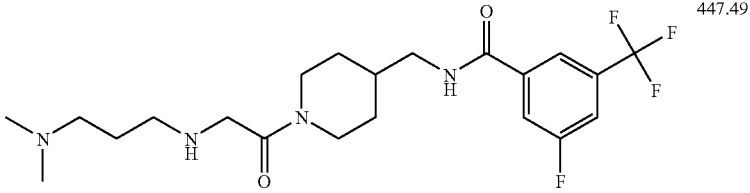 | 447.49 |
| 272 | N-((1-(2-(cyclohexyl(methyl)amino)acetyl)piperidin-4-yl)methyl)-3-fluoro-5-(trifluoromethyl)benzamide | 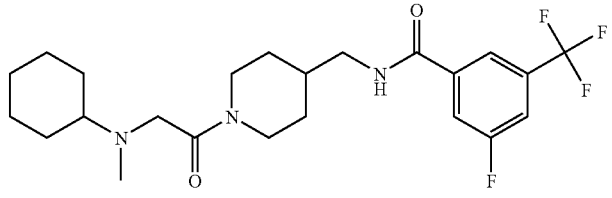 [SMILES: CN(CC(=O)N1CCC(CNC(=O)c2cc(F)cc(C(F)(F)F)c2)CC1)C1CCCCC1] | 458.51 |
| 273 | N-((1-(2-(cyclopentylamino)acetyl)piperidin-4-yl)methyl)-3-fluoro-5-(trifluoromethyl)benzamide | 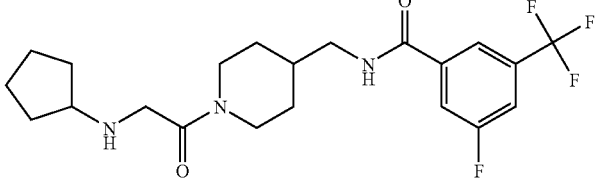 | 430.46 |
| 274 | 3-fluoro-N-((1-(2-(2-methylcyclohexyl-amino)acetyl)piperidin-4-yl)methyl)-5-(trifluoromethyl)benzamide | 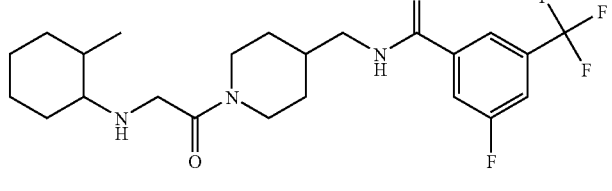 | 458.51 |
| 275 | 3-fluoro-N-((1-(2-(2-hydroxycyclohexyl-amino)acetyl)piperidin-4-yl)methyl)-5-(trifluoromethyl)benzamide | 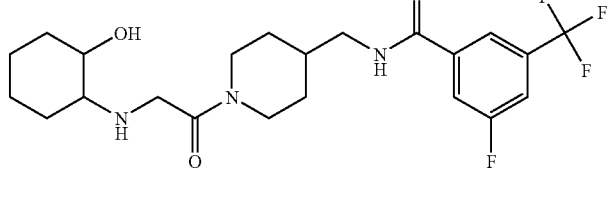 | 460.48 |

TABLE 1-continued

| Cmpd No. | Name | Structure | Mass Spec (m/z) |
|---|---|---|---|
| 276 | N-((1-(2-(cyclohexylamino)acetyl)piperidin-4-yl)methyl)-3-fluoro-5-(trifluoromethyl)benzamide | 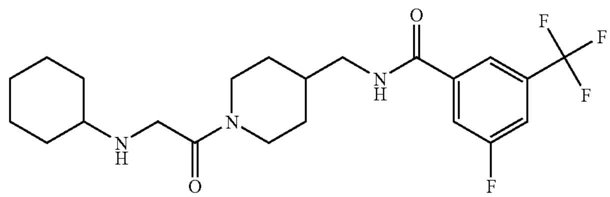 [SMILES: O=C(NCC1CCN(C(=O)CNC2CCCCC2)CC1)c1cc(F)cc(C(F)(F)F)c1] | 444.48 |
| 277 | 3-fluoro-N-((1-(2-(4-hydroxypiperidin-1-yl)acetyl)piperidin-4-yl)methyl)-5-(trifluoromethyl)benzamide | 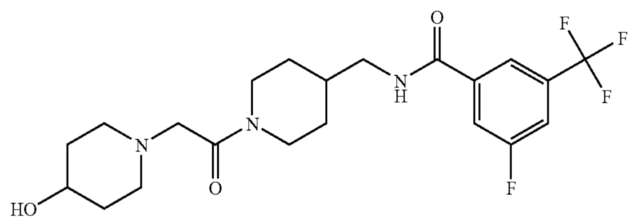 [SMILES: O=C(NCC1CCN(C(=O)CN2CCC(O)CC2)CC1)c1cc(F)cc(C(F)(F)F)c1] | 446.46 |
| 278 | 3-fluoro-N-((1-(2-(4-methoxypiperidin-1-yl)acetyl)piperidin-4-yl)methyl)-5-(trifluoromethyl)benzamide | 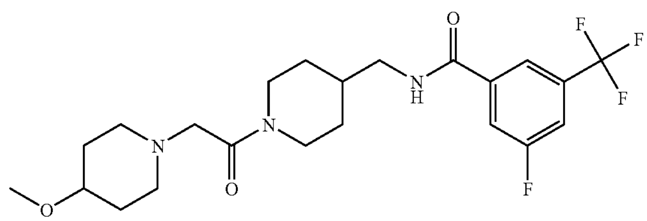 [SMILES: COC1CCN(CC(=O)N2CCC(CNC(=O)c3cc(F)cc(C(F)(F)F)c3)CC2)CC1] | 460.48 |
| 279 | (R)-3-fluoro-N-((1-(2-(2-methylpiperidin-1-yl)acetyl)piperidin-4-yl)methyl)-5-(trifluoromethyl)benzamide | 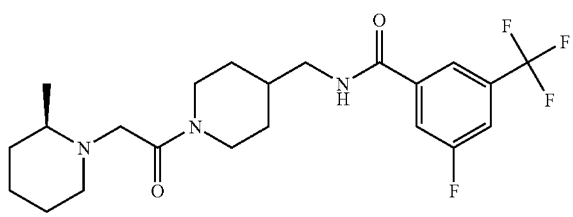 [SMILES: C[C@@H]1CCCCN1CC(=O)N1CCC(CNC(=O)c2cc(F)cc(C(F)(F)F)c2)CC1] | 444.48 |
| 280 | N-((1-(2-(2-ethylpyrrolidin-1-yl)acetyl)piperidin-4-yl)methyl)-3-fluoro-5-(trifluoromethyl)benzamide | 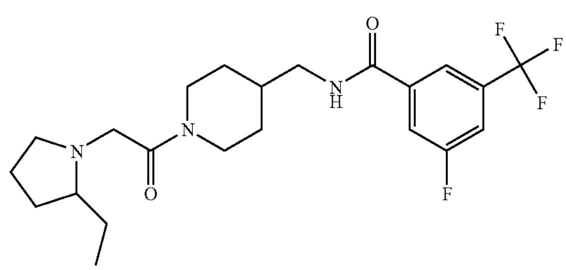 [SMILES: CCC1CCCN1CC(=O)N1CCC(CNC(=O)c2cc(F)cc(C(F)(F)F)c2)CC1] | 444.48 |
| 281 | 3-fluoro-N-((1-(2-(4-(hydroxymethyl)piperidin-1-yl)acetyl)piperidin-4-yl)methyl)-5-(trifluoromethyl)benzamide | 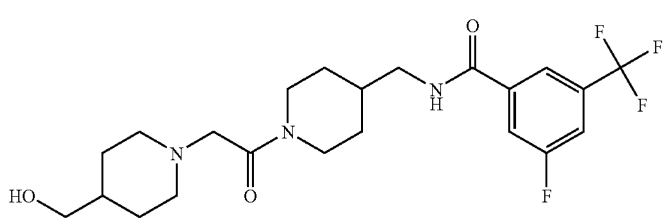 [SMILES: O=C(NCC1CCN(C(=O)CN2CCC(CO)CC2)CC1)c1cc(F)cc(C(F)(F)F)c1] | 460.48 |

| Cmpd No. | Name | Structure | Mass Spec (m/z) |
|---|---|---|---|
| 282 | 3-fluoro-5-(trifluoromethyl)-N-((1-(2-(3-(trifluoromethyl)piperidin-1-yl)acetyl)piperidin-4-yl)methyl)benzamide | 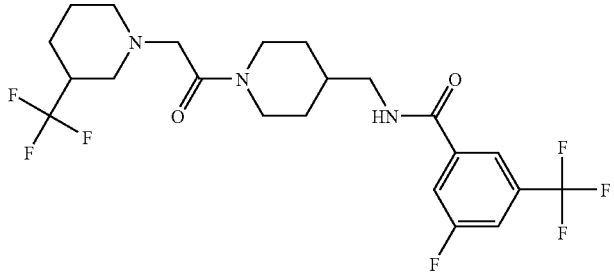 [SMILES: O=C(NCC1CCN(C(=O)CN2CCCC(C(F)(F)F)C2)CC1)c1cc(F)cc(C(F)(F)F)c1] | 498.45 |
| 283 | N-((1-(2-(3,3-difluoropiperidin-1-yl)acetyl)piperidin-4-yl)methyl)-3-fluoro-5-(trifluoromethyl)benzamide | 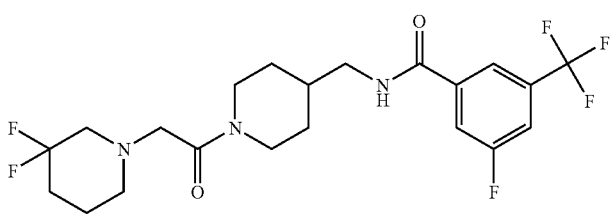 [SMILES: O=C(NCC1CCN(C(=O)CN2CCCC(F)(F)C2)CC1)c1cc(F)cc(C(F)(F)F)c1] | 466.44 |
| 284 | N-((1-(2-(cyclopropylamino)acetyl)piperidin-4-yl)methyl)-3-fluoro-5-(trifluoromethyl)benzamide | 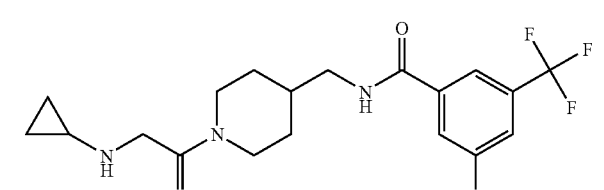 | 402.40 |
| 285 | N-((1-(2-(4-tert-butylpiperidin-1-yl)acetyl)piperidin-4-yl)methyl)-3-fluoro-5-(trifluoromethyl)benzamide | 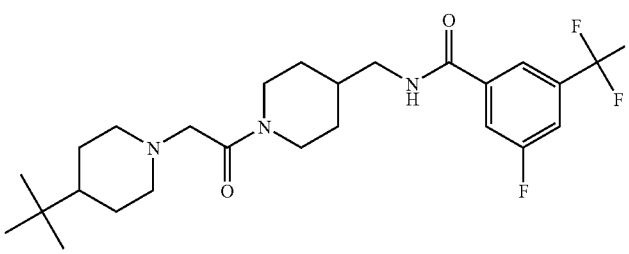 | 486.57 |
| 286 | N-((1-(2-(4-cyanopiperidin-1-yl)acetyl)piperidin-4-yl)methyl)-3-fluoro-5-(trifluoromethyl)benzamide | 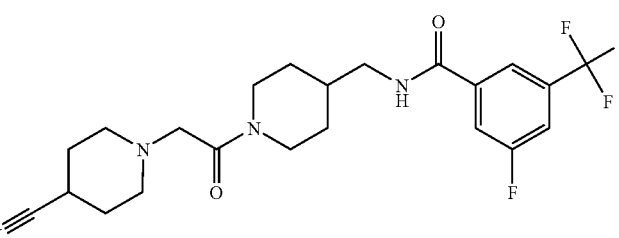 | 455.47 |
| 287 | 3-fluoro-N-((1-(2-(4-morpholinopiperidin-1-yl)acetyl)piperidin-4-yl)methyl)-5-(trifluoromethyl)benzamide | 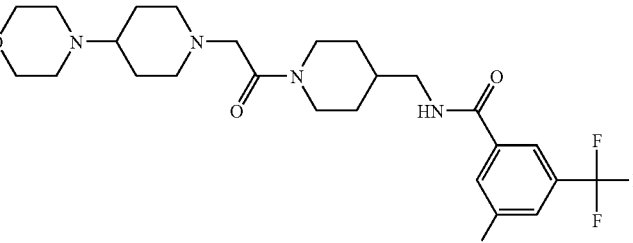 | 515.56 |

TABLE 1-continued

| Cmpd No. | Name | Mass Spec (m/z) |
|---|---|---|
| 288 | N-((1-(2-(2,6-dimethylmorpholino)acetyl)piperidin-4-yl)methyl)-3-fluoro-5-(trifluoromethyl)benzamide | 460.48 |
| 289 | 3-fluoro-N-((1-(2-morpholinoacetyl)piperidin-4-yl)methyl)-5-(trifluoromethyl)benzamide | 432.43 |
| 290 | (R)-3-fluoro-N-((1-(2-(3-hydroxypyrrolidin-1-yl)acetyl)piperidin-4-yl)methyl)-5-(trifluoromethyl)benzamide | 432.43 |
| 291 | 3-fluoro-N-((1-(2-((1r,4r)-4-methylcyclohexylamino)acetyl)piperidin-4-yl)methyl)-5-(trifluoromethyl)benzamide | 458.51 |
| 292 | N-((1-(2-pivalamidoethyl)piperidin-4-yl)methyl)-3-(trifluoromethoxy)benzamide | 430.48 |
| 293 | 3,5-difluoro-N-((1-(2-pivalamidoethyl)piperidin-4-yl)methyl)benzamide | 382.47 |
| 294 | 3-fluoro-N-((1-(2-pivalamidoethyl)piperidin-4-yl)methyl)-5-(trifluoromethyl)benzamide | 432.47 |

TABLE 1-continued

| Cmpd No. | Name | Structure | Mass Spec (m/z) |
|---|---|---|---|
| 295 | 3,5-dimethyl-N-((1-(2-pivalamidoethyl)piperidin-4-yl)methyl)benzamide | 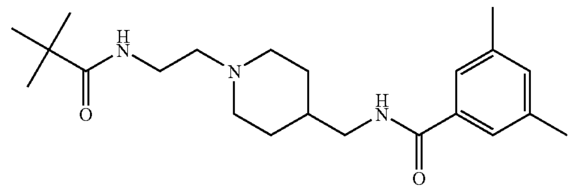 [SMILES: Cc1cc(C)cc(C(=O)NCC2CCN(CCNC(=O)C(C)(C)C)CC2)c1] | 374.54 |
| 296 | N-((1-(2-pivalamidoethyl)piperidin-4-yl)methyl)-3-(trifluoromethyl)benzamide | 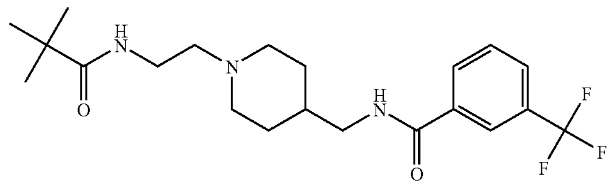 [SMILES: CC(C)(C)C(=O)NCCN1CCC(CNC(=O)c2cccc(C(F)(F)F)c2)CC1] | 414.48 |
| 297 | (E)-3-(3,5-difluorophenyl)-N-((1-(2-pivalamidoethyl)piperidin-4-yl)methyl)acrylamide | 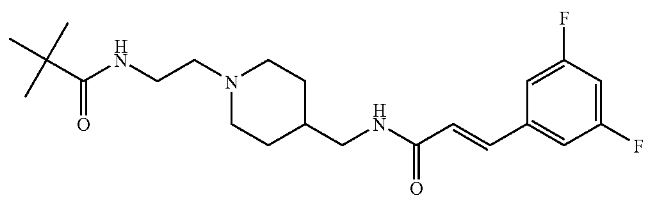 [SMILES: CC(C)(C)C(=O)NCCN1CCC(CNC(=O)/C=C/c2cc(F)cc(F)c2)CC1] | 408.50 |
| 298 | 3,5-dichloro-N-((1-(2-pivalamidoethyl)piperidin-4-yl)methyl)benzamide | 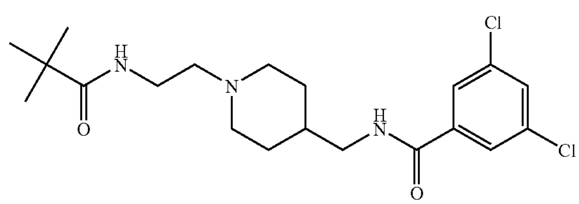 [SMILES: CC(C)(C)C(=O)NCCN1CCC(CNC(=O)c2cc(Cl)cc(Cl)c2)CC1] | 415.38 |
| 299 | 3-chloro-N-((1-(2-pivalamidoethyl)piperidin-4-yl)methyl)benzamide | 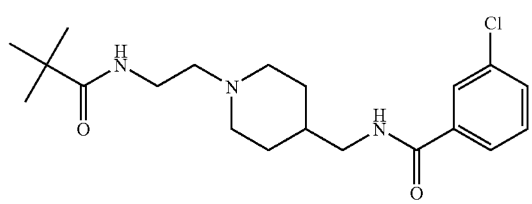 [SMILES: CC(C)(C)C(=O)NCCN1CCC(CNC(=O)c2cccc(Cl)c2)CC1] | 380.93 |
| 300 | (E)-3-(3,5-dichlorophenyl)-N-((1-(2-pivalamidoethyl)piperidin-4-yl)methyl)acrylamide | 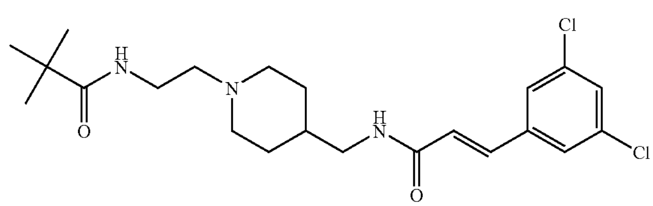 [SMILES: CC(C)(C)C(=O)NCCN1CCC(CNC(=O)/C=C/c2cc(Cl)cc(Cl)c2)CC1] | 441.41 |
| 301 | 3-chloro-N-((1-(2-pivalamidoethyl)piperidin-4-yl)methyl)-5-(trifluoromethyl)benzamide | 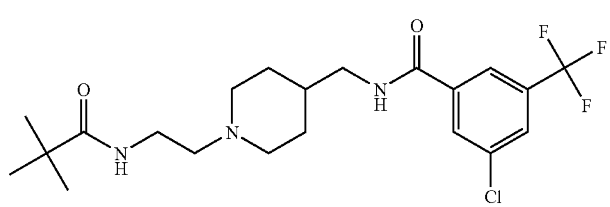 [SMILES: CC(C)(C)C(=O)NCCN1CCC(CNC(=O)c2cc(Cl)cc(C(F)(F)F)c2)CC1] | 448.93 |

TABLE 1-continued

| Cmpd No. | Name | Structure | Mass Spec (m/z) |
|---|---|---|---|
| 302 | 3-bromo-N-((1-(2-pivalamidoethyl)piperidin-4-yl)methyl)-5-(trifluoromethyl)benzamide | 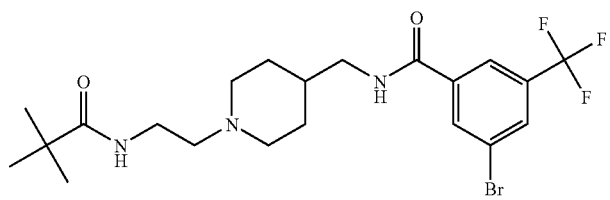 | 493.38 |
| 303 | 3-methoxy-N-((1-(2-pivalamidoethyl)piperidin-4-yl)methyl)-5-(trifluoromethyl)benzamide | 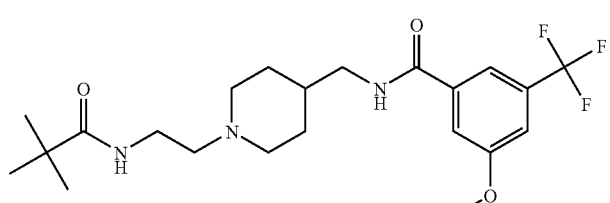 | 444.51 |
| 304 | N-((1-(2-(2-cyanopropan-2-ylamino)-2-oxoethyl)piperidin-4-yl)methyl)-3,5-bis(trifluoromethyl)benzamide | 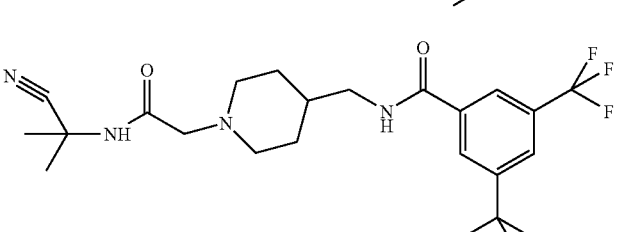 | 479.44 |
| 305 | N-((1-(2-(4-ethoxypiperidin-1-yl)-2-oxoethyl)piperidin-4-yl)methyl)-3,5-bis(trifluoromethyl)benzamide | 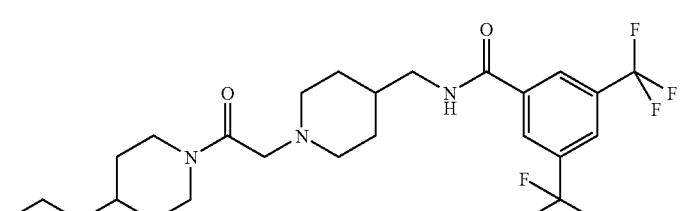 | 524.52 |
| 306 | N-((1-(2-(cyclobutanesulfonamido)ethyl)piperidin-4-yl)methyl)-3-fluoro-5-(trifluoromethyl)benzamide | 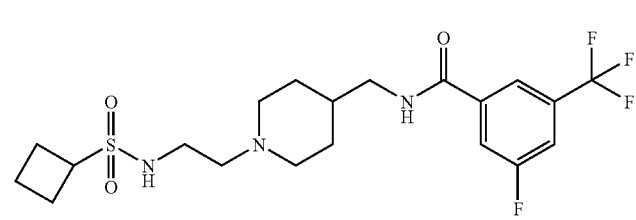 [SMILES: O=C(NCC1CCN(CCNS(=O)(=O)C2CCC2)CC1)c1cc(F)cc(C(F)(F)F)c1] | 466.51 |
| 307 | N-((1-(2-(cyclopentanesulfonamido)ethyl)piperidin-4-yl)methyl)-3-fluoro-5-(trifluoromethyl)benzamide | 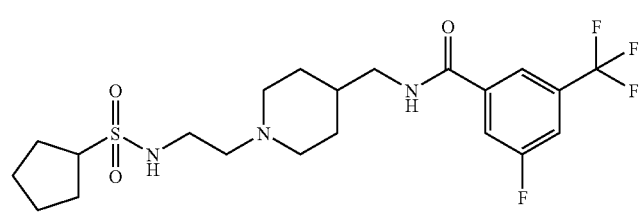 [SMILES: O=C(NCC1CCN(CCNS(=O)(=O)C2CCCC2)CC1)c1cc(F)cc(C(F)(F)F)c1] | 480.54 |
| 308 | 3-fluoro-N-((1-(2-(3-fluoro-propylsulfonamido)ethyl)piperidin-4-yl)methyl)-5-(trifluoromethyl)benzamide | 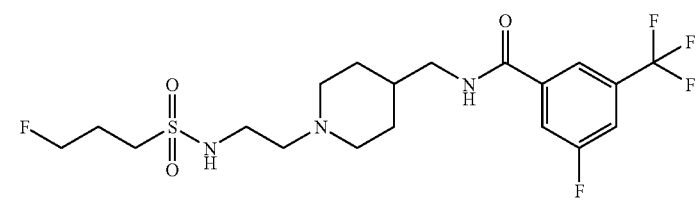 [SMILES: O=C(NCC1CCN(CCNS(=O)(=O)CCCF)CC1)c1cc(F)cc(C(F)(F)F)c1] | 472.49 |

TABLE 1-continued

| Cmpd No. | Name | Structure | Mass Spec (m/z) |
|---|---|---|---|
| 309 | 3-chloro-5-fluoro-N-((1-(2-pivalamidoethyl)piperidin-4-yl)methyl)benzamide | 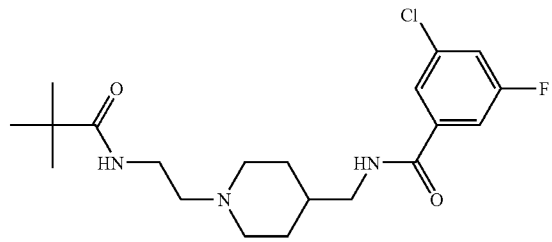 [SMILES: CC(C)(C)C(=O)NCCN1CCC(CNC(=O)c2cc(F)cc(Cl)c2)CC1] | 398.92 |
| 310 | N-((1-(2-pivalamidoethyl)piperidin-4-yl)methyl)-4-(trifluoromethyl)picolinamide | 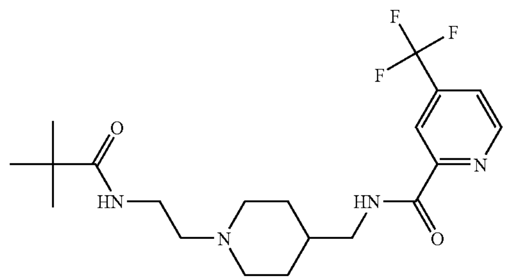 [SMILES: CC(C)(C)C(=O)NCCN1CCC(CNC(=O)c2cc(C(F)(F)F)ccn2)CC1] | 415.47 |
| 311 | N-((1-(2-(4,4,4-trifluorobutanamido)ethyl)piperidin-4-yl)methyl)-3-(trifluoromethoxy)benzamide | 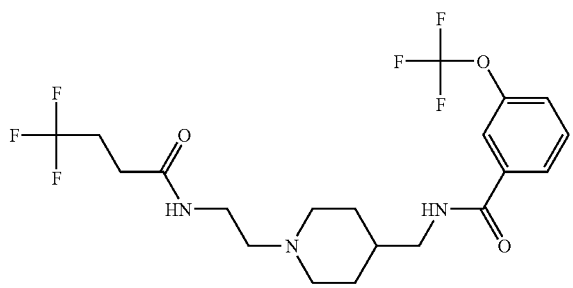 [SMILES: O=C(CCC(F)(F)F)NCCN1CCC(CNC(=O)c2cccc(OC(F)(F)F)c2)CC1] | 470.43 |
| 312 | 3,5-dimethyl-N-((1-(2-(4,4,4-trifluorobutanamido)ethyl)piperidin-4-yl)methyl)benzamide | 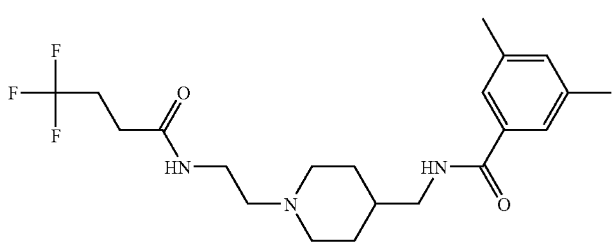 [SMILES: Cc1cc(C)cc(C(=O)NCC2CCN(CCNC(=O)CCC(F)(F)F)CC2)c1] | 414.48 |
| 313 | N-((1-(2-(4,4,4-trifluorobutanamido)ethyl)piperidin-4-yl)methyl)-3-(trifluoromethyl)benzamide | 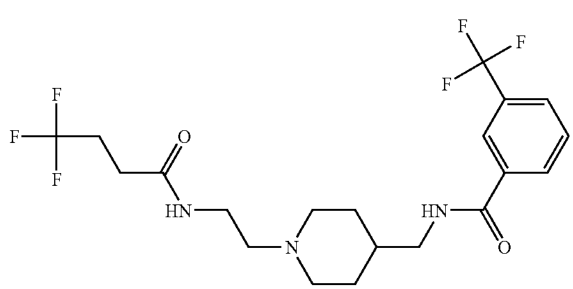 [SMILES: O=C(CCC(F)(F)F)NCCN1CCC(CNC(=O)c2cccc(C(F)(F)F)c2)CC1] | 454.43 |

TABLE 1-continued

| Cmpd No. | Name | Structure | Mass Spec (m/z) |
|---|---|---|---|
| 314 | (E)-N-(2-(4-((3-(3,5-difluorophenyl)acrylamido)methyl)piperidin-1-yl)ethyl)-4,4,4-trifluorobutanamide | 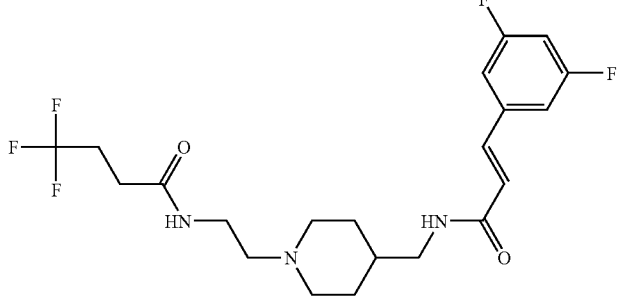 | 448.45 |
| 315 | 3-chloro-N-((1-(2-(4,4,4-trifluoro-butanamido)ethyl)piperidin-4-yl)methyl)benzamide | 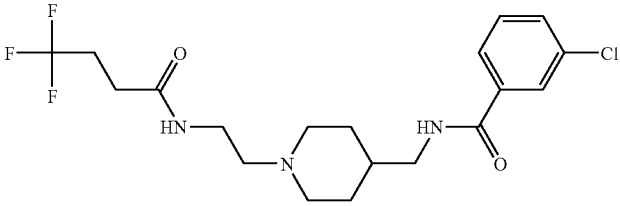 [SMILES: O=C(CCC(F)(F)F)NCCN1CCC(CNC(=O)c2cccc(Cl)c2)CC1] | 420.87 |
| 316 | (E)-N-(2-(4-((3-(3,5-dichlorophenyl)acrylamido)methyl)piperidin-1-yl)ethyl)-4,4,4-trifluorobutanamide | 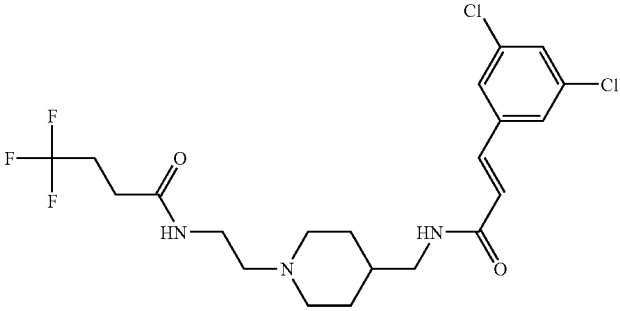 [SMILES: O=C(/C=C/c1cc(Cl)cc(Cl)c1)NCC1CCN(CCNC(=O)CCC(F)(F)F)CC1] | 481.36 |
| 317 | 3-methoxy-N-((1-(2-(4,4,4-trifluoro-butanamido)ethyl)piperidin-4-yl)methyl)-5-(trifluoromethyl)benzamide | 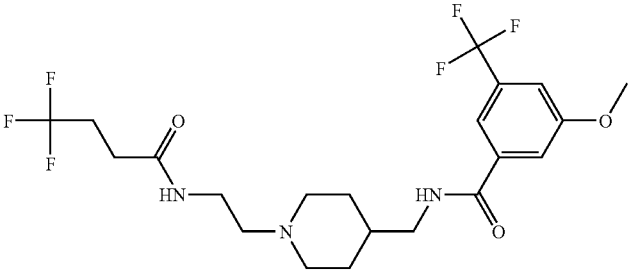 [SMILES: COc1cc(C(=O)NCC2CCN(CCNC(=O)CCC(F)(F)F)CC2)cc(C(F)(F)F)c1] | 484.45 |
| 318 | 3-fluoro-5-methoxy-N-((1-(2-(1-methyl-ethylsulfonamido)ethyl)piperidin-4-yl)methyl)benzamide | 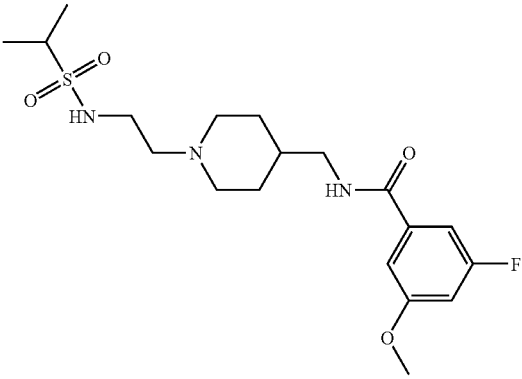 [SMILES: COc1cc(F)cc(C(=O)NCC2CCN(CCNS(=O)(=O)C(C)C)CC2)c1] | 416.53 |

TABLE 1-continued

| Cmpd No. | Name | Structure | Mass Spec (m/z) |
|---|---|---|---|
| 319 | 3,5-dibromo-N-((1-(2-(1-methylethylsulfonamido)ethyl)piperidin-4-yl)methyl)benzamide | 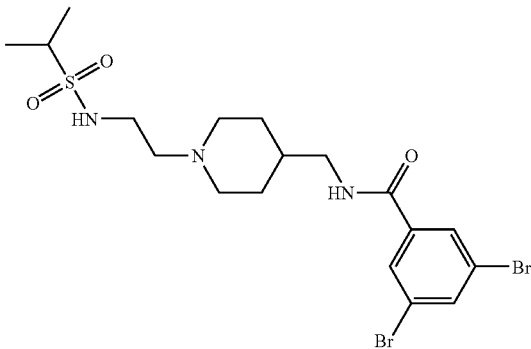 [SMILES: CC(C)S(=O)(=O)NCCN1CCC(CNC(=O)c2cc(Br)cc(Br)c2)CC1] | 526.31 |
| 320 | 3-chloro-5-methoxy-N-((1-(2-(1-methylethylsulfonamido)ethyl)piperidin-4-yl)methyl)benzamide | 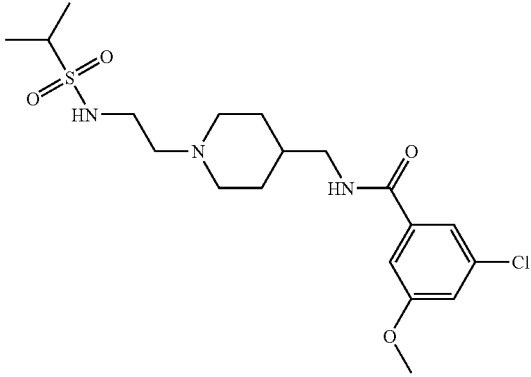 [SMILES: COc1cc(Cl)cc(C(=O)NCC2CCN(CCNS(=O)(=O)C(C)C)CC2)c1] | 432.98 |
| 321 | N-((1-(2-(cyclopropanesulfonamido)ethyl)piperidin-4-yl)methyl)-3-fluoro-5-methoxybenzamide | 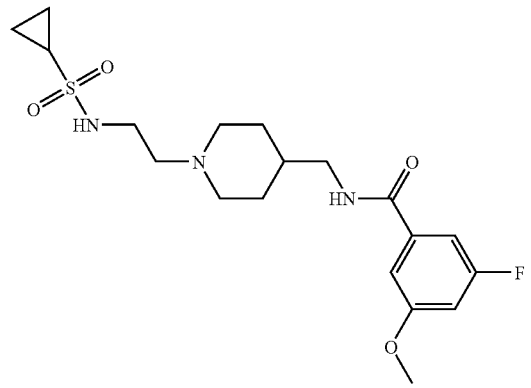 [SMILES: COc1cc(F)cc(C(=O)NCC2CCN(CCNS(=O)(=O)C3CC3)CC2)c1] | 414.51 |
| 322 | 3-chloro-N-((1-(2-(cyclopropane-sulfonamido)ethyl)piperidin-4-yl)methyl)-5-methoxybenzamide | 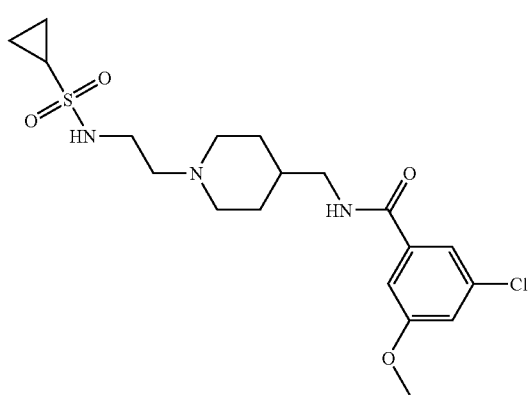 [SMILES: COc1cc(Cl)cc(C(=O)NCC2CCN(CCNS(=O)(=O)C3CC3)CC2)c1] | 430.97 |

TABLE 1-continued

| Cmpd No. | Name | Structure | Mass Spec (m/z) |
|---|---|---|---|
| 323 | 3-bromo-N-((1-(2-(cyclopropane-sulfonamido)ethyl)piperidin-4-yl)methyl)benzamide | 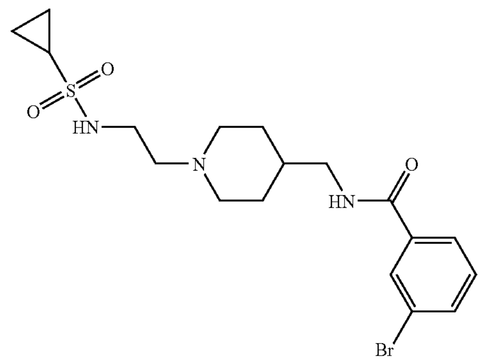 [SMILES: O=C(NCC1CCN(CCNS(=O)(=O)C2CC2)CC1)c1cccc(Br)c1] | 445.40 |
| 324 | N-((1-(2-(cyclopropanesulfonamido)ethyl)piperidin-4-yl)methyl)-3,4-dimethoxybenzamide | 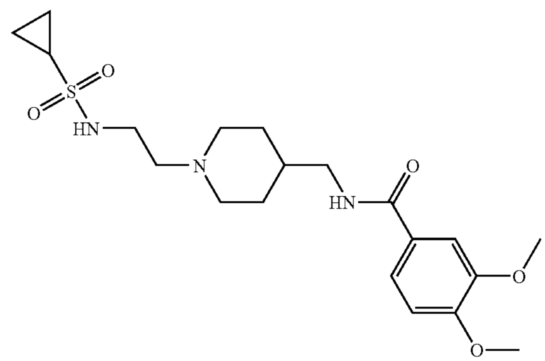 [SMILES: COc1ccc(C(=O)NCC2CCN(CCNS(=O)(=O)C3CC3)CC2)cc1OC] | 426.55 |
| 325 | 3-fluoro-5-methoxy-N-((1-(2-(trifluoromethylsulfonamido)ethyl)piperidin-4-yl)methyl)benzamide | 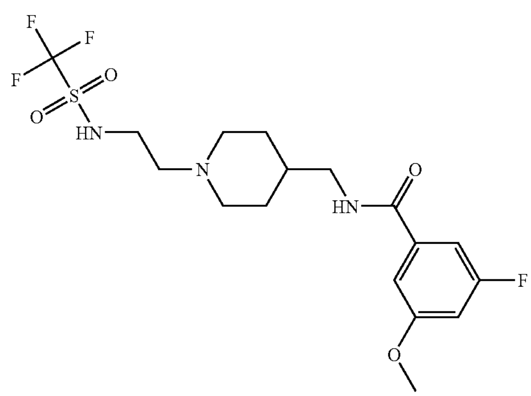 [SMILES: COc1cc(F)cc(C(=O)NCC2CCN(CCNS(=O)(=O)C(F)(F)F)CC2)c1] | 442.44 |
| 326 | 3-chloro-5-methoxy-N-((1-(2-(trifluoromethylsulfonamido)ethyl)piperidin-4-yl)methyl)benzamide | 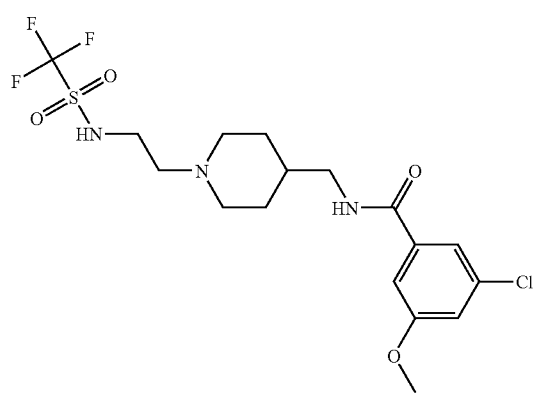 [SMILES: COc1cc(Cl)cc(C(=O)NCC2CCN(CCNS(=O)(=O)C(F)(F)F)CC2)c1] | 458.90 |

TABLE 1-continued

| Cmpd No. | Name | Structure | Mass Spec (m/z) |
|---|---|---|---|
| 327 | 3-methoxy-5-(trifluoromethyl)-N-((1-(2-(trifluoromethylsulfonamido)ethyl)piperidin-4-yl)methyl)benzamide | 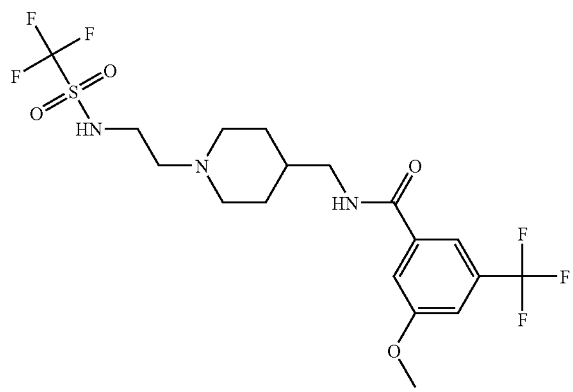 [SMILES: COc1cc(C(=O)NCC2CCN(CCNS(=O)(=O)C(F)(F)F)CC2)cc(C(F)(F)F)c1] | 492.45 |
| 328 | 3-fluoro-4-(trifluoromethyl)-N-((1-(2-(trifluoromethylsulfonamido)ethyl)piperidin-4-yl)methyl)benzamide | 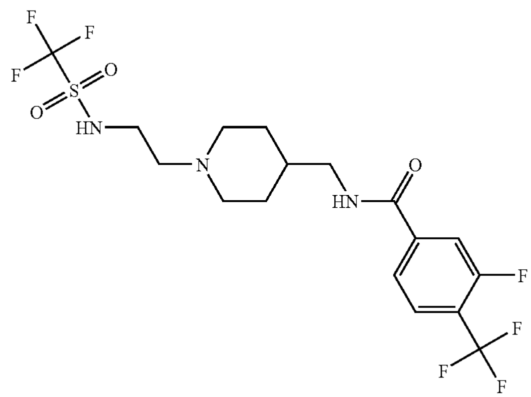 [SMILES: O=C(NCC1CCN(CCNS(=O)(=O)C(F)(F)F)CC1)c1ccc(C(F)(F)F)c(F)c1] | 480.41 |
| 329 | 3-chloro-5-fluoro-N-((1-(2-(trifluoromethylsulfonamido)ethyl)piperidin-4-yl)methyl)benzamide | 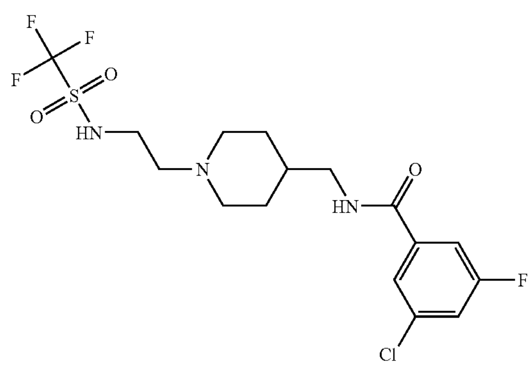 [SMILES: O=C(NCC1CCN(CCNS(=O)(=O)C(F)(F)F)CC1)c1cc(F)cc(Cl)c1] | 446.86 |
| 330 | 3-bromo-N-((1-(2-(trifluoromethylsulfonamido)ethyl)piperidin-4-yl)methyl)benzamide | 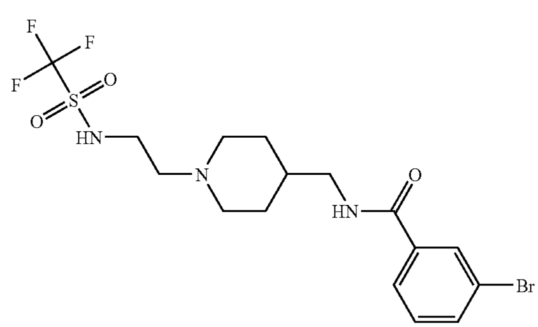 [SMILES: O=C(NCC1CCN(CCNS(=O)(=O)C(F)(F)F)CC1)c1cccc(Br)c1] | 473.33 |

TABLE 1-continued

| Cmpd No. | Name | Structure | Mass Spec (m/z) |
|---|---|---|---|
| 331 | 3-fluoro-5-methyl-N-((1-(2-(trifluoromethylsulfonamido)ethyl)piperidin-4-yl)methyl)benzamide | 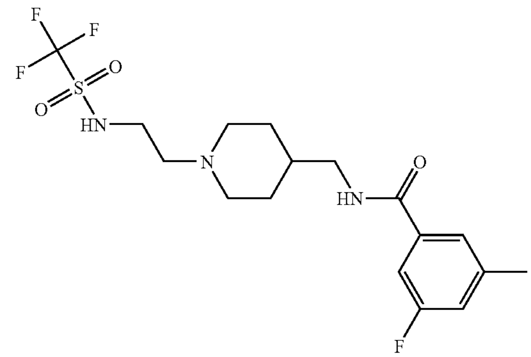 [SMILES: Cc1cc(F)cc(C(=O)NCC2CCN(CCNS(=O)(=O)C(F)(F)F)CC2)c1] | 426.44 |
| 332 | 3,4-dimethoxy-N-((1-(2-(trifluoromethylsulfonamido)ethyl)piperidin-4-yl)methyl)benzamide | 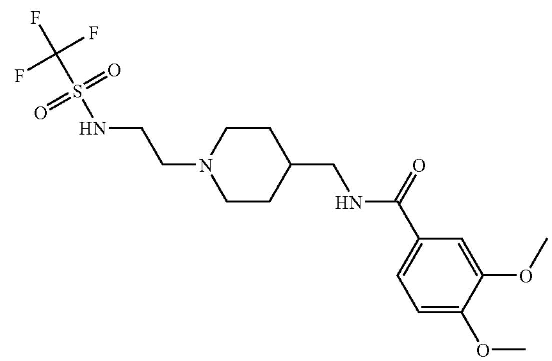 [SMILES: COc1ccc(C(=O)NCC2CCN(CCNS(=O)(=O)C(F)(F)F)CC2)cc1OC] | 454.48 |
| 333 | 2,5-dichloro-N-((1-(2-(cyclopropanesulfonamido)ethyl)piperidin-4-yl)methyl)thiophene-3-carboxamide | 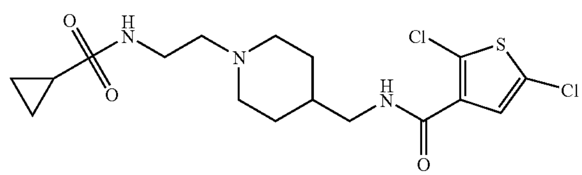 | 441.41 |
| 334 | N-(2-(4-(2-(3,5-bis(trifluoromethyl)phenylamino)-2-oxoethyl)piperidin-1-yl)ethyl)pivalamide | 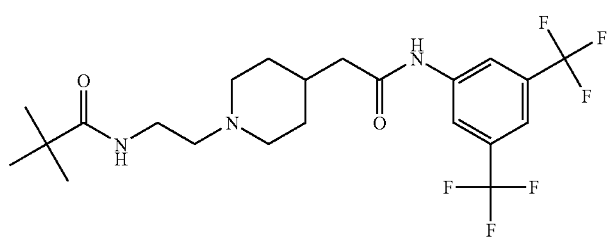 [SMILES: CC(C)(C)C(=O)NCCN1CCC(CC(=O)Nc2cc(C(F)(F)F)cc(C(F)(F)F)c2)CC1] | 482.48 |
| 335 | N-((1-(2-(2-fluoro-2-methylpropanamido)ethyl)piperidin-4-yl)methyl)-3,5-bis(trifluoromethyl)benzamide | 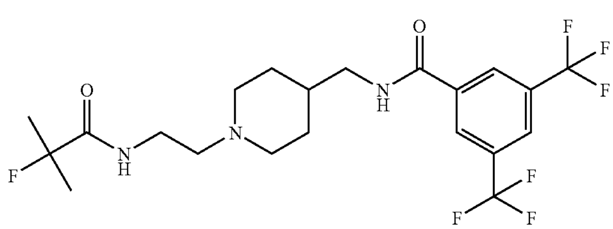 [SMILES: CC(C)(F)C(=O)NCCN1CCC(CNC(=O)c2cc(C(F)(F)F)cc(C(F)(F)F)c2)CC1] | 486.44 |
| 336 | 3-fluoro-N-((1-(2-(2-fluoro-2-methylpropanamido)ethyl)piperidin-4-yl)methyl)-5-(trifluoromethyl)benzamide | 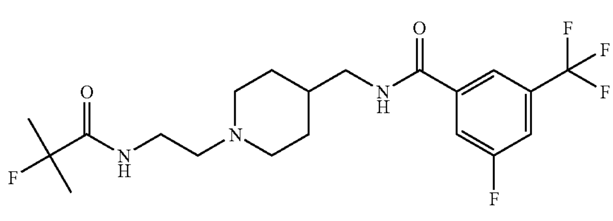 [SMILES: CC(C)(F)C(=O)NCCN1CCC(CNC(=O)c2cc(F)cc(C(F)(F)F)c2)CC1] | 436.44 |

TABLE 1-continued

| Cmpd No. | Name | Structure | Mass Spec (m/z) |
|---|---|---|---|
| 337 | N-((1-(2-(1-methylcyclopropane-carboxamido)ethyl)piperidin-4-yl)methyl)-3,5-bis(trifluoromethyl)benzamide | 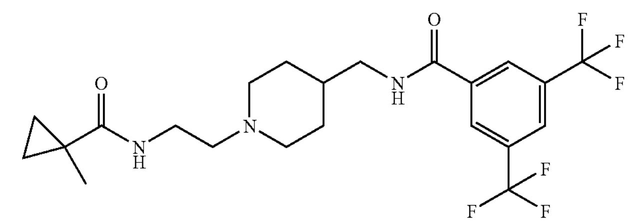 [SMILES: CC1(C(=O)NCCN2CCC(CNC(=O)c3cc(C(F)(F)F)cc(C(F)(F)F)c3)CC2)CC1] | 480.46 |
| 338 | N-((1-(2-(3,3,3-trifluoro-2,2-dimethylpropanamido)ethyl)piperidin-4-yl)methyl)-3,5-bis(trifluoromethyl)benzamide | 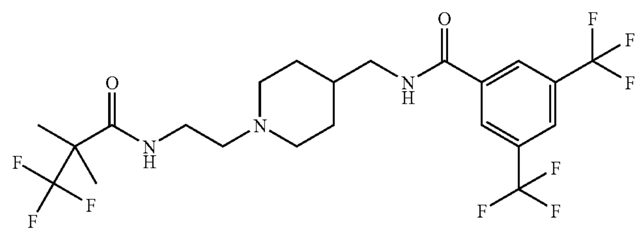 [SMILES: CC(C)(C(=O)NCCN1CCC(CNC(=O)c2cc(C(F)(F)F)cc(C(F)(F)F)c2)CC1)C(F)(F)F] | 536.45 |
| 339 | 3-fluoro-N-((1-(2-(3,3,3-trifluoro-2,2-dimethylpropanamido)ethyl)piperidin-4-yl)methyl)-5-(trifluoromethyl)benzamide | 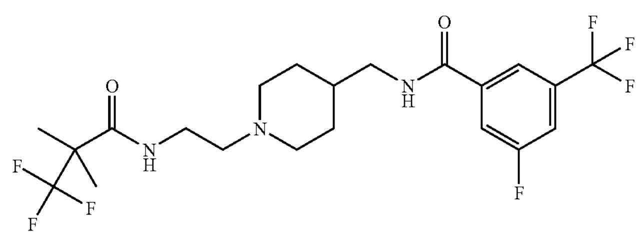 [SMILES: CC(C)(C(=O)NCCN1CCC(CNC(=O)c2cc(F)cc(C(F)(F)F)c2)CC1)C(F)(F)F] | 486.44 |
| 340 | 3,5-bis(trifluoromethyl)-N-((1-(2-(1-(trifluoromethyl)cyclopentane-carboxamido)ethyl)piperidin-4-yl)methyl)benzamide | 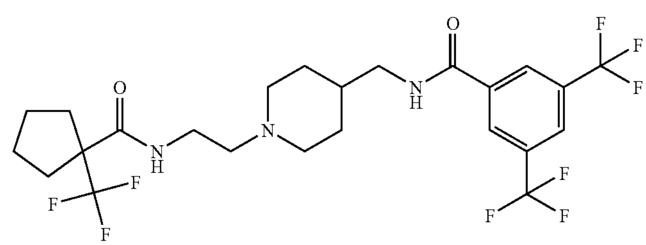 [SMILES: O=C(NCC1CCN(CCNC(=O)C2(C(F)(F)F)CCCC2)CC1)c1cc(C(F)(F)F)cc(C(F)(F)F)c1] | 562.49 |
| 341 | 3-fluoro-5-(trifluoromethyl)-N-((1-(2-(1-(trifluoromethyl)cyclopentane-carboxamido)ethyl)piperidin-4-yl)methyl)benzamide | 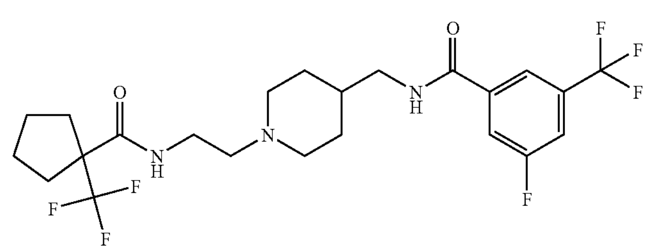 [SMILES: O=C(NCC1CCN(CCNC(=O)C2(C(F)(F)F)CCCC2)CC1)c1cc(F)cc(C(F)(F)F)c1] | 512.48 |
| 342 | 3,5-bis(trifluoromethyl)-N-((1-(2-(1-(trifluoromethyl)cyclopropane-carboxamido)ethyl)piperidin-4-yl)methyl)benzamide | 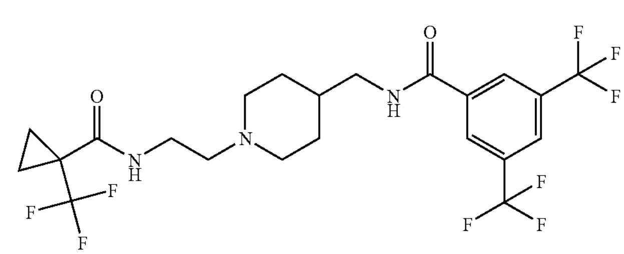 [SMILES: O=C(NCC1CCN(CCNC(=O)C2(C(F)(F)F)CC2)CC1)c1cc(C(F)(F)F)cc(C(F)(F)F)c1] | 534.43 |

TABLE 1-continued

| Cmpd No. | Name | Structure | Mass Spec (m/z) |
|---|---|---|---|
| 343 | 3-fluoro-5-(trifluoromethyl)-N-((1-(2-(1-(trifluoromethyl)cyclopropane-carboxamido)ethyl)piperidin-4-yl)methyl)benzamide | 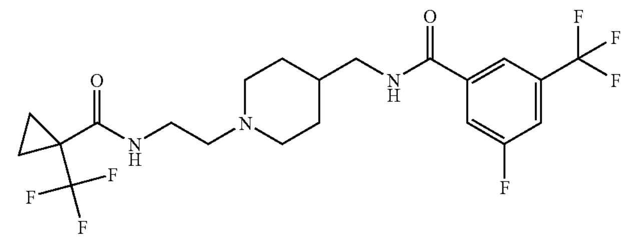 [SMILES: O=C(NCC1CCN(CCNC(=O)C2(C(F)(F)F)CC2)CC1)c1cc(F)cc(C(F)(F)F)c1] | 484.43 |
| 344 | N-((1-(2-(isopropylamino)-2-oxoethyl)piperidin-4-yl)methyl)-3,5-bis(trifluoromethyl)benzamide | 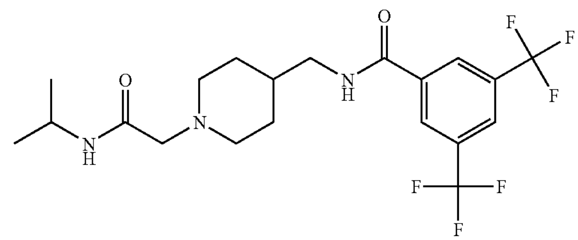 [SMILES: CC(C)NC(=O)CN1CCC(CNC(=O)c2cc(C(F)(F)F)cc(C(F)(F)F)c2)CC1] | 454.43 |
| 345 | N-((1-(2-oxo-2-(propylamino)ethyl)piperidin-4-yl)methyl)-3,5-bis(trifluoromethyl)benzamide | 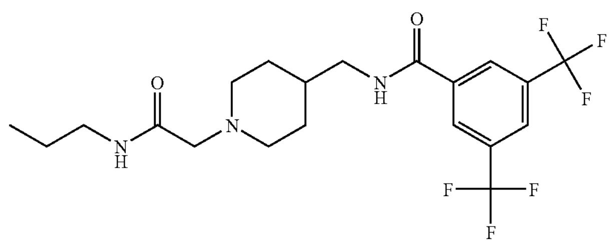 [SMILES: CCCNC(=O)CN1CCC(CNC(=O)c2cc(C(F)(F)F)cc(C(F)(F)F)c2)CC1] | 454.43 |
| 346 | N-((1-(2-oxo-2-(tert-pentylamino)ethyl)piperidin-4-yl)methyl)-3,5-bis(trifluoromethyl)benzamide | 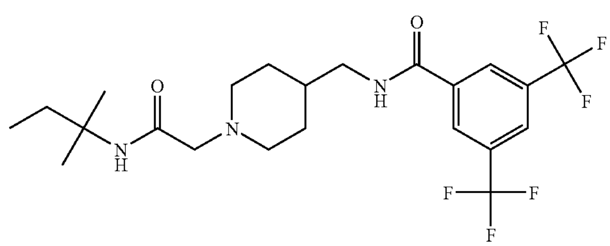 [SMILES: CCC(C)(C)NC(=O)CN1CCC(CNC(=O)c2cc(C(F)(F)F)cc(C(F)(F)F)c2)CC1] | 482.48 |
| 347 | N-((1-(2-(1,3-dimethoxypropan-2-ylamino)-2-oxoethyl)piperidin-4-yl)methyl)-3,5-bis(trifluoromethyl)benzamide | 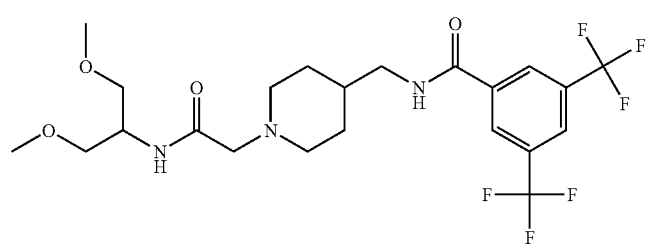 [SMILES: COCC(COC)NC(=O)CN1CCC(CNC(=O)c2cc(C(F)(F)F)cc(C(F)(F)F)c2)CC1] | 514.48 |
| 348 | (S)-N-((1-(2-oxo-2-(3-(trifluoromethyl)pyrrolidin-1-yl)ethyl)piperidin-4-yl)methyl)-3,5-bis(trifluoromethyl)benzamide | 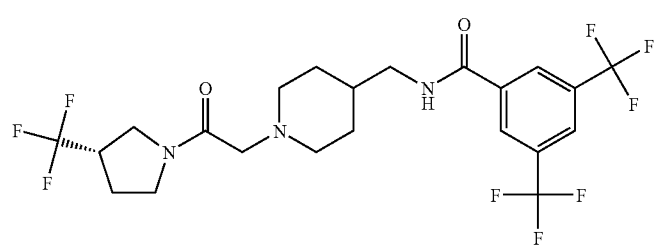 [SMILES: O=C(NCC1CCN(CC(=O)N2CC[C@H](C(F)(F)F)C2)CC1)c1cc(C(F)(F)F)cc(C(F)(F)F)c1] | 534.43 |

TABLE 1-continued

| Cmpd No. | Name | Mass Spec (m/z) |
|---|---|---|
| 349 | N-((1-(2-(4-fluoropiperidin-1-yl)-2-oxoethyl)piperidin-4-yl)methyl)-3,5-bis(trifluoromethyl)benzamide | 498.45 |
| 350 | 3-fluoro-N-((1-(2-(isopropylamino)-2-oxoethyl)piperidin-4-yl)methyl)-5-(trifluoromethyl)benzamide | 404.42 |
| 351 | 3-fluoro-N-((1-(2-oxo-2-(propylamino)ethyl)piperidin-4-yl)methyl)-5-(trifluoromethyl)benzamide | 404.42 |
| 352 | 3-fluoro-N-((1-(2-(1-methylcyclobutyl-amino)-2-oxoethyl)piperidin-4-yl)methyl)-5-(trifluoromethyl)benzamide | 430.46 |
| 353 | 3-fluoro-N-((1-(2-oxo-2-(tert-pentylamino)ethyl)piperidin-4-yl)methyl)-5-(trifluoromethyl)benzamide | 432.47 |
| 354 | N-((1-(2-(1,3-dimethoxypropan-2-ylamino)-2-oxoethyl)piperidin-4-yl)methyl)-3-fluoro-5-(trifluoromethyl)benzamide | 464.47 |
| 355 | (S)-3-fluoro-N-((1-(2-oxo-2-(3-(trifluoromethyl)pyrrolidin-1-yl)ethyl)piperidin-4-yl)methyl)-5-(trifluoromethyl)benzamide | 484.43 |

TABLE 1-continued

| Cmpd No. | Name | Structure | Mass Spec (m/z) |
|---|---|---|---|
| 356 | 3-fluoro-N-((1-(2-(4-fluoropiperidin-1-yl)-2-oxoethyl)piperidin-4-yl)methyl)-5-(trifluoromethyl)benzamide | 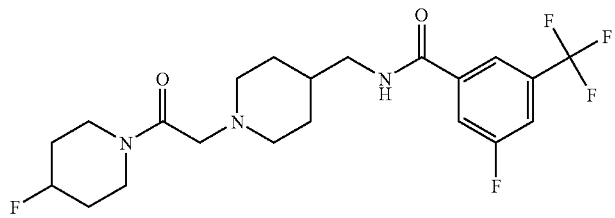 [SMILES: O=C(NCC1CCN(CC(=O)N2CCC(F)CC2)CC1)c1cc(F)cc(C(F)(F)F)c1] | 448.45 |
| 357 | N-((1-((1-(methylsulfonamido)cyclopropyl)methyl)piperidin-4-yl)methyl)-3,5-bis(trifluoromethyl)benzamide | 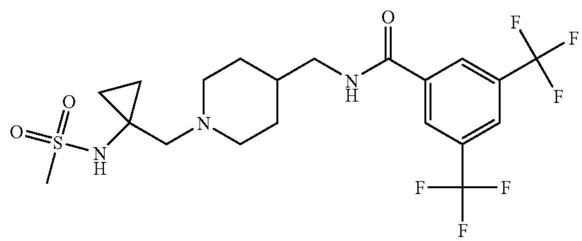 [SMILES: CS(=O)(=O)NC1(CN2CCC(CNC(=O)c3cc(C(F)(F)F)cc(C(F)(F)F)c3)CC2)CC1] | 502.49 |
| 358 | N-((1-((1-(ethylsulfonamido)cyclopropyl)methyl)piperidin-4-yl)methyl)-3,5-bis(trifluoromethyl)benzamide | 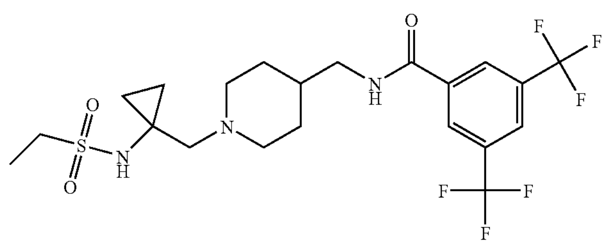 [SMILES: CCS(=O)(=O)NC1(CN2CCC(CNC(=O)c3cc(C(F)(F)F)cc(C(F)(F)F)c3)CC2)CC1] | 516.52 |
| 359 | N-((1-((1-(cyclopropanesulfonamido)cyclopropyl)methyl)piperidin-4-yl)methyl)-3,5-bis(trifluoromethyl)benzamide | 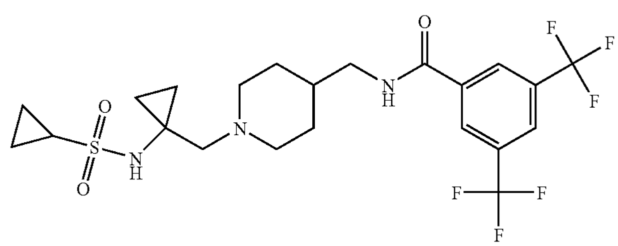 [SMILES: O=C(NCC1CCN(CC2(NS(=O)(=O)C3CC3)CC2)CC1)c1cc(C(F)(F)F)cc(C(F)(F)F)c1] | 528.53 |
| 360 | 3,5-bis(trifluoromethyl)-N-((1-((1-(3,3,3-trifluoropropylsulfonamido)cyclopropyl)methyl)piperidin-4-yl)methyl)benzamide | 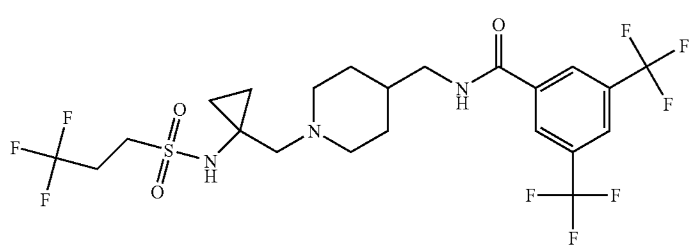 [SMILES: O=C(NCC1CCN(CC2(NS(=O)(=O)CCC(F)(F)F)CC2)CC1)c1cc(C(F)(F)F)cc(C(F)(F)F)c1] | 584.51 |
| 361 | N-((1-((1-pivalamidocyclopropyl)methyl)piperidin-4-yl)methyl)-3,5-bis(trifluoromethyl)benzamide | 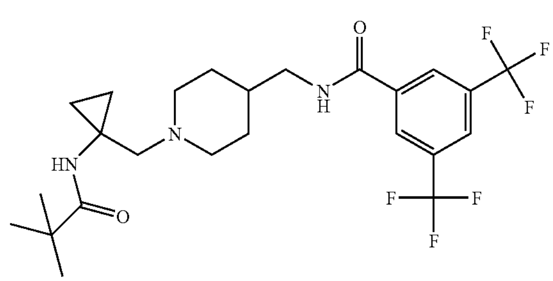 [SMILES: CC(C)(C)C(=O)NC1(CN2CCC(CNC(=O)c3cc(C(F)(F)F)cc(C(F)(F)F)c3)CC2)CC1] | 508.52 |

TABLE 1-continued

| Cmpd No. | Name | Structure | Mass Spec (m/z) |
|---|---|---|---|
| 362 | N-((1-(2-(tert-butylamino)-2-oxoethyl)piperidin-4-yl)methyl)-3,5-dimethylbenzamide | 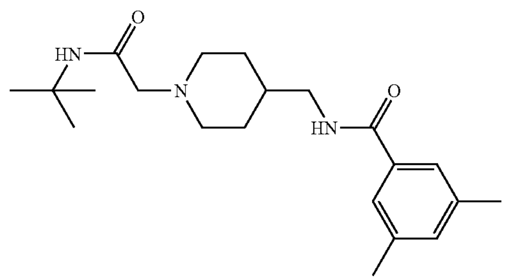 [SMILES: Cc1cc(C)cc(C(=O)NCC2CCN(CC(=O)NC(C)(C)C)CC2)c1] | 360.51 |
| 363 | N-((1-(2-(tert-butylamino)-2-oxoethyl)piperidin-4-yl)methyl)-3-fluoro-5-methylbenzamide | 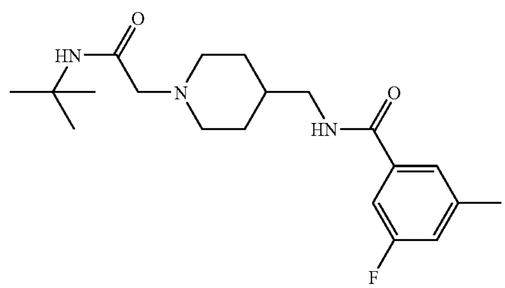 [SMILES: Cc1cc(F)cc(C(=O)NCC2CCN(CC(=O)NC(C)(C)C)CC2)c1] | 364.48 |
| 364 | N-((1-(2-(tert-butylamino)-2-oxoethyl)piperidin-4-yl)methyl)-3-chlorobenzamide | 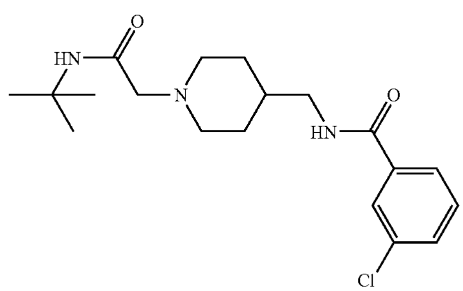 [SMILES: CC(C)(C)NC(=O)CN1CCC(CNC(=O)c2cccc(Cl)c2)CC1] | 366.90 |
| 365 | N-((1-(2-(tert-butylamino)-2-oxoethyl)piperidin-4-yl)methyl)-3,5-difluorobenzamide | 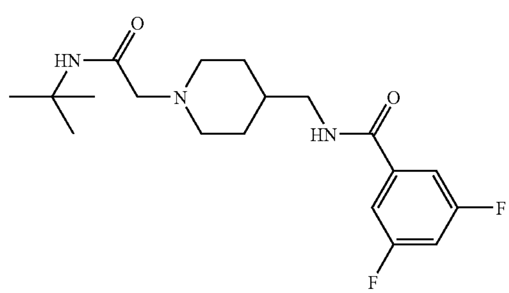 [SMILES: CC(C)(C)NC(=O)CN1CCC(CNC(=O)c2cc(F)cc(F)c2)CC1] | 368.44 |
| 366 | N-((1-(2-(tert-butylamino)-2-oxoethyl)piperidin-4-yl)methyl)-3-fluoro-5-methoxybenzamide | 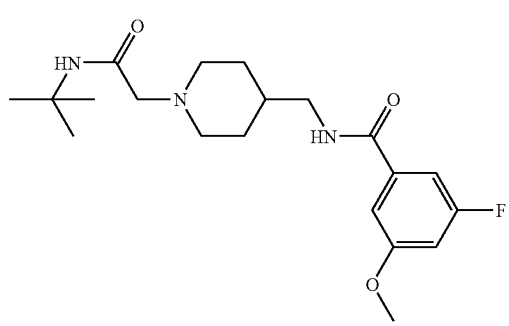 [SMILES: COc1cc(F)cc(C(=O)NCC2CCN(CC(=O)NC(C)(C)C)CC2)c1] | 380.48 |

TABLE 1-continued

| Cmpd No. | Name | Structure | Mass Spec (m/z) |
|---|---|---|---|
| 367 | N-((1-(2-(tert-butylamino)-2-oxoethyl)piperidin-4-yl)methyl)-3-chloro-5-fluorobenzamide | 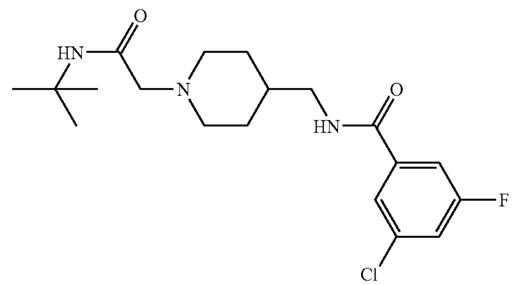 [SMILES: CC(C)(C)NC(=O)CN1CCC(CNC(=O)c2cc(F)cc(Cl)c2)CC1] | 384.89 |
| 368 | N-((1-(2-(tert-butylamino)-2-oxoethyl)piperidin-4-yl)methyl)-3,5-dimethoxybenzamide | 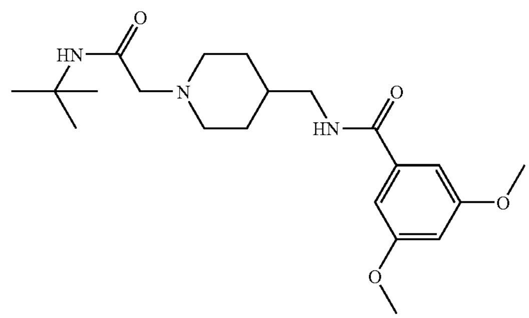 [SMILES: COc1cc(OC)cc(C(=O)NCC2CCN(CC(=O)NC(C)(C)C)CC2)c1] | 392.51 |
| 369 | (E)-N-((1-(2-(tert-butylamino)-2-oxoethyl)piperidin-4-yl)methyl)-3-(3,5-difluorophenyl)acrylamide | 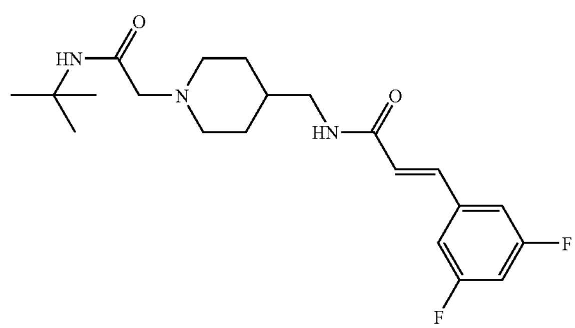 [SMILES: CC(C)(C)NC(=O)CN1CCC(CNC(=O)/C=C/c2cc(F)cc(F)c2)CC1] | 394.48 |
| 370 | N-((1-(2-(tert-butylamino)-2-oxoethyl)piperidin-4-yl)methyl)-3,5-dichlorobenzamide | 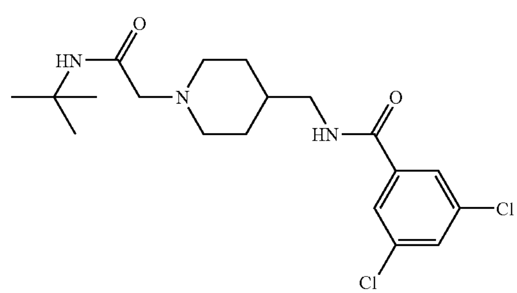 [SMILES: CC(C)(C)NC(=O)CN1CCC(CNC(=O)c2cc(Cl)cc(Cl)c2)CC1] | 401.35 |
| 371 | N-((1-(2-(tert-butylamino)-2-oxoethyl)piperidin-4-yl)methyl)-3-(trifluoromethyl)benzamide | 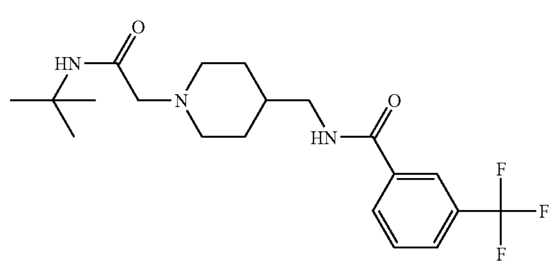 [SMILES: CC(C)(C)NC(=O)CN1CCC(CNC(=O)c2cccc(C(F)(F)F)c2)CC1] | 400.46 |

TABLE 1-continued

| Cmpd No. | Name | Structure | Mass Spec (m/z) |
|---|---|---|---|
| 372 | N-((1-(2-(tert-butylamino)-2-oxoethyl)piperidin-4-yl)methyl)-4-(trifluoromethyl)picolinamide | 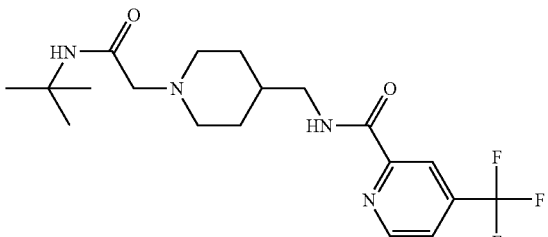 | 401.44 |
| 373 | N-((1-(2-(tert-butylamino)-2-oxoethyl)piperidin-4-yl)methyl)-2-(pyrrolidin-1-yl)isonicotinamide | 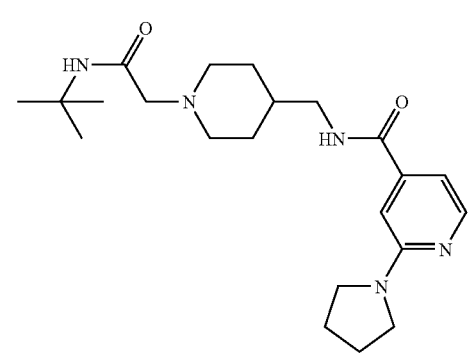 [SMILES: CC(C)(C)NC(=O)CN1CCC(CNC(=O)c2ccnc(N3CCCC3)c2)CC1] | 402.55 |
| 374 | 3-bromo-N-((1-(2-(tert-butylamino)-2-oxoethyl)piperidin-4-yl)methyl)benzamide | 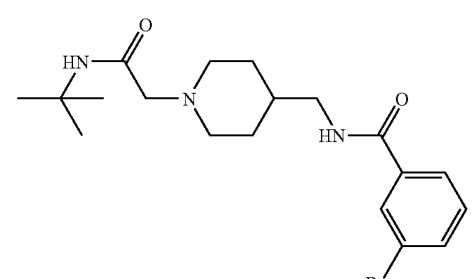 | 411.36 |
| 375 | N-((1-(2-(tert-butylamino)-2-oxoethyl)piperidin-4-yl)methyl)-3-(trifluoromethoxy)benzamide | 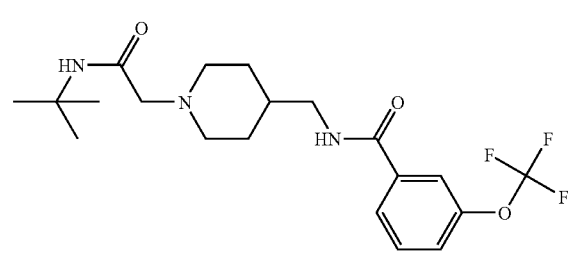 [SMILES: CC(C)(C)NC(=O)CN1CCC(CNC(=O)c2cccc(OC(F)(F)F)c2)CC1] | 416.46 |
| 376 | N-((1-(2-(tert-butylamino)-2-oxoethyl)piperidin-4-yl)methyl)-3-fluoro-5-(trifluoromethyl)benzamide | 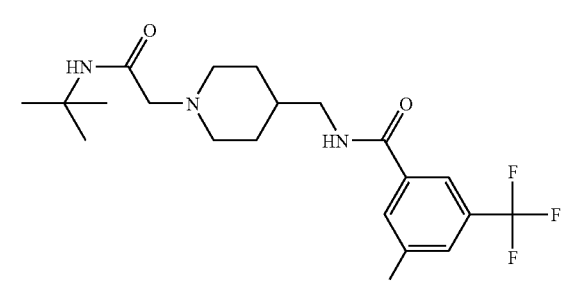 | 418.45 |

TABLE 1-continued

| Cmpd No. | Name | Structure | Mass Spec (m/z) |
|---|---|---|---|
| 377 | N-((1-(2-(tert-butylamino)-2-oxoethyl)piperidin-4-yl)methyl)-3,5-diethoxybenzamide | 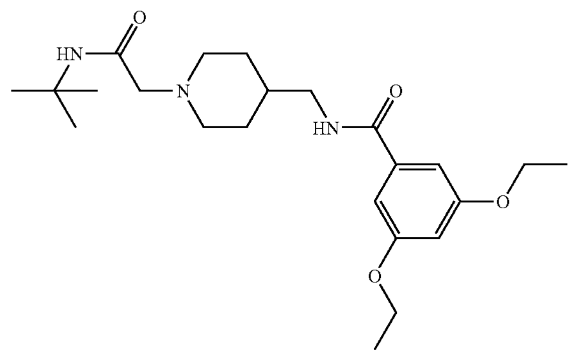 [SMILES: CCOc1cc(OCC)cc(C(=O)NCC2CCN(CC(=O)NC(C)(C)C)CC2)c1] | 420.57 |
| 378 | (E)-N-((1-(2-(tert-butylamino)-2-oxoethyl)piperidin-4-yl)methyl)-3-(3,5-dichlorophenyl)acrylamide | 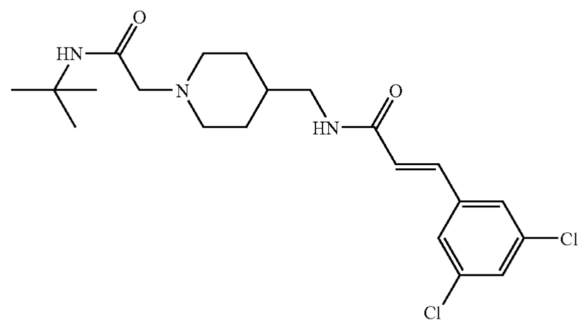 [SMILES: CC(C)(C)NC(=O)CN1CCC(CNC(=O)/C=C/c2cc(Cl)cc(Cl)c2)CC1] | 427.39 |
| 379 | N-((1-(2-(tert-butylamino)-2-oxoethyl)piperidin-4-yl)methyl)-3-methoxy-5-(trifluoromethyl)benzamide | 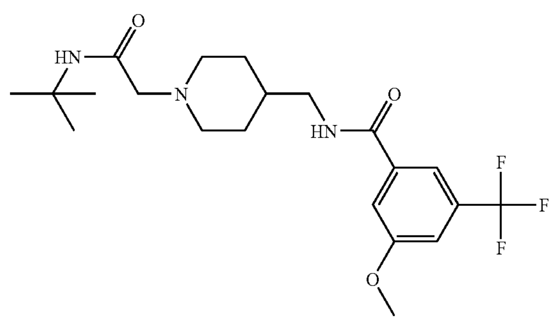 [SMILES: COc1cc(C(=O)NCC2CCN(CC(=O)NC(C)(C)C)CC2)cc(C(F)(F)F)c1] | 430.48 |
| 380 | N-((1-(2-(tert-butylamino)-2-oxoethyl)piperidin-4-yl)methyl)-3-chloro-5-(trifluoromethyl)benzamide | 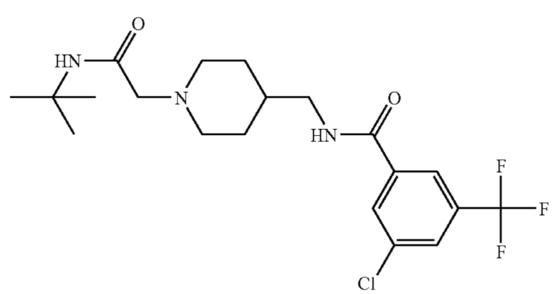 [SMILES: CC(C)(C)NC(=O)CN1CCC(CNC(=O)c2cc(Cl)cc(C(F)(F)F)c2)CC1] | 434.90 |
| 381 | 3-bromo-N-((1-(2-(tert-butylamino)-2-oxoethyl)piperidin-4-yl)methyl)-5-chlorobenzamide | 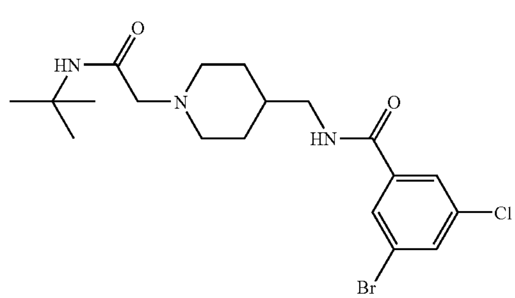 [SMILES: CC(C)(C)NC(=O)CN1CCC(CNC(=O)c2cc(Cl)cc(Br)c2)CC1] | 445.81 |

TABLE 1-continued

| Cmpd No. | Name | Structure | Mass Spec (m/z) |
|---|---|---|---|
| 382 | 3-bromo-N-((1-(2-(tert-butylamino)-2-oxoethyl)piperidin-4-yl)methyl)-5-(trifluoromethyl)benzamide | 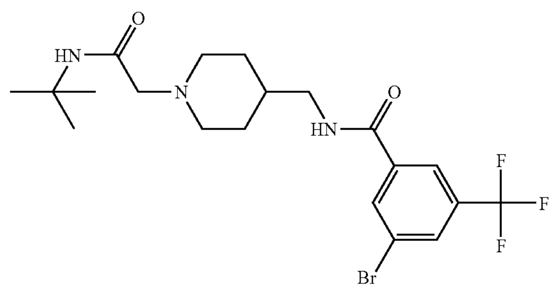 [SMILES: CC(C)(C)NC(=O)CN1CCC(CNC(=O)c2cc(Br)cc(C(F)(F)F)c2)CC1] | 479.36 |
| 383 | 2-(3,5-bis(trifluoromethyl)phenyl)-N-((1-(2-(tert-butylamino)-2-oxoethyl)piperidin-4-yl)methyl)acetamide | 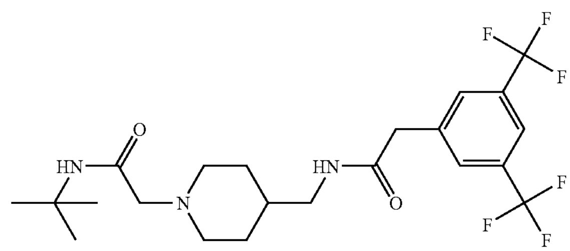 [SMILES: CC(C)(C)NC(=O)CN1CCC(CNC(=O)Cc2cc(C(F)(F)F)cc(C(F)(F)F)c2)CC1] | 482.48 |
| 384 | 3,5-dibromo-N-((1-(2-(tert-butylamino)-2-oxoethyl)piperidin-4-yl)methyl)benzamide | 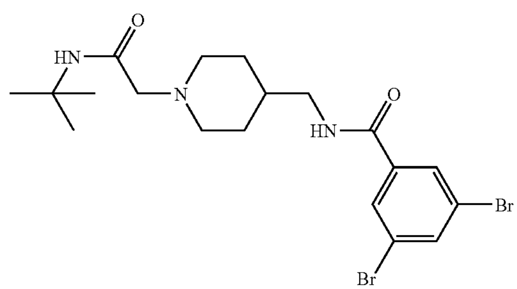 [SMILES: CC(C)(C)NC(=O)CN1CCC(CNC(=O)c2cc(Br)cc(Br)c2)CC1] | 490.26 |
| 385 | 3-chloro-5-fluoro-N-((1-(2-(1-methylethylsulfonamido)ethyl)piperidin-4-yl)methyl)benzamide | 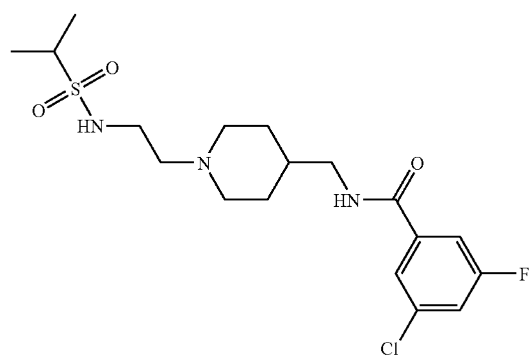 [SMILES: CC(C)S(=O)(=O)NCCN1CCC(CNC(=O)c2cc(F)cc(Cl)c2)CC1] | 420.95 |
| 386 | 3-bromo-N-((1-(2-(1-methylethyl-sulfonamido)ethyl)piperidin-4-yl)methyl)benzamide | 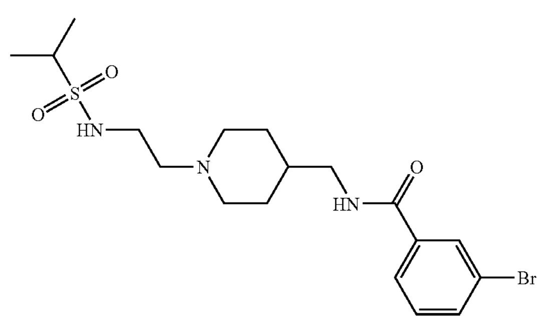 [SMILES: CC(C)S(=O)(=O)NCCN1CCC(CNC(=O)c2cccc(Br)c2)CC1] | 447.41 |

TABLE 1-continued

| Cmpd No. | Name | Structure | Mass Spec (m/z) |
|---|---|---|---|
| 387 | N-((1-(2-(cyclopropanesulfonamido)ethyl)piperidin-4-yl)methyl)-3-fluoro-4-(trifluoromethyl)benzamide | 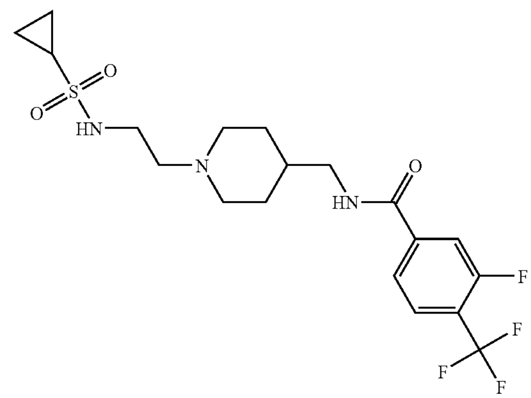 [SMILES: O=C(NCC1CCN(CCNS(=O)(=O)C2CC2)CC1)c1ccc(C(F)(F)F)c(F)c1] | 452.48 |
| 388 | 3,5-dibromo-N-((1-(2-(trifluoromethyl-sulfonamido)ethyl)piperidin-4-yl)methyl)benzamide | 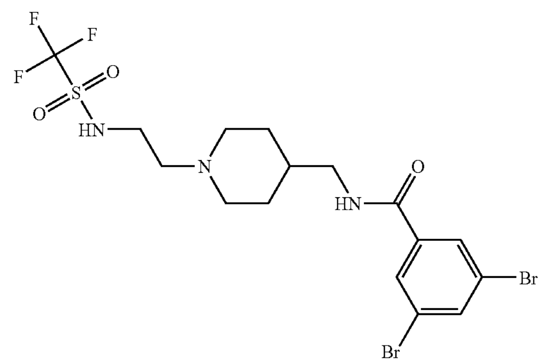 [SMILES: O=C(NCC1CCN(CCNS(=O)(=O)C(F)(F)F)CC1)c1cc(Br)cc(Br)c1] | 552.23 |
| 389 | 4-(trifluoromethoxy)-N-((1-(2-(trifluoromethylsulfonamido)ethyl)piperidin-4-yl)methyl)benzamide | 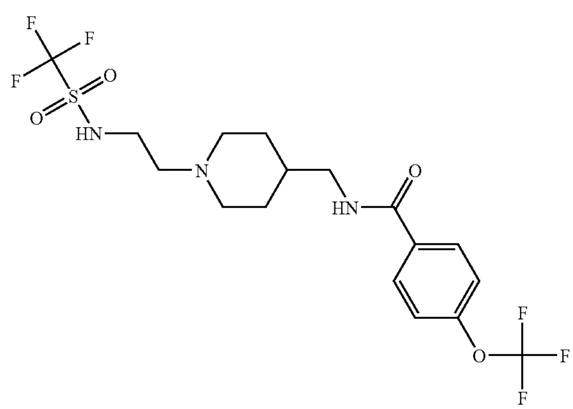 [SMILES: O=C(NCC1CCN(CCNS(=O)(=O)C(F)(F)F)CC1)c1ccc(OC(F)(F)F)cc1] | 478.42 |
| 390 | 3-chloro-N-((1-(2-(cyclopropane-sulfonamido)ethyl)piperidin-4-yl)methyl)-5-fluorobenzamide | 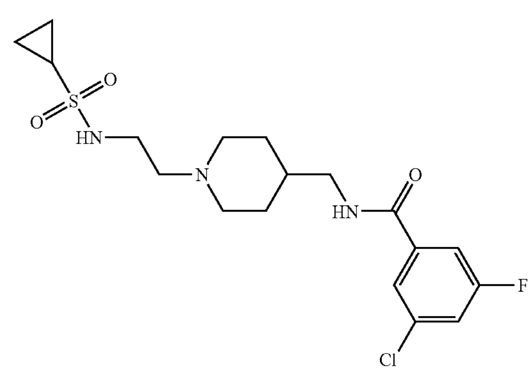 [SMILES: O=C(NCC1CCN(CCNS(=O)(=O)C2CC2)CC1)c1cc(F)cc(Cl)c1] | 418.93 |

TABLE 1-continued

| Cmpd No. | Name | Structure | Mass Spec (m/z) |
|---|---|---|---|
| 391 | N-(3-bromo-5-(trifluoromethyl)phenyl)-2-(1-(2-(1-methylethylsulfonamido)ethyl)piperidin-4-yl)acetamide | 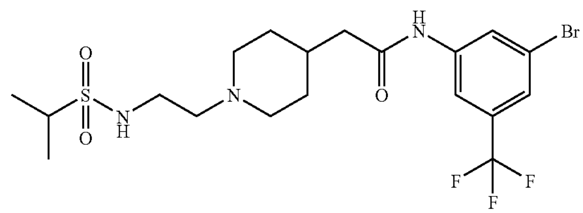 [SMILES: CC(C)S(=O)(=O)NCCN1CCC(CC(=O)Nc2cc(Br)cc(C(F)(F)F)c2)CC1] | 515.41 |
| 392 | N-((1-(2-(cyclopentanecarboxamido)ethyl)piperidin-4-yl)methyl)-3,5-dimethylbenzamide | 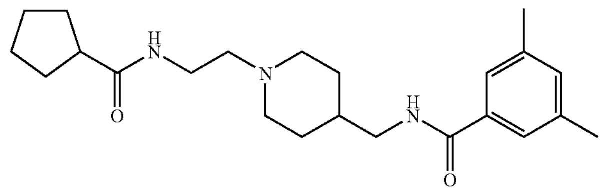 [SMILES: Cc1cc(C)cc(C(=O)NCC2CCN(CCNC(=O)C3CCCC3)CC2)c1] | 386.55 |
| 393 | N-((1-(2-(cyclopentanecarboxamido)ethyl)piperidin-4-yl)methyl)-3-fluoro-5-methylbenzamide | 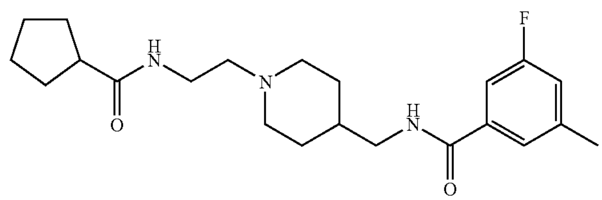 [SMILES: Cc1cc(F)cc(C(=O)NCC2CCN(CCNC(=O)C3CCCC3)CC2)c1] | 390.51 |
| 394 | 3-chloro-N-((1-(2-(cyclopentanecarboxamido)ethyl)piperidin-4-yl)methyl)benzamide | 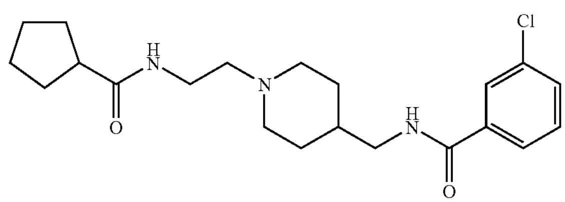 [SMILES: O=C(NCC1CCN(CCNC(=O)C2CCCC2)CC1)c1cccc(Cl)c1] | 392.94 |
| 395 | N-((1-(2-(cyclopentanecarboxamido)ethyl)piperidin-4-yl)methyl)-3,5-difluorobenzamide | 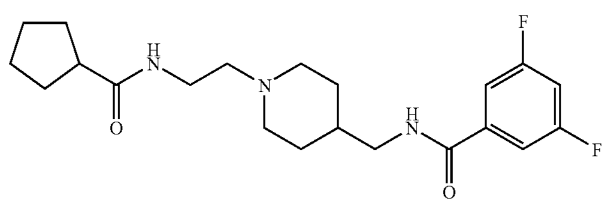 | 394.48 |
| 396 | N-((1-(2-(cyclopentanecarboxamido)ethyl)piperidin-4-yl)methyl)-3-fluoro-5-methoxybenzamide | 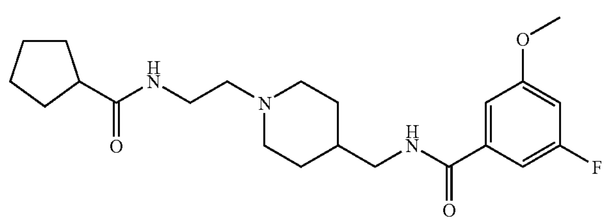 [SMILES: COc1cc(F)cc(C(=O)NCC2CCN(CCNC(=O)C3CCCC3)CC2)c1] | 406.51 |
| 397 | 3-chloro-N-((1-(2-(cyclopentanecarboxamido)ethyl)piperidin-4-yl)methyl)-5-fluorobenzamide | 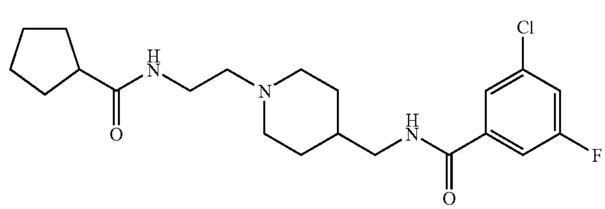 [SMILES: O=C(NCC1CCN(CCNC(=O)C2CCCC2)CC1)c1cc(F)cc(Cl)c1] | 410.93 |

TABLE 1-continued

| Cmpd No. | Name | Structure | Mass Spec (m/z) |
|---|---|---|---|
| 398 | N-((1-(2-(cyclopentanecarboxamido)ethyl)piperidin-4-yl)methyl)-3-(trifluoromethyl)benzamide | 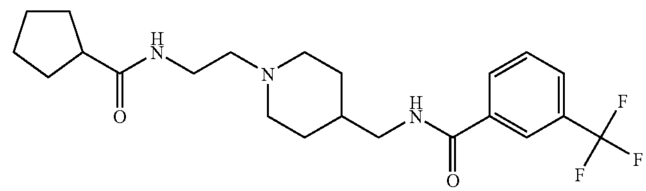 [SMILES: O=C(NCC1CCN(CCNC(=O)C2CCCC2)CC1)c1cccc(C(F)(F)F)c1] | 426.49 |
| 399 | N-((1-(2-(cyclopentanecarboxamido)ethyl)piperidin-4-yl)methyl)-2-(pyrrolidin-1-yl)isonicotinamide | 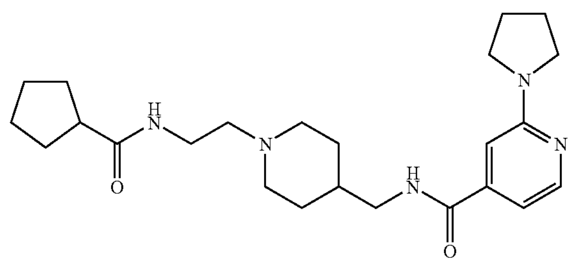 [SMILES: O=C(NCC1CCN(CCNC(=O)C2CCCC2)CC1)c1ccnc(N2CCCC2)c1] | 428.59 |
| 400 | 3-bromo-N-((1-(2-(cyclopentanecarboxamido)ethyl)piperidin-4-yl)methyl)benzamide | 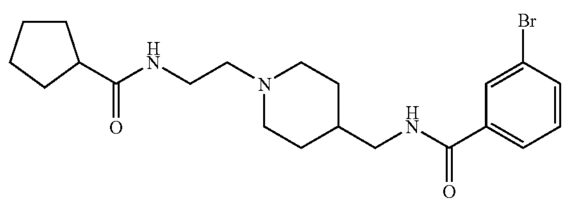 | 437.40 |
| 401 | N-((1-(2-(cyclopentanecarboxamido)ethyl)piperidin-4-yl)methyl)-3-(trifluoromethoxy)benzamide | 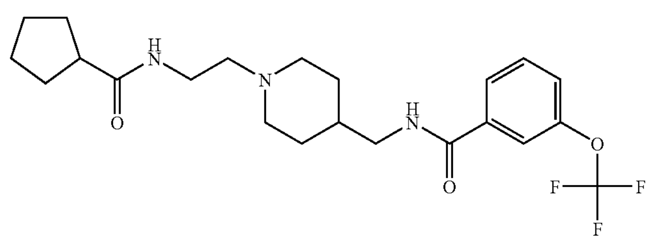 [SMILES: O=C(NCC1CCN(CCNC(=O)C2CCCC2)CC1)c1cccc(OC(F)(F)F)c1] | 442.49 |
| 402 | N-((1-(2-(cyclopentanecarboxamido)ethyl)piperidin-4-yl)methyl)-3-fluoro-5-(trifluoromethyl)benzamide | 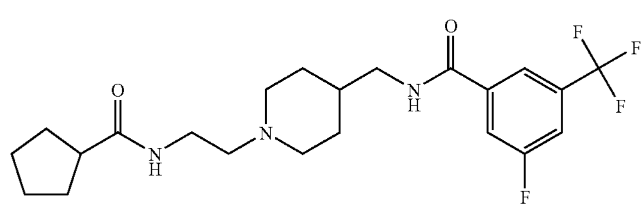 [SMILES: O=C(NCC1CCN(CCNC(=O)C2CCCC2)CC1)c1cc(F)cc(C(F)(F)F)c1] | 444.48 |
| 403 | N-((1-(2-(cyclopentanecarboxamido)ethyl)piperidin-4-yl)methyl)-3,5-diethoxybenzamide | 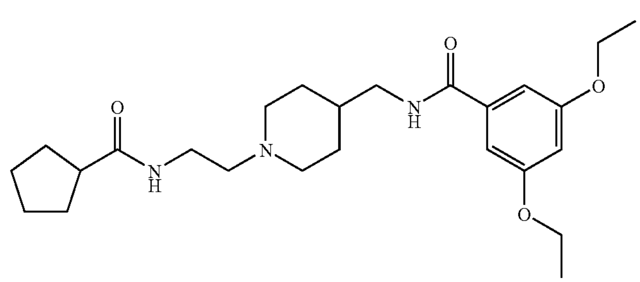 [SMILES: CCOc1cc(OCC)cc(C(=O)NCC2CCN(CCNC(=O)C3CCCC3)CC2)c1] | 446.60 |

TABLE 1-continued

| Cmpd No. | Name | Structure | Mass Spec (m/z) |
|---|---|---|---|
| 404 | N-((1-(2-(cyclopentanecarboxamido)ethyl)piperidin-4-yl)methyl)-3-methoxy-5-(trifluoromethyl)benzamide | 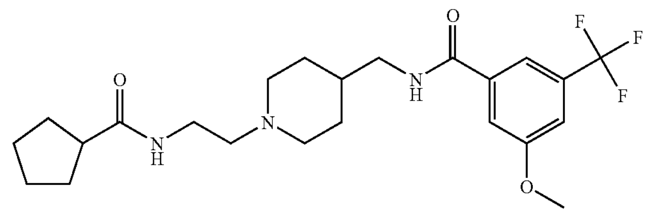 [SMILES: COc1cc(C(=O)NCC2CCN(CCNC(=O)C3CCCC3)CC2)cc(C(F)(F)F)c1] | 456.52 |
| 405 | 3-chloro-N-((1-(2-(cyclopentane-carboxamido)ethyl)piperidin-4-yl)methyl)-5-(trifluoromethyl)benzamide | 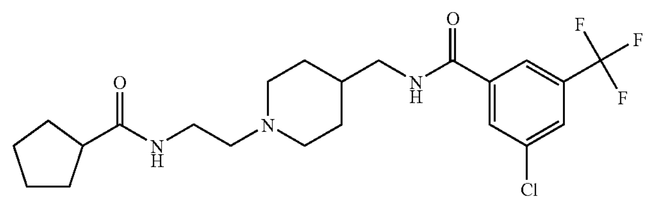 [SMILES: O=C(NCC1CCN(CCNC(=O)C2CCCC2)CC1)c1cc(Cl)cc(C(F)(F)F)c1] | 460.94 |
| 406 | 3-bromo-5-chloro-N-((1-(2-(cyclopentane-carboxamido)ethyl)piperidin-4-yl)methyl)benzamide | 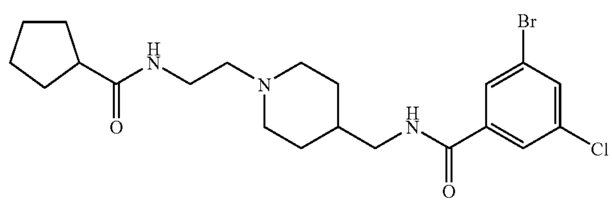 [SMILES: O=C(NCC1CCN(CCNC(=O)C2CCCC2)CC1)c1cc(Cl)cc(Br)c1] | 471.84 |
| 407 | 3-bromo-N-((1-(2-(cyclopentane-carboxamido)ethyl)piperidin-4-yl)methyl)-5-(trifluoromethyl)benzamide | 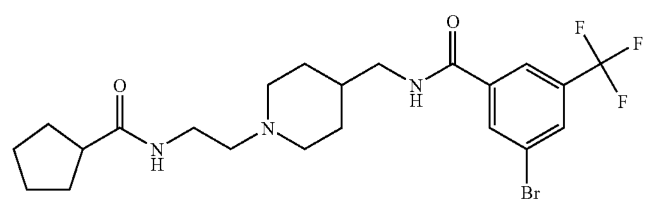 [SMILES: O=C(NCC1CCN(CCNC(=O)C2CCCC2)CC1)c1cc(Br)cc(C(F)(F)F)c1] | 505.40 |
| 408 | N-(2-(4-((2-(3,5-bis(trifluoromethyl)phenyl)acetamido)methyl)piperidin-1-yl)ethyl)cyclopentanecarboxamide | 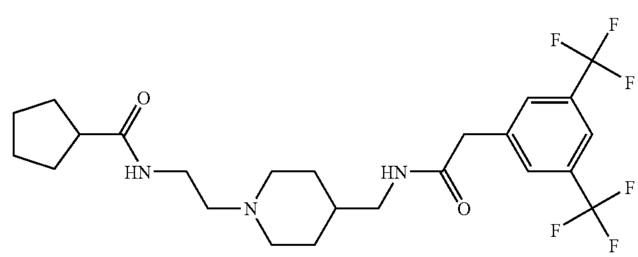 [SMILES: O=C(Cc1cc(C(F)(F)F)cc(C(F)(F)F)c1)NCC1CCN(CCNC(=O)C2CCCC2)CC1] | 508.52 |
| 409 | 3,5-dibromo-N-((1-(2-(cyclopentane-carboxamido)ethyl)piperidin-4-yl)methyl)benzamide | 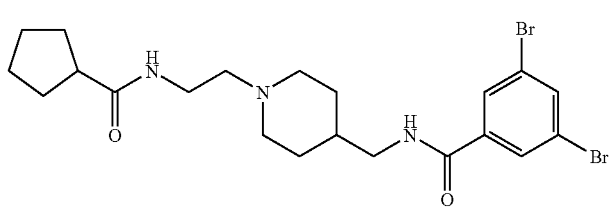 [SMILES: O=C(NCC1CCN(CCNC(=O)C2CCCC2)CC1)c1cc(Br)cc(Br)c1] | 516.30 |

TABLE 1-continued

| Cmpd No. | Name | Mass Spec (m/z) |
|---|---|---|
| 410 | (S)-N-tert-butyl-2-((4-((3-fluoro-5-(trifluoromethyl)benzamido)methyl)piperidin-1-yl)methyl)pyrrolidine-1-carboxamide | 487.55 |
| 411 | N-((1-(2-(3-tert-butylureido)ethyl)piperidin-4-yl)methyl)-3-fluoro-N-methyl-5-(trifluoromethyl)benzamide | 461.52 |
| 412 | 3-fluoro-N-methyl-N-((1-(2-pivalamidoethyl)piperidin-4-yl)methyl)-5-(trifluoromethyl)benzamide | 446.50 |
| 413 | N-((1-(2-(3,3-dimethylbutanamido)ethyl)piperidin-4-yl)methyl)-3-fluoro-N-methyl-5-(trifluoromethyl)benzamide | 460.53 |
| 414 | N-((1-(2-(cyclopentanecarboxamido)ethyl)piperidin-4-yl)methyl)-3-fluoro-N-methyl-5-(trifluoromethyl)benzamide | 458.51 |
| 415 | 3-fluoro-N-methyl-N-((1-(2-(4,4,4-trifluorobutanamido)ethyl)piperidin-4-yl)methyl)-5-(trifluoromethyl)benzamide | 486.44 |
| 416 | (S)-3-fluoro-N-((1-((1-(methylsulfonyl)pyrrolidin-2-yl)methyl)piperidin-4-yl)methyl)-5-(trifluoromethyl)benzamide | 466.51 |

TABLE 1-continued

| Cmpd No. | Name | Structure | Mass Spec (m/z) |
|---|---|---|---|
| 417 | (S)-N-((1-((1-(ethylsulfonyl)pyrrolidin-2-yl)methyl)piperidin-4-yl)methyl)-3-fluoro-5-(trifluoromethyl)benzamide | 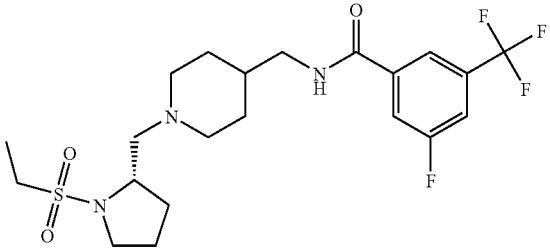 [SMILES: CCS(=O)(=O)N1CCC[C@H]1CN1CCC(CNC(=O)c2cc(F)cc(C(F)(F)F)c2)CC1] | 480.54 |
| 418 | (S)-N-((1-((1-(cyclopropylsulfonyl)pyrrolidin-2-yl)methyl)piperidin-4-yl)methyl)-3-fluoro-5-(trifluoromethyl)benzamide | 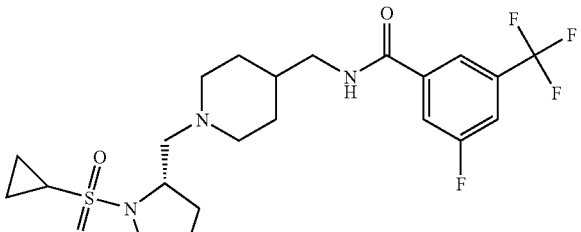 | 492.55 |
| 419 | (S)-N-((1-((1-(cyclobutylsulfonyl)pyrrolidin-2-yl)methyl)piperidin-4-yl)methyl)-3-fluoro-5-(trifluoromethyl)benzamide | 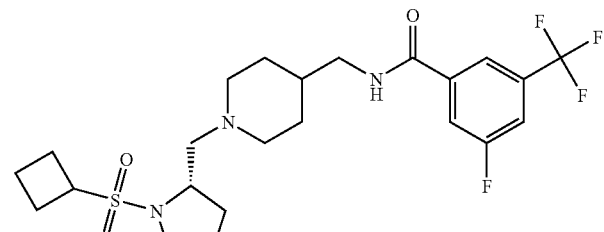 | 506.57 |
| 420 | (S)-N-((1-((1-(cyclopentylsulfonyl)pyrrolidin-2-yl)methyl)piperidin-4-yl)methyl)-3-fluoro-5-(trifluoromethyl)benzamide | 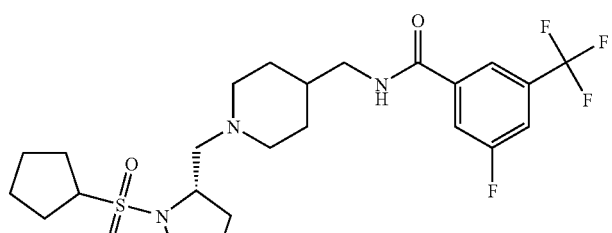 | 520.60 |
| 421 | (S)-N-((1-((1-(cyclopropylmethylsulfonyl)pyrrolidin-2-yl)methyl)piperidin-4-yl)methyl)-3-fluoro-5-(trifluoromethyl)benzamide | 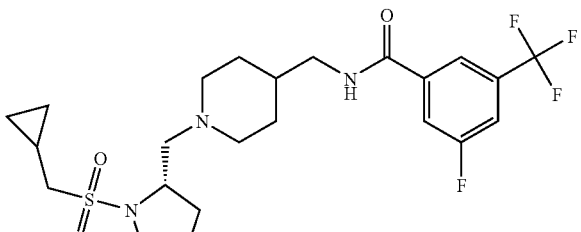 | 506.57 |

TABLE 1-continued

| Cmpd No. | Name | Structure | Mass Spec (m/z) |
|---|---|---|---|
| 422 | (S)-3-fluoro-5-(trifluoromethyl)-N-((1-((1-(3,3,3-trifluoropropylsulfonyl)pyrrolidin-2-yl)methyl)piperidin-4-yl)methyl)benzamide | 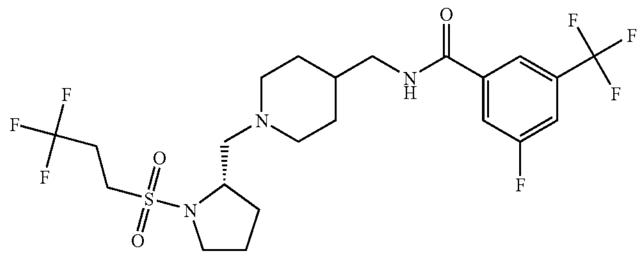 [SMILES: O=C(NCC1CCN(C[C@@H]2CCCN2S(=O)(=O)CCC(F)(F)F)CC1)c1cc(F)cc(C(F)(F)F)c1] | 548.53 |
| 423 | (S)-3-fluoro-N-((1-((1-pivaloylpyrrolidin-2-yl)methyl)piperidin-4-yl)methyl)-5-(trifluoromethyl)benzamide | 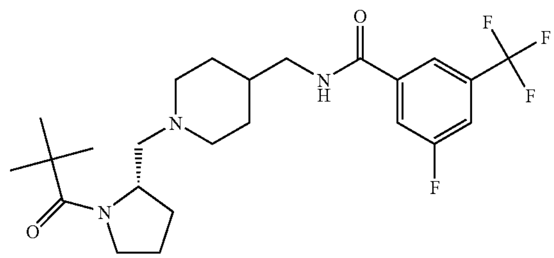 [SMILES: CC(C)(C)C(=O)N1CCC[C@H]1CN1CCC(CNC(=O)c2cc(F)cc(C(F)(F)F)c2)CC1] | 472.54 |
| 424 | (S)-N-((1-((1-(3,3-dimethylbutanoyl)pyrrolidin-2-yl)methyl)piperidin-4-yl)methyl)-3-fluoro-5-(trifluoromethyl)benzamide | 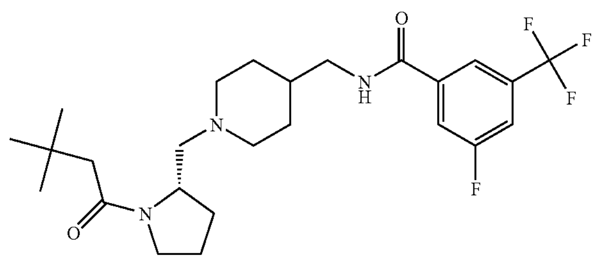 [SMILES: CC(C)(C)CC(=O)N1CCC[C@H]1CN1CCC(CNC(=O)c2cc(F)cc(C(F)(F)F)c2)CC1] | 486.57 |
| 425 | (S)-N-((1-((1-(cyclopentanecarbonyl)pyrrolidin-2-yl)methyl)piperidin-4-yl)methyl)-3-fluoro-5-(trifluoromethyl)benzamide | 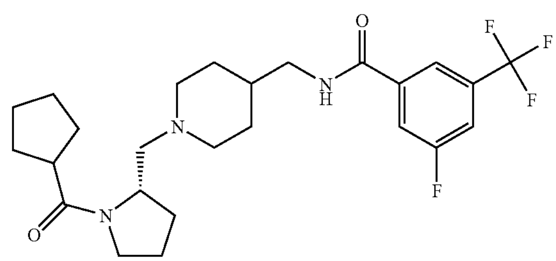 [SMILES: O=C(NCC1CCN(C[C@@H]2CCCN2C(=O)C2CCCC2)CC1)c1cc(F)cc(C(F)(F)F)c1] | 484.55 |
| 426 | (S)-3-fluoro-N-((1-((1-(4,4,4-trifluorobutanoyl)pyrrolidin-2-yl)methyl)piperidin-4-yl)methyl)-5-(trifluoromethyl)benzamide | 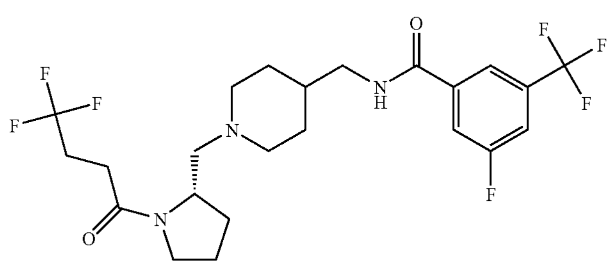 [SMILES: O=C(NCC1CCN(C[C@@H]2CCCN2C(=O)CCC(F)(F)F)CC1)c1cc(F)cc(C(F)(F)F)c1] | 512.48 |
| 427 | N-(3-fluoro-5-(trifluoromethyl)phenyl)-2-(1-(2-(2-methylpropylsulfonamido)ethyl)piperidin-4-yl)acetamide | 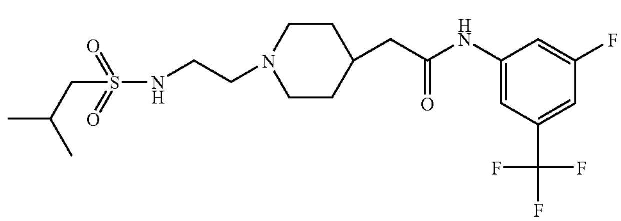 [SMILES: CC(C)CS(=O)(=O)NCCN1CCC(CC(=O)Nc2cc(F)cc(C(F)(F)F)c2)CC1] | 468.53 |

TABLE 1-continued

| Cmpd No. | Name | Structure | Mass Spec (m/z) |
|---|---|---|---|
| 428 | N-((1-(2-(tert-butylamino)-2-oxoethyl)piperidin-4-yl)methyl)-1-(4-chlorophenyl)cyclopentanecarboxamide | 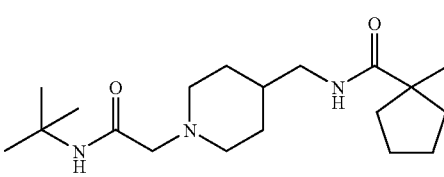 | 435.02 |
| 429 | 3-bromo-N-((1-(2-(tert-butylamino)-2-oxoethyl)piperidin-4-yl)methyl)-5-(trifluoromethoxy)benzamide | 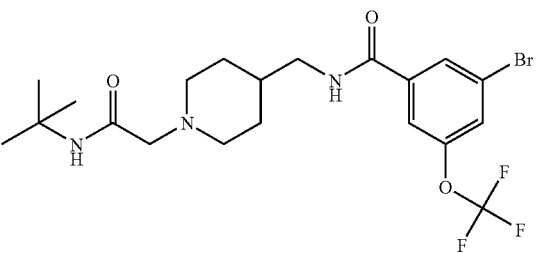 [SMILES: CC(C)(C)NC(=O)CN1CCC(CNC(=O)c2cc(Br)cc(OC(F)(F)F)c2)CC1] | 495.36 |
| 430 | N-((1-(2-(1-hydroxy-2-methylpropan-2-ylamino)-2-oxoethyl)piperidin-4-yl)methyl)-3,5-bis(trifluoromethyl)benzamide | 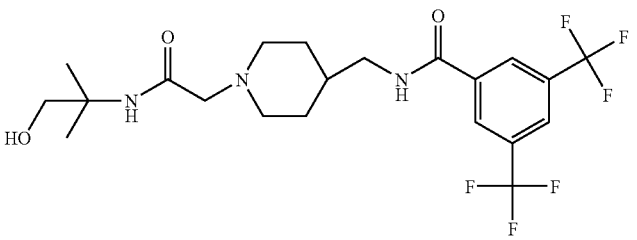 [SMILES: CC(C)(CO)NC(=O)CN1CCC(CNC(=O)c2cc(C(F)(F)F)cc(C(F)(F)F)c2)CC1] | 484.45 |
| 431 | N-((1-(2-(1-methylcyclohexylamino)-2-oxoethyl)piperidin-4-yl)methyl)-3,5-bis(trifluoromethyl)benzamide | 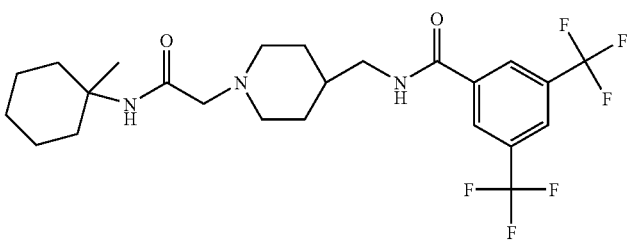 [SMILES: CC1(NC(=O)CN2CCC(CNC(=O)c3cc(C(F)(F)F)cc(C(F)(F)F)c3)CC2)CCCCC1] | 508.52 |
| 432 | N-((1-(2-(tert-butylamino)-2-oxoethyl)piperidin-4-yl)methyl)-1-phenylcyclopentanecarboxamide | 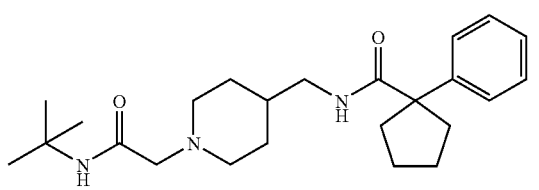 [SMILES: CC(C)(C)NC(=O)CN1CCC(CNC(=O)C2(c3ccccc3)CCCC2)CC1] | 400.58 |
| 433 | N-(2,6-dimethylphenyl)-2-(1-(2-(1-methylethylsulfonamido)ethyl)piperidin-4-yl)acetamide | 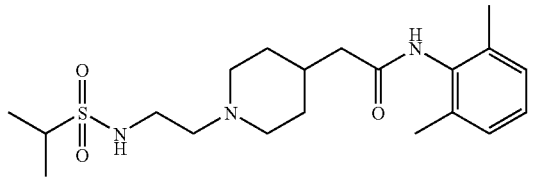 [SMILES: Cc1cccc(C)c1NC(=O)CC1CCN(CCNS(=O)(=O)C(C)C)CC1] | 396.57 |
| 434 | 3,5-bis(trifluoromethyl)-N-((1-(2-(1-(trifluoromethyl)cyclobutanecarboxamido)ethyl)piperidin-4-yl)methyl)benzamide | 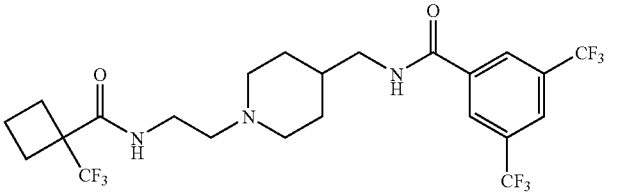 [SMILES: O=C(NCC1CCN(CCNC(=O)C2(C(F)(F)F)CCC2)CC1)c1cc(C(F)(F)F)cc(C(F)(F)F)c1] | 548.19 |

TABLE 1-continued

| Cmpd No. | Name | Structure | Mass Spec (m/z) |
|---|---|---|---|
| 435 | 3-fluoro-5-(trifluoromethyl)-N-((1-(2-(1-(trifluoromethyl)cyclobutanecarboxamido)ethyl)piperidin-4-yl)methyl)benzamide | 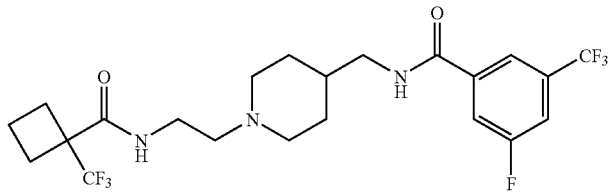 [SMILES: O=C(NCC1CCN(CCNC(=O)C2(C(F)(F)F)CCC2)CC1)c1cc(F)cc(C(F)(F)F)c1] | 498.19 |
| 436 | N-((1-(2-(isopropylamino)-2-oxoethyl)piperidin-4-yl)methyl)-3,5-dimethylbenzamide | 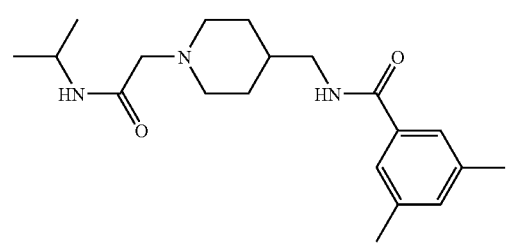 [SMILES: Cc1cc(C)cc(C(=O)NCC2CCN(CC(=O)NC(C)C)CC2)c1] | 346.24 |
| 437 | 3-fluoro-N-((1-(2-(isopropylamino)-2-oxoethyl)piperidin-4-yl)methyl)-5-methylbenzamide | 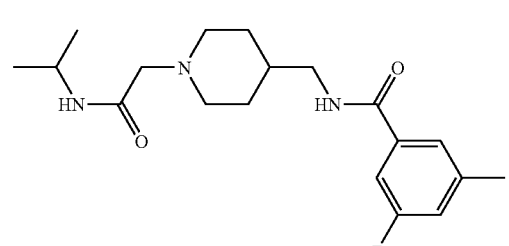 | 350.22 |
| 438 | 3-fluoro-N-((1-(2-(isopropylamino)-2-oxoethyl)piperidin-4-yl)methyl)-5-methoxybenzamide | 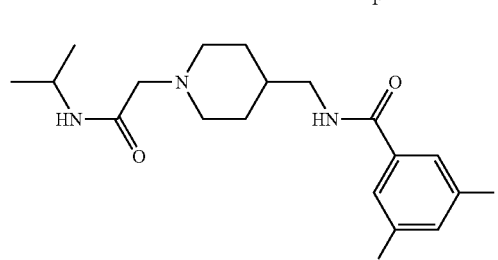 | 366.21 |
| 439 | N-((1-(2-(isopropylamino)-2-oxoethyl)piperidin-4-yl)methyl)-3,5-dimethoxybenzamide | 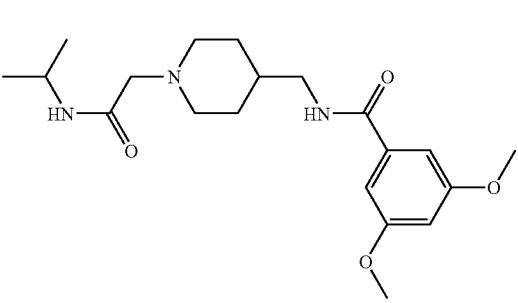 [SMILES: COc1cc(OC)cc(C(=O)NCC2CCN(CC(=O)NC(C)C)CC2)c1] | 378.23 |
| 440 | N-((1-(2-(isopropylamino)-2-oxoethyl)piperidin-4-yl)methyl)-3-(trifluoromethyl)benzamide | 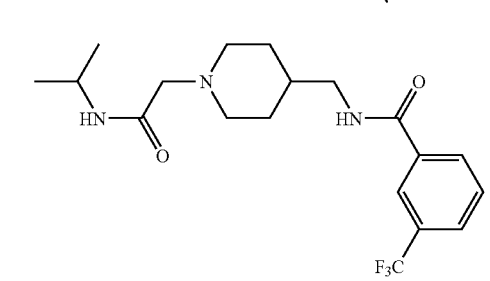 | 386.20 |

TABLE 1-continued

| Cmpd No. | Name | Structure | Mass Spec (m/z) |
|---|---|---|---|
| 441 | 3-bromo-N-((1-(2-(isopropylamino)-2-oxoethyl)piperidin-4-yl)methyl)benzamide | 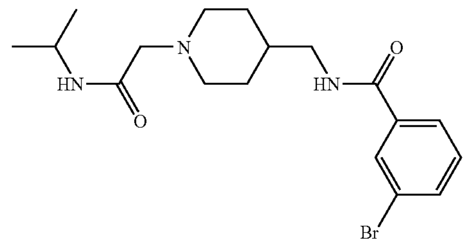 [SMILES: CC(C)NC(=O)CN1CCC(CNC(=O)c2cccc(Br)c2)CC1] | 396.12 |
| 442 | 3-chloro-N-((1-(2-(isopropylamino)-2-oxoethyl)piperidin-4-yl)methyl)benzamide | 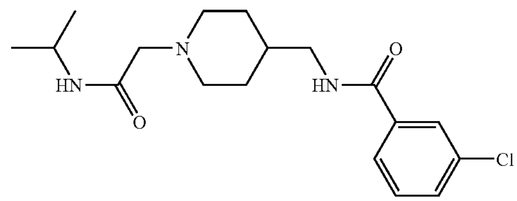 [SMILES: CC(C)NC(=O)CN1CCC(CNC(=O)c2cccc(Cl)c2)CC1] | 352.17 |
| 443 | 3-chloro-5-fluoro-N-((1-(2-(isopropylamino)-2-oxoethyl)piperidin-4-yl)methyl)benzamide | 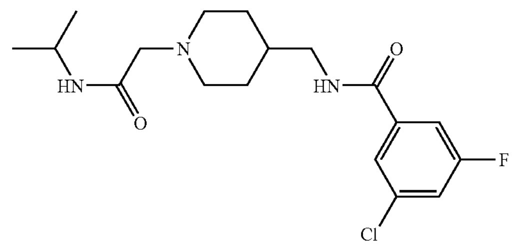 [SMILES: CC(C)NC(=O)CN1CCC(CNC(=O)c2cc(F)cc(Cl)c2)CC1] | 370.16 |
| 444 | N-((1-(2-(isopropylamino)-2-oxoethyl)piperidin-4-yl)methyl)-3-(trifluoromethoxy)benzamide | 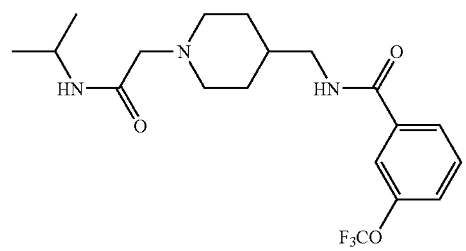 [SMILES: CC(C)NC(=O)CN1CCC(CNC(=O)c2cccc(OC(F)(F)F)c2)CC1] | 402.19 |
| 445 | 3,5-dimethyl-N-((1-(2-oxo-2-(propylamino)ethyl)piperidin-4-yl)methyl)benzamide | 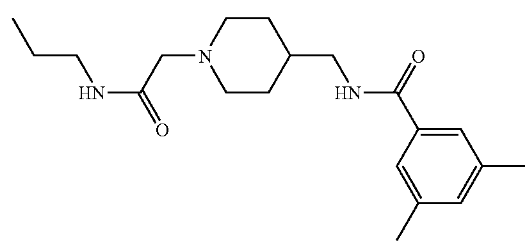 [SMILES: CCCNC(=O)CN1CCC(CNC(=O)c2cc(C)cc(C)c2)CC1] | 346.24 |
| 446 | 3-fluoro-5-methyl-N-((1-(2-oxo-2-(propylamino)ethyl)piperidin-4-yl)methyl)benzamide | 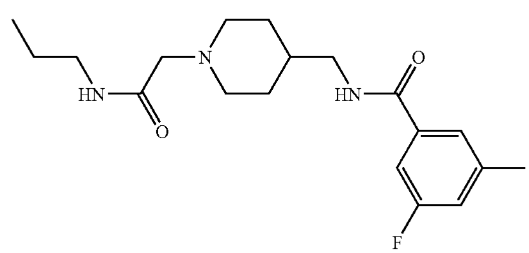 [SMILES: CCCNC(=O)CN1CCC(CNC(=O)c2cc(C)cc(F)c2)CC1] | 350.22 |

TABLE 1-continued

| Cmpd No. | Name | Structure | Mass Spec (m/z) |
|---|---|---|---|
| 447 | 3-fluoro-5-methoxy-N-((1-(2-oxo-2-(propylamino)ethyl)piperidin-4-yl)methyl)benzamide | 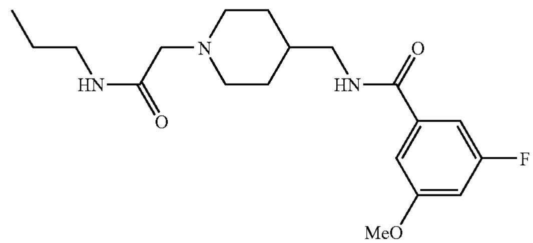 [SMILES: CCCNC(=O)CN1CCC(CNC(=O)c2cc(F)cc(OC)c2)CC1] | 366.21 |
| 448 | 3,5-dimethoxy-N-((1-(2-oxo-2-(propylamino)ethyl)piperidin-4-yl)methyl)benzamide | 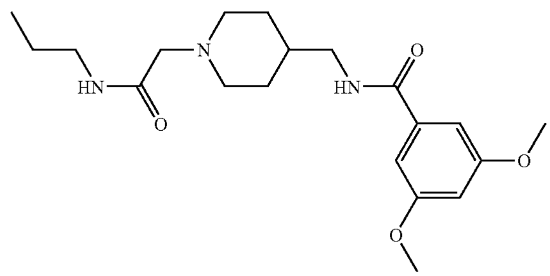 [SMILES: CCCNC(=O)CN1CCC(CNC(=O)c2cc(OC)cc(OC)c2)CC1] | 378.23 |
| 449 | N-((1-(2-oxo-2-(propylamino)ethyl)piperidin-4-yl)methyl)-3-(trifluoromethyl)benzamide | 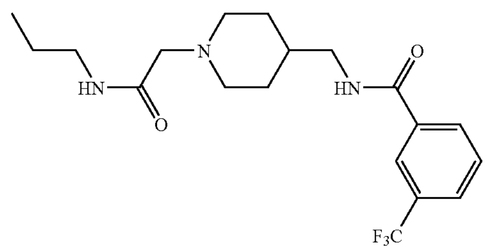 [SMILES: CCCNC(=O)CN1CCC(CNC(=O)c2cccc(C(F)(F)F)c2)CC1] | 386.20 |
| 450 | 3-bromo-N-((1-(2-oxo-2-(propylamino)ethyl)piperidin-4-yl)methyl)benzamide | 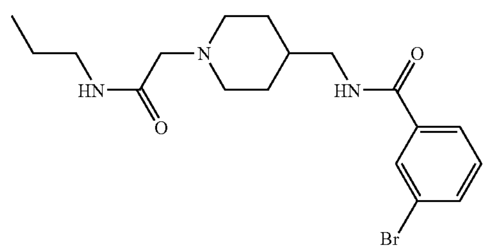 [SMILES: CCCNC(=O)CN1CCC(CNC(=O)c2cccc(Br)c2)CC1] | 396.12 |
| 451 | 3-chloro-N-((1-(2-oxo-2-(propylamino)ethyl)piperidin-4-yl)methyl)benzamide | 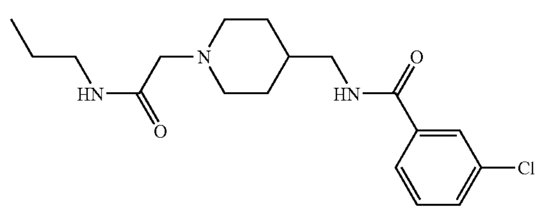 [SMILES: CCCNC(=O)CN1CCC(CNC(=O)c2cccc(Cl)c2)CC1] | 352.17 |
| 452 | 3-chloro-5-fluoro-N-((1-(2-oxo-2-(propylamino)ethyl)piperidin-4-yl)methyl)benzamide | 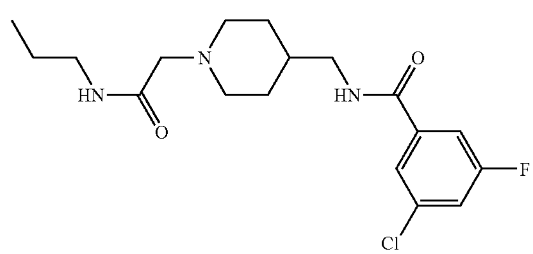 [SMILES: CCCNC(=O)CN1CCC(CNC(=O)c2cc(F)cc(Cl)c2)CC1] | 370.16 |

TABLE 1-continued

| Cmpd No. | Name | Structure | Mass Spec (m/z) |
|---|---|---|---|
| 453 | N-((1-(2-oxo-2-(propylamino)ethyl)piperidin-4-yl)methyl)-3-(trifluoromethoxy)benzamide | 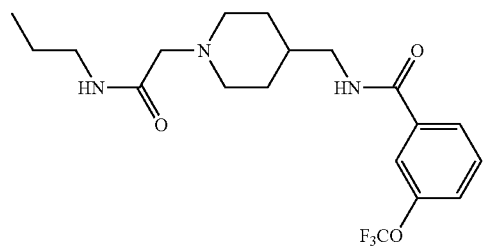 [SMILES: CCCNC(=O)CN1CCC(CNC(=O)c2cccc(OC(F)(F)F)c2)CC1] | 402.19 |
| 454 | 3,5-dimethyl-N-((1-(2-oxo-2-(1,1,1-trifluoro-2-methylpropan-2-ylamino)ethyl)piperidin-4-yl)methyl)benzamide | 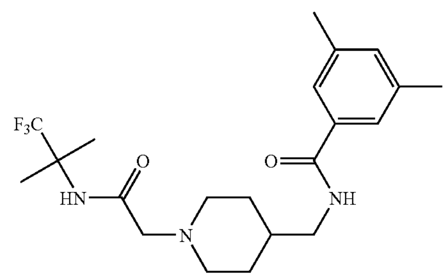 [SMILES: Cc1cc(C)cc(C(=O)NCC2CCN(CC(=O)NC(C)(C)C(F)(F)F)CC2)c1] | 414.23 |
| 455 | 3-fluoro-5-methyl-N-((1-(2-oxo-2-(1,1,1-trifluoro-2-methylpropan-2-ylamino)ethyl)piperidin-4-yl)methyl)benzamide | 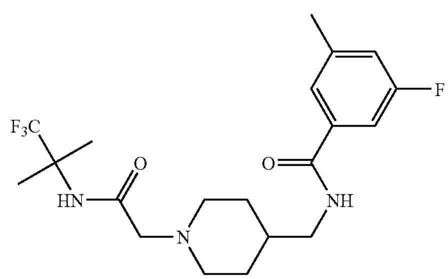 [SMILES: Cc1cc(F)cc(C(=O)NCC2CCN(CC(=O)NC(C)(C)C(F)(F)F)CC2)c1] | 418.20 |
| 456 | 3-fluoro-5-methoxy-N-((1-(2-oxo-2-(1,1,1-trifluoro-2-methylpropan-2-ylamino)ethyl)piperidin-4-yl)methyl)benzamide | 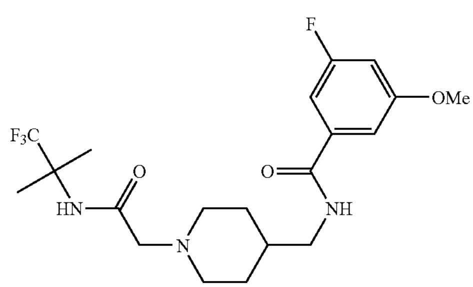 [SMILES: COc1cc(F)cc(C(=O)NCC2CCN(CC(=O)NC(C)(C)C(F)(F)F)CC2)c1] | 434.20 |
| 457 | 3,5-dimethoxy-N-((1-(2-oxo-2-(1,1,1-trifluoro-2-methylpropan-2-ylamino)ethyl)piperidin-4-yl)methyl)benzamide | 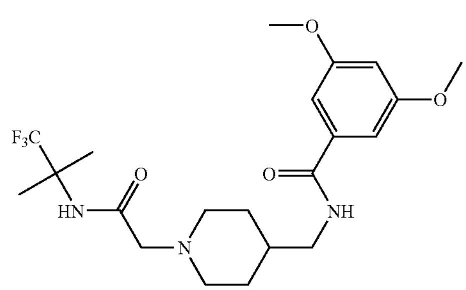 [SMILES: COc1cc(OC)cc(C(=O)NCC2CCN(CC(=O)NC(C)(C)C(F)(F)F)CC2)c1] | 446.22 |

TABLE 1-continued

| Cmpd No. | Name | Structure | Mass Spec (m/z) |
|---|---|---|---|
| 458 | N-((1-(2-oxo-2-(1,1,1-trifluoro-2-methylpropan-2-ylamino)ethyl)piperidin-4-yl)methyl)-3-(trifluoromethyl)benzamide | 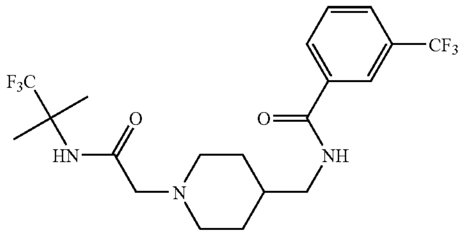 [SMILES: CC(C)(NC(=O)CN1CCC(CNC(=O)c2cccc(C(F)(F)F)c2)CC1)C(F)(F)F] | 454.19 |
| 459 | 3-bromo-N-((1-(2-oxo-2-(1,1,1-trifluoro-2-methylpropan-2-ylamino)ethyl)piperidin-4-yl)methyl)benzamide | 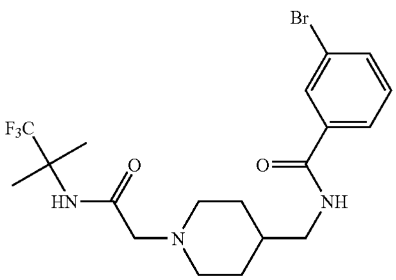 [SMILES: CC(C)(NC(=O)CN1CCC(CNC(=O)c2cccc(Br)c2)CC1)C(F)(F)F] | 464.11 |
| 460 | 3-chloro-N-((1-(2-oxo-2-(1,1,1-trifluoro-2-methylpropan-2-ylamino)ethyl)piperidin-4-yl)methyl)benzamide | 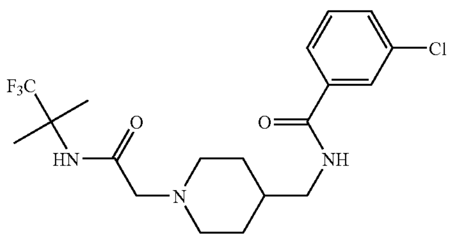 [SMILES: CC(C)(NC(=O)CN1CCC(CNC(=O)c2cccc(Cl)c2)CC1)C(F)(F)F] | 420.16 |
| 461 | 3-chloro-5-fluoro-N-((1-(2-oxo-2-(1,1,1-trifluoro-2-methylpropan-2-ylamino)ethyl)piperidin-4-yl)methyl)benzamide | 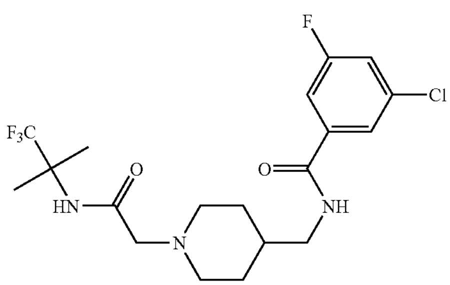 [SMILES: CC(C)(NC(=O)CN1CCC(CNC(=O)c2cc(F)cc(Cl)c2)CC1)C(F)(F)F] | 438.15 |
| 462 | N-((1-(2-oxo-2-(1,1,1-trifluoro-2-methylpropan-2-ylamino)ethyl)piperidin-4-yl)methyl)-3-(trifluoromethoxy)benzamide | 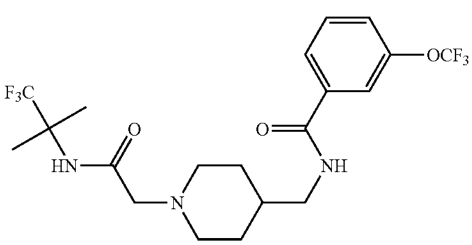 [SMILES: CC(C)(NC(=O)CN1CCC(CNC(=O)c2cccc(OC(F)(F)F)c2)CC1)C(F)(F)F] | 470.18 |
| 463 | (S)-3,5-dimethyl-N-((1-(2-oxo-2-(2-(trifluoromethyl)pyrrolidin-1-yl)ethyl)piperidin-4-yl)methyl)benzamide | 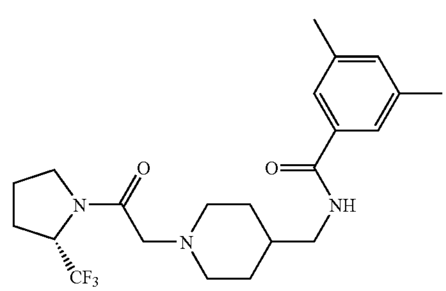 [SMILES: Cc1cc(C)cc(C(=O)NCC2CCN(CC(=O)N3CCC[C@H]3C(F)(F)F)CC2)c1] | 426.23 |

TABLE 1-continued

| Cmpd No. | Name | Structure | Mass Spec (m/z) |
|---|---|---|---|
| 464 | (S)-3-fluoro-5-methyl-N-((1-(2-oxo-2-(2-(trifluoromethyl)pyrrolidin-1-yl)ethyl)piperidin-4-yl)methyl)benzamide | 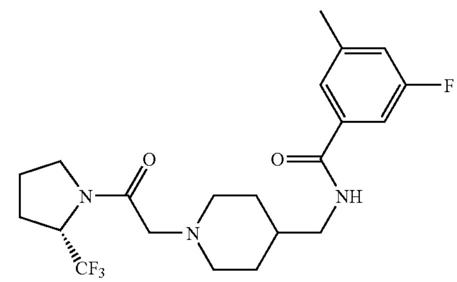 [SMILES: Cc1cc(F)cc(C(=O)NCC2CCN(CC(=O)N3CCC[C@H]3C(F)(F)F)CC2)c1] | 430.20 |
| 465 | (S)-3-fluoro-5-methoxy-N-((1-(2-oxo-2-(2-(trifluoromethyl)pyrrolidin-1-yl)ethyl)piperidin-4-yl)methyl)benzamide | 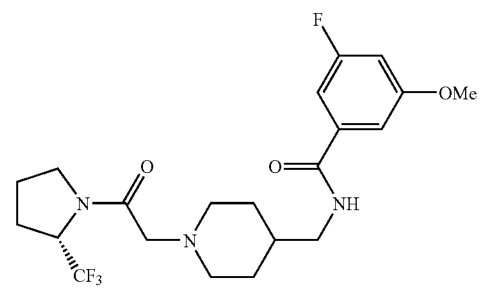 [SMILES: COc1cc(F)cc(C(=O)NCC2CCN(CC(=O)N3CCC[C@H]3C(F)(F)F)CC2)c1] | 446.20 |
| 466 | (S)-3,5-dimethoxy-N-((1-(2-oxo-2-(2-(trifluoromethyl)pyrrolidin-1-yl)ethyl)piperidin-4-yl)methyl)benzamide | 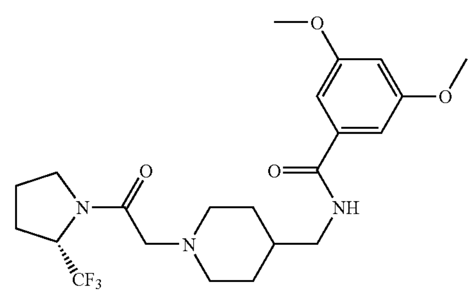 [SMILES: COc1cc(OC)cc(C(=O)NCC2CCN(CC(=O)N3CCC[C@H]3C(F)(F)F)CC2)c1] | 458.22 |
| 467 | (S)-N-((1-(2-oxo-2-(2-(trifluoromethyl)pyrrolidin-1-yl)ethyl)piperidin-4-yl)methyl)-3-(trifluoromethyl)benzamide | 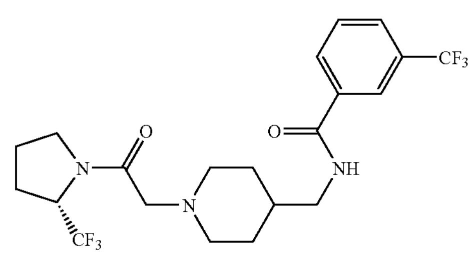 [SMILES: O=C(NCC1CCN(CC(=O)N2CCC[C@H]2C(F)(F)F)CC1)c1cccc(C(F)(F)F)c1] | 466.19 |
| 468 | (S)-3-bromo-N-((1-(2-oxo-2-(2-(trifluoromethyl)pyrrolidin-1-yl)ethyl)piperidin-4-yl)methyl)benzamide | 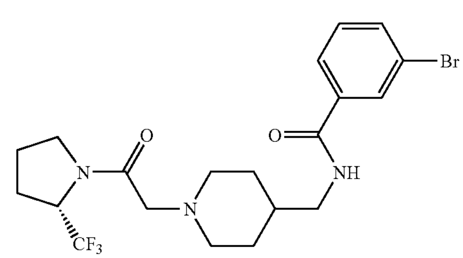 [SMILES: O=C(NCC1CCN(CC(=O)N2CCC[C@H]2C(F)(F)F)CC1)c1cccc(Br)c1] | 476.11 |

TABLE 1-continued

| Cmpd No. | Name | Mass Spec (m/z) |
|---|---|---|
| 469 | (S)-3-chloro-N-((1-(2-oxo-2-(2-(trifluoromethyl)pyrrolidin-1-yl)ethyl)piperidin-4-yl)methyl)benzamide | 432.16 |
| 470 | (S)-3-chloro-5-fluoro-N-((1-(2-oxo-2-(2-(trifluoromethyl)pyrrolidin-1-yl)ethyl)piperidin-4-yl)methyl)benzamide | 450.15 |
| 471 | (S)-N-((1-(2-oxo-2-(2-(trifluoromethyl)pyrrolidin-1-yl)ethyl)piperidin-4-yl)methyl)-3-(trifluoromethoxy)benzamide | 482.18 |
| 472 | 3-chloro-5-fluoro-N-((1-(2-(1-(trifluoromethyl)cyclopropanecarboxamido)ethyl)piperidin-4-yl)methyl)benzamide | 450.15 |
| 473 | 3-(trifluoromethyl)-N-((1-(2-(1-(trifluoromethyl)cyclopropanecarboxamido)ethyl)piperidin-4-yl)methyl)benzamide | 466.19 |

TABLE 1-continued

| Cmpd No. | Name | Structure | Mass Spec (m/z) |
|---|---|---|---|
| 474 | 3-(trifluoromethoxy)-N-((1-(2-(1-(trifluoromethyl)cyclopropane-carboxamido)ethyl)piperidin-4-yl)methyl)benzamide | 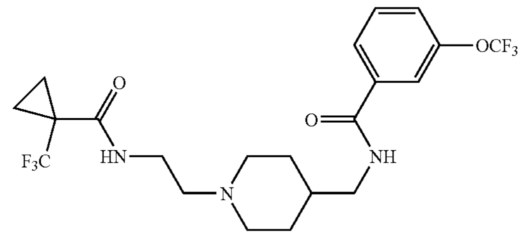 [SMILES: O=C(NCC1CCN(CCNC(=O)C2(C(F)(F)F)CC2)CC1)c1cccc(OC(F)(F)F)c1] | 482.18 |
| 475 | 3,5-dimethyl-N-((1-(2-(1-methylcyclobutylamino)-2-oxoethyl)piperidin-4-yl)methyl)benzamide | 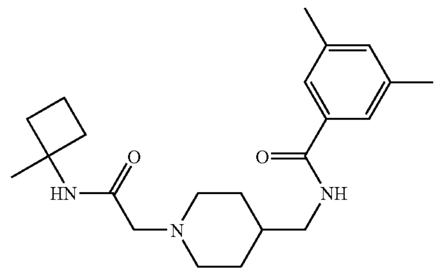 | 372.26 |
| 476 | 3-fluoro-5-methyl-N-((1-(2-(1-methylcyclobutylamino)-2-oxoethyl)piperidin-4-yl)methyl)benzamide | 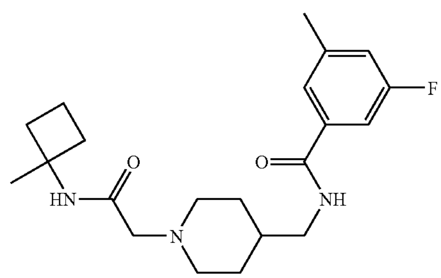 [SMILES: Cc1cc(F)cc(C(=O)NCC2CCN(CC(=O)NC3(C)CCC3)CC2)c1] | 376.23 |
| 477 | 3-fluoro-5-methoxy-N-((1-(2-(1-methylcyclobutylamino)-2-oxoethyl)piperidin-4-yl)methyl)benzamide | 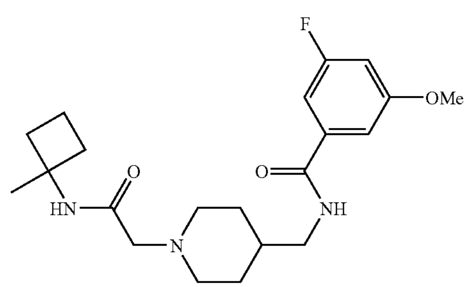 [SMILES: COc1cc(F)cc(C(=O)NCC2CCN(CC(=O)NC3(C)CCC3)CC2)c1] | 392.23 |
| 478 | 3,5-dimethoxy-N-((1-(2-(1-methylcyclobutylamino)-2-oxoethyl)piperidin-4-yl)methyl)benzamide | 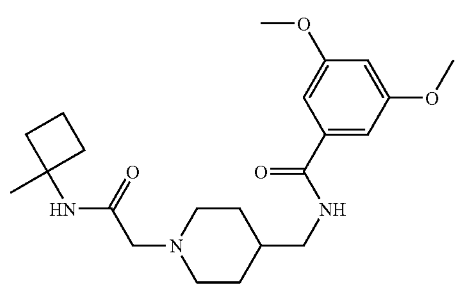 | 404.25 |

| Cmpd No. | Name | Structure | Mass Spec (m/z) |
|---|---|---|---|
| 479 | N-((1-(2-(1-methylcyclobutylamino)-2-oxoethyl)piperidin-4-yl)methyl)-3-(trifluoromethyl)benzamide | 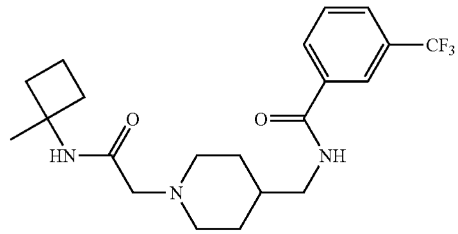 [SMILES: CC1(NC(=O)CN2CCC(CNC(=O)c3cccc(C(F)(F)F)c3)CC2)CCC1] | 412.21 |
| 480 | 3-bromo-N-((1-(2-(1-methylcyclobutylamino)-2-oxoethyl)piperidin-4-yl)methyl)benzamide | 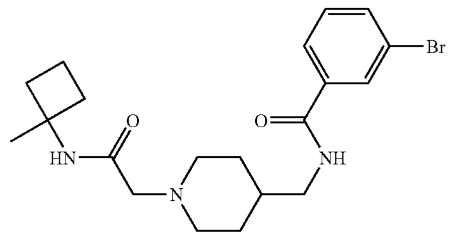 [SMILES: CC1(NC(=O)CN2CCC(CNC(=O)c3cccc(Br)c3)CC2)CCC1] | 422.14 |
| 481 | 3-chloro-N-((1-(2-(1-methylcyclobutylamino)-2-oxoethyl)piperidin-4-yl)methyl)benzamide | 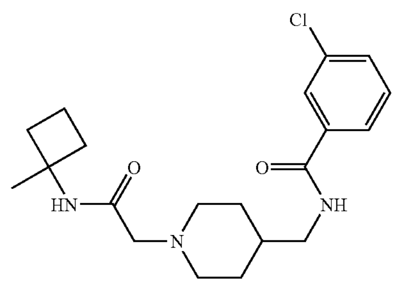 [SMILES: CC1(NC(=O)CN2CCC(CNC(=O)c3cccc(Cl)c3)CC2)CCC1] | 378.19 |
| 482 | 3-chloro-5-fluoro-N-((1-(2-(1-methylcyclobutylamino)-2-oxoethyl)piperidin-4-yl)methyl)benzamide | 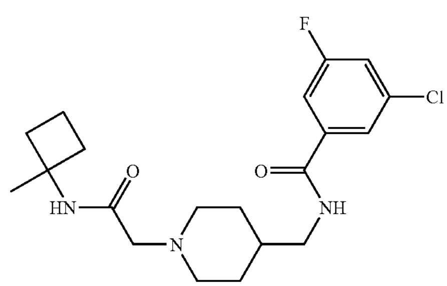 [SMILES: CC1(NC(=O)CN2CCC(CNC(=O)c3cc(F)cc(Cl)c3)CC2)CCC1] | 396.18 |
| 483 | N-((1-(2-(1-methylcyclobutylamino)-2-oxoethyl)piperidin-4-yl)methyl)-3-(trifluoromethoxy)benzamide | 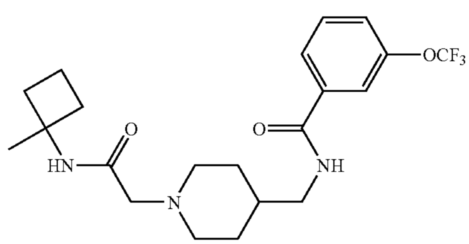 [SMILES: CC1(NC(=O)CN2CCC(CNC(=O)c3cccc(OC(F)(F)F)c3)CC2)CCC1] | 428.21 |
| 484 | N-((1-(2-(2,5-dioxopyrrolidin-1-yl)ethyl)piperidin-4-yl)methyl)-3-fluoro-5-(trifluoromethyl)benzamide | 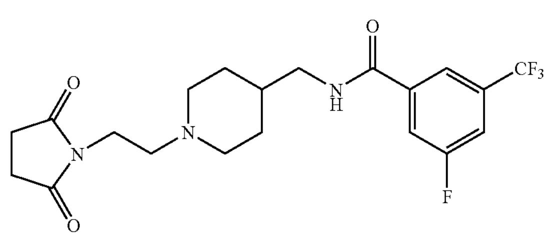 [SMILES: O=C(NCC1CCN(CCN2C(=O)CCC2=O)CC1)c1cc(F)cc(C(F)(F)F)c1] | 430.17 |

TABLE 1-continued

| Cmpd No. | Name | Structure | Mass Spec (m/z) |
|---|---|---|---|
| 485 | N-((1-(2-(methoxyamino)-2-oxoethyl)piperidin-4-yl)methyl)-3,5-bis(trifluoromethyl)benzamide | 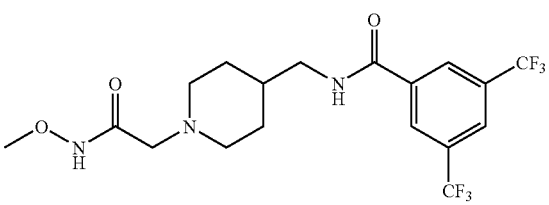 [SMILES: CONC(=O)CN1CCC(CNC(=O)c2cc(C(F)(F)F)cc(C(F)(F)F)c2)CC1] | 442.15 |
| 486 | N-((1-(2-(ethoxyamino)-2-oxoethyl)piperidin-4-yl)methyl)-3,5-bis(trifluoromethyl)benzamide | 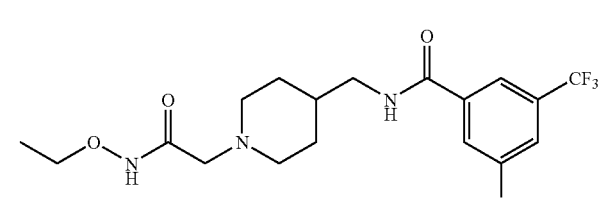 | 456.16 |
| 487 | 3-fluoro-N-((1-(2-(2-oxopyrrolidin-1-yl)ethyl)piperidin-4-yl)methyl)-5-(trifluoromethyl)benzamide | 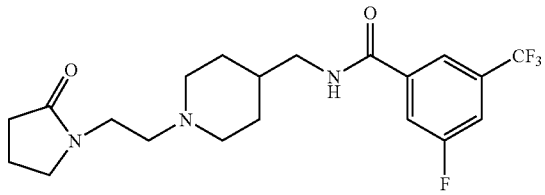 [SMILES: O=C(NCC1CCN(CCN2CCCC2=O)CC1)c1cc(F)cc(C(F)(F)F)c1] | 416.19 |
| 488 | 3,5-dimethyl-N-((1-(2-(3,3,3-trifluoro-2,2-dimethylpropanamido)ethyl)piperidin-4-yl)methyl)benzamide | 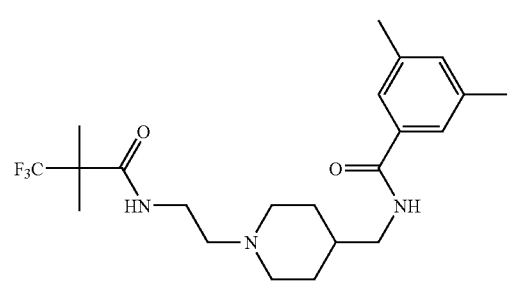 [SMILES: Cc1cc(C)cc(C(=O)NCC2CCN(CCNC(=O)C(C)(C)C(F)(F)F)CC2)c1] | 428.24 |
| 489 | 3-fluoro-5-methyl-N-((1-(2-(3,3,3-trifluoro-2,2-dimethylpropanamido)ethyl)piperidin-4-yl)methyl)benzamide | 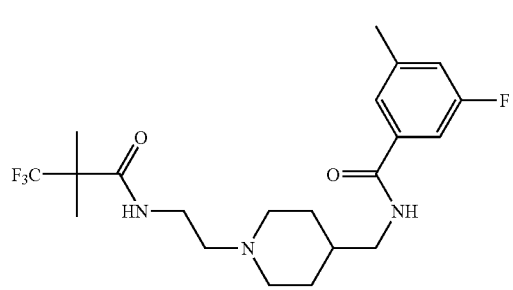 [SMILES: Cc1cc(F)cc(C(=O)NCC2CCN(CCNC(=O)C(C)(C)C(F)(F)F)CC2)c1] | 432.22 |
| 490 | 3-fluoro-5-methoxy-N-((1-(2-(3,3,3-trifluoro-2,2-dimethylpropanamido)ethyl)piperidin-4-yl)methyl)benzamide | 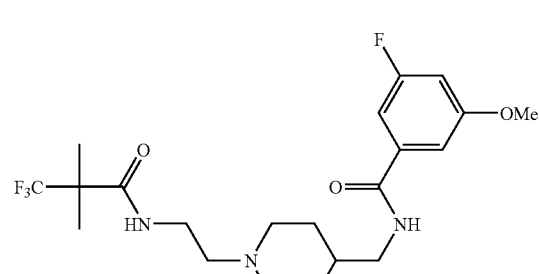 | 448.21 |

TABLE 1-continued

| Cmpd No. | Name | Structure | Mass Spec (m/z) |
|---|---|---|---|
| 491 | 3,5-dimethoxy-N-((1-(2-(3,3,3-trifluoro-2,2-dimethylpropanamido)ethyl)piperidin-4-yl)methyl)benzamide | 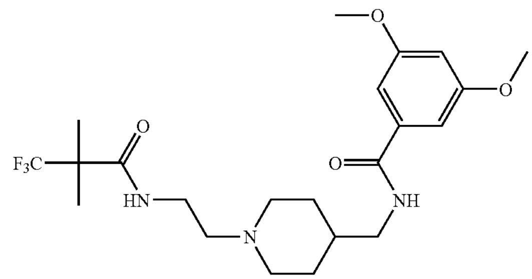 [SMILES: COc1cc(OC)cc(C(=O)NCC2CCN(CCNC(=O)C(C)(C)C(F)(F)F)CC2)c1] | 460.23 |
| 492 | N-((1-(2-(3,3,3-trifluoro-2,2-dimethylpropanamido)ethyl)piperidin-4-yl)methyl)-3-(trifluoromethyl)benzamide | 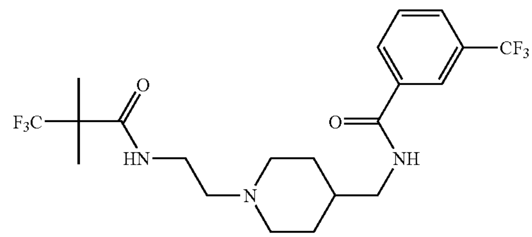 [SMILES: CC(C)(C(=O)NCCN1CCC(CNC(=O)c2cccc(C(F)(F)F)c2)CC1)C(F)(F)F] | 468.20 |
| 493 | 3-bromo-N-((1-(2-(3,3,3-trifluoro-2,2-dimethylpropanamido)ethyl)piperidin-4-yl)methyl)benzamide | 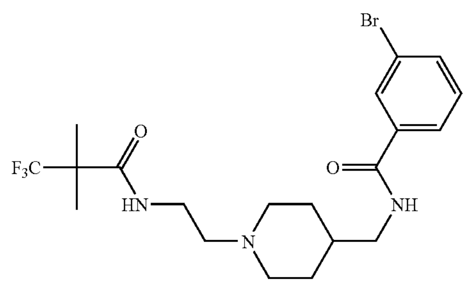 [SMILES: CC(C)(C(=O)NCCN1CCC(CNC(=O)c2cccc(Br)c2)CC1)C(F)(F)F] | 478.12 |
| 494 | 3-chloro-N-((1-(2-(3,3,3-trifluoro-2,2-dimethylpropanamido)ethyl)piperidin-4-yl)methyl)benzamide | 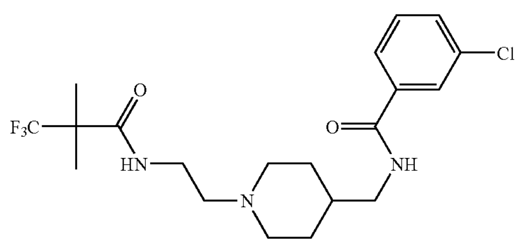 [SMILES: CC(C)(C(=O)NCCN1CCC(CNC(=O)c2cccc(Cl)c2)CC1)C(F)(F)F] | 434.17 |
| 495 | 3-chloro-5-fluoro-N-((1-(2-(3,3,3-trifluoro-2,2-dimethylpropanamido)ethyl)piperidin-4-yl)methyl)benzamide | 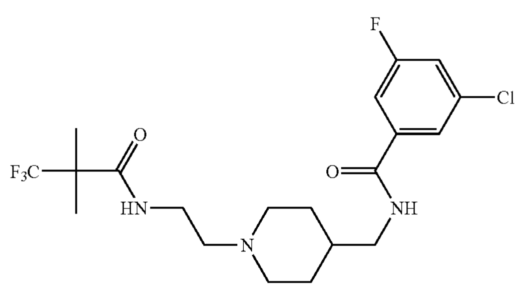 [SMILES: CC(C)(C(=O)NCCN1CCC(CNC(=O)c2cc(F)cc(Cl)c2)CC1)C(F)(F)F] | 452.16 |
| 496 | N-((1-(2-(3,3,3-trifluoro-2,2-dimethylpropanamido)ethyl)piperidin-4-yl)methyl)-3-(trifluoromethoxy)benzamide | 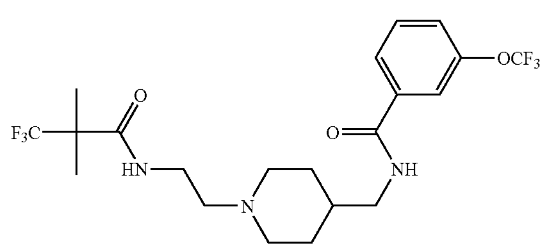 [SMILES: CC(C)(C(=O)NCCN1CCC(CNC(=O)c2cccc(OC(F)(F)F)c2)CC1)C(F)(F)F] | 484.20 |

TABLE 1-continued

| Cmpd No. | Name | Structure | Mass Spec (m/z) |
|---|---|---|---|
| 497 | 3,5-dimethyl-N-((1-(2-(1-(trifluoromethyl)cyclopropane-carboxamido)ethyl)piperidin-4-yl)methyl)benzamide | 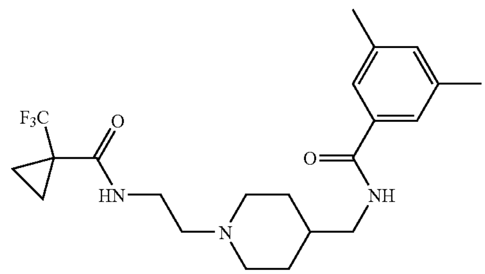 [SMILES: Cc1cc(C)cc(C(=O)NCC2CCN(CCNC(=O)C3(C(F)(F)F)CC3)CC2)c1] | 426.23 |
| 498 | 3-fluoro-5-methyl-N-((1-(2-(1-(trifluoromethyl)cyclopropane-carboxamido)ethyl)piperidin-4-yl)methyl)benzamide | 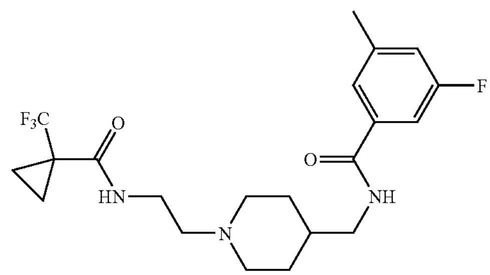 [SMILES: Cc1cc(F)cc(C(=O)NCC2CCN(CCNC(=O)C3(C(F)(F)F)CC3)CC2)c1] | 430.20 |
| 499 | 3-fluoro-5-methoxy-N-((1-(2-(1-(trifluoromethyl)cyclopropane-carboxamido)ethyl)piperidin-4-yl)methyl)benzamide | 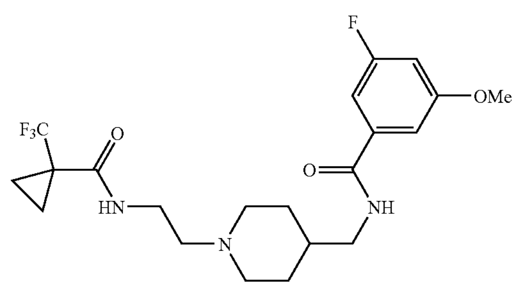 [SMILES: COc1cc(F)cc(C(=O)NCC2CCN(CCNC(=O)C3(C(F)(F)F)CC3)CC2)c1] | 446.20 |
| 500 | 3,5-dimethoxy-N-((1-(2-(1-(trifluoromethyl)cyclopropane-carboxamido)ethyl)piperidin-4-yl)methyl)benzamide | 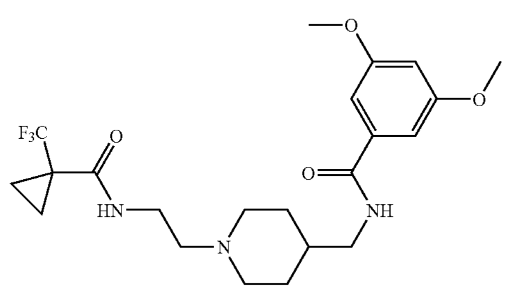 [SMILES: COc1cc(OC)cc(C(=O)NCC2CCN(CCNC(=O)C3(C(F)(F)F)CC3)CC2)c1] | 458.22 |
| 501 | 3-bromo-N-((1-(2-(1-(trifluoromethyl)cyclopropanecarboxamido)ethyl)piperidin-4-yl)methyl)benzamide | 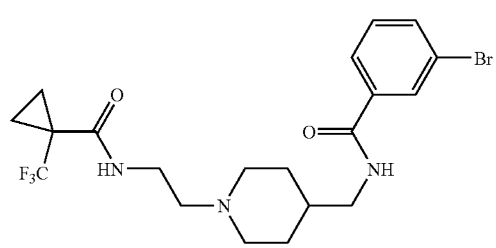 [SMILES: O=C(NCC1CCN(CCNC(=O)C2(C(F)(F)F)CC2)CC1)c1cccc(Br)c1] | 476.11 |

TABLE 1-continued

| Cmpd No. | Name | Structure | Mass Spec (m/z) |
|---|---|---|---|
| 502 | 3-chloro-N-((1-(2-(1-(trifluoromethyl) cyclopropanecarboxamido)ethyl)piperidin-4-yl)methyl)benzamide | 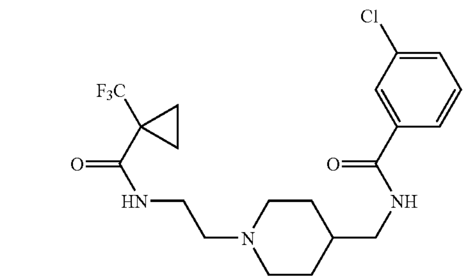 [SMILES: O=C(NCC1CCN(CCNC(=O)C2(C(F)(F)F)CC2)CC1)c1cccc(Cl)c1] | 432.16 |
| 503 | (Z)-N-((1-(2-(tert-butylamino)-2-(cyanoimino)ethyl)piperidin-4-yl)methyl)-3,5-bis(trifluoromethyl)benzamide | 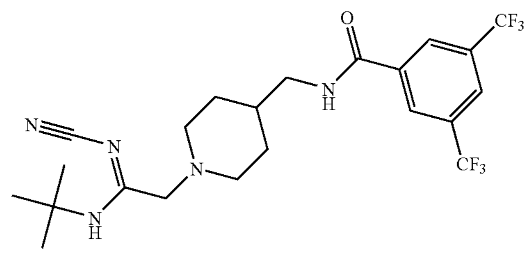 [SMILES: CC(C)(C)N/C(CN1CCC(CNC(=O)c2cc(C(F)(F)F)cc(C(F)(F)F)c2)CC1)=N\C#N] | 492.21 |
| 504 | (R)-3-chloro-5-fluoro-N-((1-(2-oxo-2-(2-(trifluoromethyl)pyrrolidin-1-yl)ethyl)piperidin-4-yl)methyl)benzamide | 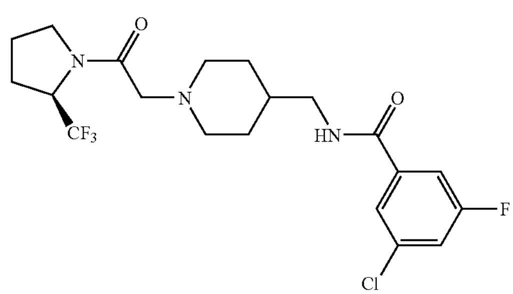 [SMILES: O=C(NCC1CCN(CC(=O)N2CCC[C@@H]2C(F)(F)F)CC1)c1cc(F)cc(Cl)c1] | 450.15 |
| 505 | (R)-3-fluoro-5-methoxy-N-((1-(2-oxo-2-(2-(trifluoromethyl)pyrrolidin-1-yl)ethyl)piperidin-4-yl)methyl)benzamide | 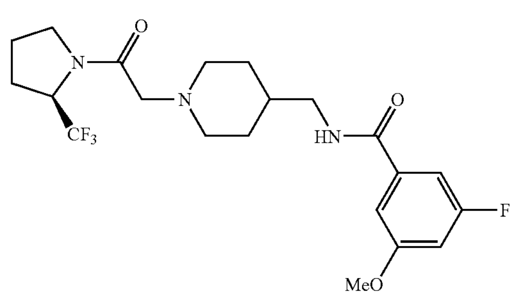 [SMILES: COc1cc(F)cc(C(=O)NCC2CCN(CC(=O)N3CCC[C@@H]3C(F)(F)F)CC2)c1] | 446.20 |
| 506 | (R)-3-fluoro-5-methyl-N-((1-(2-oxo-2-(2-(trifluoromethyl)pyrrolidin-1-yl)ethyl)piperidin-4-yl)methyl)benzamide | 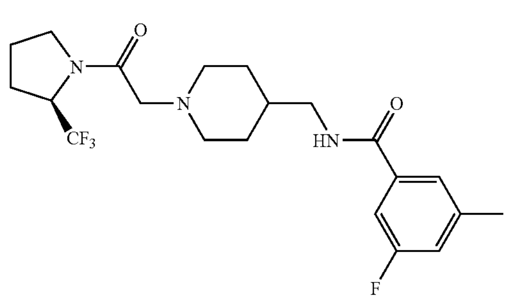 [SMILES: Cc1cc(F)cc(C(=O)NCC2CCN(CC(=O)N3CCC[C@@H]3C(F)(F)F)CC2)c1] | 430.20 |

TABLE 1-continued

| Cmpd No. | Name | Structure | Mass Spec (m/z) |
|---|---|---|---|
| 507 | (R)-3-chloro-N-((1-(2-oxo-2-(2-(trifluoromethyl)pyrrolidin-1-yl)ethyl)piperidin-4-yl)methyl)benzamide | 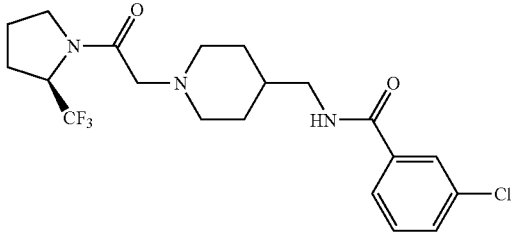 [SMILES: O=C(NCC1CCN(CC(=O)N2CCC[C@@H]2C(F)(F)F)CC1)c1cccc(Cl)c1] | 432.16 |
| 508 | (R)-3-fluoro-N-((1-(2-oxo-2-(2-(trifluoromethyl)pyrrolidin-1-yl)ethyl)piperidin-4-yl)methyl)benzamide | 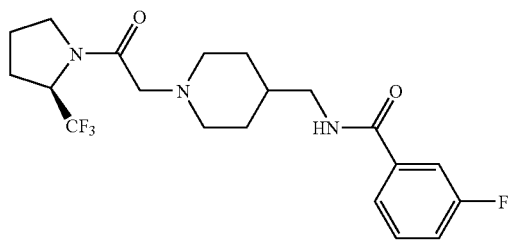 [SMILES: O=C(NCC1CCN(CC(=O)N2CCC[C@@H]2C(F)(F)F)CC1)c1cccc(F)c1] | 416.19 |
| 509 | 3-fluoro-N-((1-((1R,2R)-2-pivalamidocyclohexyl)piperidin-4-yl)methyl)-5-(trifluoromethyl)benzamide | 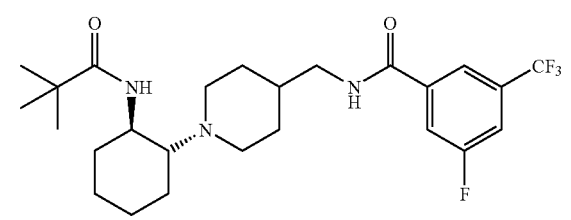 | 486.27 |
| 510 | (Z)-N-((1-(2-(tert-butylamino)-2-(cyanoimino)ethyl)piperidin-4-yl)methyl)-3-fluoro-5-(trifluoromethyl)benzamide | 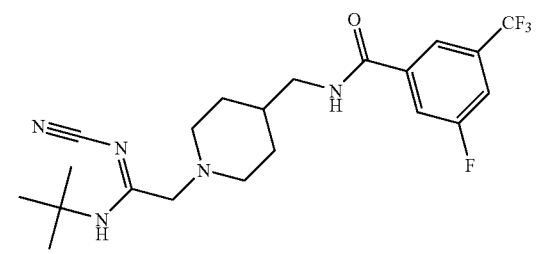 [SMILES: CC(C)(C)N/C(CN1CCC(CNC(=O)c2cc(F)cc(C(F)(F)F)c2)CC1)=N\C#N] | 442.22 |
| 511 | 3-chloro-5-fluoro-N-((1-(2-(1-(trifluoromethyl)cyclobutanecarboxamido)ethyl)piperidin-4-yl)methyl)benzamide | 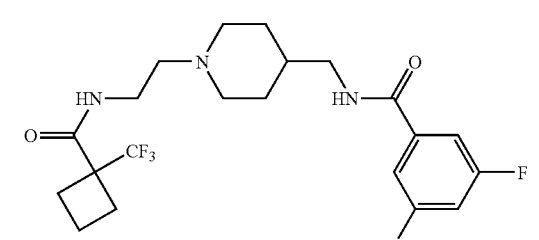 | 464.16 |
| 512 | 3-chloro-N-((1-(2-(1-(trifluoromethyl)cyclobutanecarboxamido)ethyl)piperidin-4-yl)methyl)benzamide | 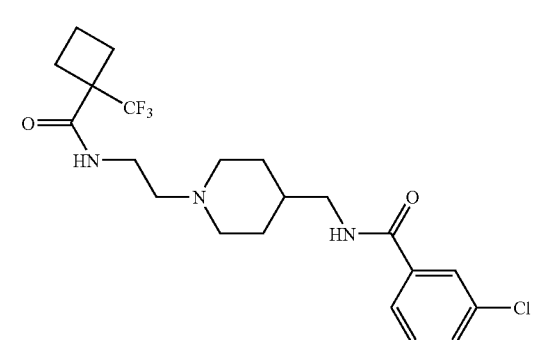 | 446.17 |

TABLE 1-continued

| Cmpd No. | Name | Mass Spec (m/z) |
|---|---|---|
| 513 | 3-fluoro-5-methoxy-N-((1-(2-(1-(trifluoromethyl)cyclobutanecarboxamido)ethyl)piperidin-4-yl)methyl)benzamide | 460.21 |
| 514 | N-((1-(2-(N-tert-butylsulfamoyl)ethyl)piperidin-4-yl)methyl)-3-fluoro-5-(trifluoromethyl)benzamide | 468.19 |
| 515 | 3-fluoro-N-((1-(2-(N-methylpivalamido)ethyl)piperidin-4-yl)methyl)-5-(trifluoromethyl)benzamide | 446.24 |
| 516 | 3-fluoro-N-((1-(2-(N-methylcyclopentanecarboxamido)ethyl)piperidin-4-yl)methyl)-5-(trifluoromethyl)benzamide | 458.24 |
| 517 | 3-fluoro-N-((1-(2-(4,4,4-trifluoro-N-methylbutanamido)ethyl)piperidin-4-yl)methyl)-5-(trifluoromethyl)benzamide | 486.19 |
| 518 | N-((1-(2-(N,1-dimethylcyclopropanecarboxamido)ethyl)piperidin-4-yl)methyl)-3-fluoro-5-(trifluoromethyl)benzamide | 444.22 |

TABLE 1-continued

| Cmpd No. | Name | Structure | Mass Spec (m/z) |
|---|---|---|---|
| 519 | N-((1-(2-(N,4-dimethylcyclohexane-carboxamido)ethyl)piperidin-4-yl)methyl)-3-fluoro-5-(trifluoromethyl)benzamide | 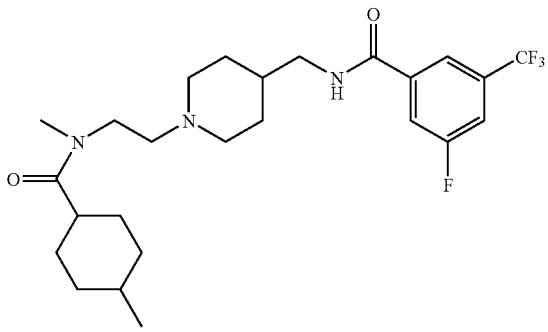 [SMILES: CC1CCC(C(=O)N(C)CCN2CCC(CNC(=O)c3cc(F)cc(C(F)(F)F)c3)CC2)CC1] | 486.27 |
| 520 | 3-fluoro-N-((1-(2-(N-methyl-1-(trifluoromethyl)cyclopropane-carboxamido)ethyl)piperidin-4-yl)methyl)-5-(trifluoromethyl)benzamide | 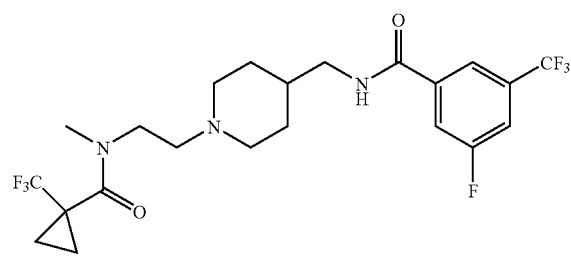 [SMILES: CN(CCN1CCC(CNC(=O)c2cc(F)cc(C(F)(F)F)c2)CC1)C(=O)C1(C(F)(F)F)CC1] | 498.19 |
| 521 | 3-fluoro-N-((1-(2-(3,3,3-trifluoro-N,2,2-trimethylpropanamido)ethyl)piperidin-4-yl)methyl)-5-(trifluoromethyl)benzamide | 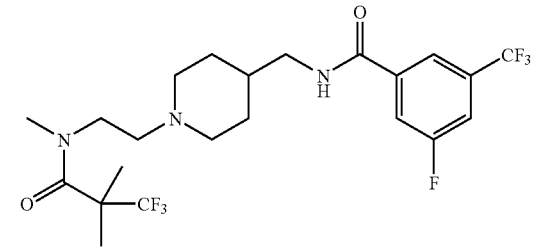 [SMILES: CN(CCN1CCC(CNC(=O)c2cc(F)cc(C(F)(F)F)c2)CC1)C(=O)C(C)(C)C(F)(F)F] | 500.21 |
| 522 | 3-fluoro-N-((1-(2-(N-methyl-1-(trifluoromethyl)cyclopentane-carboxamido)ethyl)piperidin-4-yl)methyl)-5-(trifluoromethyl)benzamide | 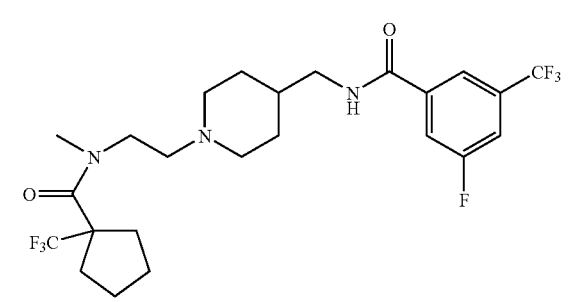 [SMILES: CN(CCN1CCC(CNC(=O)c2cc(F)cc(C(F)(F)F)c2)CC1)C(=O)C1(C(F)(F)F)CCCC1] | 526.22 |
| 523 | N-((1-(2-(3-tert-butyl-1-methylureido)ethyl)piperidin-4-yl)methyl)-3-fluoro-5-(trifluoromethyl)benzamide | 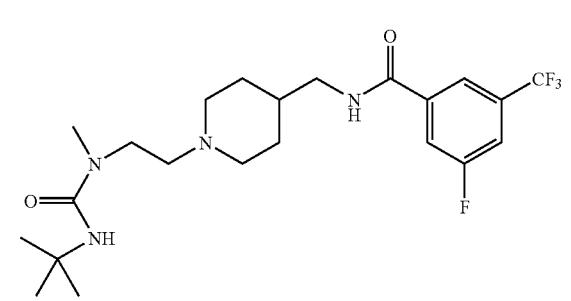 [SMILES: CN(CCN1CCC(CNC(=O)c2cc(F)cc(C(F)(F)F)c2)CC1)C(=O)NC(C)(C)C] | 461.25 |

TABLE 1-continued

| Cmpd No. | Name | Structure | Mass Spec (m/z) |
|---|---|---|---|
| 524 | N-((1-(2-(3-ethyl-1-methylureido)ethyl)piperidin-4-yl)methyl)-3-fluoro-5-(trifluoromethyl)benzamide | 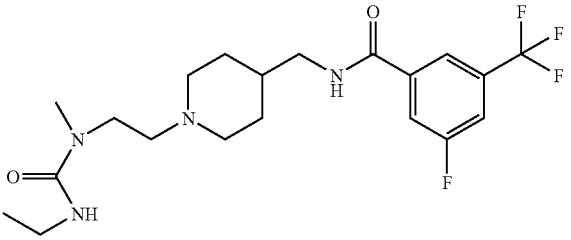 [SMILES: CCNC(=O)N(C)CCN1CCC(CNC(=O)c2cc(F)cc(C(F)(F)F)c2)CC1] | 433.21 |
| 525 | N-((1-(2-(3-cyclohexyl-1-methylureido)ethyl)piperidin-4-yl)methyl)-3-fluoro-5-(trifluoromethyl)benzamide | 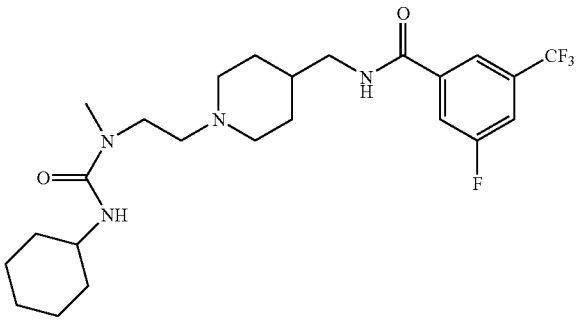 [SMILES: CN(CCN1CCC(CNC(=O)c2cc(F)cc(C(F)(F)F)c2)CC1)C(=O)NC1CCCCC1] | 487.26 |
| 526 | 3-fluoro-N-((1-(2-(1-methyl-3-propylureido)ethyl)piperidin-4-yl)methyl)-5-(trifluoromethyl)benzamide | 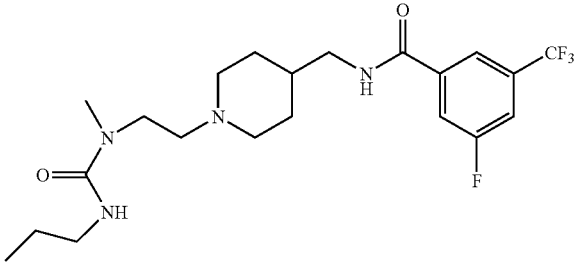 [SMILES: CCCNC(=O)N(C)CCN1CCC(CNC(=O)c2cc(F)cc(C(F)(F)F)c2)CC1] | 447.23 |
| 527 | 3-chloro-N-((1-(2-oxo-2-(piperidin-1-ylamino)ethyl)piperidin-4-yl)methyl)benzamide | 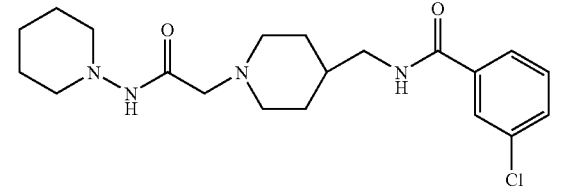 [SMILES: O=C(CN1CCC(CNC(=O)c2cccc(Cl)c2)CC1)NN1CCCCC1] | 393.20 |
| 528 | N-((1-(2-(1-methylcyclobutylamino)-2-oxoethyl)piperidin-4-yl)methyl)benzamide | 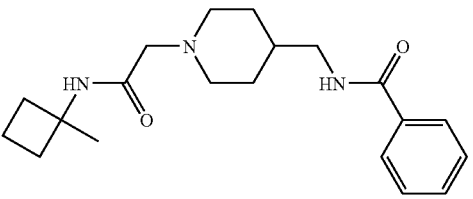 [SMILES: CC1(NC(=O)CN2CCC(CNC(=O)c3ccccc3)CC2)CCC1] | 344.23 |
| 529 | 4-fluoro-N-((1-(2-(1-methylcyclobutylamino)-2-oxoethyl)piperidin-4-yl)methyl)benzamide | 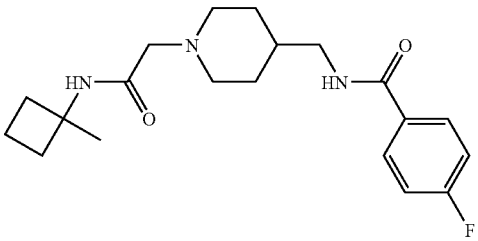 [SMILES: CC1(NC(=O)CN2CCC(CNC(=O)c3ccc(F)cc3)CC2)CCC1] | 362.22 |

TABLE 1-continued

| Cmpd No. | Name | Structure | Mass Spec (m/z) |
|---|---|---|---|
| 530 | 2-(4-((3-fluoro-5-(trifluoromethyl)benzamido)methyl)piperidin-1-yl)ethyl cyclohexylcarbamate | 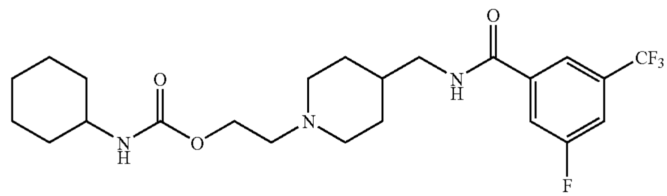 [SMILES: O=C(NC1CCCCC1)OCCN1CCC(CNC(=O)c2cc(F)cc(C(F)(F)F)c2)CC1] | 474.23 |
| 531 | 3-chloro-N-((1-(2-(cyclopentylamino)-2-oxoethyl)piperidin-4-yl)methyl)-5-fluorobenzamide | 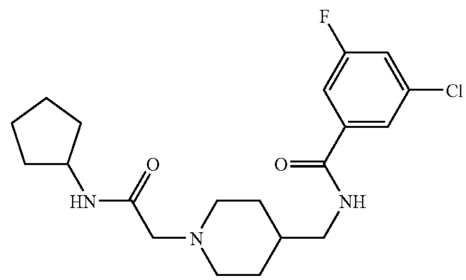 [SMILES: O=C(CN1CCC(CNC(=O)c2cc(F)cc(Cl)c2)CC1)NC1CCCC1] | 396.18 |
| 532 | N-((1-(2-(cyclopentylamino)-2-oxoethyl)piperidin-4-yl)methyl)-3-fluoro-5-methoxybenzamide | 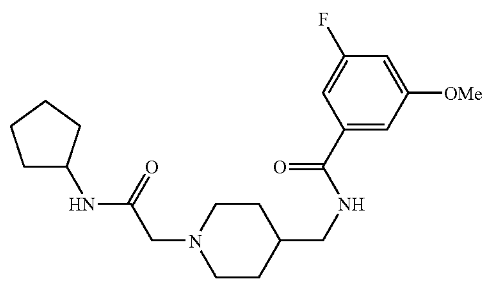 [SMILES: COc1cc(F)cc(C(=O)NCC2CCN(CC(=O)NC3CCCC3)CC2)c1] | 392.23 |
| 533 | N-((1-(2-(cyclopentylamino)-2-oxoethyl)piperidin-4-yl)methyl)-3-fluoro-5-methylbenzamide | 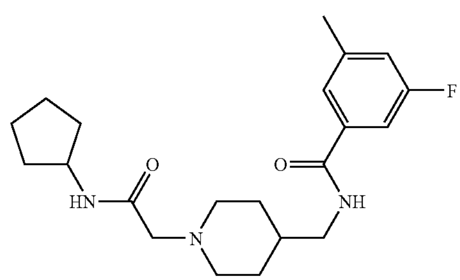 [SMILES: Cc1cc(F)cc(C(=O)NCC2CCN(CC(=O)NC3CCCC3)CC2)c1] | 376.23 |
| 534 | 3-chloro-N-((1-(2-(cyclopentylamino)-2-oxoethyl)piperidin-4-yl)methyl)benzamide | 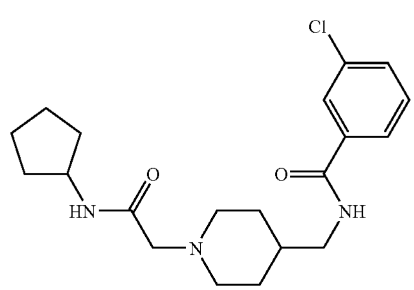 | 378.19 |

TABLE 1-continued

| Cmpd No. | Name | Structure | Mass Spec (m/z) |
|---|---|---|---|
| 535 | N-((1-(2-(cyclopentylamino)-2-oxoethyl)piperidin-4-yl)methyl)-3-fluorobenzamide | 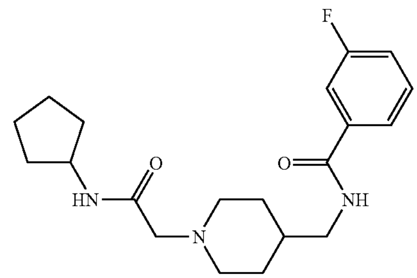 [SMILES: O=C(CN1CCC(CNC(=O)c2cccc(F)c2)CC1)NC1CCCC1] | 362.22 |
| 536 | N-((1-(2-(cyclopentylamino)-2-oxoethyl)piperidin-4-yl)methyl)-3-(trifluoromethoxy)benzamide | 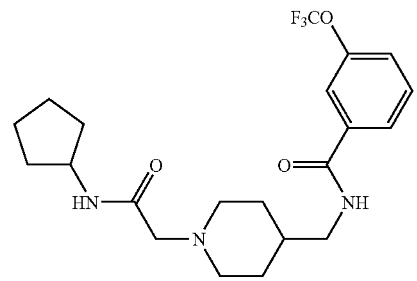 [SMILES: O=C(CN1CCC(CNC(=O)c2cccc(OC(F)(F)F)c2)CC1)NC1CCCC1] | 428.21 |
| 537 | N-((1-(2-(1,1-dimethylethylsulfinamido)ethyl)piperidin-4-yl)methyl)-3-fluoro-5-(trifluoromethyl)benzamide | 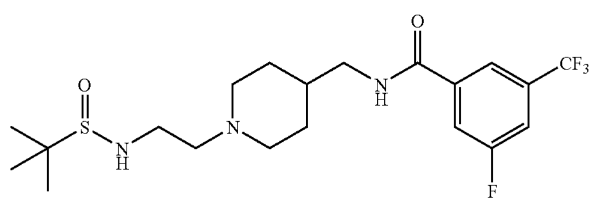 [SMILES: CC(C)(C)S(=O)NCCN1CCC(CNC(=O)c2cc(F)cc(C(F)(F)F)c2)CC1] | 452.19 |
| 538 | 3-chloro-5-fluoro-N-((1-(2-(1-methoxy-2-methylpropan-2-ylamino)-2-oxoethyl)piperidin-4-yl)methyl)benzamide | 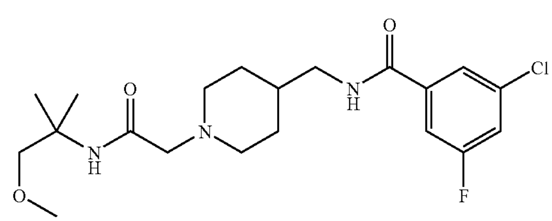 [SMILES: COCC(C)(C)NC(=O)CN1CCC(CNC(=O)c2cc(F)cc(Cl)c2)CC1] | 414.19 |
| 539 | N-((1-(2-(tert-butyl(methyl)amino)-2-oxoethyl)piperidin-4-yl)methyl)-3,5-dimethylbenzamide | 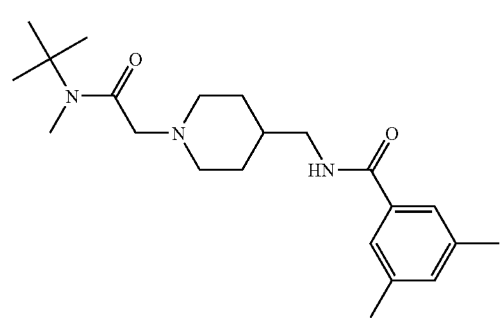 [SMILES: Cc1cc(C)cc(C(=O)NCC2CCN(CC(=O)N(C)C(C)(C)C)CC2)c1] | 374.27 |

TABLE 1-continued

| Cmpd No. | Name | Structure | Mass Spec (m/z) |
|---|---|---|---|
| 540 | N-((1-(2-(tert-butyl(methyl)amino)-2-oxoethyl)piperidin-4-yl)methyl)-3-fluoro-5-methylbenzamide | 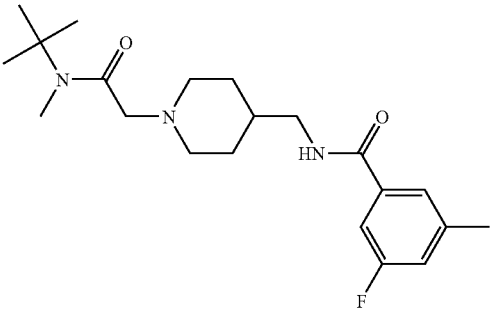 [SMILES: Cc1cc(F)cc(C(=O)NCC2CCN(CC(=O)N(C)C(C)(C)C)CC2)c1] | 378.25 |
| 541 | N-((1-(2-(tert-butyl(methyl)amino)-2-oxoethyl)piperidin-4-yl)methyl)-3-fluoro-5-methoxybenzamide | 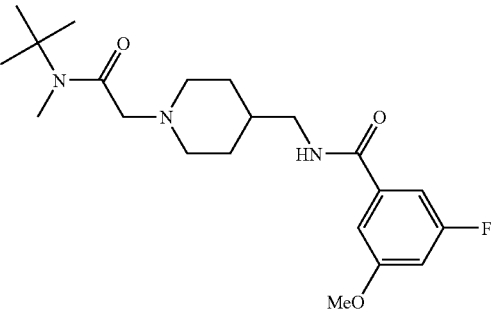 [SMILES: COc1cc(F)cc(C(=O)NCC2CCN(CC(=O)N(C)C(C)(C)C)CC2)c1] | 394.24 |
| 542 | N-((1-(2-(tert-butyl(methyl)amino)-2-oxoethyl)piperidin-4-yl)methyl)-3-(trifluoromethyl)benzamide | 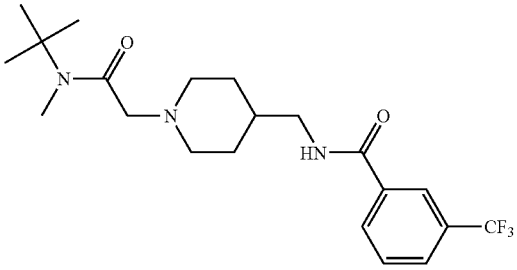 [SMILES: CN(C(=O)CN1CCC(CNC(=O)c2cccc(C(F)(F)F)c2)CC1)C(C)(C)C] | 414.23 |
| 543 | N-((1-(2-(tert-butyl(methyl)amino)-2-oxoethyl)piperidin-4-yl)methyl)-3-chlorobenzamide | 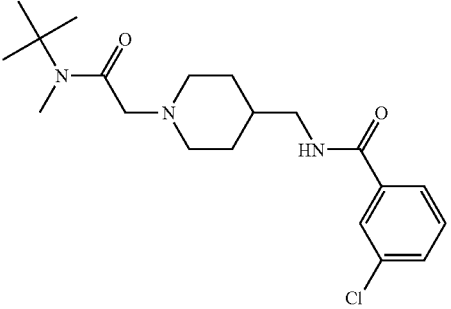 [SMILES: CN(C(=O)CN1CCC(CNC(=O)c2cccc(Cl)c2)CC1)C(C)(C)C] | 380.20 |
| 544 | N-((1-(2-(tert-butyl(methyl)amino)-2-oxoethyl)piperidin-4-yl)methyl)-3-chloro-5-fluorobenzamide | 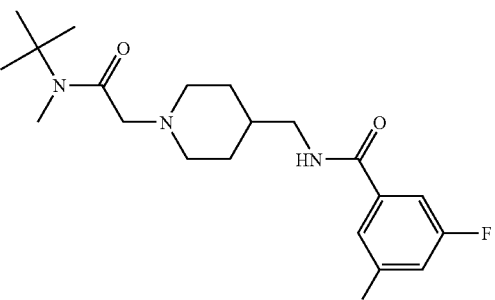 | 398.19 |

TABLE 1-continued

| Cmpd No. | Name | Structure | Mass Spec (m/z) |
|---|---|---|---|
| 545 | N-((1-(2-(tert-butyl(methyl)amino)-2-oxoethyl)piperidin-4-yl)methyl)-3-(trifluoromethoxy)benzamide | 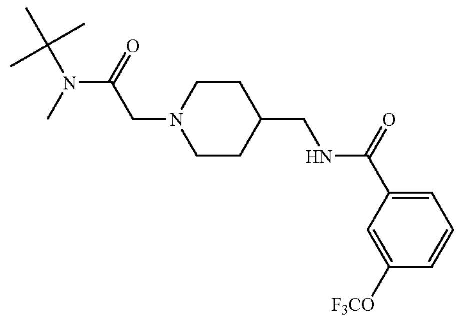 [SMILES: CN(C(=O)CN1CCC(CNC(=O)c2cccc(OC(F)(F)F)c2)CC1)C(C)(C)C] | 430.22 |
| 546 | N-((1-(1-(tert-butylamino)-1-oxopropan-2-yl)piperidin-4-yl)methyl)-3-chloro-5-fluorobenzamide | 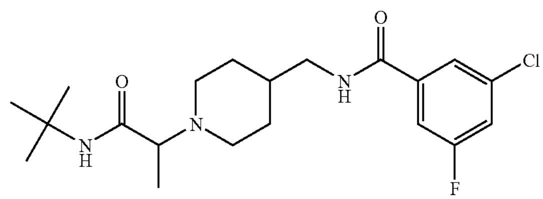 [SMILES: CC(C(=O)NC(C)(C)C)N1CCC(CNC(=O)c2cc(F)cc(Cl)c2)CC1] | 398.19 |
| 547 | 3-chloro-5-fluoro-N-((1-(1-oxo-1-(1,1,1-trifluoro-2-methylpropan-2-ylamino)propan-2-yl)piperidin-4-yl)methyl)benzamide | 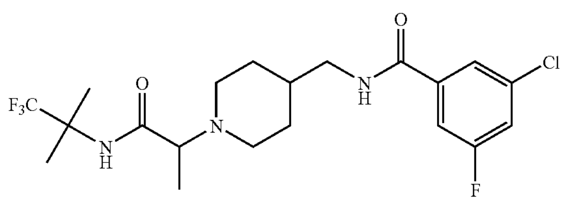 [SMILES: CC(C(=O)NC(C)(C)C(F)(F)F)N1CCC(CNC(=O)c2cc(F)cc(Cl)c2)CC1] | 452.16 |
| 548 | 3-chloro-5-fluoro-N-((1-(1-oxo-1-((S)-2-(trifluoromethyl)pyrrolidin-1-yl)propan-2-yl)piperidin-4-yl)methyl)benzamide | 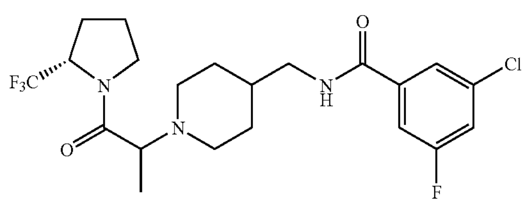 [SMILES: CC(C(=O)N1CCC[C@H]1C(F)(F)F)N1CCC(CNC(=O)c2cc(F)cc(Cl)c2)CC1] | 464.16 |
| 549 | 3-chloro-N-((1-(1-(cyclopentylamino)-1-oxopropan-2-yl)piperidin-4-yl)methyl)-5-fluorobenzamide | 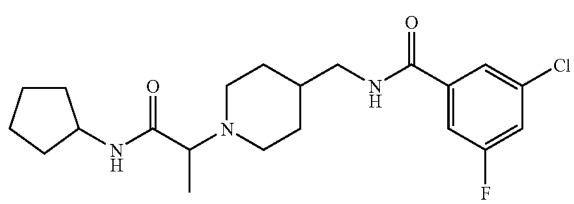 [SMILES: CC(C(=O)NC1CCCC1)N1CCC(CNC(=O)c2cc(F)cc(Cl)c2)CC1] | 410.19 |
| 550 | 3-chloro-5-fluoro-N-((1-(1-(1-methylcyclohexylamino)-1-oxopropan-2-yl)piperidin-4-yl)methyl)benzamide | 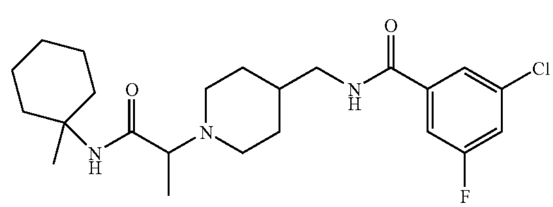 [SMILES: CC(C(=O)NC1(C)CCCCC1)N1CCC(CNC(=O)c2cc(F)cc(Cl)c2)CC1] | 438.22 |
| 551 | 3-chloro-5-fluoro-N-((1-(1-(1-methoxy-2-methylpropan-2-ylamino)-1-oxopropan-2-yl)piperidin-4-yl)methyl)benzamide | 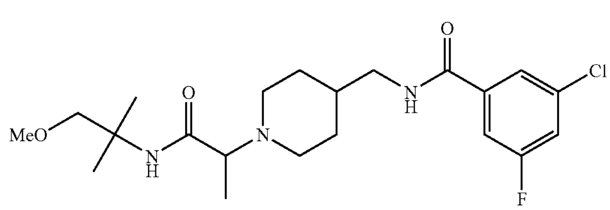 [SMILES: COCC(C)(C)NC(=O)C(C)N1CCC(CNC(=O)c2cc(F)cc(Cl)c2)CC1] | 428.20 |

TABLE 1-continued

| Cmpd No. | Name | Structure | Mass Spec (m/z) |
|---|---|---|---|
| 552 | N-((1-(2-(tert-butyl(methyl)amino)-2-oxoethyl)piperidin-4-yl)methyl)-3,5-dichlorobenzamide | 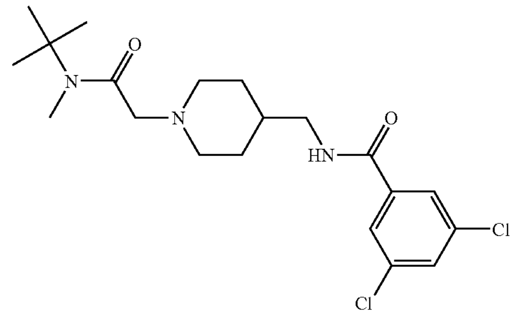 [SMILES: CN(C(=O)CN1CCC(CNC(=O)c2cc(Cl)cc(Cl)c2)CC1)C(C)(C)C] | 414.16 |
| 553 | 3-chloro-5-fluoro-N-((1-(2-(2-fluoropropylamino)-2-oxoethyl)piperidin-4-yl)methyl)benzamide compound with ethane (1:1) | 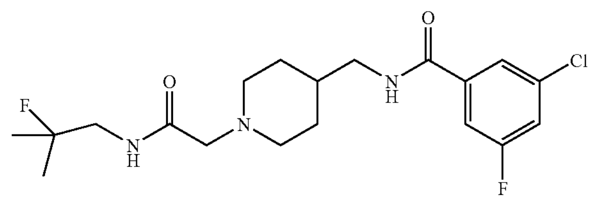 [SMILES: CC(C)(F)CNC(=O)CN1CCC(CNC(=O)c2cc(F)cc(Cl)c2)CC1] | 388.15 |
| 554 | 3-chloro-N-((1-(2-(2-fluoro-2-methylpropylamino)-2-oxoethyl)piperidin-4-yl)methyl)benzamide | 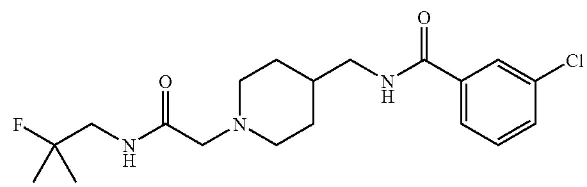 [SMILES: CC(C)(F)CNC(=O)CN1CCC(CNC(=O)c2cccc(Cl)c2)CC1] | 384.18 |
| 555 | N-((1-(2-(2-fluoro-2-methylpropylamino)-2-oxoethyl)piperidin-4-yl)methyl)-3,5-bis(trifluoromethyl)benzamide | 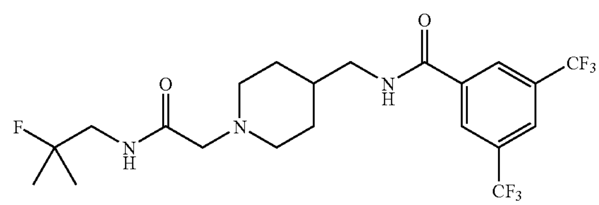 [SMILES: CC(C)(F)CNC(=O)CN1CCC(CNC(=O)c2cc(C(F)(F)F)cc(C(F)(F)F)c2)CC1] | 486.19 |
| 556 | 3-fluoro-N-((1-(2-(2-fluoro-2-methylpropylamino)-2-oxoethyl)piperidin-4-yl)methyl)-5-(trifluoromethyl)benzamide | 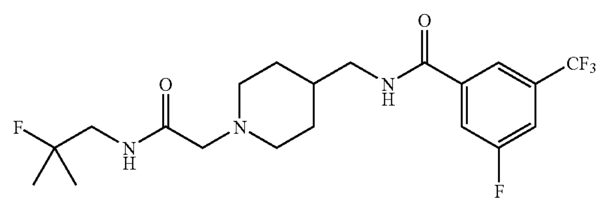 [SMILES: CC(C)(F)CNC(=O)CN1CCC(CNC(=O)c2cc(F)cc(C(F)(F)F)c2)CC1] | 436.19 |
| 557 | 3-fluoro-N-((1-(2-(2-fluoro-2-methylpropylamino)-2-oxoethyl)piperidin-4-yl)methyl)-5-methoxybenzamide | 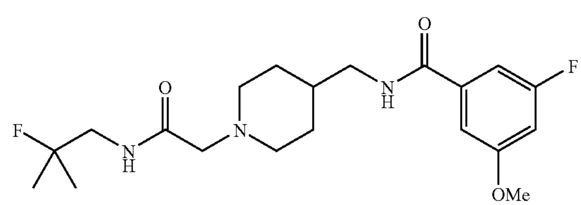 [SMILES: COc1cc(F)cc(C(=O)NCC2CCN(CC(=O)NCC(C)(C)F)CC2)c1] | 398.22 |
| 558 | 3-chloro-5-fluoro-N-((1-(1-oxo-1-((R)-2-(trifluoromethyl)pyrrolidin-1-yl)propan-2-yl)piperidin-4-yl)methyl)benzamide | 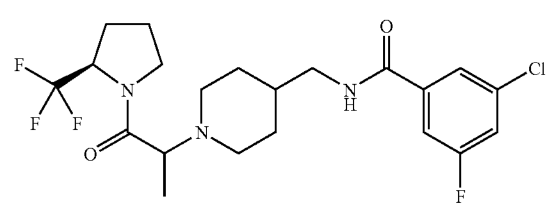 [SMILES: CC(C(=O)N1CCC[C@@H]1C(F)(F)F)N1CCC(CNC(=O)c2cc(F)cc(Cl)c2)CC1] | 464.16 |

TABLE 1-continued

| Cmpd No. | Name | Structure | Mass Spec (m/z) |
|---|---|---|---|
| 559 | 3-chloro-5-fluoro-N-((1-(1-oxo-1-(thiazolidin-3-yl)propan-2-yl)piperidin-4-yl)methyl)benzamide | 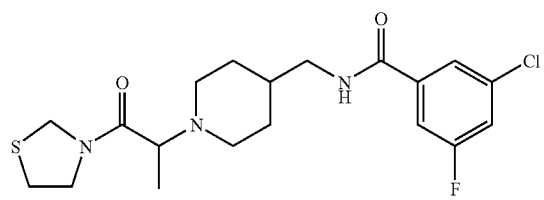 [SMILES: CC(C(=O)N1CCSC1)N1CCC(CNC(=O)c2cc(F)cc(Cl)c2)CC1] | 414.13 |
| 560 | N-((1-(2-(tert-butoxyamino)-2-oxoethyl)piperidin-4-yl)methyl)-3,5-bis(trifluoromethyl)benzamide | 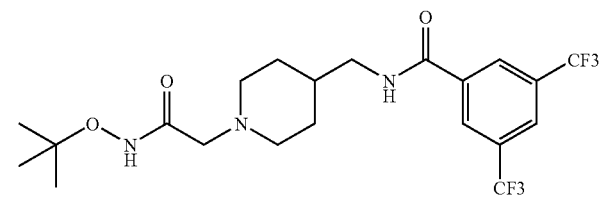 [SMILES: CC(C)(C)ONC(=O)CN1CCC(CNC(=O)c2cc(C(F)(F)F)cc(C(F)(F)F)c2)CC1] | 484.20 |
| 561 | 3-fluoro-N-((1-(2-oxo-2-(1-(tetrahydro-2H-pyran-4-yl)cyclopropylamino)ethyl)piperidin-4-yl)methyl)-5-(trifluoromethyl)benzamide | 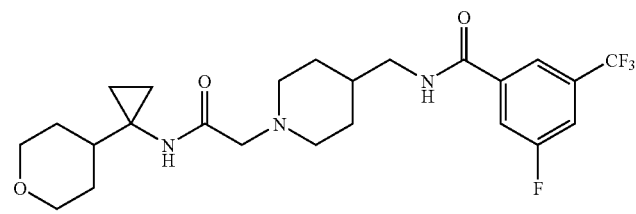 [SMILES: O=C(CN1CCC(CNC(=O)c2cc(F)cc(C(F)(F)F)c2)CC1)NC1(C2CCOCC2)CC1] | 486.23 |
| 562 | 3-fluoro-5-methoxy-N-((1-(2-oxo-2-(1-(tetrahydro-2H-pyran-4-yl)cyclopropylamino)ethyl)piperidin-4-yl)methyl)benzamide | 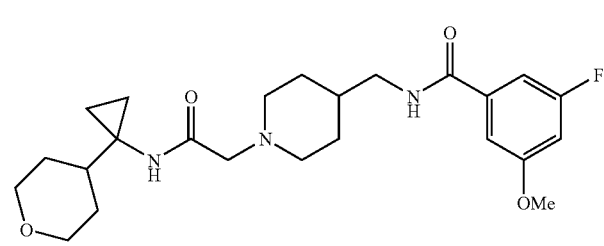 [SMILES: COc1cc(F)cc(C(=O)NCC2CCN(CC(=O)NC3(C4CCOCC4)CC3)CC2)c1] | 448.25 |
| 563 | 3-chloro-5-fluoro-N-((1-(2-oxo-2-(1-(tetrahydro-2H-pyran-4-yl)cyclopropylamino)ethyl)piperidin-4-yl)methyl)benzamide | 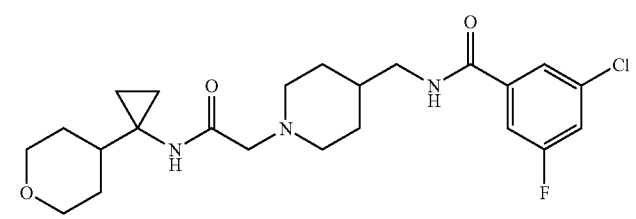 [SMILES: O=C(CN1CCC(CNC(=O)c2cc(F)cc(Cl)c2)CC1)NC1(C2CCOCC2)CC1] | 452.20 |
| 564 | 3-fluoro-N-((1-(2-(1-methoxy-2-methylpropan-2-ylamino)-2-oxoethyl)piperidin-4-yl)methyl)-5-(trifluoromethyl)benzamide | 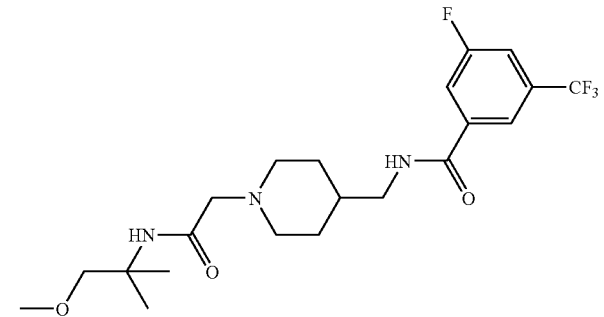 [SMILES: COCC(C)(C)NC(=O)CN1CCC(CNC(=O)c2cc(F)cc(C(F)(F)F)c2)CC1] | 448.21 |

TABLE 1-continued

| Cmpd No. | Name | Structure | Mass Spec (m/z) |
|---|---|---|---|
| 565 | 3-chloro-N-((1-(2-(1,1-dimethylethyl-sulfonamido)ethyl)piperidin-4-yl)methyl)-5-fluorobenzamide | 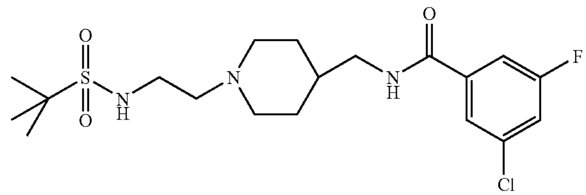 [SMILES: CC(C)(C)S(=O)(=O)NCCN1CCC(CNC(=O)c2cc(F)cc(Cl)c2)CC1] | 434.16 |
| 566 | 3-chloro-N-((1-(2-(1-methoxy-2-methylpropan-2-ylamino)-2-oxoethyl)piperidin-4-yl)methyl)benzamide | 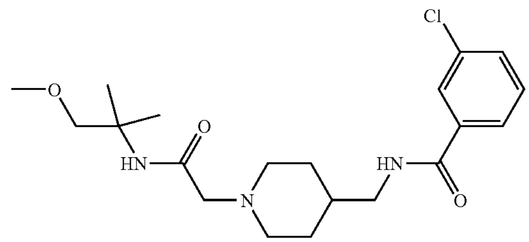 [SMILES: COCC(C)(C)NC(=O)CN1CCC(CNC(=O)c2cccc(Cl)c2)CC1] | 396.20 |
| 567 | 3-fluoro-5-methoxy-N-((1-(2-(1-methoxy-2-methylpropan-2-ylamino)-2-oxoethyl)piperidin-4-yl)methyl)benzamide | 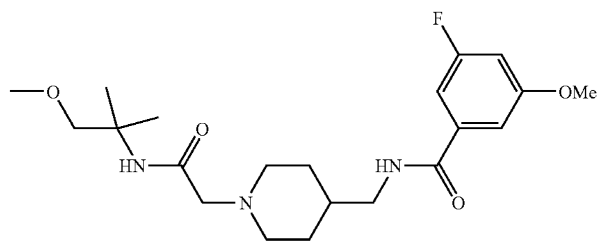 [SMILES: COCC(C)(C)NC(=O)CN1CCC(CNC(=O)c2cc(F)cc(OC)c2)CC1] | 410.24 |
| 568 | N-((1-(2-(2,4-dioxo-1,3-diazaspiro[4.5]decan-3-yl)ethyl)piperidin-4-yl)methyl)-3-fluoro-5-(trifluoromethyl)benzamide | 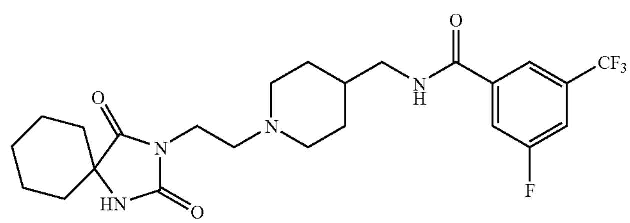 [SMILES: O=C(NCC1CCN(CCN2C(=O)NC3(CCCCC3)C2=O)CC1)c1cc(F)cc(C(F)(F)F)c1] | 499.23 |
| 569 | N-((1-(2-(6,8-dioxo-5,7-diazaspiro[3.4]octan-7-yl)ethyl)piperidin-4-yl)methyl)-3-fluoro-5-(trifluoromethyl)benzamide | 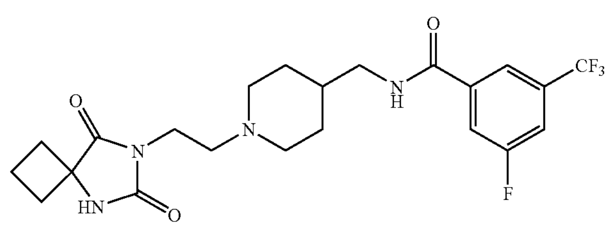 [SMILES: O=C(NCC1CCN(CCN2C(=O)NC3(CCC3)C2=O)CC1)c1cc(F)cc(C(F)(F)F)c1] | 471.19 |
| 570 | N-((1-(2-(1-aminocyclohexane-carboxamido)ethyl)piperidin-4-yl)methyl)-3-fluoro-5-(trifluoromethyl)benzamide | 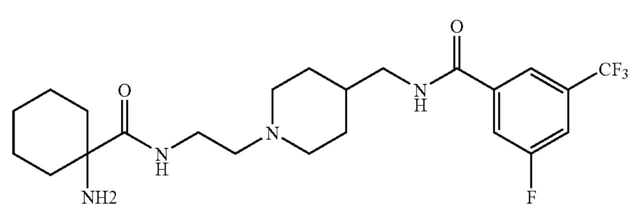 [SMILES: NC1(C(=O)NCCN2CCC(CNC(=O)c3cc(F)cc(C(F)(F)F)c3)CC2)CCCCC1] | 473.25 |
| 571 | N-((1-(2-(1-aminocyclobutane-carboxamido)ethyl)piperidin-4-yl)methyl)-3-fluoro-5-(trifluoromethyl)benzamide | 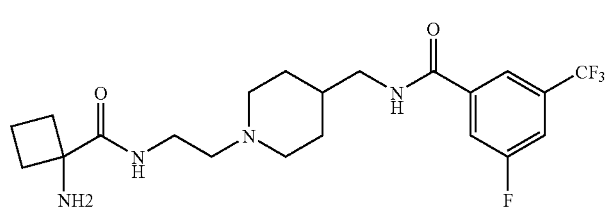 [SMILES: NC1(C(=O)NCCN2CCC(CNC(=O)c3cc(F)cc(C(F)(F)F)c3)CC2)CCC1] | 445.21 |

TABLE 1-continued

| Cmpd No. | Name | Structure | Mass Spec (m/z) |
|---|---|---|---|
| 572 | tert-butyl 1-(2-(4-((3-fluoro-5-(trifluoromethyl)benzamido)methyl)piperidin-1-yl)ethylcarbamoyl)cyclobutylcarbamate | 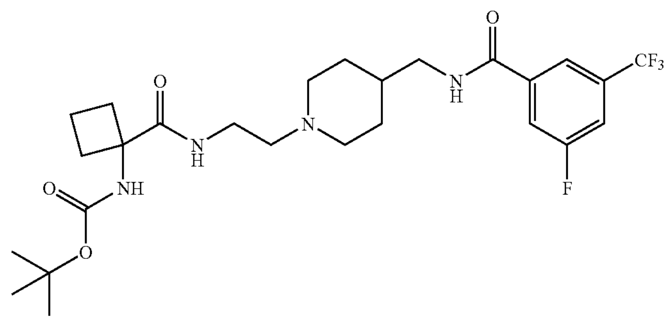 [SMILES: CC(C)(C)OC(=O)NC1(C(=O)NCCN2CCC(CNC(=O)c3cc(F)cc(C(F)(F)F)c3)CC2)CCC1] | 545.27 |
| 573 | 3-chloro-N-((1-(2-(1,1-dimethylethyl-sulfonamido)ethyl)piperidin-4-yl)methyl)benzamide | 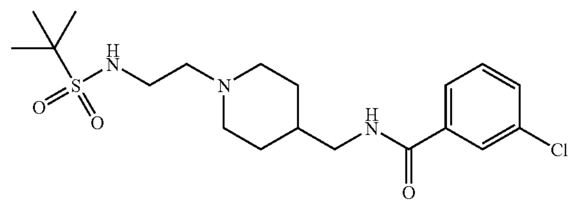 [SMILES: CC(C)(C)S(=O)(=O)NCCN1CCC(CNC(=O)c2cccc(Cl)c2)CC1] | 416.17 |
| 574 | N-((1-(2-(1,1-dimethylethylsulfonamido)ethyl)piperidin-4-yl)methyl)-3-(trifluoromethoxy)benzamide | 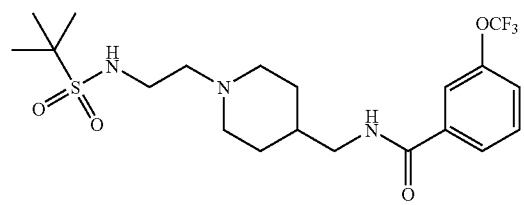 [SMILES: CC(C)(C)S(=O)(=O)NCCN1CCC(CNC(=O)c2cccc(OC(F)(F)F)c2)CC1] | 466.19 |
| 575 | N-((1-(2-(1,1-dimethylethylsulfonamido)ethyl)piperidin-4-yl)methyl)-3-fluoro-5-methylbenzamide | 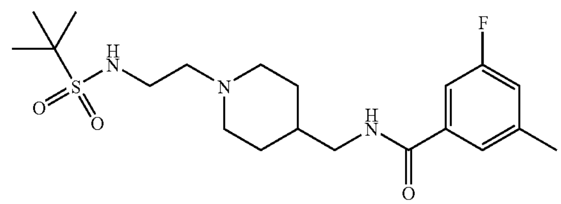 [SMILES: Cc1cc(F)cc(C(=O)NCC2CCN(CCNS(=O)(=O)C(C)(C)C)CC2)c1] | 414.21 |
| 576 | N-((1-(2-(1,1-dimethylethylsulfonamido)ethyl)piperidin-4-yl)methyl)-3,5-dimethoxybenzamide | 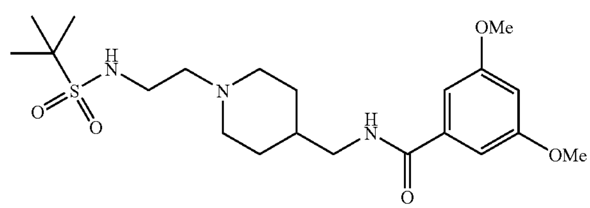 [SMILES: COc1cc(OC)cc(C(=O)NCC2CCN(CCNS(=O)(=O)C(C)(C)C)CC2)c1] | 442.23 |
| 577 | N-((1-(2-(1,1-dimethylethylsulfonamido)ethyl)piperidin-4-yl)methyl)-3-fluoro-5-methoxybenzamide | 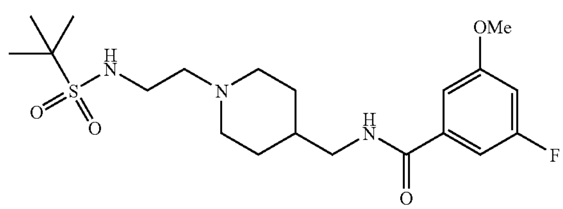 [SMILES: COc1cc(F)cc(C(=O)NCC2CCN(CCNS(=O)(=O)C(C)(C)C)CC2)c1] | 430.21 |

TABLE 1-continued

| Cmpd No. | Name | Structure | Mass Spec (m/z) |
|---|---|---|---|
| 578 | N-((1-(2-(3,3-dimethylmorpholino)-2-oxoethyl)piperidin-4-yl)methyl)-3,5-bis(trifluoromethyl)benzamide | 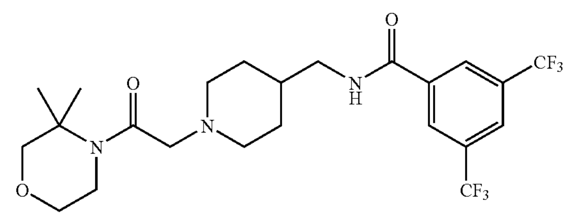 [SMILES: CC1(C)COCCN1C(=O)CN1CCC(CNC(=O)c2cc(C(F)(F)F)cc(C(F)(F)F)c2)CC1] | 510.21 |
| 579 | 3-chloro-5-fluoro-N-((1-(2-(methyl(1,1,1-trifluoro-2-methylpropan-2-yl)amino)-2-oxoethyl)piperidin-4-yl)methyl)benzamide | 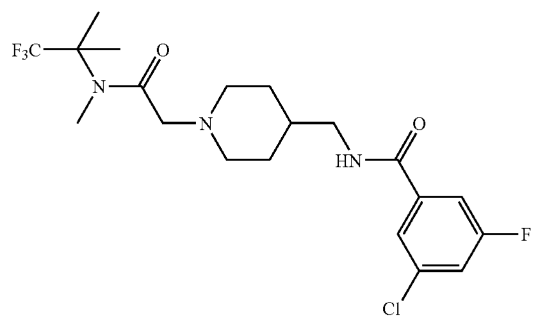 [SMILES: CN(C(=O)CN1CCC(CNC(=O)c2cc(F)cc(Cl)c2)CC1)C(C)(C)C(F)(F)F] | 452.16 |
| 580 | 3-chloro-N-((1-(2-(methyl(1,1,1-trifluoro-2-methylpropan-2-yl)amino)-2-oxoethyl)piperidin-4-yl)methyl)benzamide | 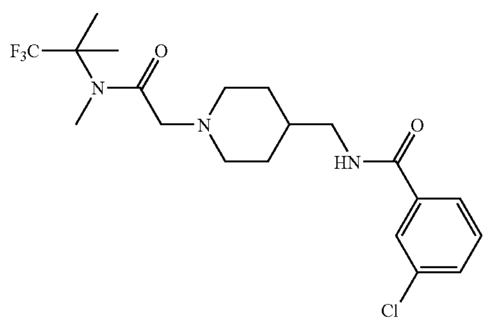 [SMILES: CN(C(=O)CN1CCC(CNC(=O)c2cccc(Cl)c2)CC1)C(C)(C)C(F)(F)F] | 434.17 |
| 581 | 3-fluoro-5-methoxy-N-((1-(2-(methyl(1,1,1-trifluoro-2-methylpropan-2-yl)amino)-2-oxoethyl)piperidin-4-yl)methyl)benzamide | 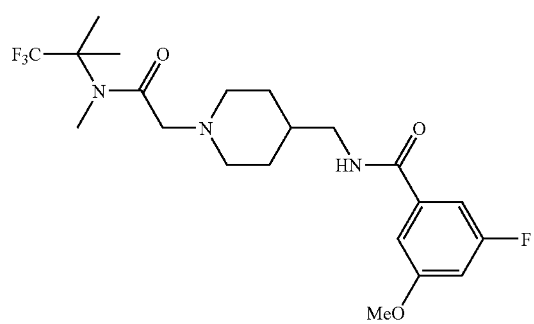 [SMILES: COc1cc(F)cc(C(=O)NCC2CCN(CC(=O)N(C)C(C)(C)C(F)(F)F)CC2)c1] | 448.21 |
| 582 | N-((1-(2-(2,2-dimethylpyrrolidin-1-yl)-2-oxoethyl)piperidin-4-yl)methyl)-3,5-bis(trifluoromethyl)benzamide | 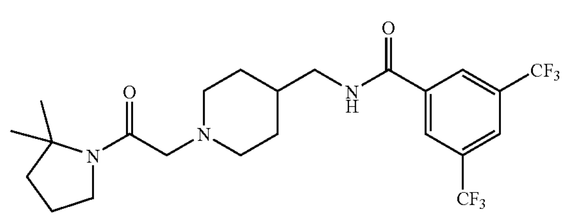 [SMILES: CC1(C)CCCN1C(=O)CN1CCC(CNC(=O)c2cc(C(F)(F)F)cc(C(F)(F)F)c2)CC1] | 494.22 |

TABLE 1-continued

| Cmpd No. | Name | Structure | Mass Spec (m/z) |
|---|---|---|---|
| 583 | 3-chloro-5-fluoro-N-((1-(2-(methyl(1-methylcyclobutyl)amino)-2-oxoethyl)piperidin-4-yl)methyl)benzamide | 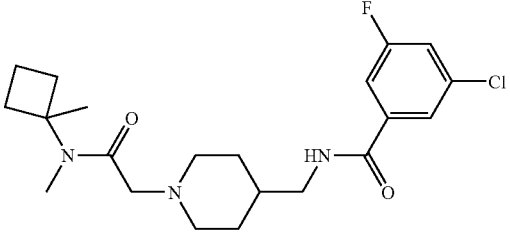 [SMILES: CN(C(=O)CN1CCC(CNC(=O)c2cc(F)cc(Cl)c2)CC1)C1(C)CCC1] | 410.19 |
| 584 | 3-fluoro-5-methoxy-N-((1-(2-(methyl(1-methylcyclobutyl)amino)-2-oxoethyl)piperidin-4-yl)methyl)benzamide | 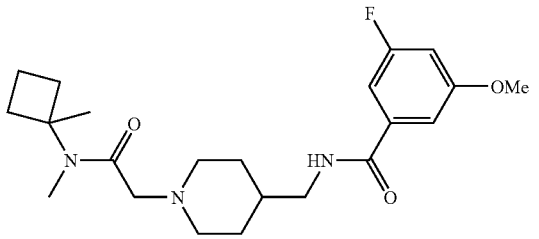 [SMILES: COc1cc(F)cc(C(=O)NCC2CCN(CC(=O)N(C)C3(C)CCC3)CC2)c1] | 406.24 |
| 585 | N-((1-(2-(cyclopentylamino)-2-oxoethyl)piperidin-4-yl)methyl)-3-(methylsulfonyl)-5-(trifluoromethyl)benzamide | 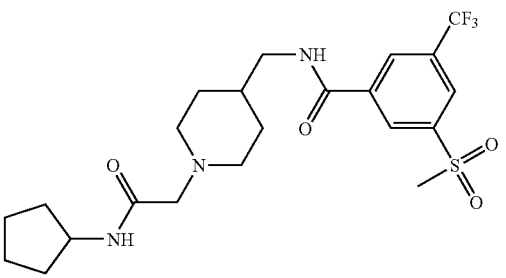 [SMILES: CS(=O)(=O)c1cc(C(=O)NCC2CCN(CC(=O)NC3CCCC3)CC2)cc(C(F)(F)F)c1] | 490.19 |
| 586 | 3-(methylsulfonyl)-5-(trifluoromethyl)-N-((1-(2-(1-(trifluoromethyl)cyclobutane-carboxamido)ethyl)piperidin-4-yl)methyl)benzamide | 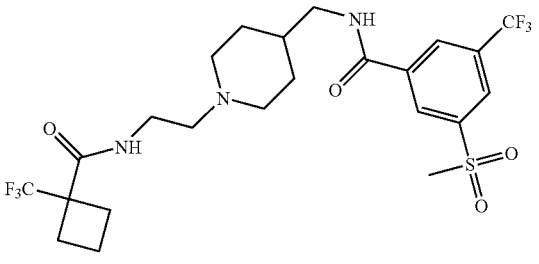 [SMILES: CS(=O)(=O)c1cc(C(=O)NCC2CCN(CCNC(=O)C3(C(F)(F)F)CCC3)CC2)cc(C(F)(F)F)c1] | 558.18 |
| 587 | 3-(methylsulfonyl)-N-((1-(2-(3,3,3-trifluoro-2,2-dimethylpropanamido)ethyl)piperidin-4-yl)methyl)-5-(trifluoromethyl)benzamide | 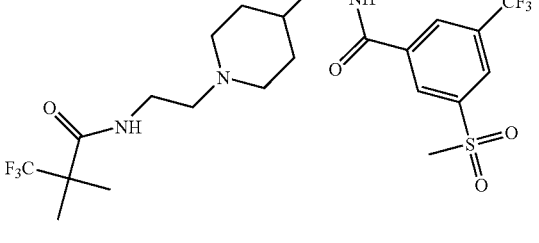 | 546.18 |
| 588 | N-((1-(2-(cyclopropanesulfonamido)ethyl)piperidin-4-yl)methyl)-3-(methylsulfonyl)-5-(trifluoromethyl)benzamide | 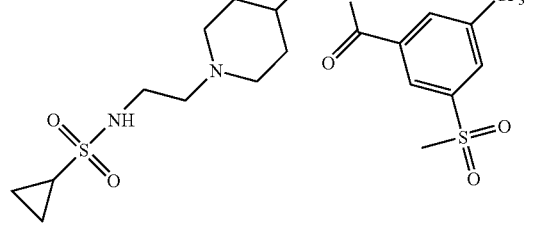 | 512.14 |

TABLE 1-continued

| Cmpd No. | Name | Structure | Mass Spec (m/z) |
|---|---|---|---|
| 589 | (R)-3-(methylsulfonyl)-N-((1-(2-oxo-2-(2-(trifluoromethyl)pyrrolidin-1-yl)ethyl)piperidin-4-yl)methyl)-5-(trifluoromethyl)benzamide | 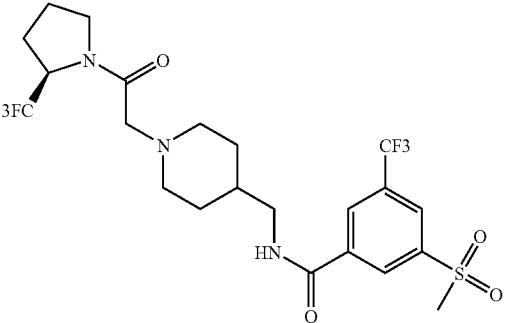 | 544.16 |
| 590 | 3-chloro-5-methoxy-N-((1-(2-(1-(trifluoromethyl)cyclopropane-carboxamido)ethyl)piperidin-4-yl)methyl)benzamide | 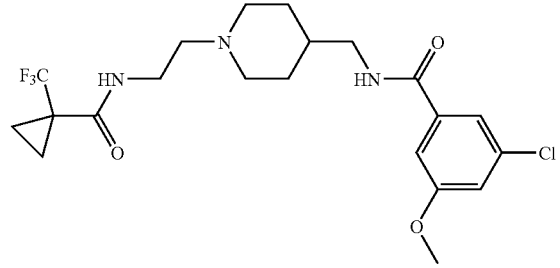 [SMILES: COc1cc(Cl)cc(C(=O)NCC2CCN(CCNC(=O)C3(C(F)(F)F)CC3)CC2)c1] | 462.17 |
| 591 | 3-chloro-5-methoxy-N-((1-(2-(methyl(1-methylcyclobutyl)amino)-2-oxoethyl)piperidin-4-yl)methyl)benzamide | 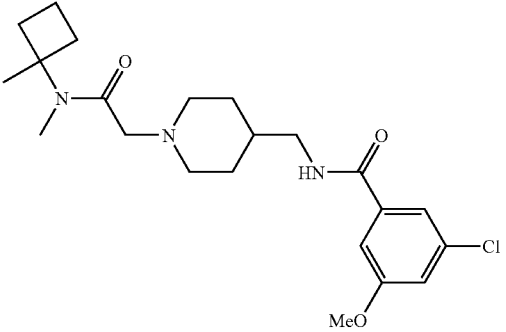 [SMILES: COc1cc(Cl)cc(C(=O)NCC2CCN(CC(=O)N(C)C3(C)CCC3)CC2)c1] | 422.21 |
| 592 | 3,5-dichloro-N-((1-(2-(methyl(1-methylcyclobutyl)amino)-2-oxoethyl)piperidin-4-yl)methyl)benzamide | 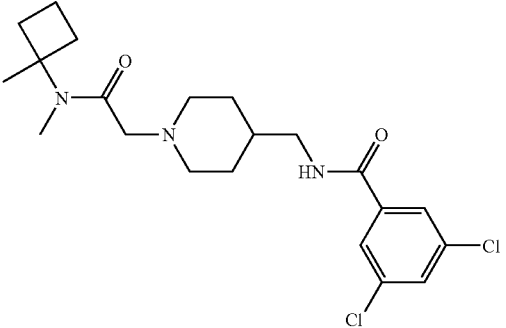 [SMILES: CN(C(=O)CN1CCC(CNC(=O)c2cc(Cl)cc(Cl)c2)CC1)C1(C)CCC1] | 426.16 |

TABLE 1-continued

| Cmpd No. | Name | Structure | Mass Spec (m/z) |
|---|---|---|---|
| 593 | 3-bromo-N-((1-(2-(methyl(1-methyl-cyclobutyl)amino)-2-oxoethyl)piperidin-4-yl)methyl)benzamide | 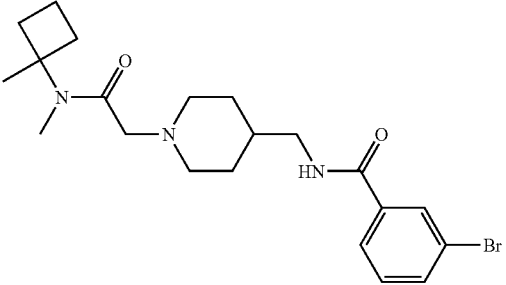 [SMILES: CN(C(=O)CN1CCC(CNC(=O)c2cccc(Br)c2)CC1)C1(C)CCC1] | 436.15 |
| 594 | 3-fluoro-N-((1-(2-(methyl(1-methyl-cyclobutyl)amino)-2-oxoethyl)piperidin-4-yl)methyl)-5-(trifluoromethyl)benzamide | 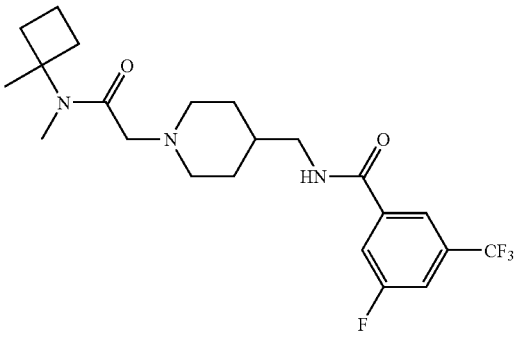 [SMILES: CN(C(=O)CN1CCC(CNC(=O)c2cc(F)cc(C(F)(F)F)c2)CC1)C1(C)CCC1] | 444.22 |
| 595 | 3-bromo-5-chloro-N-((1-(2-(methyl(1-methylcyclobutyl)amino)-2-oxoethyl)piperidin-4-yl)methyl)benzamide | 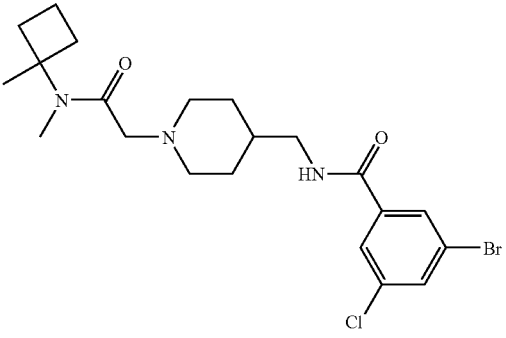 [SMILES: CN(C(=O)CN1CCC(CNC(=O)c2cc(Cl)cc(Br)c2)CC1)C1(C)CCC1] | 470.11 |
| 596 | N-((1-(2-(tert-butyl(methyl)amino)-2-oxoethyl)piperidin-4-yl)methyl)-3-chloro-5-methoxybenzamide | 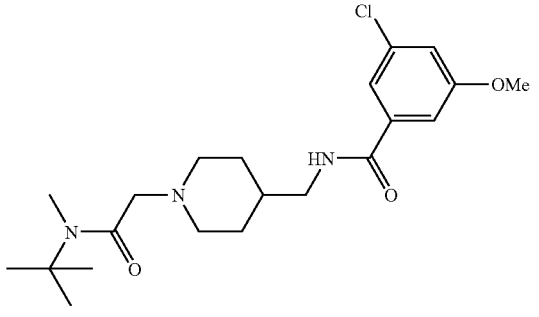 [SMILES: COc1cc(Cl)cc(C(=O)NCC2CCN(CC(=O)N(C)C(C)(C)C)CC2)c1] | 410.21 |
| 597 | tert-butyl 3-(4-((3-chloro-5-fluorobenzamido)methyl)piperidin-1-yl)azetidine-1-carboxylate | 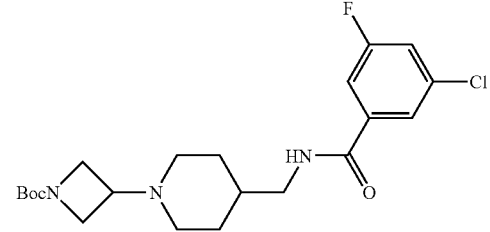 [SMILES: CC(C)(C)OC(=O)N1CC(N2CCC(CNC(=O)c3cc(F)cc(Cl)c3)CC2)C1] | 426.19 |

TABLE 1-continued

| Cmpd No. | Name | Structure | Mass Spec (m/z) |
|---|---|---|---|
| 598 | tert-butyl 4-((4-((3-chloro-5-fluorobenzamido)methyl)piperidin-1-yl)methyl)-4-hydroxypiperidine-1-carboxylate | 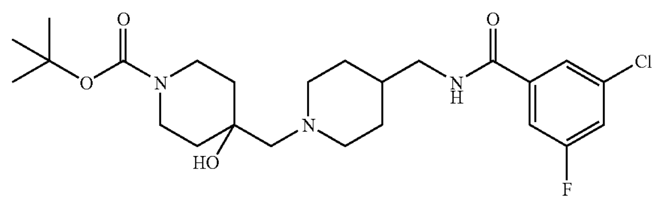 [SMILES: CC(C)(C)OC(=O)N1CCC(O)(CN2CCC(CNC(=O)c3cc(F)cc(Cl)c3)CC2)CC1] | 484.23 |
| 599 | tert-butyl 4-((4-((3-fluoro-5-(trifluoromethyl)benzamido)methyl)piperidin-1-yl)methyl)-4-hydroxy-piperidine-1-carboxylate | 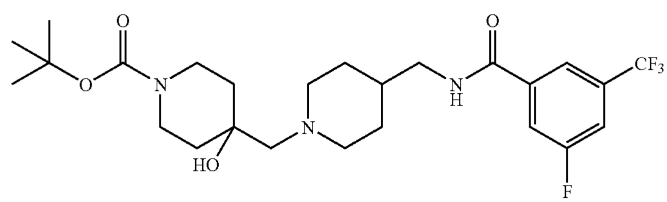 [SMILES: CC(C)(C)OC(=O)N1CCC(O)(CN2CCC(CNC(=O)c3cc(F)cc(C(F)(F)F)c3)CC2)CC1] | 518.26 |
| 600 | 3-chloro-N-((1-(1-(3-chloro-5-methoxybenzoyl)azetidin-3-yl)piperidin-4-yl)methyl)-5-fluorobenzamide | 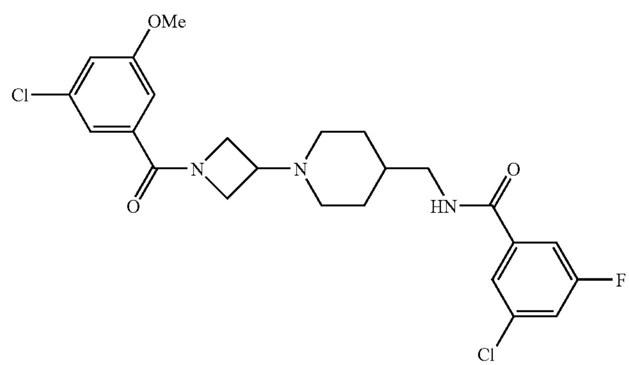 [SMILES: COc1cc(Cl)cc(C(=O)N2CC(N3CCC(CNC(=O)c4cc(F)cc(Cl)c4)CC3)C2)c1] | 494.13 |
| 601 | 3-chloro-N-((1-(1-(3,5-dichlorobenzoyl)azetidin-3-yl)piperidin-4-yl)methyl)-5-fluorobenzamide | 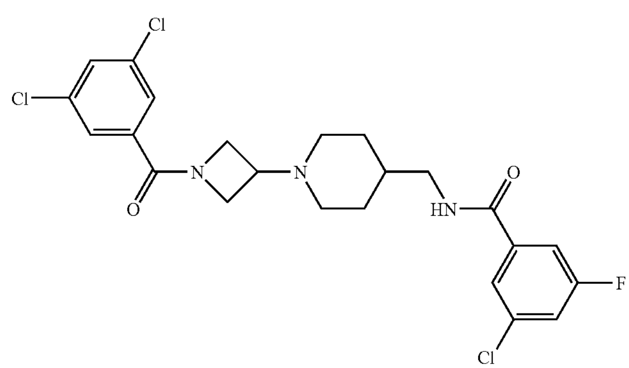 [SMILES: O=C(NCC1CCN(C2CN(C(=O)c3cc(Cl)cc(Cl)c3)C2)CC1)c1cc(F)cc(Cl)c1] | 498.08 |
| 602 | N-((1-(1-(3-bromobenzoyl)azetidin-3-yl)piperidin-4-yl)methyl)-3-chloro-5-fluorobenzamide | 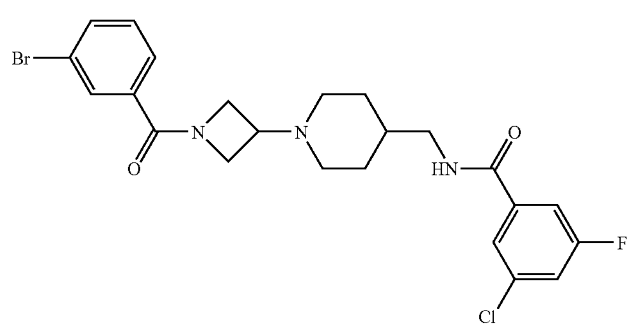 [SMILES: O=C(NCC1CCN(C2CN(C(=O)c3cccc(Br)c3)C2)CC1)c1cc(F)cc(Cl)c1] | 508.07 |

TABLE 1-continued

| Cmpd No. | Name | Structure | Mass Spec (m/z) |
|---|---|---|---|
| 603 | 3-chloro-5-fluoro-N-((1-(1-(3-(trifluoromethoxy)benzoyl)azetidin-3-yl)piperidin-4-yl)methyl)benzamide | 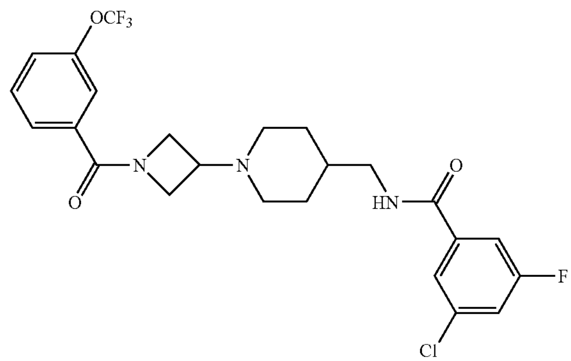 [SMILES: O=C(NCC1CCN(C2CN(C(=O)c3cccc(OC(F)(F)F)c3)C2)CC1)c1cc(F)cc(Cl)c1] | 514.14 |
| 604 | 3-chloro-5-fluoro-N-((1-(1-(3-fluoro-5-(trifluoromethyl)benzoyl)azetidin-3-yl)piperidin-4-yl)methyl)benzamide | 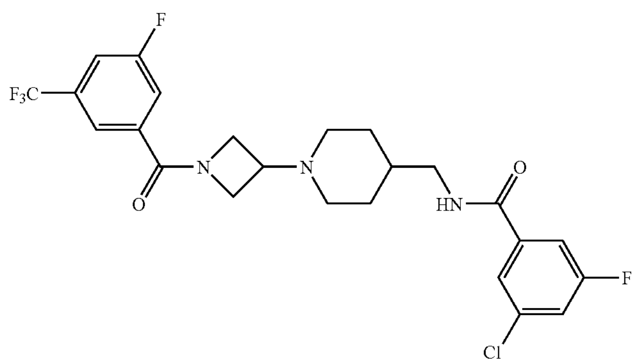 [SMILES: O=C(NCC1CCN(C2CN(C(=O)c3cc(F)cc(C(F)(F)F)c3)C2)CC1)c1cc(F)cc(Cl)c1] | 516.14 |
| 605 | 3-chloro-N-((1-(1-(3-chloro-5-fluorobenzoyl)azetidin-3-yl)piperidin-4-yl)methyl)-5-fluorobenzamide | 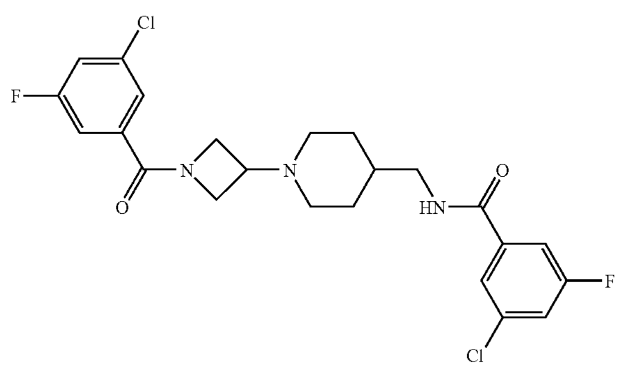 [SMILES: O=C(NCC1CCN(C2CN(C(=O)c3cc(F)cc(Cl)c3)C2)CC1)c1cc(F)cc(Cl)c1] | 482.11 |
| 606 | 3-chloro-N-((1-(1-(3-chlorobenzoyl)azetidin-3-yl)piperidin-4-yl)methyl)-5-fluorobenzamide | 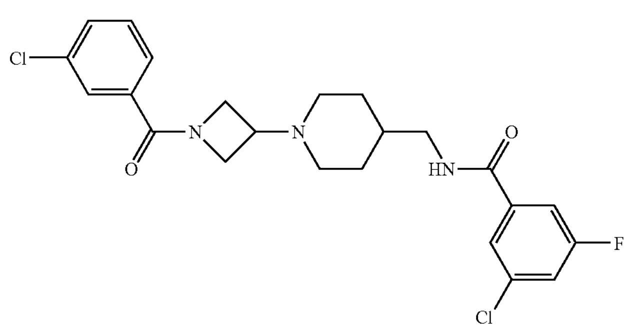 [SMILES: O=C(NCC1CCN(C2CN(C(=O)c3cccc(Cl)c3)C2)CC1)c1cc(F)cc(Cl)c1] | 464.12 |

TABLE 1-continued

| Cmpd No. | Name | Structure | Mass Spec (m/z) |
|---|---|---|---|
| 607 | 3-chloro-5-fluoro-N-((1-(1-pivaloyl-azetidin-3-yl)piperidin-4-yl)methyl)benzamide | 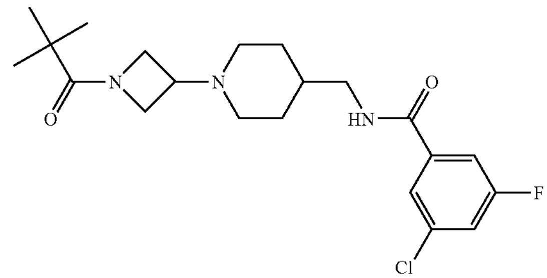 [SMILES: CC(C)(C)C(=O)N1CC(N2CCC(CNC(=O)c3cc(F)cc(Cl)c3)CC2)C1] | 410.19 |
| 608 | 3-chloro-5-fluoro-N-((1-(1-(1-methylcyclopropanecarbonyl)azetidin-3-yl)piperidin-4-yl)methyl)benzamide | 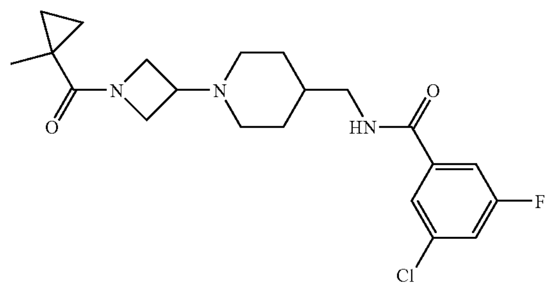 [SMILES: CC1(C(=O)N2CC(N3CCC(CNC(=O)c4cc(F)cc(Cl)c4)CC3)C2)CC1] | 408.18 |
| 609 | 3-chloro-5-fluoro-N-((1-(1-(1-(trifluoromethyl)cyclopropanecarbonyl)azetidin-3-yl)piperidin-4-yl)methyl)benzamide | 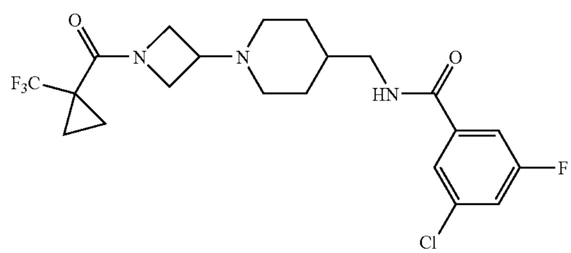 [SMILES: O=C(NCC1CCN(C2CN(C(=O)C3(C(F)(F)F)CC3)C2)CC1)c1cc(F)cc(Cl)c1] | 462.15 |
| 610 | 3-chloro-5-fluoro-N-((1-(1-(1-(trifluoromethyl)cyclobutanecarbonyl)azetidin-3-yl)piperidin-4-yl)methyl)benzamide | 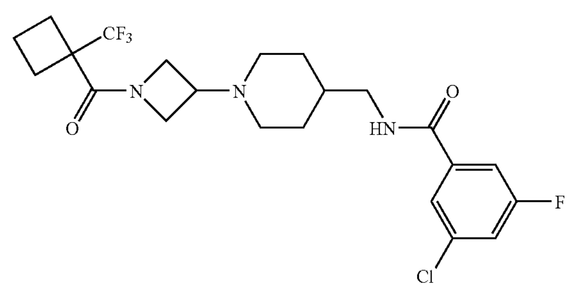 [SMILES: O=C(NCC1CCN(C2CN(C(=O)C3(C(F)(F)F)CCC3)C2)CC1)c1cc(F)cc(Cl)c1] | 476.16 |
| 611 | 3-chloro-N-((1-(1-(4,4-difluoro-1-methylcyclohexanecarbonyl)azetidin-3-yl)piperidin-4-yl)methyl)-5-fluorobenzamide | 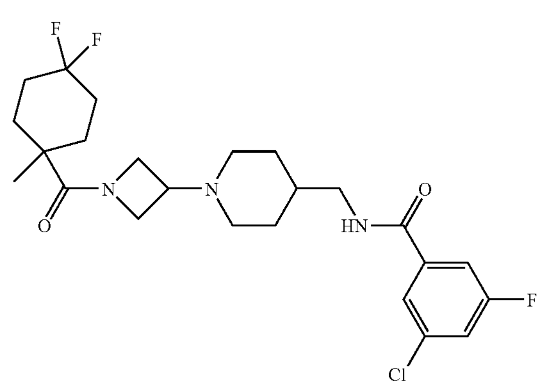 [SMILES: CC1(C(=O)N2CC(N3CCC(CNC(=O)c4cc(F)cc(Cl)c4)CC3)C2)CCC(F)(F)CC1] | 486.21 |

TABLE 1-continued

| Cmpd No. | Name | Mass Spec (m/z) |
|---|---|---|
| 612 | N-tert-butyl-3-(4-((3-chloro-5-fluorobenzamido)methyl)piperidin-1-yl)azetidine-1-carboxamide | 425.20 |
| 613 | N-((1-(2-(tert-butylamino)-2-oxoethyl)piperidin-4-yl)methyl)-2'-chlorobiphenyl-3-carboxamide | 442.22 |
| 614 | N-((1-(2-(tert-butylamino)-2-oxoethyl)piperidin-4-yl)methyl)-2',3'-dichlorobiphenyl-3-carboxamide | 476.18 |
| 615 | N-((1-(2-(tert-butylamino)-2-oxoethyl)piperidin-4-yl)methyl)-3'-chlorobiphenyl-3-carboxamide | 442.22 |
| 616 | N-((1-(2-(tert-butylamino)-2-oxoethyl)piperidin-4-yl)methyl)-2',4'-dichlorobiphenyl-3-carboxamide | 476.18 |

TABLE 1-continued

| Cmpd No. | Name | Structure | Mass Spec (m/z) |
|---|---|---|---|
| 617 | N-((1-(2-(tert-butylamino)-2-oxoethyl)piperidin-4-yl)methyl)-4'-chlorobiphenyl-3-carboxamide | 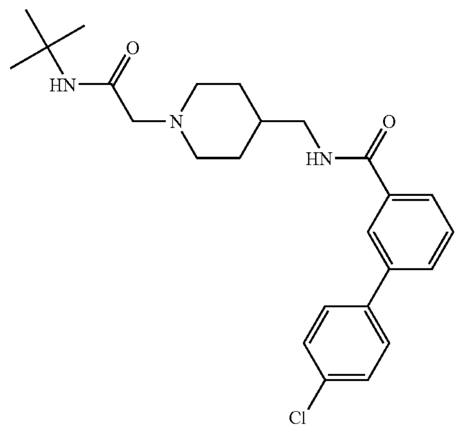 [SMILES: CC(C)(C)NC(=O)CN1CCC(CNC(=O)c2cccc(-c3ccc(Cl)cc3)c2)CC1] | 442.22 |
| 618 | N-((1-(2-(tert-butylamino)-2-oxoethyl)piperidin-4-yl)methyl)-3',4'-dichlorobiphenyl-3-carboxamide | 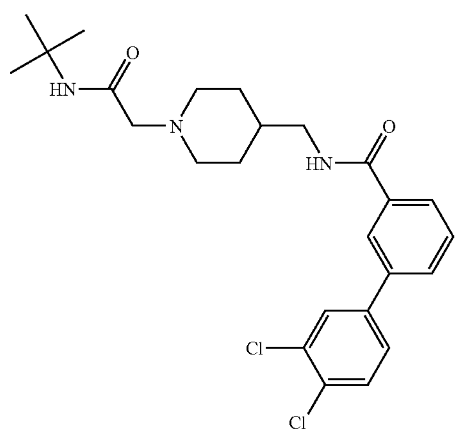 [SMILES: CC(C)(C)NC(=O)CN1CCC(CNC(=O)c2cccc(-c3ccc(Cl)c(Cl)c3)c2)CC1] | 476.18 |
| 619 | N-((1-(2-(tert-butylamino)-2-oxoethyl)piperidin-4-yl)methyl)-3'-(trifluoromethyl)biphenyl-3-carboxamide | 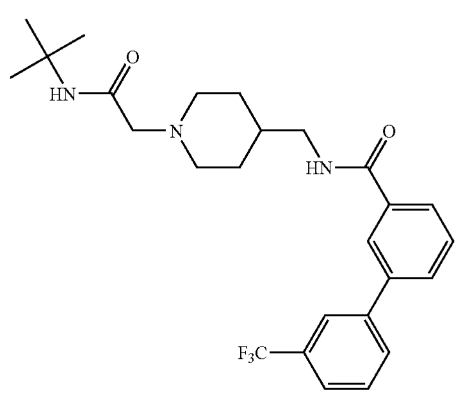 [SMILES: CC(C)(C)NC(=O)CN1CCC(CNC(=O)c2cccc(-c3cccc(C(F)(F)F)c3)c2)CC1] | 476.24 |

| Cmpd No. | Name | Structure | Mass Spec (m/z) |
|---|---|---|---|
| 620 | N-((1-(2-(tert-butylamino)-2-oxoethyl)piperidin-4-yl)methyl)-3',5'-dichlorobiphenyl-3-carboxamide | 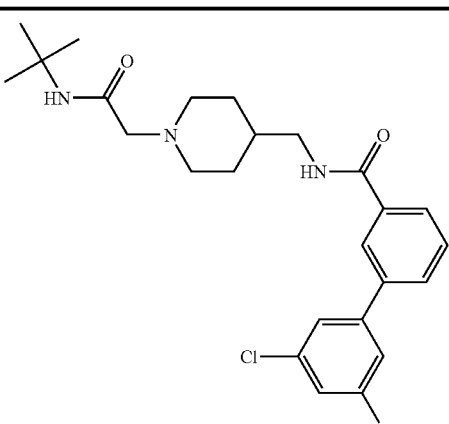 | 476.18 |

EXAMPLE 17

T-Type Channel Blocking Activities of Various Invention Compounds

A. Transformation of HEK Cells:

T-type calcium channel blocking activity was assayed in human embryonic kidney cells, HEK 293, stably transfected with the T-type calcium channel subunits. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells stably transfected using a standard calcium phosphate protocol and the appropriate calcium channel cDNA's. Fresh DMEM was supplied and the cells transferred to 28° C./5% $CO_2$. Cells were incubated for 1 to 2 days prior to whole cell recording.

Standard patch-clamp techniques were employed to identify blockers of T-type currents. Briefly, previously described HEK cell lines stably expressing human $\alpha_{1G}$, $\alpha_{1H}$ and $\alpha_{1I}$ T-type channels were used for all the recordings (passage #: 4-20, 37° C., 5% $CO_2$). Whole cell patch clamp experiments were performed using an Axopatch 200B amplifier (Axon Instruments, Burlingame, Calif.) linked to a personal computer equipped with pCLAMP software. Data were analyzed using Clampfit (Axon Instruments) and SigmaPlot 4.0 (Jandel Scientific). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal solution).

TABLE 2

| External Solution 500 ml - pH 7.4, 265.5 mOsm | | | |
|---|---|---|---|
| Salt | Final mM | Stock M | Final ml |
| CsCl | 142 | 1 | 71 |
| $CaCl_2$ | 2 | 1 | 1 |
| $MgCl_2$ | 1 | 1 | 0.5 |
| HEPES | 10 | 0.5 | 10 |
| glucose | 10 | — | 0.9 grams |

TABLE 3

| Internal Solution 50 ml - pH 7.3 with CsOH, 270 mOsm | | | |
|---|---|---|---|
| Salt | Final mM | Stock M | Final ml |
| Cs-Methanesulfonate | 126.5 | — | 1.442 gr/50 ml |
| MgCl2 | 2 | 1 | 0.1 |
| HEPES | 10 | 0.5 | 1 |
| EGTA-Cs | 11 | 0.25 | 2.2 |
| ATP | 2 | 0.2 | 0.025 |
| | | | (1 aliquot/2.5 ml) |

T-type currents were reliably obtained by using two voltage protocols:

(1) "non-inactivating", and (2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

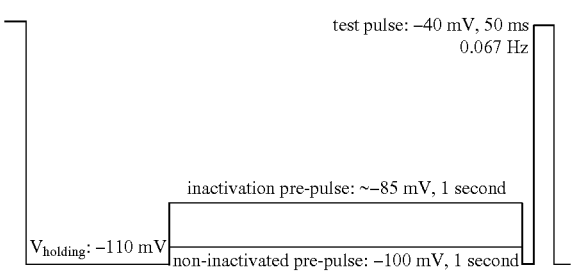

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. $IC_{50}$ values are shown for various compounds of the invention in Table 4 for the drug of interest. Values are shown in μM and values above 10 μM are simply represented as 10 μM. Similarly, $IC_{50}$ values for $\alpha_{1G}$ below 0.30 μM are simply represented as 0.30 μM.

TABLE 4

| T-type Calcium Channel Block | | |
|---|---|---|
| Compound | $\alpha_{1G}$ (μM) | $\alpha_{1H}$ (μM) |
| 1 | 1.01 | 0.37 |
| 2 | 0.30 | 0.54 |
| 3 | 0.30 | 0.55 |
| 6 | | 1.32 |
| 7 | | 4.33 |
| 8 | | 2.42 |
| 11 | 1.89 | 3.80 |
| 12 | 0.48 | 1.66 |
| 13 | 0.63 | 1.87 |
| 14 | 0.30 | 1.17 |
| 15 | 1.03 | 3.04 |
| 16 | 0.30 | 0.19 |
| 17 | 0.30 | 0.12 |
| 18 | 0.30 | 0.08 |
| 19 | 1.74 | 0.74 |
| 20 | 0.30 | 0.40 |
| 21 | 3.66 | 0.59 |
| 26 | | 0.20 |
| 27 | | 0.19 |
| 35 | 0.41 | 0.16 |
| 36 | 4.30 | 1.70 |
| 37 | 0.30 | 0.17 |
| 39 | 1.31 | 1.17 |
| 40 | 0.30 | 0.16 |
| 41 | 0.30 | 0.15 |
| 42 | 1.64 | 0.76 |
| 43 | 0.30 | 0.15 |
| 44 | 0.62 | 0.32 |
| 45 | 10.00 | |
| 47 | 3.11 | 0.88 |
| 48 | 1.57 | 0.79 |
| 49 | 0.34 | 7.30 |
| 50 | 8.97 | |
| 51 | 10.00 | |
| 53 | 10.00 | |
| 55 | 10.00 | |
| 57 | 1.05 | 10.00 |
| 58 | | 4.01 |
| 59 | | 1.66 |
| 60 | | 0.22 |
| 61 | | 10.00 |
| 62 | | 0.23 |
| 63 | | 0.43 |
| 64 | | 0.20 |

TABLE 4-continued

| T-type Calcium Channel Block | | |
|---|---|---|
| Compound | $\alpha_{1G}$ (μM) | $\alpha_{1H}$ (μM) |
| 65 | | 6.37 |
| 66 | | 0.37 |
| 68 | | 7.56 |
| 76 | 7.62 | |
| 85 | 10.00 | |
| 86 | 10.00 | |
| 88 | 10.00 | 10.00 |
| 89 | 4.10 | 10.00 |
| 90 | 4.27 | |
| 91 | 10.00 | |
| 92 | | 0.06 |
| 93 | | 0.09 |
| 94 | | 0.06 |
| 95 | | 10.00 |
| 96 | | 10.00 |
| 97 | | 0.10 |
| 98 | | 3.60 |
| 99 | | 0.21 |
| 100 | | 0.10 |
| 101 | | 0.14 |
| 102 | | 10.00 |
| 103 | | 1.21 |
| 104 | | 0.14 |
| 105 | | 0.28 |
| 106 | | 5.56 |
| 107 | | 0.16 |
| 108 | | 0.25 |
| 115 | | 0.23 |
| 116 | | 10.00 |
| 153 | 0.30 | 0.07 |
| 154 | 6.71 | |
| 157 | | 10.00 |
| 159 | 0.31 | 3.36 |
| 160 | 0.02 | 0.50 |
| 166 | 10.00 | |
| 169 | 0.30 | 0.23 |
| 172 | 1.62 | 10.00 |
| 174 | 2.48 | 10.00 |
| 175 | 10.00 | |
| 176 | 10.00 | |
| 177 | 10.00 | |
| 178 | 0.72 | 5.10 |
| 179 | 0.002 | 0.08 |
| 190 | 10.00 | |
| 191 | 10.00 | |
| 194 | 10.00 | |
| 195 | 4.78 | 1.97 |
| 196 | 10.00 | 10.00 |
| 197 | 10.00 | |
| 198 | 0.40 | 1.30 |
| 201 | 10.00 | |
| 206 | 10.00 | |
| 207 | 10.00 | |
| 208 | 10.00 | |
| 209 | 8.60 | |
| 217 | 5.82 | |
| 219 | 10.00 | |
| 220 | 6.91 | |
| 221 | 4.08 | 10.00 |
| 222 | 2.03 | 10.00 |
| 223 | 8.15 | |
| 224 | 3.76 | 6.19 |
| 225 | 0.52 | 0.77 |
| 226 | 10.00 | 10.00 |
| 228 | 1.67 | 2.35 |
| 229 | 10.00 | 10.00 |
| 230 | 4.76 | 0.85 |
| 231 | 10.00 | 10.00 |
| 232 | 5.01 | 2.87 |
| 233 | 2.04 | 1.38 |
| 234 | 1.45 | 0.97 |
| 235 | 0.30 | 0.44 |
| 236 | 0.86 | 1.72 |
| 238 | 10.00 | 10.00 |
| 239 | 0.30 | 1.73 |
| 240 | 10.00 | 10.00 |

TABLE 4-continued

T-type Calcium Channel Block

| Compound | $\alpha_{1G}$ (μM) | $\alpha_{1H}$ (μM) |
|---|---|---|
| 241 | 0.30 | 0.52 |
| 242 | 2.48 | 1.19 |
| 243 | 0.53 | 0.81 |
| 244 | 7.19 | 10.00 |
| 246 | 1.31 | 1.13 |
| 247 | 0.30 | 0.50 |
| 248 | 0.30 | 0.48 |
| 249 | 0.30 | 0.58 |
| 251 | 10.00 | 10.00 |
| 252 | 2.43 | 2.34 |
| 253 | 0.48 | 1.31 |
| 255 | 0.57 | 2.34 |
| 256 | 5.57 | 10.00 |
| 257 | 3.21 | 2.42 |
| 258 | 1.18 | 3.24 |
| 259 | 10.00 | |
| 263 | | 10.00 |
| 264 | 0.30 | 0.53 |
| 265 | 2.06 | 3.76 |
| 267 | 0.39 | 0.87 |
| 268 | 10.00 | 10.00 |
| 269 | 1.40 | 3.14 |
| 270 | 10.00 | |
| 272 | 2.84 | 10.00 |
| 273 | 0.36 | 1.42 |
| 274 | 0.30 | 0.66 |
| 275 | 1.99 | 10.00 |
| 276 | 0.31 | 1.09 |
| 279 | 10.00 | 10.00 |
| 280 | 9.70 | 5.59 |
| 282 | 2.50 | 7.16 |
| 284 | | 10.00 |
| 285 | 4.94 | 10.00 |
| 291 | 0.30 | 0.51 |
| 292 | 0.36 | 0.74 |
| 293 | 5.18 | 4.07 |
| 294 | 0.57 | 0.81 |
| 295 | 1.34 | 1.26 |
| 296 | 0.61 | 1.10 |
| 297 | 10.00 | 10.00 |
| 298 | 0.30 | 0.28 |
| 299 | 1.21 | 1.98 |
| 300 | 2.81 | 3.25 |
| 301 | 0.30 | 0.45 |
| 302 | 0.30 | 0.30 |
| 303 | 0.30 | 0.60 |
| 304 | 0.30 | 0.37 |
| 305 | 7.42 | 4.45 |
| 306 | 0.34 | 0.39 |
| 307 | 0.30 | 0.34 |
| 308 | 1.23 | 0.88 |
| 309 | 0.85 | 0.35 |
| 310 | 10.00 | 10.00 |
| 311 | 2.65 | 0.33 |
| 312 | 4.26 | 0.75 |
| 313 | 6.31 | 0.62 |
| 314 | 10.00 | 9.24 |
| 315 | 9.90 | 1.47 |
| 316 | 10.00 | 5.83 |
| 317 | 0.66 | 0.56 |
| 318 | 0.50 | 0.87 |
| 319 | 0.30 | 0.15 |
| 320 | 0.76 | 1.62 |
| 321 | 1.33 | 1.92 |
| 322 | 4.05 | 2.14 |
| 323 | 1.87 | 2.66 |
| 324 | 10.00 | 10.00 |
| 325 | 6.58 | 3.39 |
| 326 | 10.00 | 6.99 |
| 327 | 0.30 | 0.74 |
| 328 | 1.03 | 1.55 |
| 329 | 3.24 | 4.05 |
| 330 | 10.00 | 10.00 |
| 331 | 10.00 | 10.00 |
| 332 | 10.00 | |
| 333 | 0.80 | 2.42 |
| 334 | 0.30 | 0.22 |
| 335 | 0.33 | 0.31 |
| 336 | 1.75 | 1.16 |
| 337 | 0.27 | 0.37 |
| 338 | 0.30 | 0.16 |
| 339 | 0.30 | 0.13 |
| 340 | 0.30 | 0.12 |
| 341 | 0.30 | 0.12 |
| 342 | 0.30 | 0.07 |
| 343 | 0.33 | 0.13 |
| 344 | 0.30 | 0.12 |
| 345 | 0.30 | 0.11 |
| 346 | 0.30 | 0.05 |
| 347 | 0.30 | 0.24 |
| 348 | 0.30 | 0.11 |
| 349 | 0.30 | 0.30 |
| 350 | 0.91 | 0.75 |
| 351 | 1.72 | 1.30 |
| 352 | 0.30 | 0.08 |
| 353 | 0.30 | 0.06 |
| 354 | 1.84 | 2.14 |
| 355 | 0.30 | 0.16 |
| 356 | 0.55 | 0.83 |
| 357 | 2.15 | 1.27 |
| 358 | 0.52 | 0.53 |
| 359 | 0.38 | 0.49 |
| 360 | 0.30 | 0.25 |
| 361 | 0.70 | 0.60 |
| 362 | 0.30 | 0.17 |
| 363 | 0.30 | 0.20 |
| 364 | 0.30 | 0.23 |
| 365 | 0.80 | 0.56 |
| 366 | 0.30 | 0.12 |
| 367 | 0.30 | 0.05 |
| 368 | 0.30 | 0.17 |
| 369 | 6.91 | 7.01 |
| 370 | 0.30 | 0.04 |
| 371 | 0.30 | 0.14 |
| 372 | 10.00 | 10.00 |
| 373 | 10.00 | 10.00 |
| 374 | 0.30 | 0.09 |
| 375 | 0.30 | 0.07 |
| 376 | 0.30 | 0.16 |
| 377 | 0.30 | 0.45 |
| 378 | 1.60 | 1.44 |
| 379 | 0.30 | 0.13 |
| 380 | 0.30 | 0.11 |
| 381 | 0.30 | 0.08 |
| 382 | 0.30 | 0.09 |
| 383 | 1.22 | 1.35 |
| 384 | 0.30 | 0.09 |
| 385 | 0.58 | 0.80 |
| 386 | 0.87 | 0.49 |
| 387 | 0.99 | 0.72 |
| 388 | 0.30 | 0.16 |
| 389 | 10.00 | 10.00 |
| 390 | 0.30 | |
| 391 | 0.30 | |
| 392 | 2.01 | |
| 393 | 6.04 | |
| 394 | 4.61 | |
| 395 | 10.00 | |
| 396 | 2.91 | |
| 397 | 1.78 | |
| 398 | 3.53 | |
| 400 | 1.50 | |
| 401 | 0.91 | |
| 402 | 0.54 | |
| 403 | 1.11 | |
| 404 | 0.38 | |
| 405 | 0.30 | |
| 406 | 0.30 | |
| 407 | 0.30 | |
| 408 | 3.36 | |
| 409 | 0.30 | |
| 410 | 1.15 | |

TABLE 4-continued

T-type Calcium Channel Block

| Compound | $\alpha_{1G}$ (μM) | $\alpha_{1H}$ (μM) |
|---|---|---|
| 411 | 10.00 | |
| 412 | 10.00 | |
| 413 | 10.00 | |
| 416 | 10.00 | |
| 417 | 9.49 | |
| 418 | 2.17 | |
| 419 | 1.63 | |
| 420 | 0.70 | |
| 421 | 4.04 | |
| 422 | 1.93 | |
| 423 | 2.08 | |
| 424 | 0.44 | |
| 425 | 0.30 | |
| 426 | 0.30 | |
| 427 | 0.30 | |
| 428 | 0.30 | |
| 429 | 0.30 | |
| 430 | 0.30 | |
| 431 | 0.30 | |
| 432 | 0.30 | |
| 433 | 10.00 | |
| 434 | 0.300 | 0.06 |
| 435 | 0.300 | 0.09 |
| 436 | 10.00 | 10.00 |
| 437 | 10.00 | 10.00 |
| 438 | 3.91 | 1.71 |
| 439 | 3.28 | 2.17 |
| 440 | 10.00 | 10.00 |
| 441 | 9.48 | 10.00 |
| 442 | 10.00 | 10.00 |
| 443 | 3.31 | 2.81 |
| 444 | 7.40 | 10.00 |
| 445 | 10.00 | 10.00 |
| 446 | 10.00 | 10.00 |
| 447 | 9.15 | 3.08 |
| 448 | 9.73 | 4.64 |
| 449 | 10.00 | 10.00 |
| 450 | 8.88 | 10.00 |
| 451 | 10.00 | 10.00 |
| 452 | 4.24 | 7.92 |
| 453 | 8.24 | 10.00 |
| 454 | 0.30 | 0.04 |
| 455 | 0.30 | 0.03 |
| 456 | 0.30 | 0.02 |
| 457 | 0.30 | 0.05 |
| 458 | 0.30 | 0.04 |
| 459 | 0.30 | 0.02 |
| 460 | 0.30 | 0.03 |
| 461 | 0.30 | 0.02 |
| 462 | 0.30 | 0.03 |
| 463 | 0.30 | 0.21 |
| 464 | 0.30 | 0.14 |
| 465 | 0.30 | 0.17 |
| 466 | 0.30 | 0.27 |
| 467 | 0.30 | 0.17 |
| 468 | 0.30 | 0.09 |
| 469 | 0.30 | 0.12 |
| 470 | 0.30 | 0.07 |
| 471 | 0.30 | 0.06 |
| 472 | 0.30 | 0.04 |
| 473 | 0.68 | 0.13 |
| 474 | 0.30 | 0.04 |
| 475 | 0.30 | 0.17 |
| 476 | 0.30 | 0.14 |
| 477 | 0.30 | 0.06 |
| 478 | 0.30 | 0.11 |
| 479 | 0.30 | 0.15 |
| 480 | 0.30 | 0.18 |
| 481 | 0.30 | 0.25 |
| 482 | 0.30 | 0.08 |
| 483 | 0.30 | 0.11 |
| 486 | 10.00 | 10.00 |
| 487 | | 10.00 |
| 488 | 0.42 | 0.13 |
| 489 | 0.37 | 0.12 |
| 490 | 0.30 | 0.15 |
| 491 | 0.30 | 0.19 |
| 492 | 0.30 | 0.09 |
| 493 | 0.30 | 0.06 |
| 494 | 0.30 | 0.16 |
| 495 | 0.30 | 0.09 |
| 496 | 0.30 | 0.09 |
| 497 | 0.77 | 0.16 |
| 498 | 0.77 | 0.22 |
| 499 | 0.30 | 0.14 |
| 500 | 0.30 | 0.18 |
| 501 | 0.30 | 0.12 |
| 502 | 0.59 | 0.23 |
| 503 | 1.55 | 7.20 |
| 504 | 0.42 | 0.42 |
| 505 | 0.77 | 0.58 |
| 506 | 5.36 | 1.48 |
| 507 | 2.98 | 1.48 |
| 508 | 10.00 | 9.22 |
| 510 | 3.97 | 10.00 |
| 511 | 0.30 | 0.09 |
| 512 | 0.30 | 0.19 |
| 513 | 0.30 | 0.09 |
| 514 | 0.30 | 0.31 |
| 515 | 0.31 | 0.31 |
| 516 | 0.46 | 0.22 |
| 517 | 1.10 | 0.42 |
| 518 | 1.31 | 0.81 |
| 519 | 0.30 | 0.24 |
| 520 | 0.30 | 0.19 |
| 522 | 0.30 | 0.14 |
| 523 | 5.74 | 0.91 |
| 524 | 10.00 | 10.00 |
| 525 | 2.36 | 0.77 |
| 526 | 10.00 | 3.24 |
| 527 | 2.65 | 2.84 |
| 528 | 10.00 | 8.54 |
| 529 | 5.44 | 2.51 |
| 530 | 0.59 | 0.86 |
| 531 | 0.30 | 0.08 |
| 532 | 0.30 | 0.13 |
| 533 | 0.43 | 0.40 |
| 534 | 0.38 | 0.42 |
| 535 | 3.62 | 2.14 |
| 536 | 0.30 | 0.12 |
| 537 | 2.47 | 0.36 |
| 538 | 0.30 | 0.06 |
| 539 | 1.68 | 0.51 |
| 540 | 1.40 | 0.55 |
| 541 | 0.31 | 0.41 |
| 542 | 0.98 | 0.45 |
| 543 | 0.58 | 0.41 |
| 544 | 0.30 | 0.17 |
| 545 | 0.47 | 0.21 |
| 546 | 0.30 | 0.13 |
| 547 | 0.30 | 0.03 |
| 548 | 0.30 | 0.16 |
| 549 | 0.30 | 0.11 |
| 550 | 0.30 | 0.02 |
| 551 | 0.37 | 0.14 |
| 552 | 0.30 | 0.06 |
| 553 | 2.52 | 1.73 |
| 554 | 10.00 | 10.00 |
| 555 | 0.53 | 0.89 |
| 556 | 1.37 | 1.77 |
| 557 | 3.58 | 1.31 |
| 558 | 0.30 | 0.46 |
| 559 | 9.06 | 10.00 |
| 560 | 0.47 | 0.59 |
| 561 | 0.30 | 0.27 |
| 562 | 0.40 | 0.66 |
| 563 | 0.30 | 0.31 |
| 564 | 0.30 | 0.10 |
| 565 | 0.31 | 0.22 |
| 566 | 0.76 | 0.82 |
| 567 | 0.30 | 0.35 |
| 568 | 1.36 | 0.89 |

TABLE 4-continued

T-type Calcium Channel Block

| Compound | $\alpha_{1G}$ (µM) | $\alpha_{1H}$ (µM) |
| --- | --- | --- |
| 579 | 3.79 | 4.35 |
| 570 | 2.06 | 2.36 |
| 571 | 10.00 | 10.00 |
| 572 | 0.49 | 1.56 |
| 573 | 1.27 | 1.01 |
| 574 | 0.30 | 0.20 |
| 575 | 1.25 | 1.04 |
| 576 | 0.43 | 0.93 |
| 577 | 0.30 | 0.45 |
| 578 | 0.30 | 0.16 |
| 579 | 0.30 | 0.05 |
| 580 | 0.30 | 0.22 |
| 581 | 0.30 | 0.21 |
| 583 | 0.30 | 0.15 |
| 584 | 0.30 | 0.28 |
| 585 | 10.00 | 10.00 |
| 586 | 10.00 | 4.80 |
| 587 | 10.00 | 3.59 |
| 589 |  | 10.00 |
| 590 | 0.30 | 0.07 |
| 591 |  | 0.17 |
| 592 |  | 0.08 |
| 593 |  | 0.26 |
| 594 |  | 0.16 |
| 595 |  | 0.08 |
| 596 |  | 0.16 |
| 597 |  | 6.52 |
| 598 |  | 1.65 |
| 599 |  | 1.47 |
| 600 |  | 2.05 |
| 601 |  | 1.87 |
| 602 |  | 2.41 |
| 603 |  | 0.81 |
| 604 |  | 1.90 |
| 605 |  | 3.58 |
| 606 |  | 3.30 |
| 607 |  | 3.17 |
| 608 |  | 10.00 |
| 609 |  | 3.05 |
| 610 |  | 0.77 |
| 611 |  | 0.29 |
| 612 |  | 10.00 |

TABLE 5 hERG K⁺ Channel Block

| Compound | hERG (µM) |
| --- | --- |
| 26 | 2.60 |
| 59 | 2.80 |
| 115 | 8.30 |
| 153 | 2.80 |
| 159 | 1.30 |
| 160 | 0.19 |
| 178 | 1.60 |
| 179 | 0.33 |
| 334 | 0.92 |
| 343 | 6.20 |
| 344 | 9.10 |
| 362 | 8.30 |
| 363 | 8.30 |
| 364 | 8.30 |
| 366 | 8.30 |
| 367 | 8.30 |
| 368 | 8.30 |
| 371 | 14.70 |
| 374 | 7.80 |
| 375 | 8.80 |
| 376 | 11.00 |
| 391 | 0.63 |
| 427 | 0.45 |
| 457 | 16.60 |

TABLE 5-continued hERG K⁺ Channel Block

| Compound | hERG (µM) |
| --- | --- |
| 460 | 6.90 |
| 461 | 7.40 |
| 462 | 4.10 |
| 468 | 4.20 |
| 469 | 9.50 |
| 470 | 2.60 |
| 471 | 2.30 |
| 472 | 2.80 |
| 473 | 2.20 |
| 476 | 16.60 |
| 477 | 16.60 |
| 478 | 16.60 |
| 482 | 7.90 |
| 489 | 8.80 |
| 490 | 10.90 |
| 492 | 4.70 |
| 493 | 2.50 |
| 495 | 4.10 |
| 499 | 11.10 |
| 500 | 5.50 |
| 501 | 5.60 |
| 511 | 2.90 |
| 513 | 16.60 |
| 531 | 2.40 |
| 537 | 17.00 |
| 538 | 13.00 |
| 541 | 17.00 |
| 542 | 6.40 |
| 543 | 5.20 |
| 544 | 6.00 |
| 545 | 6.60 |
| 552 | 1.80 |
| 567 | 17.00 |
| 574 | 4.10 |
| 577 | 17.00 |
| 578 | 5.40 |
| 580 | 8.30 |
| 581 | 11.00 |
| 583 | 1.70 |
| 594 | 17.00 |
| 590 | 2.20 |

EXAMPLE 18

L5/L6 Spinal Nerve Ligation (SNL)—Chung Pain Model

The Spinal Nerve Ligation is an animal model representing peripheral nerve injury generating a neuropathic pain syndrome. In this model experimental animals develop the clinical symptoms of tactile allodynia and hyperalgesia. L5/L6 Spinal nerve ligation (SNL) injury may be induced using the procedure of Kim and Chung (Kim, S. H., et al., *Pain* (1992) 50:355-363) in male Sprague-Dawley rats (Harlan; Indianapolis, Ind.) weighing 200 to 250 grams.

Anaesthesia may be induced with 2% isofluorane in $O_2$ at 2 L/min and maintained with 0.5% isofluorane in $O_2$. Rats can then be shaved and aseptically prepared for surgeries. A 2 cm paraspinal incision can be made at the level of L4-S2. L4/L5 can be exposed by removing the transverse process above the nerves with a small rongeur. The L5 spinal nerve is the larger of the two visible nerves below the transverse process and lies closest to the spine. The L6 spinal nerve is located beneath the corner of the slope bone. A home-made glass Chung rod can be used to hook L5 or L6 and a pre-made slip knot of 4.0 silk suture can be placed on the tip of the rod just above the nerve and pulled underneath to allow for the tight ligation. The L5 and L6 spinal nerves can be tightly ligated distal to the dorsal root ganglion. The incision may be closed, and the animals allowed to recover for 5 days. Rats that exhibited motor deficiency (such as paw-dragging) or failure to exhibit subsequent tactile allodynia should be excluded from further testing.

Sham control rats may undergo the same operation and handling as the experimental animals, but without SNL.

Prior to initiating drug delivery, baseline behavioural testing data should be obtained. At selected times after infusion of the Test or Control Article behavioural data can then be collected again.

A. Assessment of Tactile Allodynia—Von Frey

The assessment of tactile allodynia consists of measuring the withdrawal threshold of the paw ipsilateral to the site of nerve injury in response to probing with a series of calibrated von Frey filaments (innocuous stimuli). Animals should be acclimated to the suspended wire-mesh cages for 30 min before testing. Each von Frey filament may be applied perpendicularly to the plantar surface of the ligated paw of rats for 5 sec. A positive response is indicated by a sharp withdrawal of the paw. For rats, the first testing filament is 4.31. Measurements can be taken before and after administration of test articles. The paw withdrawal threshold is determined by the non-parametric method of Dixon (Dixon, W., *Ann. Rev. Pharmacol. Toxicol.* (1980) 20:441-462), in which the stimulus is incrementally increased until a positive response was obtained, and then decreased until a negative result is observed. The protocol can be repeated until three changes in behaviour were determined ("up and down" method) (Chaplan, S. R., et al., *J. Neuroscience Methods* (1994) 53:55-63). The 50% paw withdrawal threshold can be determined as $(10^{[X_f+k\delta]})/10,000$, where $X_f$=the value of the last von Frey filament employed, k=Dixon value for the positive/negative pattern, and $\delta$=the logarithmic difference between stimuli. The cut-off values for rats may be no less than 0.2 g and no higher than 15 g (5.18 filament); for mice no less than 0.03 g and no higher than 2.34 g (4.56 filament). A significant drop of the paw withdrawal threshold compared to the pre-treatment baseline is considered tactile allodynia.

B. Assessment of Thermal Hypersensitivity—Hargreaves

The method of Hargreaves and colleagues (Hargreaves, K., et al., *Pain* (1988) 32:77-8) can be employed to assess paw-withdrawal latency to a noxious thermal stimulus.

Rats may be allowed to acclimate within a Plexiglas enclosure on a clear glass plate for 30 minutes. A radiant heat source (i.e., halogen bulb coupled to an infrared filter) can then be activated with a timer and focused onto the plantar surface of the affected paw of treated rats. Paw-withdrawal latency can be determined by a photocell that halted both lamp and timer when the paw is withdrawn. The latency to withdrawal of the paw from the radiant heat source can be determined prior to L5/L6 SNL, 7-14 days after L5/L6 SNL but before drug, as well as after drug administration. A maximal cut-off of 33 seconds is employed to prevent tissue damage. Paw withdrawal latency can thus be determined to the nearest 0.1 second. A significant drop of the paw withdrawal latency from the baseline indicates the status of thermal hyperalgesia. Antinociception is indicated by a reversal of thermal hyperalgesia to the pre-treatment baseline or a significant ($p<0.05$) increase in paw withdrawal latency above this baseline. Data is converted to % anti hyperalgesia or % anti nociception by the formula: (100×(test latency−baseline latency)/(cut-off−baseline latency) where cut-off is 21 seconds for determining anti hyperalgesia and 40 seconds for determining anti nociception.

EXAMPLE 19

Electroconvulsive Shock (ECS) Threshold Test Epilepsy Model

The proconvulsant or anticonvulsant activity of compounds can be evaluated using the electroconvulsive shock threshold test following the method described by Swinyard et al., (J. Pharmacol. Exp. Ther., 106, 319-330, 1952).

To elicit tonic convulsions, a rectangular electroconvulsive shock is administered to OF1 mice for 0.4 s at 50 Hz, via corneal electrodes connected to a constant current shock generator (Ugo Basile: Type 7801). The threshold for tonic convulsions is determined as follows: The first animal is exposed to 30 mA. If the first animal does not exhibit tonic convulsions within 5 seconds, the second animal is exposed to 40 mA, and so on (increments of 10 mA) until the first tonic convulsion is observed. Once the first tonic convulsion is observed, the intensity of ECS is decreased by 5 mA for the next animal and then the intensity is decreased or increased by 5 mA from animal to animal depending on whether the previous animal convulsed or not. The minimum intensity given is 5 mA and the maximum intensity given is 95 mA.

Each treatment group consists of a number mice that are all exposed to ECS, but only the first 3 animals are used to estimate the threshold current and are not included in the analysis.

For optimal results, each test substance is evaluated at multiple doses, administered i.p. or p.o., prior to ECS to coincide with times of peak optimal effect (Tmax), and compared with a vehicle control group. Diazepam administered under the same experimental conditions can be used as reference substance and the vehicle alone can be administered as a vehicle control.

The results are reported as the mean intensity administered, number of deaths and percent change from control for each treatment group for approximately 30 minutes after the animal receives the ECS. A positive percent change indicates an anticonvulsant effect whereas a negative percent change indicates a proconvulsant effect. For the test substances, data (intensity) can be analyzed using a one-way ANOVA followed by Dunnett's t test in case of a significant group effect. The effects of the reference substance (diazepam) can be analyzed using a Student's t test.

EXAMPLE 20

GAERS (Genetic Absence Epilepsy Rats from Strasbourg) Epilepsy Model

The GAERS (Genetic Absence Epilepsy Rats from Strasbourg) is noted for its long and frequently recurring absence seizure episodes. Investigators have determined, using electrophysiological recordings from neurons within the thalamus, that the activity and expression of the low-voltage calcium channels is significantly increased in GAERS. Eight female GAERS rats, bred in the Ludwig Institute for Cancer Research, were used for this study. Rats weighed between 180 and 250 g and aged between 18 and 26 weeks at the start of the experiment.

Electrodes were made in our laboratory by soldering together gold-plated sockets (220-S02 Ginder Scientific, VA, Canada), stainless steel teflon coated wire (SDR clinical technology, NSW, Australia) and a small stainless steel screw (1.4×3 mm, Mr. Specks, Australia). Animals were anaethetised with inhalation of Isoflurane in equal parts of medical air and oxygen (5% induction, 2.5-1.5% maintenance) or alternatively by intraperitoneal injection with xylazine (10 mg/kg) and ketamine (75 mg/kg). The animals were fixated in a stereotaxic frame by means of ear bars. A midline incision on the scalp was made, skin and connective tissue was scraped and pushed laterally to expose underlying skull. 6 holes were drilled bilaterally, 2 in the frontal bone and 4 in the parietal bone, approximately 2 mm anterior to bregma, and 4 and 10 mm posterior to bregma. 6 electrodes were implanted in the holes, and gold-plated sockets were clipped into 9-pin ABS plug (GS09PLG-220, Ginder Scientific, Canada). 2 two side-anchoring screws were placed laterally into skull to improve strength of cap fixation, then caps were held in place with dental cement.

Post-operatively, animals were given the analgesic Rimadyl (4 mg/kg), placed in their cages on a heat mat, and observed until recovery. Rats were caged separately throughout the study, weighed and health-checked daily, and were allowed 7 days to recover prior to commencement of the experimental procedures. Rats were allowed free access to rodent chow (brand, WA stock feeders) and water under 12:12 light dark conditions in the Biological Research Facility of the Department of Medicine (RMH).

Prior to first drug treatment, rats were tested for absence-type seizures, which are accompanied by generalised spike and wave discharges (SWD) on an EEG recording. Testing, and all further experiments were performed in a quiet, well lit room with rats in their home cages. Rats were connected via 6-channel wire cables, which were cut and soldered to 6 gold-plated pins inserted into a 9 pin socket. Cables were connected to a computer running Compumedics™ EEG acquisition software (Melbourne, Australia). 3 rats which did not have adequate baseline seizures at the start of the study were commenced in week 2 and their treatments were made up for at the end according to the schedule (see table 2). On week 1, day 1 after the acclimation period following surgical implantation of subdural electrodes, 4 animals (#1-4) were habituated with the cable connected for 15 minutes, then had their SWDs recorded for 60 minutes as baseline. Immediately following baseline, rats were given one of the test, reference or control articles according to the treatment schedule, and target period was recorded from 15 after injection for 120 minutes. Animals were monitored throughout the experiment, and were kept quietly wakeful during baseline and target periods The seizure expression for the 60 minutes pre-injection and 120 minutes post-injection EEG recording (starting 15 minutes post-drug administration) was quantified by marking the start and finish of the burst of SWDs. This was done with the assistance of SWCFinder® software which has been custom designed to quantitate GAERS seizures, and researchers were blinded to the nature of the drug administered, whereby the analysis was performed blinded. Standard criteria for GAERS seizures is an SWD burst of amplitude of more than three times baseline, a frequency of 7 to 12 Hz, and a duration of longer than 0.5 s. From this, the total percent time spent in seizure over the 120 minutes post-injection EEG recording was determined (percentage time in seizure) as the primary outcome variable.

Table 6 shows the average percentage time in seizure of vehicle, compounds 365 and 368 administered IP with a 30 mg/kg dose compared to baseline. Both compounds 365 and 368 demonstrated a significant decrease in the percentage of time in seizure activity compared to both baseline and vehicle.

TABLE 6

| | Percent Recording Time in Seizure Activity | |
|---|---|---|
| Cmpd No. | Baseline | Post-injection |
| Vehicle | 13.85 ± 2.89 | 9.67 ± 1.92 |
| 364 | 12.12 ± 1.82 | 0.45 ± 0.20 |
| 367 | 9.99 ± 2.07 | 0.87 ± 0.44 |

The invention claimed is:

1. A pharmaceutical composition comprising a compound having the structure:

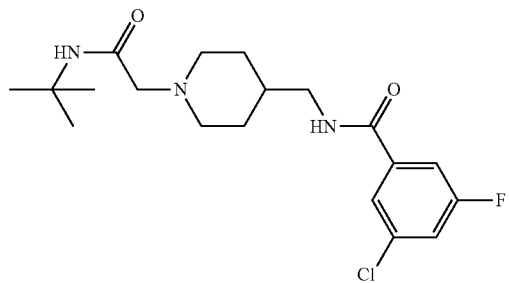 [SMILES: CC(C)(C)NC(=O)CN1CCC(CNC(=O)c2cc(F)cc(Cl)c2)CC1]

or a pharmaceutically acceptable salt or conjugate thereof in admixture with a pharmaceutically acceptable excipient.

2. A method to treat epilepsy, said method comprising administering to a subject in need of such treatment an amount of the pharmaceutical composition of claim 1 effective to ameliorate epilepsy.

* * * * *

UNITED STATES PATENT AND TRADEMARK OFFICE
CERTIFICATE OF CORRECTION

PATENT NO. : 8,377,968 B2
APPLICATION NO. : 12/420793
DATED : February 19, 2013
INVENTOR(S) : Pajouhesh et al.

Page 1 of 1

It is certified that error appears in the above-identified patent and that said Letters Patent is hereby corrected as shown below:

In the Specification

Column 1, Line 49, replace "Regulation nad Clinical" with --Regulation and Clinical--.

Column 3, Line 17, replace "heteroakenylene" with --heteroalkenylene--.

Column 6, Lines 24-25, replace "substitents" with --substituents--.

Column 8, Lines 25-26, replace "calcum channel" with --calcium channel--.

Signed and Sealed this
Twenty-fourth Day of September, 2013

Teresa Stanek Rea
*Deputy Director of the United States Patent and Trademark Office*